(12) United States Patent
Allen et al.

(10) Patent No.: US 10,507,141 B2
(45) Date of Patent: Dec. 17, 2019

(54) APPARATUSES AND METHODS FOR NEGATIVE PRESSURE WOUND THERAPY

(71) Applicant: Smith & Nephew PLC, Watford, Hertfordshire (GB)

(72) Inventors: Julie Allen, Hull (GB); Ben Alan Askem, Brough (GB); Sarah Jenny Collinson, Hull (GB); Philip Gowans, York (GB); Steven Carl Mehta, Lincoln (GB); Derek Nicolini, Hull (GB); Carol Zagrabski, Cheektowaga, NY (US)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 15/890,218

(22) Filed: Feb. 6, 2018

(65) Prior Publication Data

US 2018/0168869 A1 Jun. 21, 2018

Related U.S. Application Data

(63) Continuation of application No. 14/403,036, filed as application No. PCT/IB2013/001469 on May 22, 2013, now Pat. No. 9,907,703.
(Continued)

(51) Int. Cl.
*A61M 1/00* (2006.01)
*A61F 13/02* (2006.01)
*A61F 13/00* (2006.01)

(52) U.S. Cl.
CPC ...... *A61F 13/022* (2013.01); *A61F 13/00068* (2013.01); *A61F 13/0216* (2013.01);
(Continued)

(58) Field of Classification Search
CPC .............. A61F 13/022; A61F 13/00068; A61F 13/0216; A61F 2013/00238;
(Continued)

(56) References Cited

U.S. PATENT DOCUMENTS

| 2,905,174 A | 9/1959 | Smith |
| 3,285,245 A | 11/1966 | Eldredge et al. |

(Continued)

FOREIGN PATENT DOCUMENTS

| AU | 674837 B2 | 1/1997 |
| CN | 1212613 A | 3/1999 |

(Continued)

OTHER PUBLICATIONS

US 7,186,244 B1, 03/2007, Hunt et al. (withdrawn)
(Continued)

*Primary Examiner* — Andrew J Mensh
(74) *Attorney, Agent, or Firm* — Knobbe, Martens, Olson & Bear LLP

(57) ABSTRACT

Disclosed herein are several embodiments of a negative pressure appliance and methods of using the same in the treatment of wounds. Some embodiments are directed towards wound dressings comprising a liquid and gas permeable transmission layer, an absorbent layer for absorbing wound exudate, the absorbent layer overlying the transmission layer, a gas impermeable cover layer overlying the absorbent layer and comprising a first orifice, wherein the cover layer is moisture vapor permeable. Some embodiments are directed to improved fluidic connectors or suction adapters for connecting to a wound site, for example using softer, kink-free conformable suction adapters.

14 Claims, 99 Drawing Sheets

Related U.S. Application Data

(60) Provisional application No. 61/650,904, filed on May 23, 2012, provisional application No. 61/785,927, filed on Mar. 14, 2013.

(52) U.S. Cl.
CPC ........ *A61M 1/0056* (2013.01); *A61M 1/0086* (2014.02); *A61M 1/0088* (2013.01); *A61F 2013/00238* (2013.01); *A61M 1/008* (2013.01); *A61M 2205/583* (2013.01); *A61M 2205/7536* (2013.01)

(58) Field of Classification Search
CPC .............. A61M 1/0086; A61M 1/0056; A61M 1/0088; A61M 1/008; A61M 2205/583; A61M 2205/7536
USPC ........................................................ 604/319
See application file for complete search history.

(56) References Cited

U.S. PATENT DOCUMENTS

| | | | |
|---|---|---|---|
| 3,568,675 A | 3/1971 | Harvey | |
| 3,687,136 A | 8/1972 | Carmody | |
| 3,935,863 A | 2/1976 | Kliger | |
| 3,943,734 A | 3/1976 | Fleissner | |
| 3,972,328 A | 8/1976 | Chen | |
| 4,029,598 A | 6/1977 | Neisius et al. | |
| 4,093,277 A | 6/1978 | Nolan et al. | |
| 4,605,399 A | 8/1986 | Weston et al. | |
| 4,728,499 A | 3/1988 | Fehder | |
| 4,798,603 A | 1/1989 | Meyer et al. | |
| 4,813,942 A | 3/1989 | Alvarez | |
| 4,834,735 A | 5/1989 | Alemany et al. | |
| 4,846,164 A | 7/1989 | Martz | |
| 4,968,181 A | 11/1990 | Goldman | |
| 4,969,880 A | 11/1990 | Zamierowski | |
| 4,973,325 A | 11/1990 | Sherrod et al. | |
| 4,988,344 A | 1/1991 | Reising et al. | |
| 4,988,345 A | 1/1991 | Reising | |
| 5,000,172 A | 3/1991 | Ward | |
| 5,018,515 A | 5/1991 | Gilman | |
| 5,021,050 A | 6/1991 | Iskra | |
| 5,037,409 A | 8/1991 | Chen et al. | |
| 5,056,510 A | 10/1991 | Gilman | |
| 5,061,258 A * | 10/1991 | Martz ................... A61F 13/023 128/898 |
| 5,065,600 A | 11/1991 | Byles | |
| 5,100,396 A | 3/1992 | Zamierowski | |
| 5,115,801 A | 5/1992 | Cartmell et al. | |
| 5,124,197 A | 6/1992 | Bernardin et al. | |
| 5,149,334 A | 9/1992 | Lahrman et al. | |
| 5,151,091 A | 9/1992 | Glaug et al. | |
| 5,160,328 A | 11/1992 | Cartmell et al. | |
| 5,171,391 A | 12/1992 | Chmielewski et al. | |
| 5,175,046 A | 12/1992 | Nguyen | |
| 5,181,905 A | 1/1993 | Flam | |
| 5,197,945 A | 3/1993 | Cole et al. | |
| 5,217,445 A | 6/1993 | Young et al. | |
| 5,236,427 A | 8/1993 | Hamajima et al. | |
| 5,238,732 A | 8/1993 | Krishnan | |
| 5,242,435 A | 9/1993 | Murji et al. | |
| 5,257,982 A | 11/1993 | Cohen et al. | |
| 5,261,893 A | 11/1993 | Zamierowski | |
| 5,271,987 A | 12/1993 | Iskra | |
| 5,281,208 A | 1/1994 | Thompson et al. | |
| 5,294,478 A | 3/1994 | Wanek et al. | |
| 5,296,290 A | 3/1994 | Brassington | |
| 5,314,743 A | 5/1994 | Meirowitz et al. | |
| 5,318,554 A | 6/1994 | Young et al. | |
| 5,330,456 A | 7/1994 | Robinson | |
| 5,336,219 A | 8/1994 | Krantz | |
| 5,342,336 A | 8/1994 | Meirowitz et al. | |
| 5,348,547 A | 9/1994 | Payne et al. | |
| 5,354,261 A | 10/1994 | Clark et al. | |
| 5,356,405 A | 10/1994 | Thompson et al. | |
| 5,358,492 A | 10/1994 | Feibus | |
| 5,360,420 A | 11/1994 | Cook et al. | |
| 5,364,381 A | 11/1994 | Soga et al. | |
| 5,364,382 A | 11/1994 | Latimer et al. | |
| 5,366,451 A | 11/1994 | Levesque | |
| 5,368,909 A | 11/1994 | Langdon et al. | |
| 5,368,926 A | 11/1994 | Thompson et al. | |
| 5,374,260 A | 12/1994 | Lemay et al. | |
| 5,380,294 A | 1/1995 | Persson | |
| 5,382,245 A | 1/1995 | Thompson et al. | |
| 5,387,208 A | 2/1995 | Ashton et al. | |
| 5,397,316 A | 3/1995 | Lavon et al. | |
| 5,401,267 A | 3/1995 | Couture-Dorschner et al. | |
| 5,425,725 A | 6/1995 | Tanzer et al. | |
| 5,431,643 A | 7/1995 | Ouellette et al. | |
| 5,447,492 A | 9/1995 | Cartmell et al. | |
| 5,454,800 A | 10/1995 | Hirt et al. | |
| 5,456,660 A | 10/1995 | Reich et al. | |
| 5,465,735 A | 11/1995 | Patel | |
| 5,470,326 A | 11/1995 | Dabi et al. | |
| H1511 H | 12/1995 | Chappell et al. | |
| 5,480,377 A | 1/1996 | Cartmell et al. | |
| 5,486,167 A | 1/1996 | Dragoo et al. | |
| 5,487,736 A | 1/1996 | Van Phan | |
| 5,497,788 A | 3/1996 | Inman et al. | |
| 5,500,270 A | 3/1996 | Langdon et al. | |
| 5,501,661 A | 3/1996 | Cartmell et al. | |
| 5,505,719 A | 4/1996 | Cohen et al. | |
| 5,509,914 A | 4/1996 | Osborn, III | |
| 5,514,120 A | 5/1996 | Johnston et al. | |
| 5,525,407 A | 6/1996 | Yang | |
| 5,527,293 A | 6/1996 | Zamierowski | |
| 5,536,264 A | 7/1996 | Hsueh et al. | |
| 5,538,500 A | 7/1996 | Peterson | |
| H1585 H | 8/1996 | Ahr | |
| 5,545,155 A | 8/1996 | Hseih et al. | |
| 5,549,584 A | 8/1996 | Gross | |
| 5,549,589 A | 8/1996 | Horney et al. | |
| 5,562,107 A | 10/1996 | Lavender et al. | |
| 5,562,646 A | 10/1996 | Goldman et al. | |
| 5,562,650 A | 10/1996 | Everett et al. | |
| 5,579,765 A | 12/1996 | Cox et al. | |
| 5,591,148 A | 1/1997 | McFall et al. | |
| 5,591,149 A | 1/1997 | Cree et al. | |
| 5,599,289 A | 2/1997 | Castellana | |
| 5,603,707 A | 2/1997 | Trombetta et al. | |
| 5,603,946 A | 2/1997 | Constantine | |
| 5,609,588 A | 3/1997 | DiPalma et al. | |
| 5,613,960 A | 3/1997 | Mizutani | |
| 5,614,283 A | 3/1997 | Pontis et al. | |
| 5,614,295 A | 3/1997 | Quincy, III et al. | |
| 5,628,736 A | 5/1997 | Thompson | |
| 5,632,731 A | 5/1997 | Patel | |
| H1657 H | 6/1997 | Hammons et al. | |
| 5,634,915 A | 6/1997 | Osterdahl | |
| 5,636,643 A | 6/1997 | Argenta et al. | |
| 5,637,080 A | 6/1997 | Geng | |
| 5,643,238 A | 7/1997 | Baker | |
| 5,645,081 A | 7/1997 | Argenta et al. | |
| 5,648,142 A | 7/1997 | Phillips | |
| 5,649,915 A | 7/1997 | Chauvette et al. | |
| 5,649,916 A | 7/1997 | DiPalma et al. | |
| 5,662,599 A | 9/1997 | Reich et al. | |
| 5,665,082 A | 9/1997 | Boulanger | |
| 5,669,895 A | 9/1997 | Murakami et al. | |
| 5,675,079 A | 10/1997 | Gilman et al. | |
| 5,678,564 A | 10/1997 | Lawrence et al. | |
| 5,700,254 A | 12/1997 | McDowall et al. | |
| 5,701,917 A | 12/1997 | Khouri | |
| 5,702,356 A | 12/1997 | Hathman | |
| 5,704,905 A | 1/1998 | Jensen et al. | |
| 5,707,499 A | 1/1998 | Joshi et al. | |
| 5,713,384 A | 2/1998 | Roach et al. | |
| 5,713,842 A | 2/1998 | Kay | |
| 5,716,703 A | 2/1998 | Payne | |
| 5,728,084 A | 3/1998 | Palumbo et al. | |
| 5,728,085 A | 3/1998 | Widlund et al. | |

(56) References Cited

U.S. PATENT DOCUMENTS

| | | |
|---|---|---|
| 5,733,273 A | 3/1998 | Ahr |
| 5,752,945 A | 5/1998 | Mosley et al. |
| 5,759,570 A | 6/1998 | Arnold |
| 5,762,641 A | 6/1998 | Bewick-Sonntag et al. |
| 5,788,684 A | 8/1998 | Abuto et al. |
| 5,795,584 A | 8/1998 | Totakura et al. |
| 5,801,107 A | 9/1998 | Everhart et al. |
| 5,810,798 A | 9/1998 | Finch et al. |
| 5,817,081 A | 10/1998 | LaVon et al. |
| 5,827,213 A | 10/1998 | Jensen |
| 5,827,254 A | 10/1998 | Trombetta et al. |
| 5,830,202 A | 11/1998 | Bogdanski et al. |
| 5,837,627 A | 11/1998 | Halabisky et al. |
| 5,840,052 A | 11/1998 | Johns |
| 5,843,025 A | 12/1998 | Shaari |
| 5,843,064 A | 12/1998 | Koczab |
| 5,852,126 A | 12/1998 | Barnard et al. |
| 5,855,572 A | 1/1999 | Schmidt |
| 5,865,822 A | 2/1999 | Hamajima et al. |
| 5,865,824 A | 2/1999 | Chen et al. |
| 5,873,867 A | 2/1999 | Coles et al. |
| 5,877,097 A | 3/1999 | West et al. |
| 5,891,120 A | 4/1999 | Chmielewski |
| 5,895,379 A | 4/1999 | Litchholt et al. |
| 5,897,541 A | 4/1999 | Uitenbrock et al. |
| 5,916,507 A | 6/1999 | Dabi et al. |
| 5,925,026 A | 7/1999 | Arteman et al. |
| 5,931,823 A | 8/1999 | Stokes et al. |
| 5,938,995 A | 8/1999 | Koltisko, Jr. et al. |
| 5,941,863 A | 8/1999 | Guidotti et al. |
| 5,947,945 A | 9/1999 | Cree et al. |
| 5,951,535 A | 9/1999 | Fujiwara et al. |
| 5,961,506 A | 10/1999 | Guidotti et al. |
| 5,968,027 A | 10/1999 | Cole et al. |
| 5,968,855 A | 10/1999 | Perdelwitz, Jr. et al. |
| 5,989,478 A | 11/1999 | Ouellette et al. |
| 6,018,092 A | 1/2000 | Dunshee |
| 6,022,610 A | 2/2000 | Phan et al. |
| 6,037,518 A | 3/2000 | Guidotti et al. |
| 6,040,493 A | 3/2000 | Cooke et al. |
| 6,060,638 A | 5/2000 | Paul et al. |
| 6,068,620 A | 5/2000 | Chmielewski |
| 6,071,267 A | 6/2000 | Zamierowski |
| 6,075,177 A | 6/2000 | Bahia et al. |
| 6,077,526 A | 6/2000 | Scully et al. |
| 6,096,015 A | 8/2000 | Yeo et al. |
| 6,103,953 A | 8/2000 | Cree et al. |
| 6,103,954 A | 8/2000 | Grondin et al. |
| 6,107,539 A | 8/2000 | Palumbo et al. |
| 6,117,523 A | 9/2000 | Sugahara |
| 6,124,520 A | 9/2000 | Roberts |
| 6,124,521 A | 9/2000 | Roberts |
| 6,127,595 A | 10/2000 | Makoui et al. |
| 6,142,982 A | 11/2000 | Hunt et al. |
| 6,168,849 B1 | 1/2001 | Braverman et al. |
| 6,191,340 B1 | 2/2001 | Carlucci et al. |
| 6,206,865 B1 | 3/2001 | Chen et al. |
| 6,235,966 B1 | 5/2001 | Magnusson et al. |
| 6,241,697 B1 | 6/2001 | Augustine |
| 6,264,776 B1 | 7/2001 | DiPalma |
| 6,294,710 B1 | 9/2001 | Schmidt et al. |
| 6,297,423 B1 | 10/2001 | Schoenfeldt et al. |
| 6,344,036 B1 | 2/2002 | Ivansson |
| 6,345,623 B1 | 2/2002 | Heaton et al. |
| 6,362,390 B1 | 3/2002 | Carlucci et al. |
| 6,369,292 B1 | 4/2002 | Strack et al. |
| 6,372,952 B1 | 4/2002 | Lash et al. |
| 6,403,857 B1 | 6/2002 | Gross et al. |
| 6,458,109 B1 | 10/2002 | Henley et al. |
| 6,461,339 B1 | 10/2002 | Sugahara |
| 6,468,295 B2 | 10/2002 | Augustine et al. |
| 6,479,415 B1 | 11/2002 | Erspamer et al. |
| 6,497,688 B2 | 12/2002 | Lasko |
| 6,497,689 B2 | 12/2002 | Schmidt et al. |
| 6,506,175 B1 | 1/2003 | Goldstein |
| 6,506,960 B1 | 1/2003 | Young et al. |
| 6,521,813 B1 | 2/2003 | Chihani |
| 6,528,696 B1 | 3/2003 | Ireland |
| 6,534,149 B1 | 3/2003 | Daley et al. |
| 6,545,194 B1 | 4/2003 | Schmidt et al. |
| 6,551,295 B1 | 4/2003 | Schmidt et al. |
| 6,552,244 B1 | 4/2003 | Jacques et al. |
| 6,570,057 B1 | 5/2003 | Schmidt et al. |
| 6,570,058 B1 | 5/2003 | Fuchs et al. |
| 6,573,424 B1 | 6/2003 | Raidel et al. |
| 6,586,653 B2 | 7/2003 | Graeme, III et al. |
| 6,610,898 B1 | 8/2003 | Magnusson et al. |
| 6,610,903 B1 | 8/2003 | Latimer et al. |
| 6,613,028 B1 | 9/2003 | Daley et al. |
| 6,613,953 B1 | 9/2003 | Altura |
| 6,613,955 B1 | 9/2003 | Lindsay et al. |
| 6,626,891 B2 | 9/2003 | Ohmstede |
| 6,630,611 B1 | 10/2003 | Malowaniec |
| 6,648,862 B2 | 11/2003 | Watson |
| 6,664,439 B1 | 12/2003 | Arndt et al. |
| 6,683,229 B1 | 1/2004 | Ehrnsperger et al. |
| 6,685,681 B2 | 2/2004 | Lockwood et al. |
| 6,706,940 B2 | 3/2004 | Worthley |
| 6,719,742 B1 | 4/2004 | McCormack et al. |
| 6,727,403 B1 | 4/2004 | Ehrnsperger et al. |
| 6,752,794 B2 | 6/2004 | Lockwood et al. |
| 6,755,807 B2 | 6/2004 | Risk et al. |
| 6,762,337 B2 | 7/2004 | Boukanov et al. |
| 6,764,459 B1 | 7/2004 | Donaldson |
| 6,776,769 B2 | 8/2004 | Smith |
| 6,783,837 B1 | 8/2004 | Creagan et al. |
| 6,787,682 B2 | 9/2004 | Gilman |
| 6,835,192 B1 | 12/2004 | Guidotti et al. |
| 6,841,715 B2 | 1/2005 | Roberts |
| 6,855,135 B2 | 2/2005 | Lockwood et al. |
| 6,936,037 B2 | 8/2005 | Bubb et al. |
| 6,951,553 B2 | 10/2005 | Bubb et al. |
| 6,960,181 B2 | 11/2005 | Stevens |
| 6,979,324 B2 | 12/2005 | Bybordi et al. |
| 6,998,511 B2 | 2/2006 | Worthley |
| 7,004,915 B2 | 2/2006 | Boynton et al. |
| 7,049,478 B1 | 5/2006 | Smith et al. |
| 7,070,584 B2 | 7/2006 | Johnson et al. |
| 7,108,683 B2 | 9/2006 | Zamierowski |
| 7,112,712 B1 | 9/2006 | Ancell |
| 7,118,545 B2 | 10/2006 | Boyde |
| 7,122,023 B1 | 10/2006 | Hinoki |
| 7,122,712 B2 | 10/2006 | Lutri et al. |
| 7,195,624 B2 | 3/2007 | Lockwood |
| 7,198,046 B1 | 4/2007 | Argenta et al. |
| 7,216,651 B2 | 5/2007 | Argenta et al. |
| 7,279,612 B1 | 10/2007 | Heaton et al. |
| 7,294,751 B2 | 11/2007 | Propp et al. |
| 7,294,752 B1 | 11/2007 | Propp |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,429,689 B2 | 9/2008 | Chen et al. |
| 7,438,705 B2 | 10/2008 | Karpowicz et al. |
| 7,476,205 B2 | 1/2009 | Erdmann |
| 7,485,112 B2 | 2/2009 | Karpowicz et al. |
| 7,503,910 B2 | 3/2009 | Adahan |
| 7,511,187 B2 | 3/2009 | Kelly |
| 7,534,927 B2 | 5/2009 | Lockwood |
| 7,563,940 B2 | 7/2009 | Kurata |
| 7,569,742 B2 | 8/2009 | Haggstrom et al. |
| 7,576,256 B2 | 8/2009 | Björnberg et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,645,269 B2 | 1/2010 | Zamierowski |
| 7,670,323 B2 | 3/2010 | Hunt et al. |
| 7,676,257 B2 | 3/2010 | Suryanarayanan et al. |
| 7,678,102 B1 | 3/2010 | Heaton |
| 7,686,785 B2 | 3/2010 | Boehringer et al. |
| 7,699,823 B2 | 4/2010 | Haggstrom et al. |

(56) References Cited

U.S. PATENT DOCUMENTS

| | | |
|---|---|---|
| 7,699,831 B2 | 4/2010 | Bengtson et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,723,561 B2 | 5/2010 | Propp |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,794,438 B2 | 9/2010 | Henley et al. |
| 7,811,269 B2 | 10/2010 | Boynton et al. |
| 7,812,212 B2 | 10/2010 | Propp et al. |
| 7,838,717 B2 | 11/2010 | Haggstrom et al. |
| 7,838,719 B2 | 11/2010 | Hilton, Jr. |
| 7,838,723 B1 | 11/2010 | Schmidt et al. |
| 7,846,141 B2 | 12/2010 | Weston |
| 7,862,718 B2 | 1/2011 | Doyen et al. |
| 7,880,050 B2 | 2/2011 | Robinson et al. |
| 7,884,258 B2 | 2/2011 | Boehringer et al. |
| 7,896,864 B2 | 3/2011 | Lockwood et al. |
| 7,910,791 B2 | 3/2011 | Coffey |
| 7,922,703 B2 | 4/2011 | Riesinger |
| 7,935,066 B2 | 5/2011 | Shives et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,981,098 B2 | 7/2011 | Boehringer et al. |
| 7,988,673 B2 | 8/2011 | Wright et al. |
| 8,007,905 B2 | 8/2011 | Perez et al. |
| 8,021,347 B2 | 9/2011 | Vitaris et al. |
| 8,034,037 B2 | 10/2011 | Adams et al. |
| 8,062,272 B2 | 11/2011 | Weston |
| 8,062,331 B2 | 11/2011 | Zamierowski |
| 8,083,712 B2 | 12/2011 | Biggie et al. |
| 8,092,436 B2 | 1/2012 | Christensen |
| 8,105,295 B2 | 1/2012 | Blott et al. |
| 8,133,211 B2 | 3/2012 | Cavanaugh, II et al. |
| 8,147,468 B2 | 4/2012 | Barta et al. |
| 8,152,785 B2 | 4/2012 | Vitaris |
| 8,158,844 B2 | 4/2012 | McNeil |
| 8,162,907 B2 | 4/2012 | Heagle |
| 8,168,848 B2 | 5/2012 | Lockwood et al. |
| 8,187,237 B2 | 5/2012 | Seegert |
| 8,188,331 B2 | 5/2012 | Barta et al. |
| 8,192,409 B2 | 6/2012 | Hardman et al. |
| 8,202,261 B2 | 6/2012 | Kazala, Jr. et al. |
| 8,212,101 B2 | 7/2012 | Propp |
| 8,235,972 B2 | 8/2012 | Adahan |
| 8,241,261 B2 | 8/2012 | Randolph et al. |
| 8,246,606 B2 | 8/2012 | Stevenson et al. |
| 8,252,971 B2 | 8/2012 | Aali et al. |
| 8,267,908 B2 | 9/2012 | Coulthard |
| 8,298,200 B2 | 10/2012 | Vess et al. |
| 8,314,283 B2 | 11/2012 | Kingsford et al. |
| 8,328,858 B2 | 12/2012 | Barsky et al. |
| 8,361,043 B2 | 1/2013 | Hu et al. |
| 8,372,049 B2 | 2/2013 | Jaeb et al. |
| 8,372,050 B2 | 2/2013 | Jaeb et al. |
| 8,382,731 B2 | 2/2013 | Johannison |
| 8,403,899 B2 | 3/2013 | Sherman |
| 8,404,921 B2 | 3/2013 | Lee et al. |
| 8,409,170 B2 | 4/2013 | Locke et al. |
| 8,425,478 B2 | 4/2013 | Olson |
| 8,444,611 B2 | 5/2013 | Wilkes et al. |
| 8,454,580 B2 | 6/2013 | Locke et al. |
| 8,506,554 B2 | 8/2013 | Adahan |
| 8,513,481 B2 | 8/2013 | Gergeley et al. |
| 8,535,296 B2 | 9/2013 | Blott et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,641,691 B2 | 2/2014 | Fink |
| 8,663,198 B2 | 3/2014 | Buan et al. |
| 8,680,360 B2 | 3/2014 | Greener et al. |
| 8,715,256 B2 | 5/2014 | Greener |
| 8,764,732 B2 | 7/2014 | Hartwell |
| 8,771,244 B2 | 7/2014 | Eckstein et al. |
| 8,791,316 B2 | 7/2014 | Greener |
| 8,795,244 B2 | 8/2014 | Randolph et al. |
| 8,795,247 B2 | 8/2014 | Bennett et al. |
| 8,795,800 B2 | 8/2014 | Evans |
| 8,801,685 B2 | 8/2014 | Armstrong et al. |
| 8,808,274 B2 | 8/2014 | Hartwell |
| 8,814,842 B2 | 8/2014 | Coulthard et al. |
| 8,834,451 B2 | 9/2014 | Blott et al. |
| 8,834,452 B2 | 9/2014 | Hudspeth et al. |
| 8,915,895 B2 | 12/2014 | Jaeb et al. |
| 8,916,742 B2 | 12/2014 | Smith |
| 9,012,714 B2 | 4/2015 | Fleischmann |
| 9,033,942 B2 | 5/2015 | Vess |
| 9,061,095 B2 | 6/2015 | Adie et al. |
| 9,067,003 B2 | 6/2015 | Buan et al. |
| 9,127,665 B2 | 9/2015 | Locke et al. |
| 9,173,777 B2 | 11/2015 | Zurovcik |
| 9,199,012 B2 | 12/2015 | Vitaris et al. |
| 9,220,822 B2 | 12/2015 | Hartwell et al. |
| 9,254,353 B2 | 2/2016 | Locke et al. |
| 9,283,118 B2 | 3/2016 | Locke et al. |
| 9,302,033 B2 | 4/2016 | Riesinger |
| 9,381,283 B2 | 7/2016 | Adams et al. |
| 9,421,309 B2 | 8/2016 | Robinson et al. |
| 9,427,505 B2 | 8/2016 | Askem et al. |
| 9,446,178 B2 | 9/2016 | Blott et al. |
| 9,452,245 B2 | 9/2016 | Jaeb et al. |
| 9,474,661 B2 | 10/2016 | Fouillet et al. |
| 9,539,373 B2 | 1/2017 | Jones et al. |
| 9,681,993 B2 | 6/2017 | Wu et al. |
| 9,682,179 B2 | 6/2017 | May |
| 9,808,561 B2 | 11/2017 | Adie et al. |
| 10,039,673 B2 | 8/2018 | Mumby et al. |
| 10,080,690 B2 | 9/2018 | Stevenson et al. |
| 10,328,188 B2 | 6/2019 | Begin et al. |
| 2001/0000795 A1 | 5/2001 | Bolian, II et al. |
| 2001/0016985 A1 | 8/2001 | Insley et al. |
| 2001/0018308 A1 | 8/2001 | Quick et al. |
| 2001/0027302 A1 | 10/2001 | Glaug et al. |
| 2001/0027305 A1 | 10/2001 | Raidel et al. |
| 2001/0044610 A1 | 11/2001 | Kim et al. |
| 2001/0051165 A1 | 12/2001 | Lenz et al. |
| 2001/0051178 A1 | 12/2001 | Blatchford et al. |
| 2001/0053904 A1 | 12/2001 | Abuto |
| 2002/0007167 A1 | 1/2002 | Dan et al. |
| 2002/0007169 A1 | 1/2002 | Graef et al. |
| 2002/0019602 A1 | 2/2002 | Geng |
| 2002/0019614 A1 | 2/2002 | Woon et al. |
| 2002/0026166 A1 | 2/2002 | Graef et al. |
| 2002/0034914 A1 | 3/2002 | De Leon et al. |
| 2002/0035352 A1 | 3/2002 | Ronnberg et al. |
| 2002/0035354 A1 | 3/2002 | Mirle et al. |
| 2002/0062113 A1 | 5/2002 | Thomas et al. |
| 2002/0064639 A1 | 5/2002 | Rearick et al. |
| 2002/0087136 A1 | 7/2002 | Widlund |
| 2002/0090511 A1 | 7/2002 | Smith et al. |
| 2002/0110672 A1 | 8/2002 | Muratore-Pallatino et al. |
| 2002/0123728 A1 | 9/2002 | Graef et al. |
| 2002/0133132 A1 | 9/2002 | Copat et al. |
| 2002/0150678 A1 | 10/2002 | Cramer et al. |
| 2002/0165509 A1 | 11/2002 | Baer et al. |
| 2002/0169405 A1 | 11/2002 | Roberts |
| 2002/0176964 A1 | 11/2002 | Koslow |
| 2002/0177831 A1 | 11/2002 | Daley et al. |
| 2002/0180092 A1 | 12/2002 | Abba et al. |
| 2002/0183704 A1 | 12/2002 | Fields et al. |
| 2003/0009122 A1 | 1/2003 | Veras |
| 2003/0045707 A1 | 3/2003 | West et al. |
| 2003/0045825 A1 | 3/2003 | Etheredge, III |
| 2003/0050617 A1 | 3/2003 | Chen et al. |
| 2003/0069563 A1 | 4/2003 | Johnson |
| 2003/0070780 A1 | 4/2003 | Chen et al. |
| 2003/0073967 A1 | 4/2003 | Wahlstrom et al. |
| 2003/0088229 A1 | 5/2003 | Baker et al. |
| 2003/0088231 A1 | 5/2003 | Yoshimasa et al. |

(56) References Cited

U.S. PATENT DOCUMENTS

| | | |
|---|---|---|
| 2003/0093044 A1 | 5/2003 | Wahlstrom et al. |
| 2003/0097101 A1 | 5/2003 | Schmidt et al. |
| 2003/0097105 A1 | 5/2003 | Chen et al. |
| 2003/0097113 A1 | 5/2003 | Molee |
| 2003/0105442 A1 | 6/2003 | Johnston et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0124311 A1 | 7/2003 | Cree et al. |
| 2003/0125646 A1 | 7/2003 | Whitlock |
| 2003/0134559 A1 | 7/2003 | Delzer et al. |
| 2003/0135174 A1 | 7/2003 | Benecke et al. |
| 2003/0135177 A1 | 7/2003 | Baker |
| 2003/0150551 A1 | 8/2003 | Baker |
| 2003/0157857 A1 | 8/2003 | Cook et al. |
| 2003/0171729 A1 | 9/2003 | Kaun et al. |
| 2003/0180341 A1 | 9/2003 | Gooch et al. |
| 2003/0199800 A1 | 10/2003 | Levin |
| 2003/0208175 A1 | 11/2003 | Gross et al. |
| 2003/0212359 A1 | 11/2003 | Butler |
| 2003/0225383 A1 | 12/2003 | Glaug et al. |
| 2004/0019338 A1 | 1/2004 | Litvay et al. |
| 2004/0019339 A1 | 1/2004 | Ranganathan et al. |
| 2004/0019340 A1 | 1/2004 | McBride |
| 2004/0019342 A1 | 1/2004 | Nagasuna et al. |
| 2004/0024375 A1 | 2/2004 | Litvay |
| 2004/0033750 A1 | 2/2004 | Everett et al. |
| 2004/0049146 A1 | 3/2004 | Kolte et al. |
| 2004/0054343 A1 | 3/2004 | Barnett et al. |
| 2004/0054344 A1 | 3/2004 | Roettger et al. |
| 2004/0057855 A1 | 3/2004 | Gerlach et al. |
| 2004/0065420 A1 | 4/2004 | Graef et al. |
| 2004/0078011 A1 | 4/2004 | Stevens |
| 2004/0078016 A1 | 4/2004 | Baker |
| 2004/0087927 A1 | 5/2004 | Suzuki |
| 2004/0106888 A1 | 6/2004 | Lutri et al. |
| 2004/0111074 A1 | 6/2004 | Eliasson |
| 2004/0127862 A1 | 7/2004 | Bubb et al. |
| 2004/0138602 A1 | 7/2004 | Rossen |
| 2004/0177935 A1 | 9/2004 | Hamed et al. |
| 2004/0181199 A1 | 9/2004 | Moberg-Alehammar et al. |
| 2004/0204696 A1 | 10/2004 | Chen |
| 2004/0230173 A1 | 11/2004 | Barge et al. |
| 2004/0230184 A1 | 11/2004 | Babusik et al. |
| 2004/0243042 A1 | 12/2004 | Lipman |
| 2004/0243080 A1 | 12/2004 | Baer |
| 2004/0243081 A1 | 12/2004 | Suzuki et al. |
| 2004/0253894 A1 | 12/2004 | Fell et al. |
| 2004/0254552 A1 | 12/2004 | Mangold |
| 2005/0008825 A1 | 1/2005 | Casey et al. |
| 2005/0013992 A1 | 1/2005 | Azad et al. |
| 2005/0015036 A1 | 1/2005 | Lutri et al. |
| 2005/0049566 A1 | 3/2005 | Vukos et al. |
| 2005/0079361 A1 | 4/2005 | Hamed et al. |
| 2005/0084641 A1 | 4/2005 | Downs et al. |
| 2005/0096616 A1 | 5/2005 | Arora et al. |
| 2005/0101940 A1 | 5/2005 | Radl et al. |
| 2005/0112979 A1 | 5/2005 | Sawyer et al. |
| 2005/0119631 A1 | 6/2005 | Giloh et al. |
| 2005/0136773 A1 | 6/2005 | Yahiaoui et al. |
| 2005/0165371 A1 | 7/2005 | Giacometti |
| 2005/0215965 A1 | 9/2005 | Schmidt et al. |
| 2005/0215967 A1 | 9/2005 | Toro et al. |
| 2005/0222547 A1 | 10/2005 | Beruda et al. |
| 2005/0228353 A1 | 10/2005 | Thomas |
| 2005/0261649 A1 | 11/2005 | Cohen |
| 2005/0267429 A1 | 12/2005 | Cohen |
| 2006/0009744 A1 | 1/2006 | Edrman et al. |
| 2006/0020234 A1 | 1/2006 | Chou et al. |
| 2006/0020250 A1 | 1/2006 | Chester et al. |
| 2006/0058750 A1 | 3/2006 | Di Girolamo et al. |
| 2006/0069366 A1 | 3/2006 | Cole |
| 2006/0069367 A1 | 3/2006 | Waksmundzki et al. |
| 2006/0069375 A1 | 3/2006 | Waksmundzki et al. |
| 2006/0100586 A1 | 5/2006 | Karpowicz |
| 2006/0122548 A1 | 6/2006 | Abrams |
| 2006/0122572 A1 | 6/2006 | Suarez |
| 2006/0153904 A1 | 7/2006 | Smith et al. |
| 2006/0161122 A1 | 7/2006 | Erdman et al. |
| 2006/0178650 A1 | 8/2006 | Hakannsson et al. |
| 2006/0184147 A1 | 8/2006 | Hamed |
| 2006/0206047 A1 | 9/2006 | Lampe et al. |
| 2006/0206073 A1 | 9/2006 | Crane et al. |
| 2006/0206074 A1 | 9/2006 | Bernal et al. |
| 2006/0241542 A1 | 10/2006 | Gudnason et al. |
| 2006/0282028 A1 | 12/2006 | Howard et al. |
| 2007/0003604 A1 | 1/2007 | Jones |
| 2007/0040454 A1 | 2/2007 | Freudenberger et al. |
| 2007/0055209 A1 | 3/2007 | Patel et al. |
| 2007/0073254 A1 | 3/2007 | Ponomarenko et al. |
| 2007/0078467 A1 | 4/2007 | Mullen |
| 2007/0100308 A1 | 5/2007 | Miyairi |
| 2007/0142804 A1 | 6/2007 | Bernard |
| 2007/0167096 A1 | 7/2007 | Scott |
| 2007/0167884 A1 | 7/2007 | Mangrum et al. |
| 2007/0220692 A1 | 9/2007 | Kustin |
| 2007/0224903 A1 | 9/2007 | Chakravarty et al. |
| 2007/0225663 A1 | 9/2007 | Watt et al. |
| 2007/0254550 A1 | 11/2007 | Hamed et al. |
| 2007/0270070 A1 | 11/2007 | Hamed |
| 2007/0282236 A1 | 12/2007 | LaGreca |
| 2008/0004581 A1 | 1/2008 | Babusik et al. |
| 2008/0015532 A1 | 1/2008 | Waksmundzki |
| 2008/0031748 A1 | 2/2008 | Ihle et al. |
| 2008/0033325 A1 | 2/2008 | Van der Hulst et al. |
| 2008/0058691 A1 | 3/2008 | Sorensen |
| 2008/0082075 A1 | 4/2008 | Morrell-Schwartz |
| 2008/0090050 A1 | 4/2008 | Seyler et al. |
| 2008/0114317 A1 | 5/2008 | Seyler |
| 2008/0119586 A1 | 5/2008 | Byerly et al. |
| 2008/0132821 A1 | 6/2008 | Propp et al. |
| 2008/0147024 A1 | 6/2008 | Potts et al. |
| 2008/0167592 A1 | 7/2008 | Greer |
| 2008/0172017 A1 | 7/2008 | Carlucci et al. |
| 2008/0243100 A1 | 10/2008 | Wu et al. |
| 2008/0255533 A1 | 10/2008 | Wu et al. |
| 2008/0275409 A1 | 11/2008 | Kane et al. |
| 2008/0306456 A1 | 12/2008 | Riesinger |
| 2008/0312621 A1 | 12/2008 | Hundorf et al. |
| 2008/0312622 A1 | 12/2008 | Hundorf et al. |
| 2009/0054855 A1 | 2/2009 | Blott et al. |
| 2009/0062760 A1 | 3/2009 | Wright et al. |
| 2009/0076472 A1 | 3/2009 | Goldwasser et al. |
| 2009/0105670 A1 | 4/2009 | Bentley et al. |
| 2009/0112175 A1 | 4/2009 | Bissah et al. |
| 2009/0125004 A1 | 5/2009 | Shen et al. |
| 2009/0131892 A1 | 5/2009 | Karpowicz et al. |
| 2009/0157016 A1 | 6/2009 | Adahan |
| 2009/0157024 A1 | 6/2009 | Song |
| 2009/0204087 A1 | 8/2009 | Herfert et al. |
| 2009/0216168 A1 | 8/2009 | Eckstein et al. |
| 2009/0227935 A1 | 9/2009 | Zanella et al. |
| 2009/0234306 A1 | 9/2009 | Vitaris |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0299308 A1 | 12/2009 | Kazala et al. |
| 2009/0299340 A1 | 12/2009 | Kazala et al. |
| 2009/0326430 A1 | 12/2009 | Frederiksen et al. |
| 2010/0010461 A1 | 1/2010 | Herfert et al. |
| 2010/0030171 A1 | 2/2010 | Canada et al. |
| 2010/0036334 A1 | 2/2010 | Heagle et al. |
| 2010/0036342 A1 | 2/2010 | Carlucci et al. |
| 2010/0048072 A1 | 2/2010 | Kauscheke et al. |
| 2010/0055158 A1 | 3/2010 | Vitaris et al. |
| 2010/0069850 A1 | 3/2010 | Fabo |
| 2010/0069858 A1 | 3/2010 | Olson |
| 2010/0084074 A1 | 4/2010 | McClernon et al. |
| 2010/0106113 A1 | 4/2010 | Heinecke |

(56) References Cited

U.S. PATENT DOCUMENTS

| | | |
|---|---|---|
| 2010/0106120 A1 | 4/2010 | Holm |
| 2010/0106121 A1 | 4/2010 | Holm |
| 2010/0121298 A1 | 5/2010 | Seyler et al. |
| 2010/0125234 A1 | 5/2010 | Smith |
| 2010/0125258 A1 | 5/2010 | Coulthard et al. |
| 2010/0137775 A1 | 6/2010 | Hu et al. |
| 2010/0137890 A1 | 6/2010 | Martinez et al. |
| 2010/0168695 A1 | 7/2010 | Robles et al. |
| 2010/0191207 A1 | 7/2010 | Oba et al. |
| 2010/0217177 A1 | 8/2010 | Cali et al. |
| 2010/0256545 A1 | 10/2010 | Aali et al. |
| 2010/0256584 A1 | 10/2010 | Litvay |
| 2010/0256586 A1 | 10/2010 | Bergstrom et al. |
| 2010/0259406 A1 | 10/2010 | Caso et al. |
| 2010/0262091 A1 | 10/2010 | Larsson |
| 2010/0310845 A1 | 12/2010 | Bond et al. |
| 2010/0318047 A1 | 12/2010 | Ducker et al. |
| 2010/0318052 A1 | 12/2010 | Ha et al. |
| 2010/0324510 A1* | 12/2010 | Andresen ............ A61M 1/0088 604/319 |
| 2010/0324516 A1 | 12/2010 | Braga et al. |
| 2011/0004172 A1 | 1/2011 | Eckstein et al. |
| 2011/0022013 A1 | 1/2011 | Boynton et al. |
| 2011/0034892 A1 | 2/2011 | Buan |
| 2011/0052664 A1 | 3/2011 | Tennican et al. |
| 2011/0054422 A1 | 3/2011 | Locke et al. |
| 2011/0059329 A1 | 3/2011 | Dobrawa et al. |
| 2011/0060303 A1 | 3/2011 | Bissah et al. |
| 2011/0066123 A1 | 3/2011 | Tout et al. |
| 2011/0070391 A1 | 3/2011 | Cotton |
| 2011/0098621 A1 | 4/2011 | Fabo et al. |
| 2011/0112492 A1 | 5/2011 | Bharti et al. |
| 2011/0118683 A1 | 5/2011 | Weston |
| 2011/0125119 A1 | 5/2011 | Weismantel et al. |
| 2011/0130712 A1 | 6/2011 | Topaz |
| 2011/0137222 A1 | 6/2011 | Masini |
| 2011/0152813 A1 | 6/2011 | Ellingson |
| 2011/0160686 A1 | 6/2011 | Ueda et al. |
| 2011/0178375 A1 | 7/2011 | Forster |
| 2011/0183109 A1 | 7/2011 | Seyler et al. |
| 2011/0184364 A1 | 7/2011 | Biggs et al. |
| 2011/0184370 A1 | 7/2011 | Seyler et al. |
| 2011/0208145 A1 | 8/2011 | Zhang et al. |
| 2011/0213286 A1 | 9/2011 | Riesinger |
| 2011/0218509 A1 | 9/2011 | Dontas |
| 2011/0223413 A1 | 9/2011 | Herfert et al. |
| 2011/0224631 A1 | 9/2011 | Simmons |
| 2011/0238026 A1 | 9/2011 | Zhang et al. |
| 2011/0245788 A1 | 10/2011 | Marquez Canada |
| 2011/0247636 A1 | 10/2011 | Pollack |
| 2011/0257572 A1 | 10/2011 | Locke et al. |
| 2011/0257611 A1 | 10/2011 | Locke et al. |
| 2011/0268932 A1 | 11/2011 | Catalan et al. |
| 2011/0282309 A1* | 11/2011 | Adie .................. A61M 1/0088 604/319 |
| 2011/0313373 A1 | 12/2011 | Riesinger |
| 2012/0004632 A1 | 1/2012 | Zhang et al. |
| 2012/0045639 A1 | 2/2012 | Whitmore et al. |
| 2012/0051945 A1 | 3/2012 | Orndorff et al. |
| 2012/0053547 A1 | 3/2012 | Schroeder et al. |
| 2012/0065664 A1 | 3/2012 | Avitable et al. |
| 2012/0071848 A1 | 3/2012 | Zhang et al. |
| 2012/0095426 A1 | 4/2012 | Visscher et al. |
| 2012/0101465 A1 | 4/2012 | Mcguire, Jr. |
| 2012/0116334 A1* | 5/2012 | Albert ................. A61F 13/02 604/319 |
| 2012/0123311 A1 | 5/2012 | Weidemann-Hendrickson et al. |
| 2012/0136329 A1 | 5/2012 | Carney |
| 2012/0143158 A1 | 6/2012 | Yang et al. |
| 2012/0150078 A1 | 6/2012 | Chen et al. |
| 2012/0165765 A1 | 6/2012 | Barta et al. |
| 2012/0172778 A1 | 7/2012 | Rastegar et al. |
| 2012/0197229 A1 | 8/2012 | Buan et al. |
| 2012/0203145 A1 | 8/2012 | Nilsson |
| 2012/0203189 A1 | 8/2012 | Barta et al. |
| 2012/0220968 A1 | 8/2012 | Confalone et al. |
| 2012/0232502 A1 | 9/2012 | Lowing |
| 2012/0238932 A1 | 9/2012 | Atteia et al. |
| 2012/0283529 A1 | 11/2012 | Marchand et al. |
| 2012/0302440 A1 | 11/2012 | Theliander et al. |
| 2012/0302976 A1 | 11/2012 | Locke et al. |
| 2012/0308780 A1 | 12/2012 | Rottger et al. |
| 2012/0310186 A1 | 12/2012 | Moghe et al. |
| 2012/0310197 A1 | 12/2012 | Thomas |
| 2012/0330253 A1 | 12/2012 | Robinson et al. |
| 2013/0012902 A1 | 1/2013 | Rovaniemi |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0138054 A1 | 5/2013 | Fleischmann |
| 2013/0144227 A1 | 6/2013 | Locke et al. |
| 2013/0150814 A1 | 6/2013 | Buan |
| 2013/0165878 A1 | 6/2013 | Heagle |
| 2013/0172835 A1 | 7/2013 | Braga et al. |
| 2013/0253453 A1 | 9/2013 | Olson |
| 2013/0274688 A1 | 10/2013 | Weston |
| 2013/0296762 A1 | 11/2013 | Toth |
| 2013/0302545 A1 | 11/2013 | Schnelker et al. |
| 2014/0010673 A1 | 1/2014 | Locke et al. |
| 2014/0012213 A1 | 1/2014 | Locke et al. |
| 2014/0114268 A1 | 4/2014 | Auguste et al. |
| 2014/0127148 A1 | 5/2014 | Derain |
| 2014/0200533 A1 | 7/2014 | Whyte et al. |
| 2014/0249495 A1 | 9/2014 | Mumby et al. |
| 2014/0316359 A1 | 10/2014 | Collinson et al. |
| 2014/0350496 A1 | 11/2014 | Riesinger |
| 2015/0032035 A1 | 1/2015 | Banwell et al. |
| 2015/0057625 A1 | 2/2015 | Coulthard et al. |
| 2015/0174304 A1 | 6/2015 | Askem et al. |
| 2015/0190286 A1 | 7/2015 | Allen et al. |
| 2015/0216733 A1 | 8/2015 | Allen et al. |
| 2015/0335798 A1 | 11/2015 | De Samber et al. |
| 2015/0335799 A1 | 11/2015 | Vitaris et al. |
| 2016/0000610 A1 | 1/2016 | Riesinger |
| 2016/0000611 A1 | 1/2016 | Niederauer et al. |
| 2017/0007748 A1 | 1/2017 | Locke et al. |
| 2019/0008696 A1 | 1/2019 | Allen et al. |
| 2019/0110932 A1 | 4/2019 | Mumby et al. |
| 2019/0175418 A1 | 6/2019 | Allen et al. |

FOREIGN PATENT DOCUMENTS

| | | |
|---|---|---|
| CN | 1874806 A | 12/2006 |
| CN | 101600464 | 12/2009 |
| DE | 34 43 101 | 5/1986 |
| DE | 40 30 465 | 4/1992 |
| DE | 90 17 289 | 4/1992 |
| DE | 198 44 355 | 4/2000 |
| EP | 0 053 936 | 6/1982 |
| EP | 0 340 018 | 11/1989 |
| EP | 0 541 251 | 5/1993 |
| EP | 0 392 640 | 6/1995 |
| EP | 0 441 418 | 7/1995 |
| EP | 0 549 781 | 9/1996 |
| EP | 0 748 894 | 12/1996 |
| EP | 0 465 601 | 1/1997 |
| EP | 0 751 757 | 1/1997 |
| EP | 0 599 871 | 4/1997 |
| EP | 0 768 071 | 4/1997 |
| EP | 0 853 950 | 7/1998 |
| EP | 0 777 504 | 10/1998 |
| EP | 0 875 224 | 11/1998 |
| EP | 0 941 726 | 9/1999 |
| EP | 1 013 290 | 6/2000 |
| EP | 1 018 967 | 7/2000 |
| EP | 1 048 278 | 11/2000 |
| EP | 1 066 809 | 1/2001 |
| EP | 0 865 304 | 7/2001 |
| EP | 1 139 951 | 10/2001 |
| EP | 1 169 071 | 1/2002 |
| EP | 0 708 620 | 5/2003 |
| EP | 1 312 328 | 5/2003 |
| EP | 1 088 569 | 8/2003 |
| EP | 0 993 317 | 9/2003 |

(56) References Cited

FOREIGN PATENT DOCUMENTS

| | | |
|---|---|---|
| EP | 1 353 001 | 10/2003 |
| EP | 1 440 667 | 7/2004 |
| EP | 1 578 477 | 7/2004 |
| EP | 1 448 261 | 8/2004 |
| EP | 1 452 156 | 9/2004 |
| EP | 0 630 629 | 11/2004 |
| EP | 1 100 574 | 2/2005 |
| EP | 1 513 478 | 3/2005 |
| EP | 0 688 189 | 6/2005 |
| EP | 1 284 777 | 4/2006 |
| EP | 0 982 015 | 8/2006 |
| EP | 0 620 720 | 11/2006 |
| EP | 1 171 065 | 3/2007 |
| EP | 1 227 853 | 1/2008 |
| EP | 1 476 217 | 3/2008 |
| EP | 1 233 808 | 7/2008 |
| EP | 1 955 887 | 8/2008 |
| EP | 1 977 776 | 10/2008 |
| EP | 2 127 690 | 12/2009 |
| EP | 1 905 465 | 1/2010 |
| EP | 2 161 011 | 3/2010 |
| EP | 2 172 164 | 4/2010 |
| EP | 2 263 627 | 12/2010 |
| EP | 2 319 550 | 5/2011 |
| EP | 2 366 721 | 9/2011 |
| EP | 1 487 389 | 10/2011 |
| EP | 2 529 766 | 12/2012 |
| EP | 2 413 858 | 1/2013 |
| EP | 2 545 946 | 3/2013 |
| EP | 2 659 915 | 11/2013 |
| EP | 2 628 500 | 5/2014 |
| EP | 1 339 366 | 6/2014 |
| EP | 2 051 675 | 6/2014 |
| EP | 2 349 154 | 8/2014 |
| FR | 1 163 907 | 10/1958 |
| GB | 1255395 | 12/1971 |
| GB | 2099306 | 12/1982 |
| GB | 2307180 | 5/1997 |
| GB | 2331937 | 6/1999 |
| GB | 2336546 | 10/1999 |
| GB | 2344531 | 7/2000 |
| GB | 2355228 | 4/2001 |
| GB | 2435422 | 8/2007 |
| GB | 2435423 | 8/2007 |
| GB | 2489947 | 10/2012 |
| JP | H07-88131 | 4/1995 |
| RU | 62504 | 4/2007 |
| RU | 2432177 | 10/2011 |
| WO | WO 1983/00742 | 3/1983 |
| WO | WO 1991/11161 | 8/1991 |
| WO | WO 1991/11162 | 8/1991 |
| WO | WO 1993/01778 | 2/1993 |
| WO | WO 1993/01779 | 2/1993 |
| WO | WO 1993/01780 | 2/1993 |
| WO | WO 1993/01781 | 2/1993 |
| WO | WO 1993/09745 | 5/1993 |
| WO | WO 1993/11726 | 6/1993 |
| WO | WO 1994/23677 | 10/1994 |
| WO | WO 1995/04511 | 2/1995 |
| WO | WO 1995/13042 | 5/1995 |
| WO | WO 1995/13776 | 5/1995 |
| WO | WO 1995/13779 | 5/1995 |
| WO | WO 1995/14451 | 6/1995 |
| WO | WO 1995/16424 | 6/1995 |
| WO | WO 1995/025492 | 9/1995 |
| WO | WO 1996/07783 | 3/1996 |
| WO | WO 1996/21410 | 7/1996 |
| WO | WO 1997/11658 | 4/1997 |
| WO | WO 1997/14384 | 4/1997 |
| WO | WO 1998/20916 | 5/1998 |
| WO | WO 1998/22279 | 5/1998 |
| WO | WO 1999/04830 | 2/1999 |
| WO | WO 1999/39671 | 8/1999 |
| WO | WO 1999/45876 | 9/1999 |
| WO | WO 1999/45878 | 9/1999 |
| WO | WO 1999/56687 | 11/1999 |
| WO | WO 2000/00016 | 1/2000 |
| WO | WO 2000/00127 | 1/2000 |
| WO | WO 2000/00129 | 1/2000 |
| WO | WO 2000/00130 | 1/2000 |
| WO | WO 2000/00131 | 1/2000 |
| WO | WO 2000/07653 | 2/2000 |
| WO | WO 2000/40190 | 7/2000 |
| WO | WO 2000/42957 | 7/2000 |
| WO | WO 2000/59438 | 10/2000 |
| WO | WO 2001/054743 | 8/2001 |
| WO | WO 2001/072251 | 10/2001 |
| WO | WO 2001/90465 | 11/2001 |
| WO | WO 2002/17840 | 3/2002 |
| WO | WO 2002/24132 | 3/2002 |
| WO | WO 2002/26180 | 4/2002 |
| WO | WO 2002/38096 | 5/2002 |
| WO | WO 2002/076379 | 10/2002 |
| WO | WO 2003/057070 | 7/2003 |
| WO | WO 2003/073971 | 9/2003 |
| WO | WO 2003/086232 | 10/2003 |
| WO | WO 2004/043321 | 5/2004 |
| WO | WO 2004/073566 | 9/2004 |
| WO | WO 2004/077387 | 9/2004 |
| WO | WO 2004/098474 | 11/2004 |
| WO | WO 2005/016179 | 2/2005 |
| WO | WO 2005/061025 | 7/2005 |
| WO | WO 2005/105174 | 11/2005 |
| WO | WO 2006/052338 | 5/2006 |
| WO | WO 2006/052745 | 5/2006 |
| WO | WO 2006/105305 | 10/2006 |
| WO | WO 2006/114637 | 11/2006 |
| WO | WO 2007/006306 | 1/2007 |
| WO | WO 2007/013049 | 2/2007 |
| WO | WO 2007/013064 | 2/2007 |
| WO | WO 2007/016590 | 2/2007 |
| WO | WO 2007/019038 | 2/2007 |
| WO | WO 2007/035038 | 3/2007 |
| WO | WO 2007/040606 | 4/2007 |
| WO | WO 2007/066699 | 6/2007 |
| WO | WO 2007/077214 | 7/2007 |
| WO | WO 2007/077216 | 7/2007 |
| WO | WO 2007/085396 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/116347 | 10/2007 |
| WO | WO 2008/008032 | 1/2008 |
| WO | WO 2008/012278 | 1/2008 |
| WO | WO 2008/027449 | 3/2008 |
| WO | WO 2008/039223 | 4/2008 |
| WO | WO 2008/043067 | 4/2008 |
| WO | WO 2008/049277 | 5/2008 |
| WO | WO 2008/100437 | 8/2008 |
| WO | WO 2008/100440 | 8/2008 |
| WO | WO 2008/100446 | 8/2008 |
| WO | WO 2008/131895 | 11/2008 |
| WO | WO 2008/135997 | 11/2008 |
| WO | WO 2008/141470 | 11/2008 |
| WO | WO 2009/002260 | 12/2008 |
| WO | WO 2009/146441 | 3/2009 |
| WO | WO 2009/066104 | 5/2009 |
| WO | WO 2009/068665 | 6/2009 |
| WO | WO 2009/086580 | 7/2009 |
| WO | WO 2009/088925 | 7/2009 |
| WO | WO 2009/111655 | 9/2009 |
| WO | WO 2009/137194 | 11/2009 |
| WO | WO 2009/140376 | 11/2009 |
| WO | WO 2009/145894 | 12/2009 |
| WO | WO 2009/152021 | 12/2009 |
| WO | WO 2009/158125 | 12/2009 |
| WO | WO 2009/158126 | 12/2009 |
| WO | WO 2009/158127 | 12/2009 |
| WO | WO 2009/158129 | 12/2009 |
| WO | WO 2010/014177 | 2/2010 |
| WO | WO 2010/032951 | 3/2010 |
| WO | WO 2010/033271 | 3/2010 |
| WO | WO 2010/033272 | 3/2010 |

(56) References Cited

FOREIGN PATENT DOCUMENTS

| | | |
|---|---|---|
| WO | WO 2010/033769 | 3/2010 |
| WO | WO 2010/048480 | 4/2010 |
| WO | WO 2010/051073 | 5/2010 |
| WO | WO 2010/059712 | 5/2010 |
| WO | WO 2010/059730 | 5/2010 |
| WO | WO 2010/078166 | 7/2010 |
| WO | WO 2010/082872 | 7/2010 |
| WO | WO 2010/089448 | 8/2010 |
| WO | WO 2010/139926 | 12/2010 |
| WO | WO 2010/147533 | 12/2010 |
| WO | WO 2010/147592 | 12/2010 |
| WO | WO 2011/023650 | 3/2011 |
| WO | WO 2011/034789 | 3/2011 |
| WO | WO 2011/049562 | 4/2011 |
| WO | WO 2011/058311 | 5/2011 |
| WO | WO 2011/087871 | 7/2011 |
| WO | WO 2011/100851 | 8/2011 |
| WO | WO 2011/112794 | 9/2011 |
| WO | WO 2011/113728 | 9/2011 |
| WO | WO 2011/115908 | 9/2011 |
| WO | WO 2011/128651 | 10/2011 |
| WO | WO 2011/135284 | 11/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/152368 | 12/2011 |
| WO | WO 2012/009370 | 1/2012 |
| WO | WO 2012/035787 | 3/2012 |
| WO | WO 2012/074512 | 6/2012 |
| WO | WO 2012/142002 | 10/2012 |
| WO | WO 2012/143665 | 10/2012 |
| WO | WO 2012/146656 | 11/2012 |
| WO | WO 2012/150235 | 11/2012 |
| WO | WO 2012/166428 | 12/2012 |
| WO | WO 2012/168298 | 12/2012 |
| WO | WO 2013/014317 | 1/2013 |
| WO | WO 2013/016239 | 1/2013 |
| WO | WO 2013/019438 | 2/2013 |
| WO | WO 2013/029652 | 3/2013 |
| WO | WO 2013/043972 | 3/2013 |
| WO | WO 2013/060732 | 5/2013 |
| WO | WO 2013/064852 | 5/2013 |
| WO | WO 2013/123005 | 8/2013 |
| WO | WO 2014/043238 | 9/2014 |
| WO | WO 2014/158526 | 10/2014 |
| ZA | 9605526 | 2/1997 |

OTHER PUBLICATIONS

European Extended Search Report, re EPO Application No. 09839009.9, dated Feb. 23, 2016.
International Search Report and Written Opinion, re PCT Application No. PCT/IB2013/001469, dated Feb. 7, 2014.
Kendall ULTEC Hydrocolloid Dressing (4"×4"), product ordering page, web page downloaded Jul. 13, 2014.
Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#p.=11.
"Pico Application", YouTube video, uploaded Jun. 6, 2012, in 2 pages. URL: https://www.youtube.com/watch?v=yCifiV6RRDw from Jun. 6, 2012.
Protz, Kerstin: "Moderne Wundauflagen unterstutzen Heilungsprozess", Wundversorgung: . Indikation and Anwendung, Geriatrie Journal, Apr. 2005, pp. 3333-3339, with translation.
Smith & Nephew, "PICO Single Use Negative Pressure Wound Therapy System", spiral booklet, Mar. 2011, in 7 pages.
SNAP—BLUE Foam Dressing—color brochure (L22162 rev. 130429), Jun. 2013.
SNAP—Product Overview—Wound Care System, as captured on Wayback Machine on Nov. 17, 2011.
International Preliminary Report on Patentability, re PCT Application No. PCT/IB2013/001469, dated Dec. 4, 2014.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

\* cited by examiner

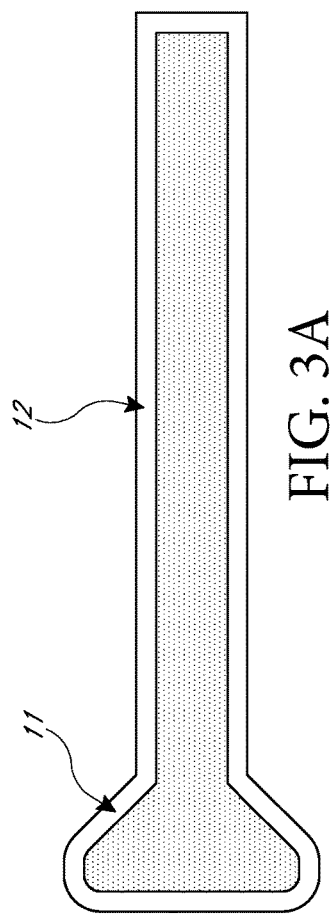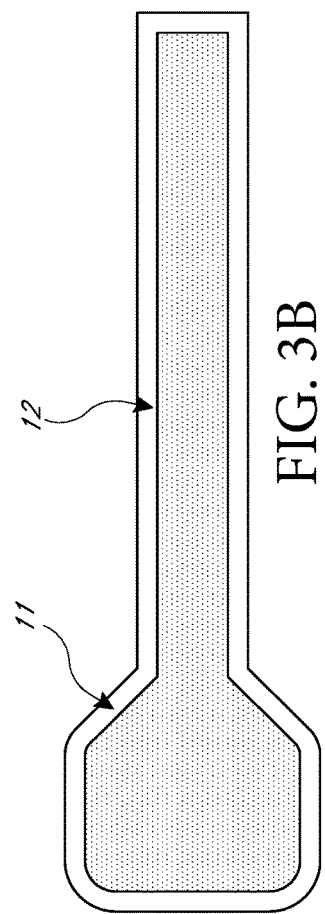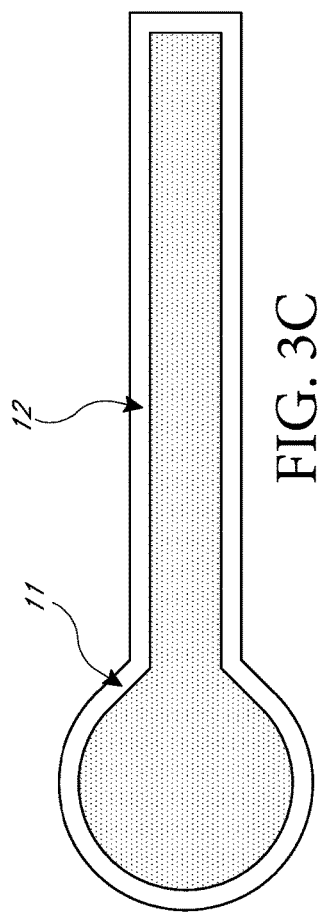

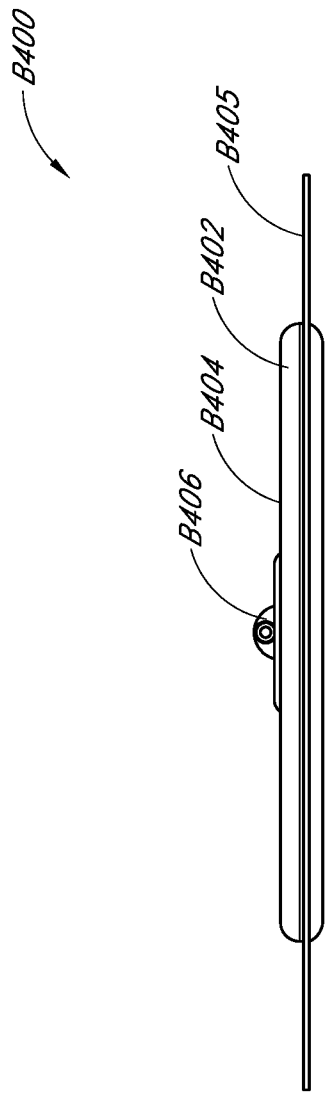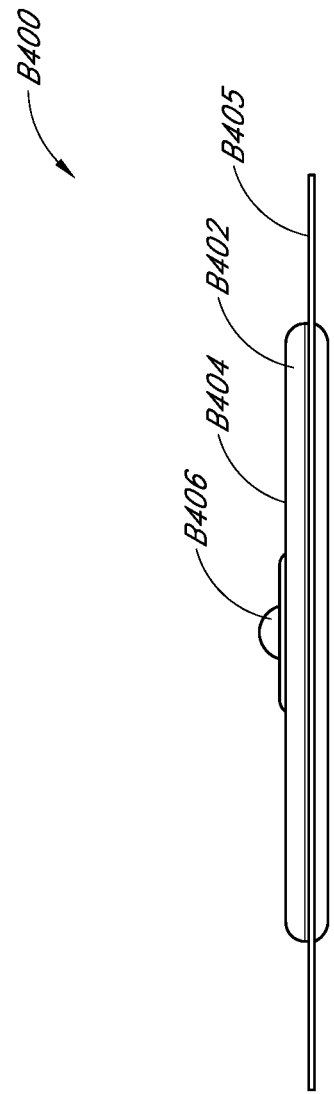
FIG. 21D
FIG. 21E

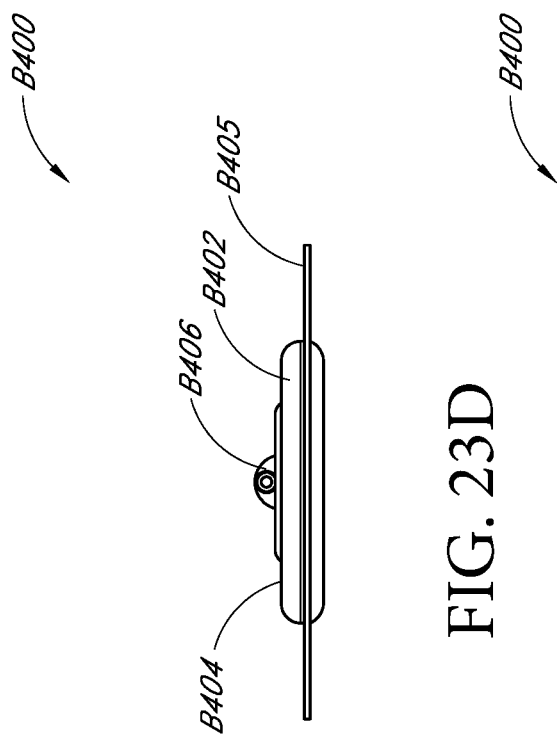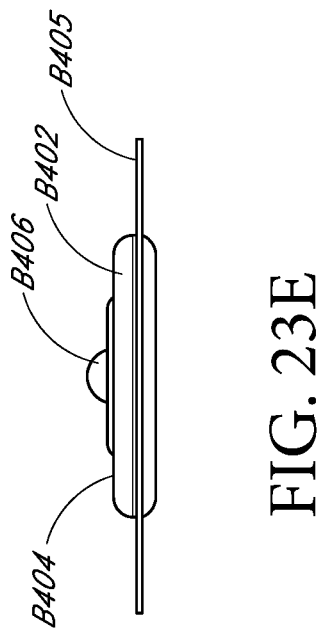
FIG. 23D
FIG. 23E

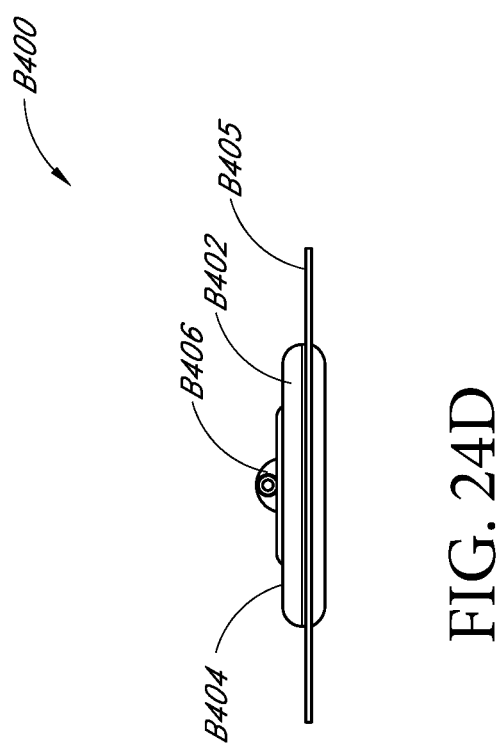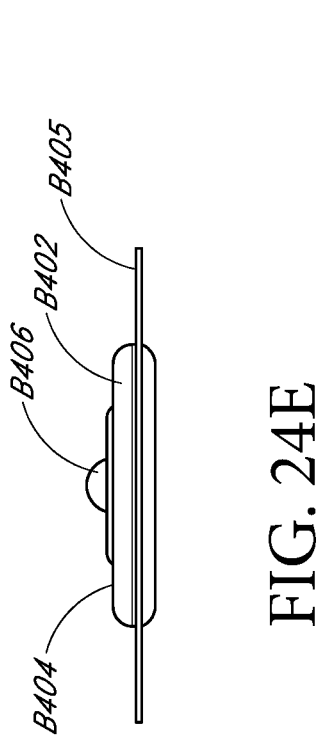

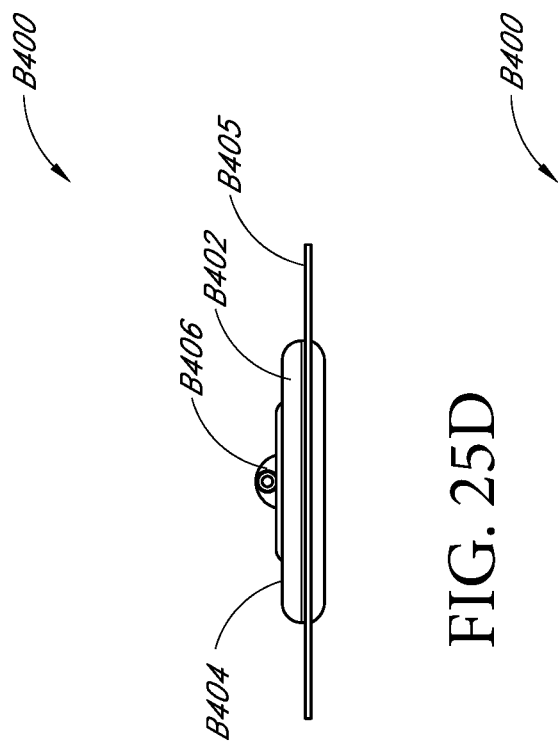
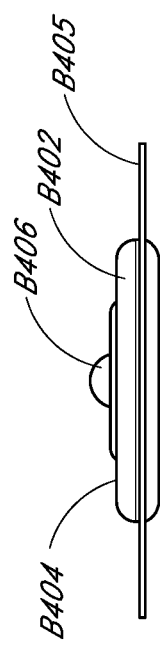
FIG. 25D
FIG. 25E

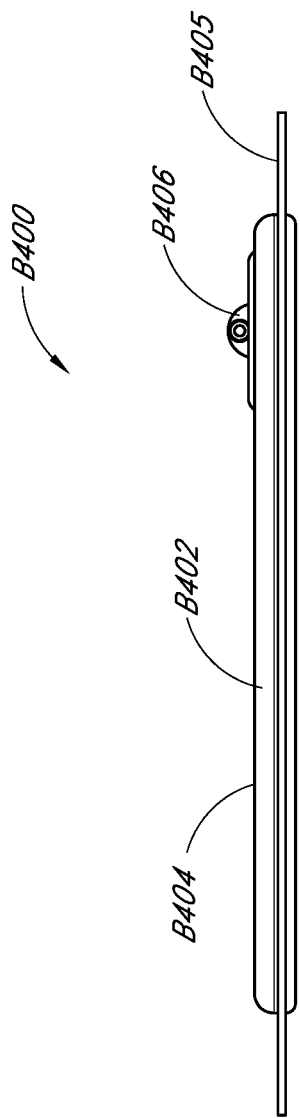
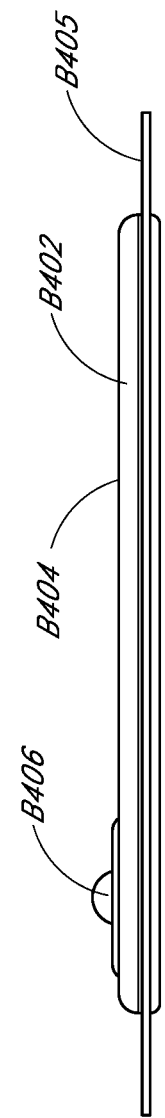
FIG. 26D
FIG. 26E

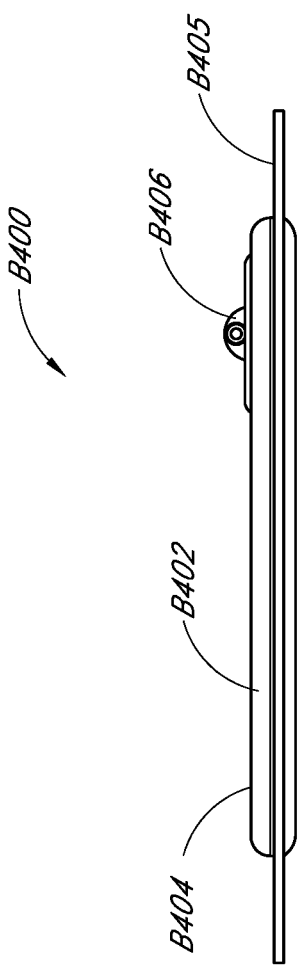
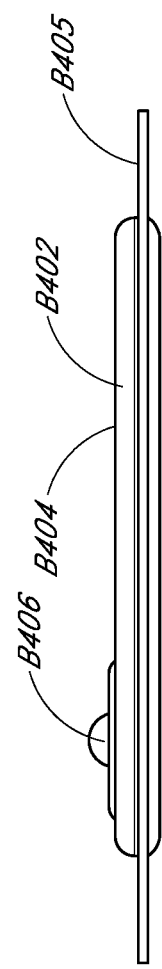
FIG. 27D
FIG. 27E

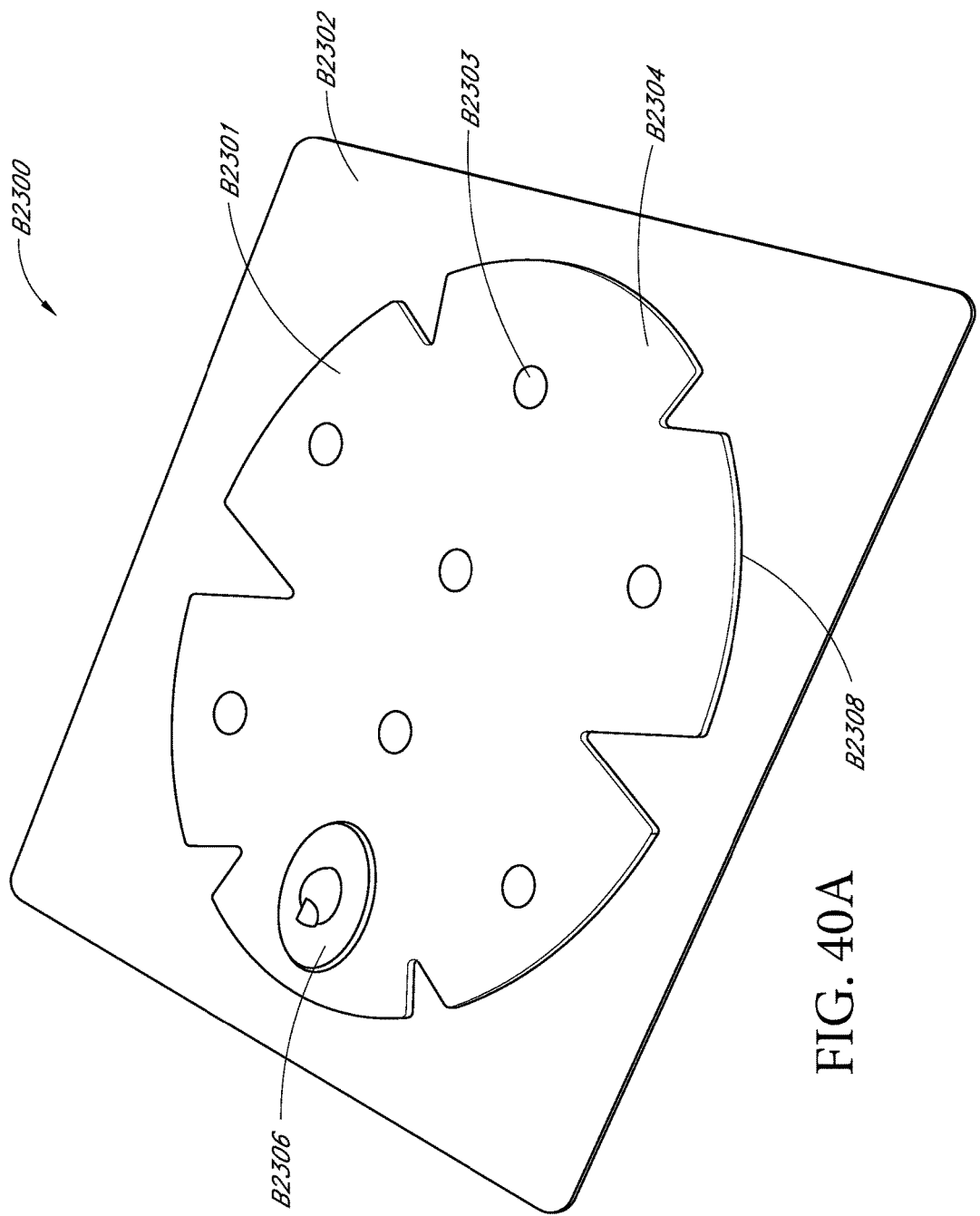

APPARATUSES AND METHODS FOR NEGATIVE PRESSURE WOUND THERAPY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE DISCLOSURE

Field of the Invention

Embodiments of the present invention relate generally to the treatment of wounds using negative pressure wound therapy, and more specifically to an improved apparatus and method thereof.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. The wound dressing may be sealed to a suction port providing connection to a length of tubing, which may be used to pump fluid out of the dressing and also to transmit negative pressure from a pump to the wound dressing. Wound exudate and other potentially harmful material is extracted from the wound region and must be stored for later disposal. A problem associated with many known techniques is that a separate canister must be provided for storage of such exudate. Provision of such canisters is costly and bulky and prone to failure.

It has been suggested as a solution to this problem that a liquid impermeable moisture vapor permeable cover layer can be utilized as an uppermost cover layer for the wound dressing. The air impermeable nature of the cover layer provides a sealing layer over the wound site so that negative pressure can be established below the dressing in the region of the wound. The moisture vapor permeability of this covering layer is selected so that liquid can constantly evaporate away from the top of the dressing. This means that as therapy is continued the dressing does not have to take up and hold all liquid exuding from the wound. Rather, some liquid is constantly escaping in the form of moisture vapor from the upper environs of the dressing.

Whilst such dressings work well in practice, the continuous evaporation of moisture vapor from the dressing can lead to the problem of crust formation in the dressing. That is to say, because of the continuous drawing of liquid away from the wound site solid particulate matter is more prone to formation and accumulation in the dressing. Under certain circumstances the build-up of such solid material can lead to blockages forming in the wound dressing in the flowpath between the wound and the source of negative pressure. This can potentially cause problems in that therapy may need to be halted to change a dressing if the blockages reach a critical level.

Further, the stiffness of the suction port in such close proximity to the wound site can adversely affect the healing process. Patient movement or pressure onto the wound dressing may bring the healing wound into contact with the inflexible suction port of the dressing. Such force can cause disturbance of a wound bed which can damage a wound site. This can potentially cause delays in healing of the wound site and discomfort for the patient.

It will also be appreciated that the tubing connected to the suction port is prone to obstruction. The tubing may become obstructed by movement of the patient, which may cause the tube to bend and form a kink or may place pressure onto the tubing, substantially or fully blocking the flow of fluid through the tubing. This can reduce or eliminate the negative pressure being transmitted to the wound site, and in embodiments employing a separate canister for fluid collection it can also result in accumulation of excess wound exudate at the wound site.

SUMMARY OF SOME EMBODIMENTS

Embodiments of the invention disclosed herein are directed to a negative pressure appliance and methods of treatment using a negative pressure appliance, and may be useful in the treatment of wounds using negative pressure. It is an aim of certain embodiments of the present invention to at least partly mitigate the above-mentioned problems.

Certain embodiments of the invention employ a wound dressing capable of absorbing and storing wound exudate in conjunction with a pump. Some wound dressing embodiments further comprise a transmission layer configured to transmit wound exudates to an absorbent layer disposed in the wound dressing. Additionally, some embodiments provide for fluidic connectors and/or suction adapters for connecting a source of negative pressure to a dressing positioned over a wound site. These fluidic connectors and/or suction adapters offer advantages over the prior art. For example and for illustrative purposes only, some of the embodiments may offer a softer, kink-free fluidic connector for connecting a wound site to a source of negative pressure for treatment. Such a fluidic connector and/or suction adapter is faster to apply, requiring fewer steps compared to prior art connectors, and offers greater patient comfort and safety by being soft and conformable, thereby avoiding pressure ulcers and other complications caused by harder connectors.

Certain embodiments provide the advantage that a wound dressing can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use.

Certain embodiments provide a wound dressing and/or method of applying topical negative pressure in which a flowpath through a wound dressing is kept open so that therapy can be continued for as long as desired by a care giver. In some embodiments, solid material, which may cause a blockage, is prevented from entering a flowpath region in the wound dressing by using a layer of the dressing to act as a bar to such material. Some embodiments prevent build-up of solid material in a flowpath region of a wound dressing by ensuring that any solid material that enters into that flowpath region can always escape into a further region of the dressing.

Certain embodiments of the invention employ fluidic connectors and/or suction adapters for connecting a source of negative pressure to a dressing positioned over a wound site. These fluidic connectors and/or suction adapters offer advantages over the prior art. For example and for illustrative purposes only, some of the embodiments may offer a softer, kink-free fluidic connector for connecting a wound site to a source of negative pressure for treatment. Such a fluidic connector and/or suction offers greater patient comfort and safety by being soft and conformable, thereby avoiding pressure ulcers and other complications caused by harder connectors.

In one embodiment, a wound treatment apparatus comprises:
  a wound dressing comprising:
    a wound contact layer configured to carry a pressure sensitive adhesive;
    a transmission layer comprising a first 3D fabric material configured to remain open upon application of negative pressure to the wound dressing, the transmission layer overlying the wound contact layer;
    an absorbent layer for absorbing wound exudate, the absorbent layer overlying the transmission layer and comprising an aperture;
    a cover layer overlying the absorbent layer and comprising an orifice, wherein the cover layer is moisture vapor permeable; and
  a suction adapter comprising:
    a sealing surface for sealing the suction adapter to the cover layer of the wound dressing, the sealing surface comprising an adhesive or weld;
    wherein the sealing surface is positioned over the orifice in the cover layer; and
    wherein the aperture in the absorbent layer is configured to permit the suction adapter to be in fluidic communication with the transmission layer; and
    a bridge having a proximal end and a distal end, the bridge comprising:
      a first fluid passage in fluid communication with a source of negative pressure, the first fluid passage comprising a second 3D fabric material; and
      at least one flexible film layer having a proximal and distal end and configured to surround the first fluid passage, the distal end of the flexible film connected to the upper surface of the sealing surface.

Further embodiments further comprise a filter configured to substantially prevent wound exudate from entering the bridge; and one or more spacer elements configured to prevent the suction adapter from contacting the transmission layer. In some embodiments, the bridge further comprises a second fluid passage positioned above the first fluid passage, and wherein the at least one flexible film layer is configured to surround the first and second fluid passages. In some embodiments, the second fluid passage is connected to an air leak.

Another embodiment provides for a method for treating a wound comprising:
  providing a wound dressing comprising:
    a transmission layer comprising a first 3D fabric material;
    an absorbent layer for absorbing wound exudate, the absorbent layer overlying the transmission layer;
    a cover layer overlying the absorbent layer and comprising an orifice, wherein the cover layer is moisture vapor permeable;
  providing a flexible suction adapter comprising:
    a top layer constructed from a liquid impermeable material;
    a bottom layer constructed from a liquid impermeable material;
    a second 3D fabric material located between the top and bottom layers;
    an aperture in the bottom layer in fluid communication with the second 3D fabric material; and
    an elongate channel extending between the top and bottom layers containing the second 3D fabric material, wherein the top layer, the bottom layer, and the second 3D knitted or 3D fabric material include enlarged distal ends with the channel extending in a proximal direction away from the enlarged distal ends, and wherein the enlarged distal ends comprise a sealing surface for securing the suction adapter to the cover layer of the dressing;
  attaching the flexible suction adapter in fluid communication with the dressing;
  positioning the dressing over a wound site to form a sealed cavity over the wound site; and
  applying negative pressure to the wound site to draw fluid through the transmission layer into the absorbent layer.

In some embodiments, applying negative pressure to the wound site comprises applying negative pressure from a pump through a connector at the distal end of the suction adapter, the connector comprising a fluidic connector, the negative pressure being transmitted through the second 3D fabric material of the suction adapter to the transmission layer through the orifice in the cover layer.

In one embodiment, an apparatus to provide suction to a wound site comprises:
  a spacer layer comprising a proximal end, an elongate middle portion and a distal end;
  a top layer constructed from a liquid impermeable material provided over the spacer layer;
  a bottom layer constructed from a liquid impermeable material provided below the spacer layer, wherein the top layer and the bottom layer substantially enclose the spacer layer;
  one or more apertures in the bottom layer beneath the distal end of the spacer layer;
  a filter positioned below the distal end of the spacer layer adjacent the one or more apertures; and
  a conduit in fluid communication with the proximal end of the spacer layer.

In further embodiments, the distal end of the spacer layer may be enlarged relative to a width of the elongate middle portion and a width of the proximal end. The filter may be positioned between the distal end of the spacer layer and the bottom layer. The filter may be below the bottom layer. The spacer layer may comprise one of a 3D knitted or 3D fabric material, foam, a porous material and non-woven material. In some embodiments, the proximal end of spacer layer may be folded. The conduit may extend into an opening in the spacer layer. In some embodiments, the opening may comprise an elongated slot. The opening may comprise a channel extending to the proximal end of the spacer layer. The conduit may extend proximally from the proximal end of the spacer layer, with a portion of the conduit extending between the top and bottom layers. The conduit may have one or more circumferential ribs to facilitate connection to the top and bottom layers. In some embodiments, a distal end of the bottom layer may comprise adhesive. In some embodiments, an elongate middle portion of the bottom layer may comprise adhesive.

In further embodiments, the distal end of the bottom layer may be adhered to a wound dressing with the aperture in the bottom layer being positioned over an opening in the wound dressing. Some embodiments may further comprise an extension conduit configured to be removably connected to the conduit in fluid communication with the proximal end of the spacer layer. The top layer may be adhered to the bottom layer to form an elongate channel holding the spacer layer therein.

In some embodiments, the filter may have a perimeter shape corresponding in shape to the distal end of the spacer layer. The distal end of the spacer layer may have a circular shape. The distal ends of the top and bottom layers may have an enlarged distal end similar in shape to an enlarged distal end of the spacer layer. The spacer layer may have a substantially rectangular cross-sectional dimension. In some embodiments, spacer layer may be adhered to at least one of the top and bottom layers.

BRIEF DESCRIPTION OF THE DRAWINGS

FIG. 3A-C illustrate various embodiments of the enlarged end of a flexible suction adapter;

FIGS. 21A-F-28A-F illustrate a perspective view, a top view, a bottom view, a front view, a back view, and a side view, respectively, of embodiments of a wound dressing including an obscuring layer and viewing windows;

FIGS. 40A-F illustrate a perspective view, a top view, a bottom view, a front view, a back view, and a side view, respectively, of an embodiment of an oval-shaped wound dressing;

DETAILED DESCRIPTION OF THE PREFERRED EMBODIMENTS

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, incisions, lacerations, abrasions, contusions, burns, diabetic ulcers, pressure ulcers, stoma, surgical wounds, trauma and venous ulcers or the like. Treatment of such wounds can be performed using negative pressure wound therapy, wherein a reduced or negative pressure can be applied to the wound to facilitate and promote healing of the wound. It will also be appreciated that the negative pressure systems and methods as disclosed herein may be applied to other parts of the body, and are not necessarily limited to treatment of wounds.

Figure 1A:
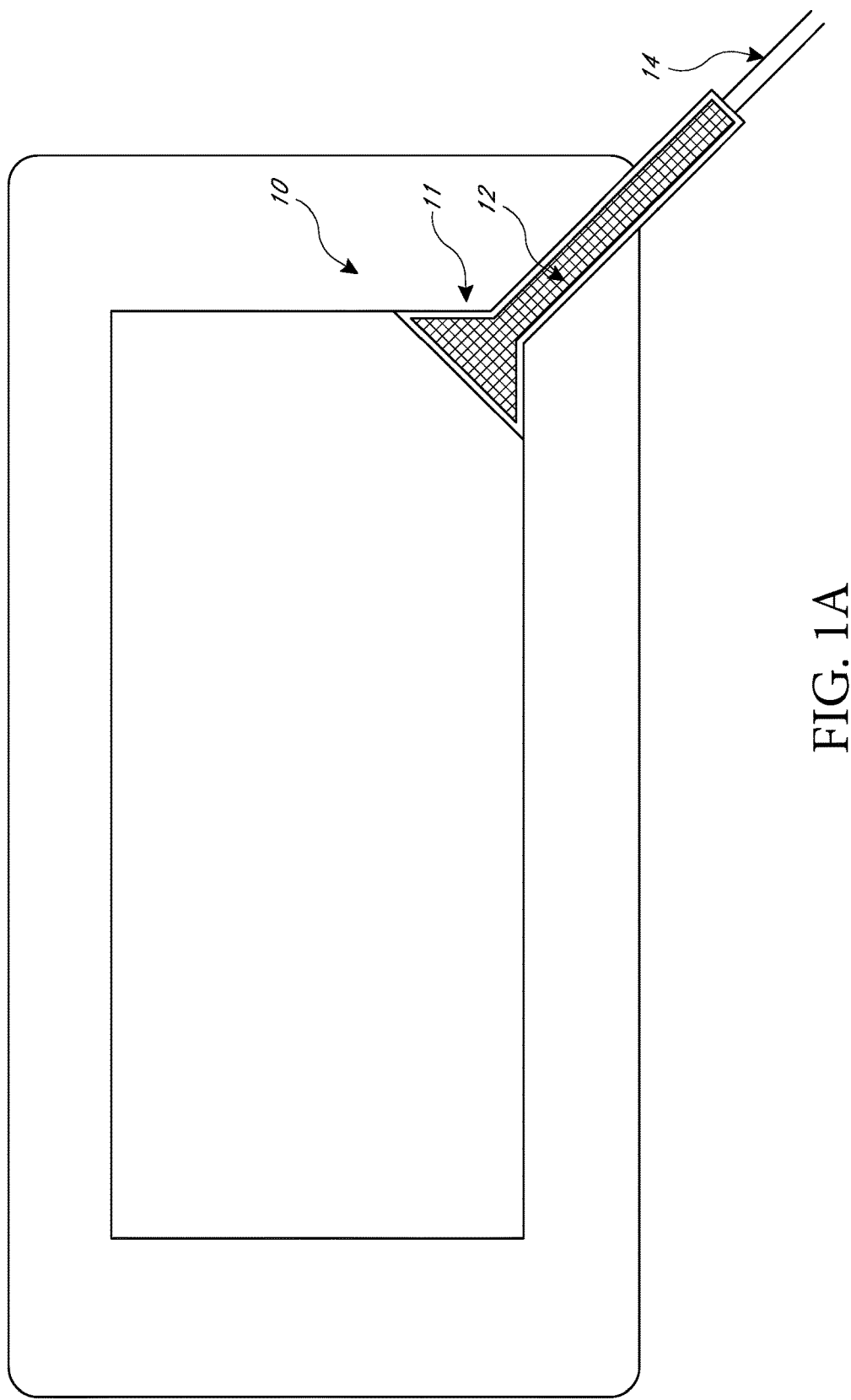
FIG. 1A illustrates an embodiment of a negative pressure wound treatment dressing capable of absorbing and storing wound exudate with a flexible suction adapter.
Figure 1B:
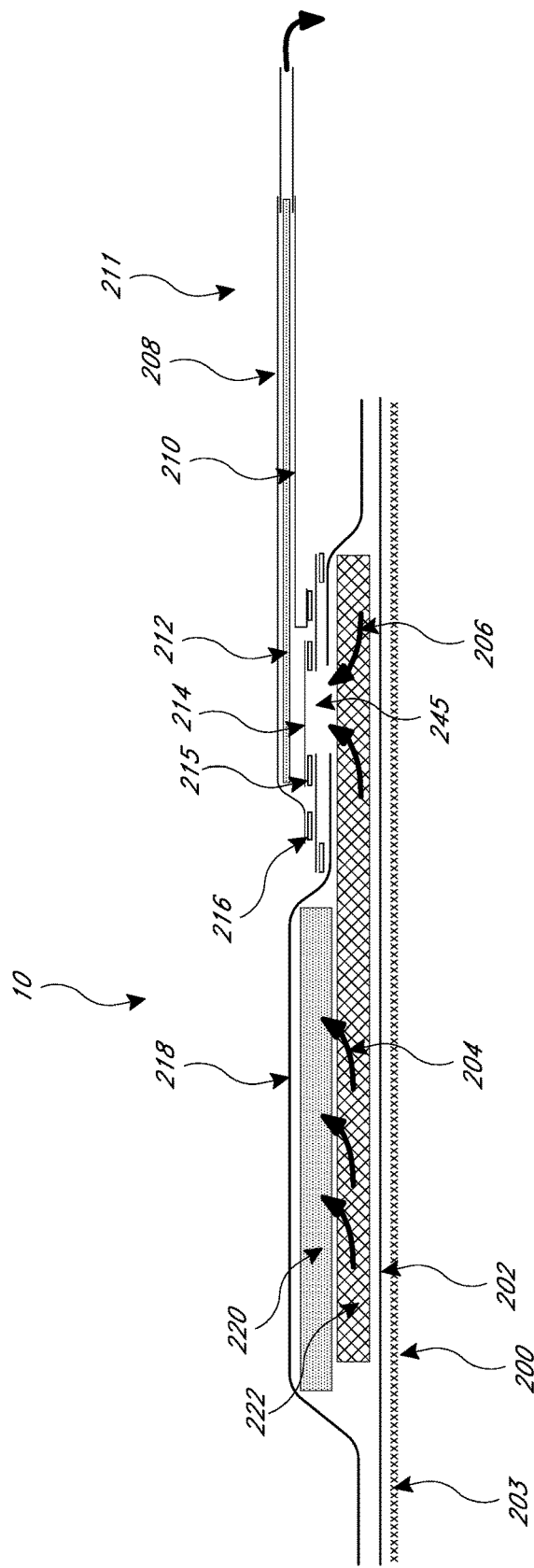
FIG. 1B illustrates a cross section of an embodiment of a negative pressure wound treatment dressing capable of absorbing and storing wound exudate with a flexible suction adapter.

With reference initially to FIGS. 1A-B, treatment of a wound with negative pressure in certain embodiments of the application uses a wound dressing 10 capable of absorbing and storing wound exudate in conjunction with a flexible suction adapter 12. In some embodiments, it may be preferable for the wound site to be filled partially or completely with a wound packing material. This wound packing material is optional, but may be desirable in certain wounds, for example deeper wounds. The wound packing material can be used in addition to the wound dressing 10. The wound packing material generally may comprise a porous and conformable material, for example foam (including reticulated foams), and gauze. Preferably, the wound packing material is sized or shaped to fit within the wound site so as to fill any empty spaces. The wound dressing 10 may then be placed over the wound site and wound packing material overlying the wound site. When a wound packing material is used, once the wound dressing 10 is sealed over the wound site, negative pressure may be transmitted from a pump or other source of negative pressure through a flexible tubing 14 via the suction adapter 12 to the wound dressing 10, through the wound packing material, and finally to the wound site. This negative pressure draws wound exudate and other fluids or secretions away from the wound site.

The suction adapter 12 preferably comprises a head 11 that is in fluidic communication with the dressing 10 as will be described in further detail below. The head 11 is illustrated here as being positioned at a corner of the dressing 10, but may also be positioned at any location on the dressing. For example, some embodiments may provide for a centrally or off-centered location not on an edge or corner of the dressing 10. In some embodiments, the dressing 10 may comprise two or more suction adapters 12, each comprising one or more heads 11, in fluidic communication therewith. In a preferred embodiment, the head 11 may measure 30 mm along its widest edge.

With reference now to FIG. 1B, certain embodiments of the wound dressing 10 may comprise a plurality of layers. A wound contact layer 203 with an upper surface 202 and a lower surface 200 may be configured to carry an adhesive on its lower surface 200 for sealing the wound dressing 10 to the wound site. A porous transmission layer 222 overlying the wound contact layer 203 may comprise a 3D knitted or 3D fabric material, and the transmission layer 222 may be configured to remain open upon application of negative pressure to the wound dressing. This facilitates fluid flow 204 through the transmission layer 222, although the transmission layer 222 does not retain a substantial amount of the fluid. An absorbent layer 220 overlying the transmission layer 222 may be configured for absorbing wound exudate. A moisture vapor permeable cover layer 218 overlays the absorbent layer 220.

The wound contact layer 203 can be a polyurethane layer or polyethylene layer or other flexible layer which is perforated, for example via a hot pin process, laser ablation process, ultrasound process or in some other way or otherwise made permeable to liquid and gas. The perforations 104 are through holes in the wound contact layer which enables fluid to flow through the layer. The wound contact layer 203 may help prevent tissue ingrowth into the other material of the wound dressing 10. The perforations are small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer 203 may help hold the whole wound dressing together and helps to create an air tight seal around the absorbent pad in order to maintain negative pressure at the wound. The wound contact layer 230 may also act as a carrier for an optional lower and upper adhesive layer (not shown). For example, a lower pressure sensitive adhesive may be provided on the underside surface 200 of the wound dressing whilst an upper pressure sensitive adhesive layer may be provided on the upper surface 202 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized this may help adhere the wound dressing 10 to the skin around a wound site.

The layer 222 of porous material is located above the wound contact layer 203. This porous layer, or transmission layer, 222 preferably allows transmission of fluid including liquid and gas away from a wound site into upper layers of the wound dressing. In particular, the transmission layer 222 ensures that an open air channel can be maintained to communicate negative pressure over the wound area even when the absorbent layer 220 has absorbed substantial amounts of exudates. The layer should remain open under the typical pressures that will be applied during negative pressure wound therapy as described above, so that the whole wound site sees an equalized negative pressure. The layer 222 is preferably formed of a material having a three dimensional structure. For example, a knitted or woven spacer fabric (for example Baltex 7970 weft knitted polyester) or a non-woven fabric could be used. The transmission layer 222 may also comprise materials such foams, including open-cell foams such as polyethylene or polyurethane foam, meshes, non-woven materials, and fluid channels.

In some embodiments, the transmission layer 222 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 220 helps lock the liquid away or itself wicks the liquid onwards towards the cover layer where it can be transpired.

Preferably, to improve the liquid flow across the transmission layer 222 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

As stated previously, the layer 220 of absorbent material is provided above the transmission layer 222. The absorbent material which may be a foam or non-woven natural or synthetic material and which may optionally include or be super-absorbent material forms a reservoir for fluid, particularly liquid, removed from the wound site and draws those fluids towards a cover layer 218. The material of the absorbent layer 220 also prevents liquid collected in the wound dressing from flowing in a sloshing manner. The absorbent layer 220 also helps distribute fluid throughout the layer via a wicking action so that fluid is drawn from the wound site and stored throughout the absorbent layer 220. This helps prevent agglomeration in areas of the absorbent layer. The capacity of the absorbent material must be sufficient to manage the exudates flow rate of a wound when negative pressure is applied. Since in use the absorbent layer 220 experiences negative pressures the material of the absorbent layer 220 is chosen to absorb liquid under such circumstances. A number of materials exist that are able to absorb liquid when under negative pressure, for example superabsorber material. The absorbent layer 220 may typically be manufactured from ALLEVYN™ foam, Freudenberg 114-224-4 and/or Chem-Posite™ 11C-450.

In some embodiments, the absorbent layer 220 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer 218 to aid increase transpiration rates of the dressing.

The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimized for wound healing.

In some embodiments, the absorbent layer 220 may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present invention. An example of a suitable material is the Product Chem-Posite™ 11 C available from Emerging Technologies Inc. (ETi) in the USA.

Optionally, according to certain embodiments of the present invention, the absorbent layer 220 may include synthetic stable fibers and/or bi-component stable fibers and/or natural stable fibers and/or super-absorbent fibers. Fibers in the absorbent layer 220 may be secured together by latex bonding or thermal bonding or hydrogen bonding or a combination of any bonding technique or other securing mechanism. In some embodiments, the absorbent layer 220 is formed by fibers which operate to lock super-absorbent particles within the absorbent layer 220. This helps ensure that super-absorbent particles do not move external to the absorbent layer 220 and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer 220.

The absorbent layer 220 may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer 220 comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. Equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

Turning now to the suction adapter 12, preferred embodiments comprise a sealing surface 216, a bridge 211 with a proximal end and a distal end, and a filter 214. The sealing surface 216 may be configured for sealing the suction adapter to the cover layer 218 of the wound dressing, and may comprise an adhesive or weld. In some embodiments, the sealing surface 216 may be placed over an orifice in the cover layer with spacer elements 215 configured to create a gap between the filter 214 and the transmission layer 222. In other embodiments, the sealing surface 216 may be positioned over an orifice in the cover layer 218 and an aperture in the absorbent layer 220, permitting the suction adapter 12 to provide air flow 206 through the transmission layer 222. In some embodiments, the bridge 211 may comprise a first fluid passage 212 in communication with a source of negative pressure, the first fluid passage 212 comprising a porous material, such as a 3D knitted material, which may be the same or different than the porous layer 222 described previously. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the suction adapter from contacting the transmission layer 222. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 10.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 222. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably the absorbent layer 220 includes at least one area 246, such as an edge or through hole, located so as to underlie the suction adapter 12 where the absorbent layer 220 is removed or not provided. It will be appreciated that multiple openings could alternatively be utilized. As shown in FIG. 1A, this area 246 preferably underlies the point where the head 11 is in fluidic communication with the dressing. Additionally, should more than one suction adapter 12 be utilized according to certain embodiments, one or multiple openings may be made in the super-absorbent layer 220 in registration with each respective suction adapter. Although not essential to certain embodiments of the present invention the use of through holes in the super-absorbent layer 220 provide a fluid flow pathway which is particularly unhindered and this is useful in certain circumstances.

Where an opening 246 is provided in the absorbent layer 220 the thickness of the layer itself will act as a stand-off separating any overlying layer from the upper surface (that is to say the surface facing away from a wound in use) of the transmission layer 222. An advantage of this is that the filter 214 is thus decoupled from the material of the transmission layer 222. This helps reduce the likelihood that the filter will be wetted out and thus will occlude and block further operation.

Use of one or more through holes in the absorption layer 220 also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the transmission layer directly to the wound facing surface of the filter and then onwards into the interior of the suction adapter.

The cover layer 218 extends across the width of the wound dressing, and is preferably gas impermeable, but moisture vapor permeable. The cover layer 218, which may for example be a polyurethane film (for example, Elastollan SP9109) having a pressure sensitive adhesive on one side, is preferably impermeable to gas and this layer thus operates to cover the wound and to seal a wound cavity over which the wound dressing is placed. In this way an effective chamber is made between the cover layer and a wound site where a negative pressure can be established. The cover layer 218 may for example be sealed to the wound contact layer 203 in a border region 200 around the circumference of the dressing, ensuring that no air is drawn in through the border area, for example via adhesive or welding techniques. The cover layer 218 protects the wound from external bacterial contamination (bacterial barrier) and allows liquid from wound exudates to be transferred through the layer and evaporated from the film outer surface. The cover layer 218 typically comprises two layers; a polyurethane film and an adhesive pattern spread onto the film. The polyurethane film is moisture vapor permeable and may be manufactured from a material that has an increased water transmission rate when wet.

In some embodiments, the absorbent layer 220 may be of a greater area than the transmission layer 222, such that the absorbent layer overlaps the edges of the transmission layer 222, thereby ensuring that the transmission layer does not contact the cover layer 218. This provides an outer channel of the absorbent layer 220 that is in direct contact with the wound contact layer 203, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks.

In order to ensure that the air channel remains open when a vacuum is applied to the wound cavity, the transmission layer 222 must be sufficiently strong and non-compliant to resist the force due to the pressure differential. However, if this layer comes into contact with the relatively delicate cover layer 218, it may cause the formation of tears, holes, or pin-hole openings in the cover layer 218 which allow air to leak into the wound cavity. This may be a particular problem when a switchable type polyurethane film is used that becomes weaker when wet. The absorbent layer 220 is generally formed of a relatively soft, non-abrasive material compared to the material of the transmission layer 222 and therefore does not cause the formation of pin-hole openings in the cover layer. Thus by providing an absorbent layer 220 that is of greater area than the transmission layer 222 and that overlaps the edges of the transmission layer 222, contact between the transmission layer 222 and the cover layer 218 is prevented, avoiding the formation of openings in the cover layer 218.

The absorbent layer 220 is positioned in fluid contact with the cover layer 218. As the absorbent layer 220 absorbs wound exudate, the exudate is drawn towards the cover layer 218, bringing the water component of the exudate into contact with the moisture vapor permeable cover layer. This water component is drawn into the cover layer itself and then evaporates from the top surface of the dressing. In this way, the water content of the wound exudate can be transpired from the dressing, reducing the volume of the remaining wound exudate that is to be absorbed by the absorbent layer 220, and increasing the time before the dressing becomes full and must be changed. This process of transpiration occurs even when negative pressure has been applied to the wound cavity, and it has been found that the pressure difference across the cover layer when a negative pressure is applied to the wound cavity has negligible impact on the moisture vapor transmission rate across the cover layer.

An orifice 245 is provided in the cover film 218 to allow a negative pressure to be applied to the dressing 10. A suction adapter 12 may be sealed to the top of the cover film 218 over the orifice 245, and communicates negative pressure through the orifice 245. A length of tubing 14 may be coupled at a first end to the suction adapter 12 and at a second end to a pump unit (not shown) to allow fluids to be pumped out of the dressing. The suction adapter 12 may be adhered and sealed to the cover film 218 using an adhesive such as an acrylic, cyanoacrylate, epoxy, UV curable or hot melt adhesive. In some embodiments, the suction adapter 12 may be separately attached to the cover film 218, while other embodiments may provide for the dressing 10 to be provided with the suction adapter 12 already attached to the cover film 218. The suction adapter 12 may be formed from a soft polymer, for example a polyethylene, a polyvinyl chloride, a silicone or polyurethane having a hardness of 30 to 90 on the Shore A scale.

As discussed above, the area or through-hole 246 may be provided in the absorbent layer 220 beneath the orifice 245 such that the orifice is connected directly to the transmission layer 222. This allows the negative pressure applied to the suction adapter 12 to be communicated to the transmission layer 222 without passing through the absorbent layer 220. This ensures that the negative pressure applied to the wound site is not inhibited by the absorbent layer as it absorbs wound exudates. In other embodiments, no aperture may be provided in the absorbent layer 220, or alternatively a plurality of apertures underlying the orifice 245 may be provided.

As shown in FIG. 1B, one embodiment of the wound dressing 10 comprises an aperture 246 in the absorbent layer 10 situated underneath the suction adapter 12. In use, for example when negative pressure is applied to the dressing 10, a wound facing portion of the suction adapter 12 may thus come into contact with the transmission layer 222, which can thus aid in transmitting negative pressure to the wound site even when the absorbent layer 220 is filled with wound fluids. Some embodiments may have the cover layer 218 be at least partly adhered to the transmission layer 222. In some embodiments, the aperture 246 is at least 1-2 mm larger than the diameter of the wound facing portion of the suction adapter 12, or the orifice 245.

Preferably, the filter element 214 is impermeable to liquids, but permeable to gases, and is provided to act as a liquid barrier and to ensure that no liquids are able to escape from the wound dressing 10. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film 218 over the orifice 245. For example, the filter element 214 may be molded into the suction adapter 12, or may be adhered to one or both of the top of the cover layer 218 and bottom of the suction adapter 12 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 10 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice 245. Liquid, particulates and pathogens however are contained in the dressing.

The wound dressing 10 may comprise spacer elements 215 in conjunction with the suction adapter 12 and the filter 214. With the addition of such spacer elements 215 the suction adapter 12 and filter 214 may be supported out of direct contact with the absorbent layer 220 and/or the transmission layer 222. The absorbent layer 220 may also act as an additional spacer element to keep the filter 214 from contacting the transmission layer 222. Accordingly, with such a configuration contact of the filter 214 with the transmission layer 222 and wound fluids during use may thus be minimized.

In particular for embodiments with a single suction adapter 12 and through hole 246, it may be preferable for the suction adapter 12 and through hole 246 to be located in an off-center position as illustrated in FIGS. 1A-B. Such a location may permit the dressing 10 to be positioned onto a patient such that the suction adapter 12 is raised in relation to the remainder of the dressing 10. So positioned, the suction adapter 12 and the filter 214 may be less likely to come into contact with wound fluids that could prematurely occlude the filter 214 so as to impair the transmission of negative pressure to the wound site.

Figure 2:
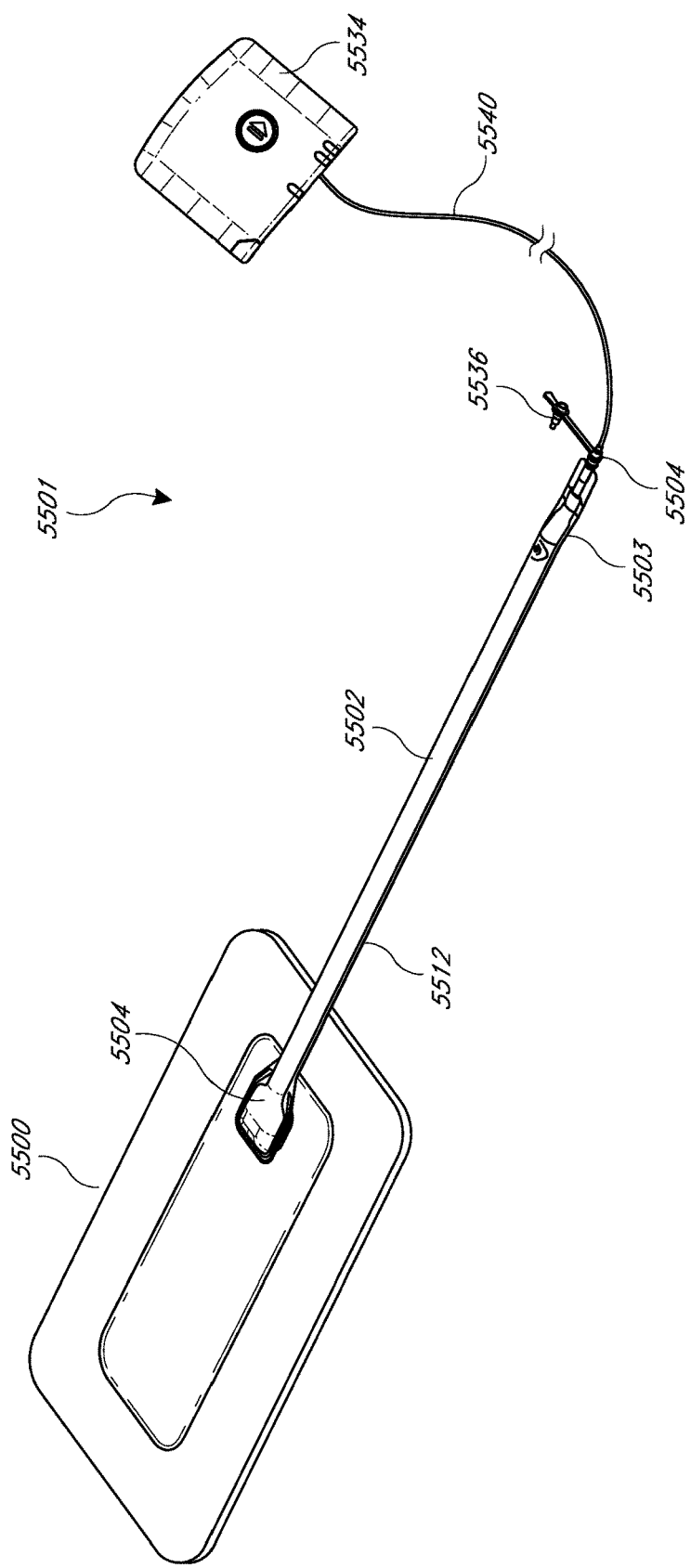
FIG. 2 illustrates an embodiment of a negative pressure wound treatment system employing a wound dressing capable of absorbing and storing wound exudate and a flexible suction adapter.

FIG. 2 illustrates an embodiment of a negative pressure wound treatment system 5501 employing a wound dressing 5500 in conjunction with a flexible suction adapter 5512. The wound dressing 5500 may be similar to the dressings illustrated in FIGS. 1A-B. Here, the flexible suction adapter 5512 may comprise a bridge 5502 having a proximal end 5503 and a distal end 5505 and an applicator 5504 at the distal end 5505 of the bridge 5502. A connector 5504 is preferably disposed at the proximal end 5503 of the bridge 5502. A cap 5536 may be provided with the system 5501 (and can in some cases, as illustrated, be attached to the connector 5504). The cap 5536 can be useful in preventing fluids from leaking out of the proximal end 5503. The system 5501 may include a source of negative pressure such as a pump or negative pressure unit 5534 capable of supplying negative pressure. The pump also preferably comprises a canister or other container for the storage of wound exudates and other fluids that may be removed from the wound. In some embodiments, this pump 5534 can be a PICO™ pump, as sold by Smith & Nephew. The pump 5534 may be connected to the connector 5504 via a tube 5540. In use, the dressing 5500 is placed over a suitably-prepared wound, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

FIGS. 3A-C illustrate various embodiments of the head 11 of the suction adapter 12. Preferably, the suction adapter 12 illustrated in FIGS. 1A-C is enlarged at the distal end to be placed over the orifice in the cover layer 218 and the aperture in the absorbent layer 220, and may form a "teardrop" or other enlarged shape. FIG. 3A illustrates a suction adapter 12 with a substantially triangular head 11. FIG. 3B illustrates a suction adapter 12 with a substantially pentagonal head 11. FIG. 3A illustrates a suction adapter 12 with a substantially circular head 11.

Figure 4A:
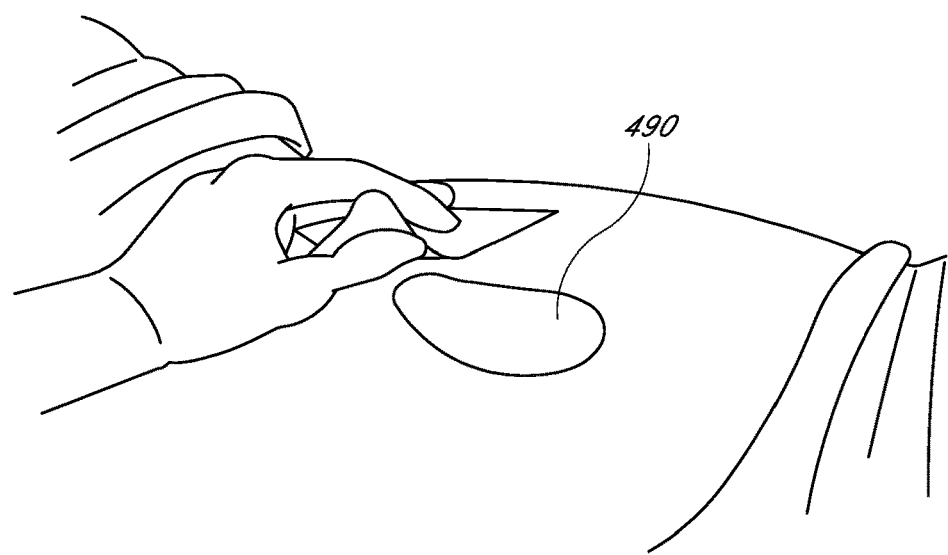
FIGS. 4A-D illustrate the use and application of an embodiment of a wound treatment system onto a patient.

FIGS. 4A-D illustrate the use of an embodiment of a negative pressure therapy wound treatment system being used to treat a wound site on a patient. FIG. 4A shows a wound site 490 being cleaned and prepared for treatment. Here, the healthy skin surrounding the wound site 490 is preferably cleaned and excess hair removed or shaved. The wound site 490 may also be irrigated with sterile saline solution if necessary. Optionally, a skin protectant may be applied to the skin surrounding the wound site 490. If necessary, a wound packing material, such as foam or gauze, may be placed in the wound site 490. This may be preferable if the wound site 490 is a deeper wound.

Figure 4B:
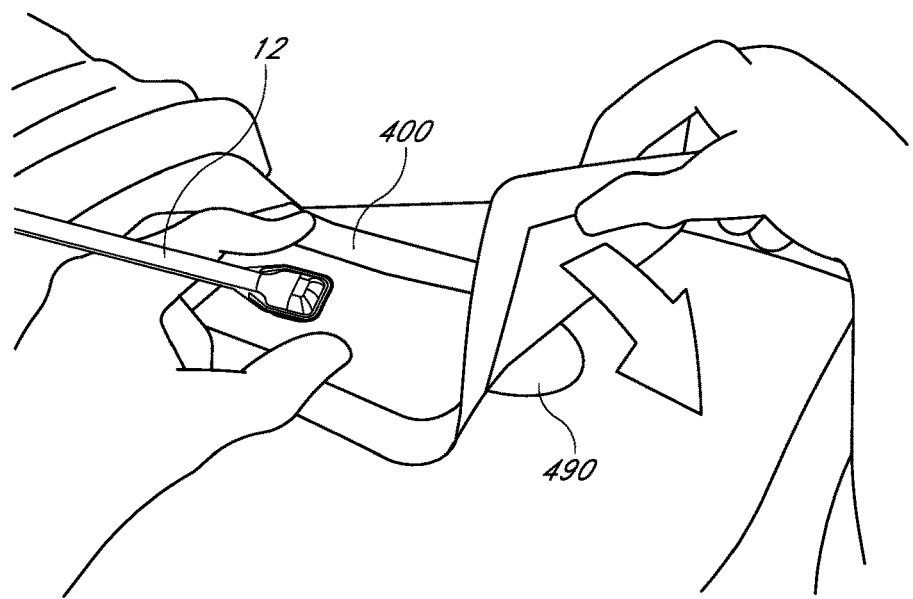

After the skin surrounding the wound site 490 is dry, and with reference now to FIG. 4B, the wound dressing 400 may be positioned and placed over the wound site 490. The wound dressing 400 may be similar to the wound dressing 10 described above in relation to FIGS. 1A-B. Preferably, the wound dressing 400 is placed with the wound contact layer 203 (illustrated in FIGS. 1A-B) over and/or in contact with the wound site 490. In some embodiments, an adhesive layer is provided on the lower surface 200 of the wound contact layer 203, which may in some cases be protected by an optional release layer to be removed prior to placement of the wound dressing 400 over the wound site 490. Preferably, the dressing 400 is positioned such that the suction adapter 12 is in a raised position with respect to the remainder of the dressing 400 so as to avoid fluid pooling around the port. In some embodiments, the dressing 400 is positioned so that the suction adapter 12 is not directly overlying the wound, and is level with or at a higher point than the wound. To help ensure adequate sealing for TNP, the edges of the dressing 400 are preferably smoothed over to avoid creases or folds.

Figure 4C:
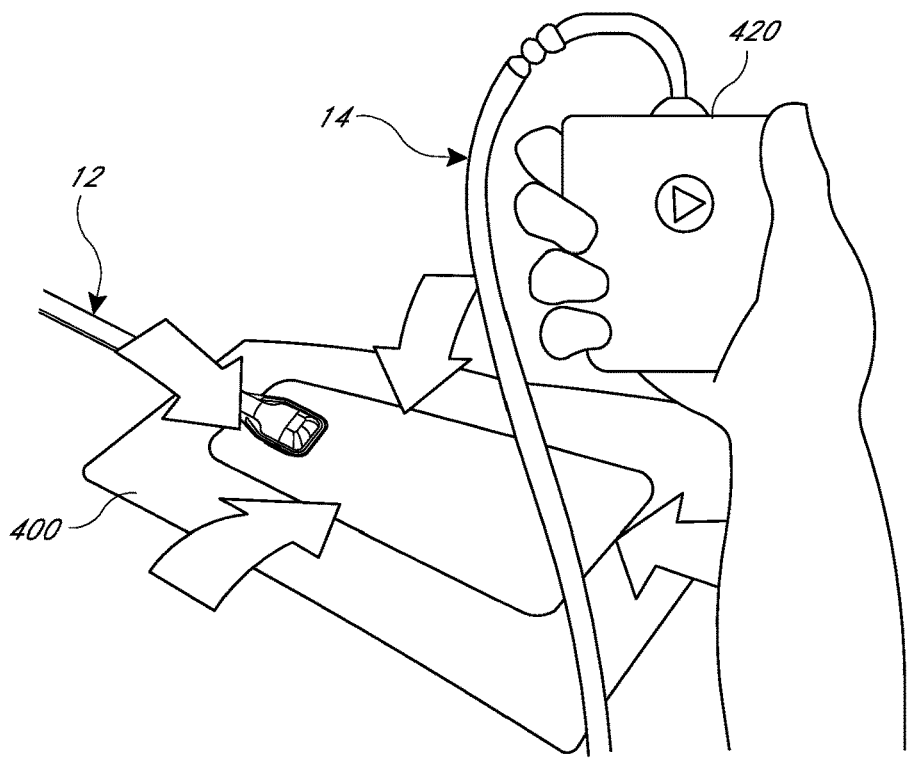

With reference now to FIG. 4C, the dressing 400 is connected to the pump 420. The pump 420 is configured to apply negative pressure to the wound site via the dressing 400, and typically through a conduit. In some embodiments, and as described above in FIG. 28, a connector may be used to join the conduit from the dressing 400 to the pump 420. Upon the application of negative pressure with the pump 420, the dressing 400 may in some embodiments partially collapse and present a wrinkled appearance as a result of the evacuation of some or all of the air underneath the dressing 400. In some embodiments, the pump 420 may be configured to detect if any leaks are present in the dressing 400, such as at the interface between the dressing 400 and the skin surrounding the wound site 490. Should a leak be found, such leak is preferably remedied prior to continuing treatment.

Figure 4D:
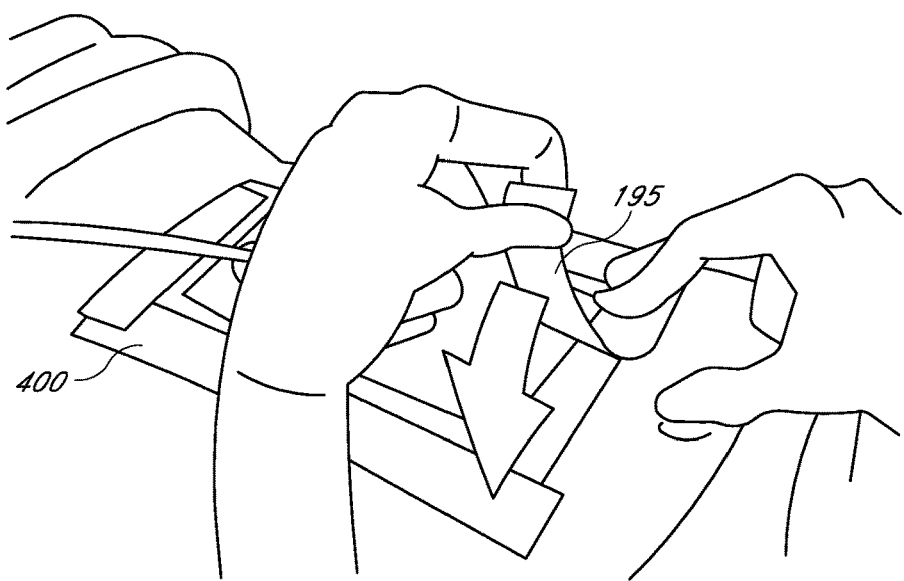

Turning to FIG. 4D, additional fixation strips 495 may also be attached around the edges of the dressing 400. Such fixation strips 495 may be advantageous in some situations so as to provide additional sealing against the skin of the patient surrounding the wound site 490. For example, the fixation strips 495 may provide additional sealing for when a patient is more mobile. In some cases, the fixation strips 495 may be used prior to activation of the pump 420, particularly if the dressing 400 is placed over a difficult to reach or contoured area.

Treatment of the wound site 490 preferably continues until the wound has reached a desired level of healing. In some embodiments, it may be desirable to replace the dressing 400 after a certain time period has elapsed, or if the dressing is full of wound fluids. During such changes, the pump 420 may be kept, with just the dressing 400 being changed.

Further details of dressings that may be used with the suction adapters, fluidic connectors or ports described herein include, but are not limited to, dressings described in Provisional Application Ser. No. 61/785,054, filed Mar. 14, 2013, the entirety of which is hereby incorporated by reference and portions of which were included as an appendix in Application Ser. No. 61/785,927 and are now described below in the section entitled "Other Negative Pressure Therapy Apparatuses, Dressings and Methods." Similarly, further details of suction adapters, fluidic connectors and other apparatuses that may be used with the dressings and other wound treatment apparatuses described herein are also described in Application Ser. No. 61/785,054, filed Mar. 14, 2013 and are described below in the section entitled "Other Negative Pressure Therapy Apparatuses, Dressings and Methods."

Figure 5A:
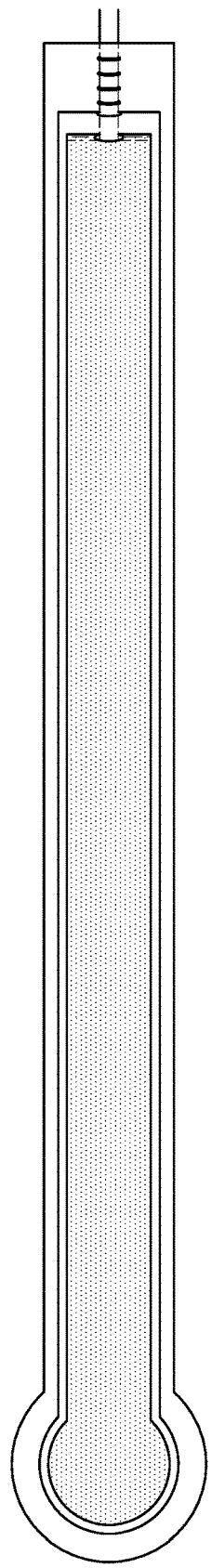
FIG. 5A illustrates a top view of an embodiment of a flexible port.
Figure 5B:
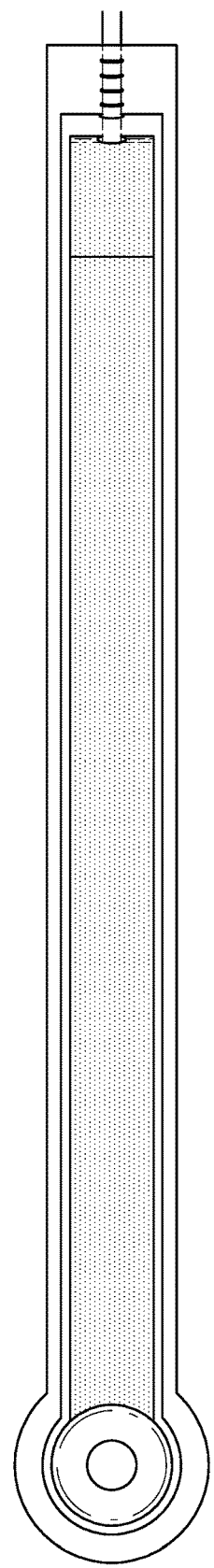
FIG. 5B illustrates a bottom view of an embodiment of a flexible port.
Figure 5C:
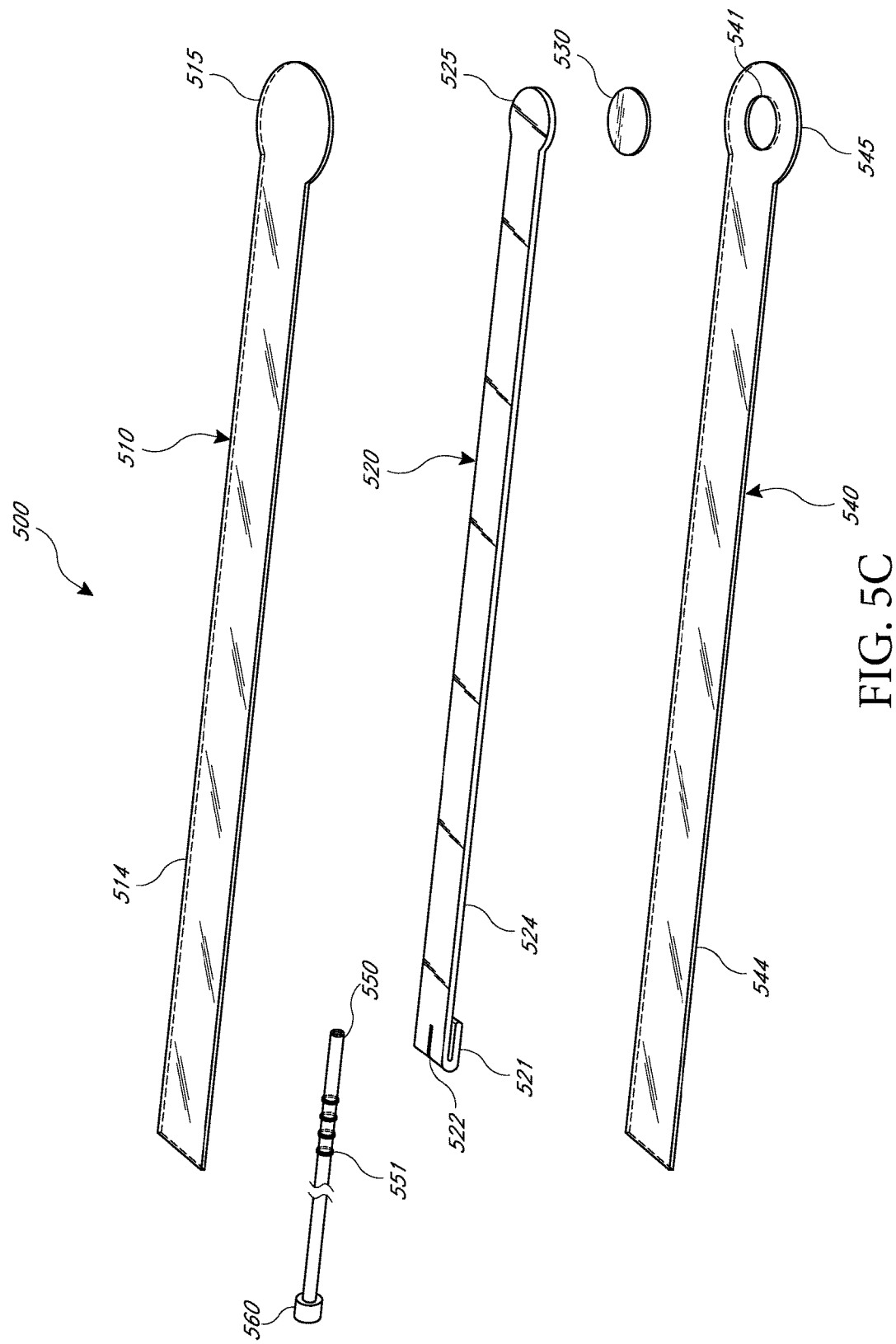
FIG. 5C illustrates a perspective exploded view of an embodiment of a flexible port.

FIGS. 5A-B illustrate an embodiment of a flexible port or fluidic connector 500. FIG. 5C illustrates a perspective exploded view the fluidic connector 500 that may be used to connect a wound dressing to a source of negative pressure. The port 500 comprises a top layer 510, a spacer layer 520, a filter element 530, a bottom layer 540, and a conduit 550. The conduit optionally comprises a connector 560. The distal end of the port 500 (the end connectable to the dressing) is depicted as having an enlarged circular shape, although it will be appreciated that any suitable shape may be used and that the distal end need not be enlarged. For example, the distal end can have any of the shapes shown in FIGS. 3A-3C above. The distal end can also have the shape shown in FIGS. 39A and 39B, discussed below.

The bottom layer 540 may comprise an elongate bridge portion 544, an enlarged (e.g., rounded or circular) sealing portion 545, and an orifice 541. In some embodiments a plurality of orifices may be provided in the bottom layer. Some embodiments of the rounded sealing portion 545 may comprise a layer of adhesive, for example a pressure sensitive adhesive, on the lower surface for use in sealing the port 500 to a dressing. For example, the port may be sealed to a cover layer of the dressing. The orifice 541 in the bottom layer 540 of the port 500 may be aligned with an orifice in the cover layer of the dressing in order to transmit negative pressure through the dressing and into a wound site.

The top layer 515 may be substantially the same shape as the bottom layer in that it comprises an elongate bridge 514 and an enlarged (e.g., rounded or circular) portion 545. The top layer 515 and the bottom layer 545 may be sealed together, for example by heat welding. In some embodiments, the bottom layer 545 may be substantially flat and the top layer 515 may be slightly larger than the bottom layer 545 in order to accommodate the height of the spacer layer 520 and seal to the bottom layer 545. In other embodiments, the top layer 515 and bottom layer 3145 may be substantially the same size, and the layers may be sealed together approximately at the middle of the height of the spacer layer 520. In some embodiments, the elongate bridge portions 544, 514 may have a length of 10 cm (or about 10 cm) or more, more preferably a length of 20 cm (or about 20 cm) or more and in some embodiments, may be about 69 cm (or 27 cm) long. Some embodiments of the entire flexible port, from a proximalmost edge of the top and bottom layers to a distalmost edge of the top and bottom layers, may be between 20 cm and 80 cm (or about 20 cm to about 80 cm) long, more preferably about 60 cm and 80 cm (or between about 60 cm and about 80 cm) long, for example about 70 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions 544, 514 to their widths may in some embodiments exceed 6:1, and may more preferably exceed 8:1 or even 10:1. The diameter of the circular portion 545, 515 may be about 3.5 cm in some embodiments.

The bottom and top layers may comprise at least one layer of a flexible film, and in some embodiments may be transparent. Some embodiments of the bottom layer 540 and top layer 515 may be polyurethane, and may be liquid impermeable.

The port 500 may comprise a spacer layer 520, such as the 3D fabric discussed above, positioned between the lower layer 540 and the top layer 510. The spacer layer 520 may be made of any suitable material, for example material resistant to collapsing in at least one direction, thereby enabling effective transmission of negative pressure therethrough. Instead of or in addition to the 3D fabric discussed above, some embodiments of the spacer layer 520 may comprise a fabric configured for lateral wicking of fluid, which may comprise viscose, polyester, polypropylene, cellulose, or a combination of some or all of these, and the material may be needle-punched. Some embodiments of the spacer layer 520 may comprise polyethylene in the range of 40-160 grams per square meter (gsm) (or about 40 to about 160 gsm), for example 80 (or about 80) gsm. Such materials may be constructed so as to resist compression under the levels of negative pressure commonly applied during negative pressure therapy.

The spacer layer 520 may comprise an elongate bridge portion 524, an enlarged (e.g., rounded or circular) portion 525, and may optionally include a fold 521. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion 525 may be slightly smaller than the diameters of the enlarged ends 545, 515, and in one embodiment is about 2 cm. Some embodiments of the spacer layer 520 may have adhesive on one or both of its proximal and distal ends (e.g., one or more dabs of adhesive) in order to secure the spacer layer 520 to the top layer 510 and/or the bottom layer 540. Adhesive may also be provided along a portion or the entire length of the spacer layer. In other embodiments, the spacer layer 520 may be freely movable within the sealed chamber of the top and bottom layers.

The fold 521 of the spacer layer may make the end of the port 500 softer and therefore more comfortable for a patient, and may also help prevent the conduit 550 from blockage. The fold 521 may further protect the end of the conduit 550 from being occluded by the top or bottom layers. The fold 521 may, in some embodiments, be between 1 cm and 3 cm (or between about 1 cm and about 3 cm) long, and in one embodiment is 2 cm (or about 2 cm) long. The spacer layer may be folded underneath itself, that is toward the bottom layer 540, and in other embodiments may be folded upward toward the top layer 510. Other embodiments of the spacer layer 520 may contain no fold. A slot or channel 522 may extend perpendicularly away from the proximal end of the fold 521, and the conduit 550 may rest in the slot or channel 522. In some embodiments the slot 522 may extend through one layer of the fold, and in others it may extend through both layers of the fold. The slot 522 may, in some embodiments, be 1 cm (or about 1 cm) long. Some embodiments may instead employ a circular or elliptical hole in the fold 521. The hole may face proximally so that the conduit 550 may be inserted into the hole and rest between the folded layers of spacer fabric. In some embodiments, the conduit 550 may be adhered to the material of the fold 3521, while in other embodiments it may not.

The port 500 may have a filter element 530 located adjacent the orifice 541, and as illustrated is located between the lower layer 540 and the spacer layer 520. The filter element 530 is impermeable to liquids, but permeable to gases. The filter element may be similar to the element described above with respect to FIG. 1B, and as illustrated may have a round or disc shape. The filter element 530 can act as a liquid barrier, to substantially prevent or inhibit liquids from escaping from the wound dressing, as well as an odor barrier. The filter element 530 may also function as a bacterial barrier. In some embodiments, the pore size of the filter element 530 can be approximately 0.2 µm. Suitable materials for the filter material of the filter element include 0.2 micron Gore™ expanded PTFE from the MMT range, PALL Versapore™ 200R, and Donaldson™ TX6628. The filter element 530 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element 530 may be adhered to one or both of top surface of the bottom layer 540 and the bottom surface of the spacer layer 520 using an adhesive such as, but not limited to, a UV cured adhesive. In other embodiments, the filter 530 may be welded to the inside of the spacer layer 520 and to the top surface of the bottom layer 540. The filter may also be provided adjacent the orifice on a lower surface of the bottom layer 540. Other possible details regarding the filter are disclosed in U.S. Patent Pub. No. 2011/0282309 and incorporated by reference herein.

The proximal end of the port 500 may be connected to the distal end of a conduit 550. The conduit 550 may comprise one or more circular ribs 551. The ribs 551 may be formed in the conduit 550 by grooves in a mold during the manufacturing of the conduit. During heat welding of the upper and lower layers 515, 545 melted material from those layers may flow around the ribs 551, advantageously providing a stronger connection between the conduit 550 and the layers. As a result, it may be more difficult to dislodge the conduit 550 out from between the layers during use of the port 500.

The proximal end of the conduit 550 may be optionally attached to a connector 560. The connector 560 may be used to connect the port 500 to a source of negative pressure, or in some embodiments to an extension conduit which may in turn be connected to a source of negative pressure. As explained in more detail below with respect to FIGS. 8A and 8B, the proximal end of the conduit 550, which is inserted into the spacer fabric 520, may be shaped in such a way to reduce the possibility of occlusion. For example, some embodiments may have a triangular portion cut out of the end of the conduit, and other embodiments may have a plurality of holes therethrough.

Figure 6:
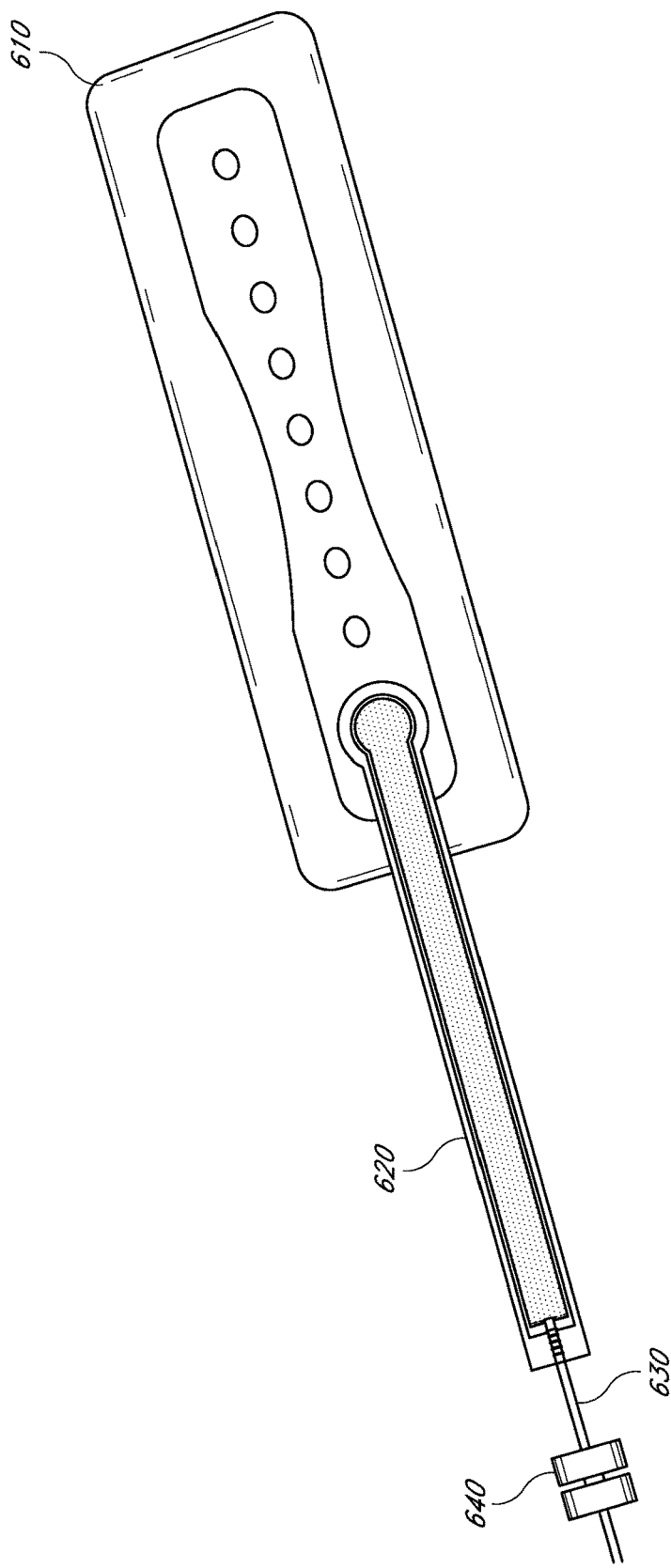
FIG. 6 illustrates an embodiment of a flexible port attached to a wound dressing.

FIG. 6 illustrates an embodiment of a wound dressing 610 with a flexible port 620 such as described above with respect to FIGS. 5A-C attached to the dressing. The port 620 may be the port described above in FIGS. 5A-C. The port 620 may comprise a conduit 630 and a connector 640 for connecting the port to a source of negative pressure or to an extension conduit. Although in this depiction the port 620 is connected over a circular window in the obscuring layer of the dressing 610, in other embodiments the port 620 may be connected over a maltese cross in the obscuring layer. In some embodiments, the maltese cross may be of a larger diameter than the port 620 and may be at least partially viewable after the port 620 is attached to the dressing 610. Further details regarding the dressing 610 and other dressings to which the port can be connected are described in Provisional Application Ser. No. 61/785,054, filed Mar. 14, 2013, incorporated by reference herein and described further below in the section entitled "Other Negative Pressure Therapy Apparatuses, Dressings and Methods."

Figure 7A:
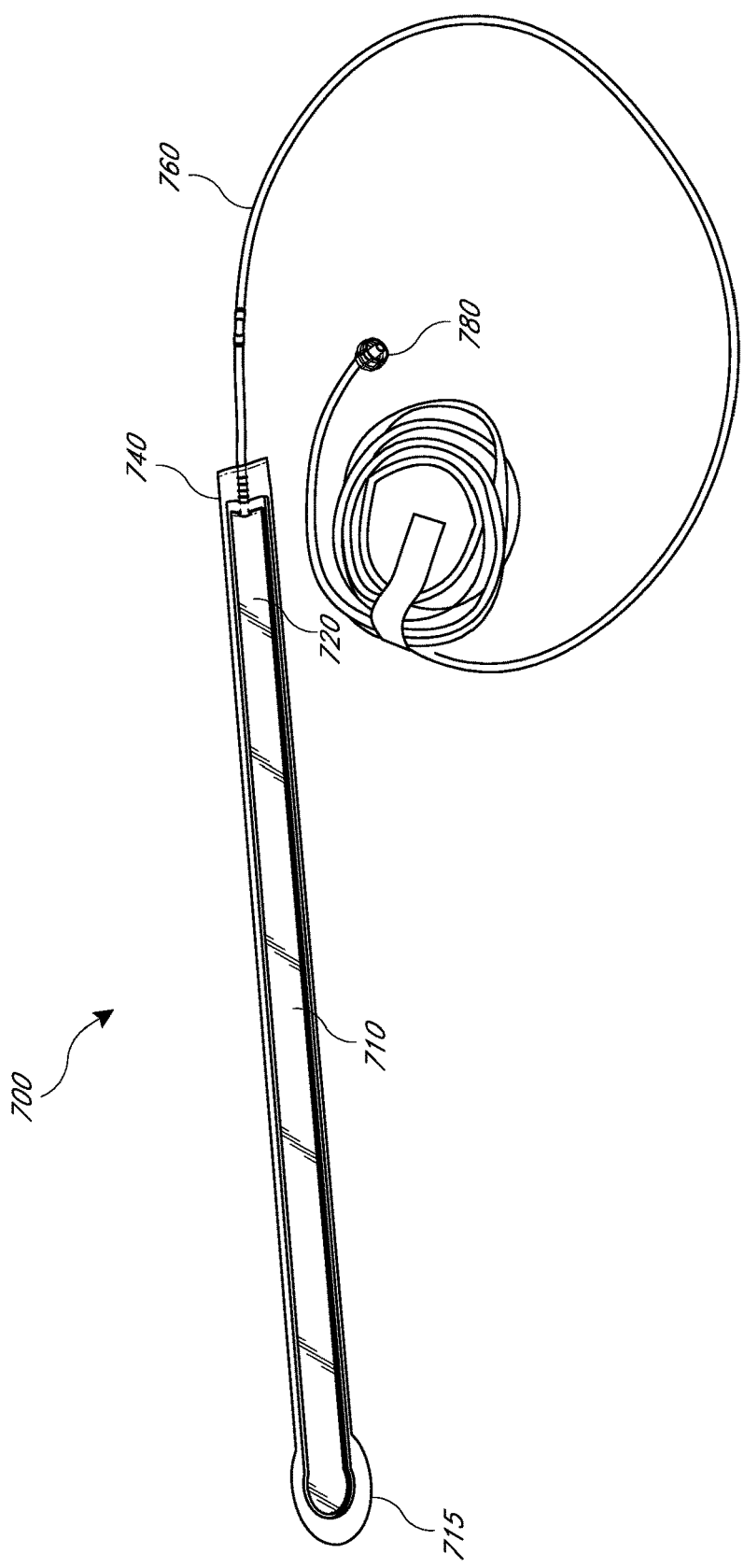
FIG. 7A illustrates a perspective view of an embodiment of a flexible port.

FIG. 7A depicts a perspective view of a flexible port 700 of the same design as shown with respect to FIGS. 5A-C. The port 700 comprises spacer fabric 710, wherein the proximal end of spacer fabric 710 comprises a fold 720, at least one layer of flexible film 740, an enlarged rounded distal end 715, a conduit 760, and a connector 780. The components of port 700 may have similar properties to the components of FIGS. 5A-C, described above.

Figure 7B:
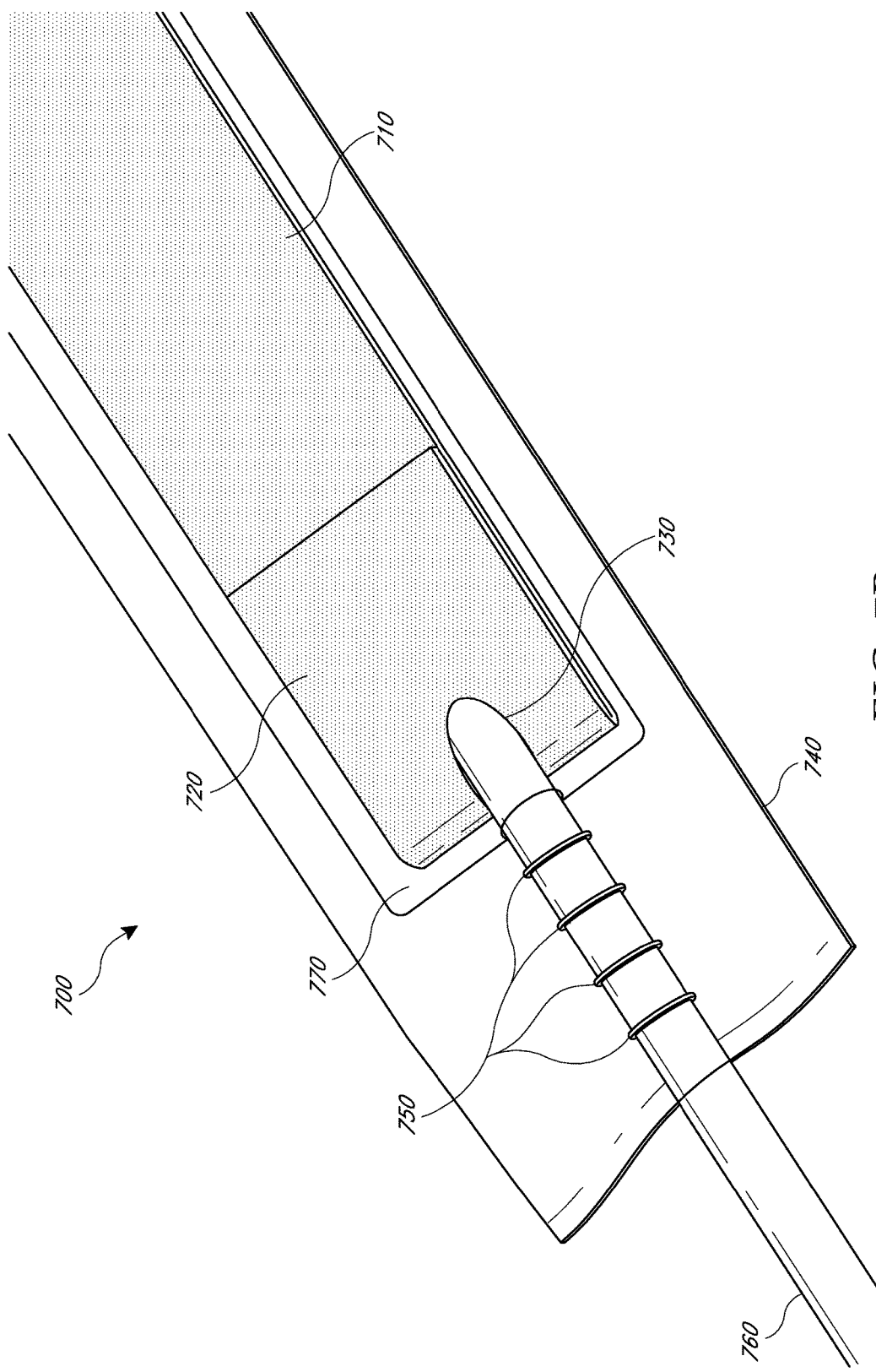
FIG. 7B illustrates a close up view of an embodiment of the proximal end of the flexible port of FIG. 7A.

FIG. 7B illustrates a close up view of an embodiment of the proximal end of the flexible port 700. The port 700 comprises spacer fabric 710 inside a sealed chamber 770 between layers of flexible film 740. The end of the spacer fabric 710 comprises a fold 720. At the proximal end of the fold, there may be a hole 730 through the fabric for inserting the conduit 760. The conduit 760 may rest between the folded portions of the spacer fabric. The conduit 760 comprises a plurality of ribs 750, which may, as described above with respect to FIGS. 5A-C, act to secure the conduit 760 between the layers of flexible film 740.

Figure 7C:
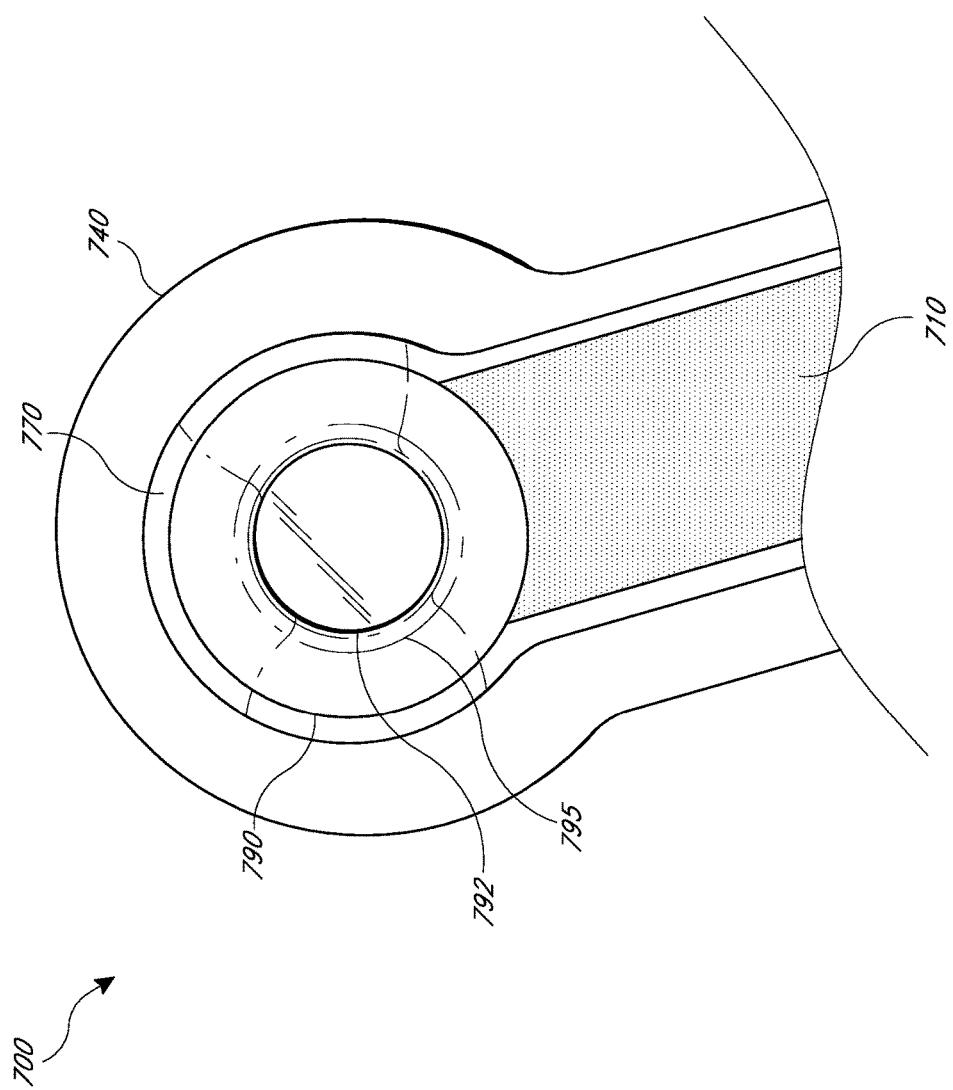
FIG. 7C illustrates a close up view of the bottom of the distal end of the flexible port of FIG. 7A.

FIG. 7C illustrates a close up view of the bottom of the distal end of the flexible port 700. The bottom of the port 700 comprises an orifice 792 for transmitting negative pressure to a dressing to which the port may be attached. The port 700 comprises a filter 790, which may have similar properties to the filters described above with respect to FIGS. 1B and 5A-C. In some embodiments, the filter 790 may have a portion 795 which is adhered to the flexible film 740 around the perimeter of the orifice 795, thereby substantially maintaining the seal of chamber 770.

Figure 8A:
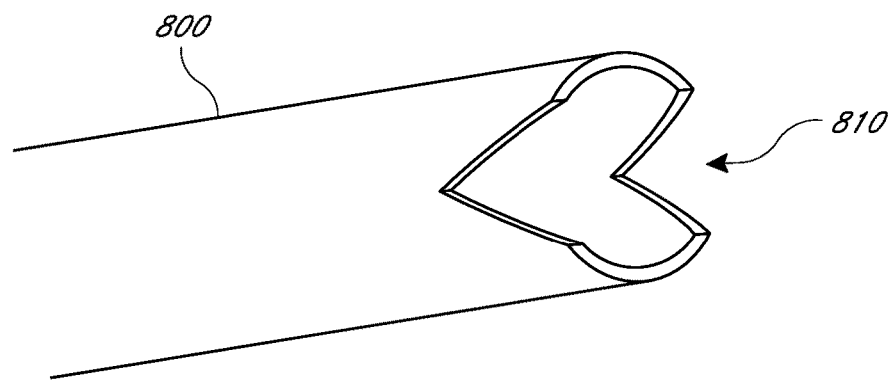
FIGS. 8A-B illustrate various embodiments of the distal end of a conduit which may be part of a flexible port.
Figure 8B:
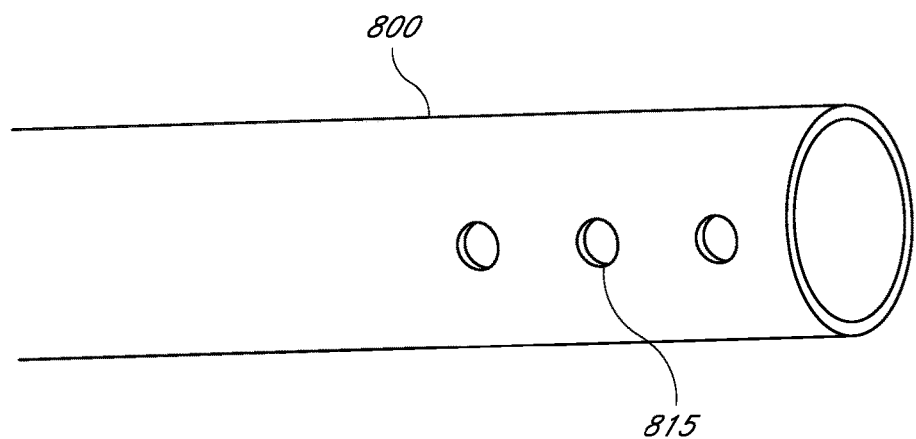
Figure 9:
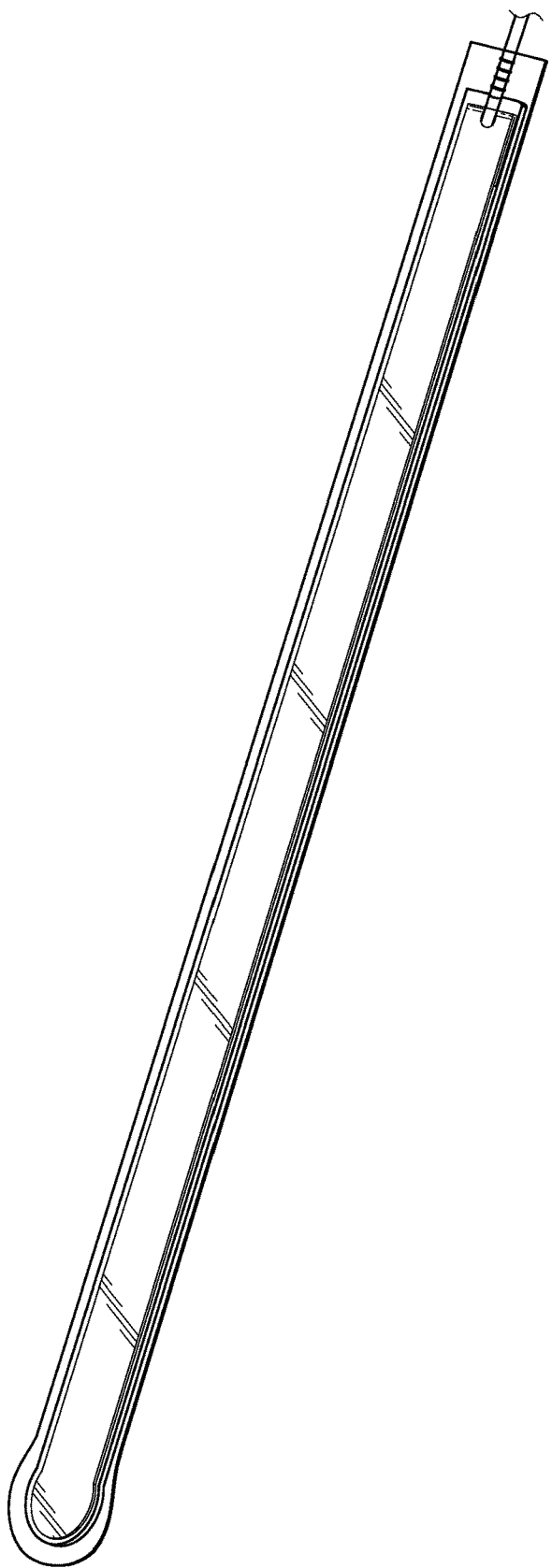
FIG. 9 illustrates a perspective top view of an ornamental design of one embodiment of a flexible port as disclosed herein.
Figure 10:
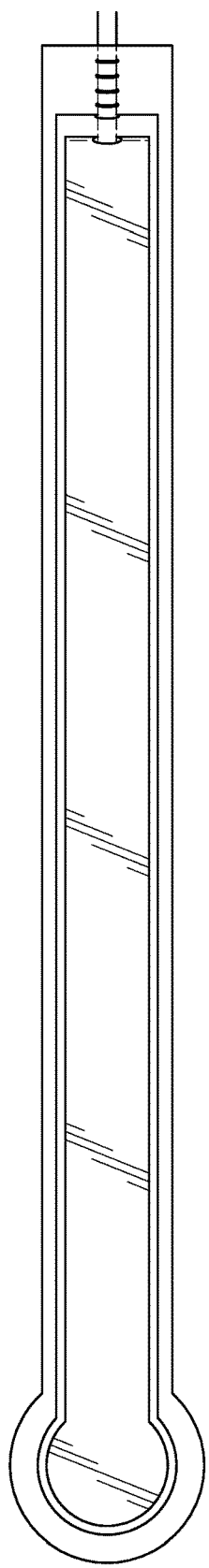
FIG. 10 illustrates a top plan view of the flexible port of FIG. 9.
Figure 11:
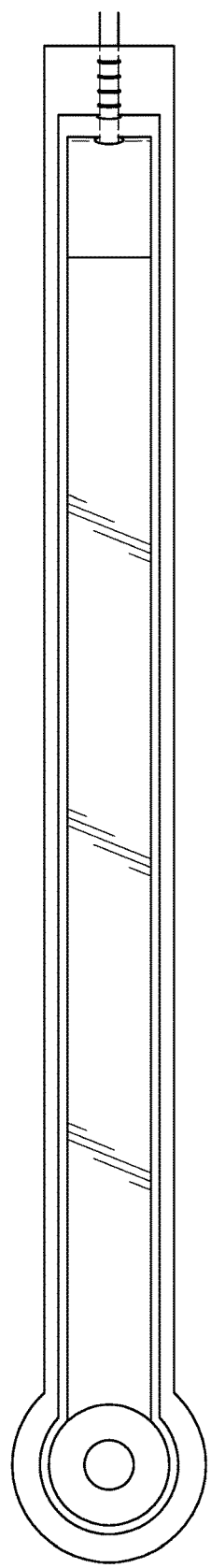
FIG. 11 illustrates a bottom view of the flexible port of FIG. 9.
Figure 12:
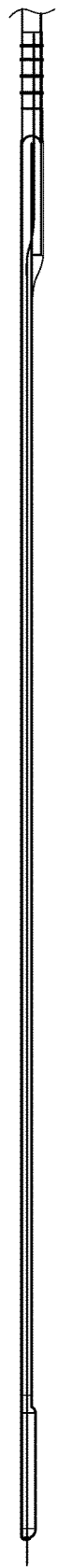
FIG. 12 is a far side view of the flexible port of FIG. 9.
Figure 13:
FIG. 13 is a near side view of the flexible port of FIG. 9.
Figure 14:
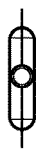
FIG. 14 is a front view of the flexible port of FIG. 9.
Figure 15:
FIG. 15 is a rear view of the flexible port of FIG. 9.
Figure 16:
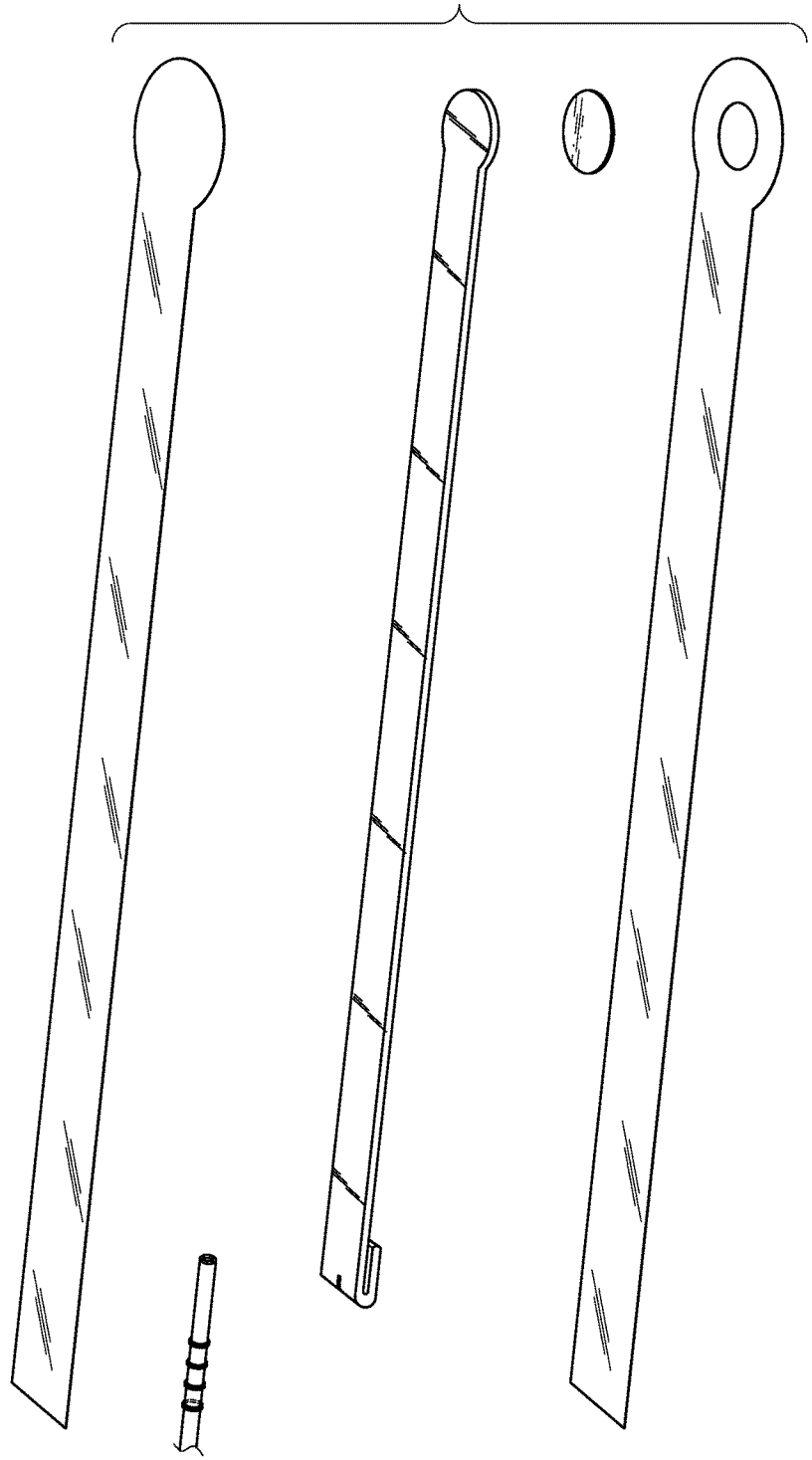
FIG. 16 is an exploded view of the flexible port of FIG. 9.

FIGS. 8A and 8B illustrate embodiments of the distal end of a conduit 800 which may be part of any of the port embodiments described above. The distal end may be shaped in such a way to reduce the possibility of occlusion. For example, the embodiment of FIG. 8A may have a triangular portion 810 cut out of the end of the conduit, and other embodiments may have a plurality of holes therethrough.

FIGS. 9-16 depict various views of an ornamental design of one embodiment of a flexible port as described herein. As will be evident from the various embodiments described herein, functionally equivalent alternative designs of such a flexible port are available, and the configuration of the design illustrated in FIGS. 9-16 was at least in part the result of aesthetic and ornamental considerations. In the case of the illustrated full flexible port design, the solid lines indicate the incorporation of the entire structure as part of one embodiment of an ornamental design for the flexible port. In the case of a partial flexible port design, any number of the solid lines may instead be depicted as broken lines to indicate that a component illustrated in broken lines is not part of that embodiment of the ornamental design.

Other Negative Pressure Therapy Apparatuses, Dressings and Methods (Incorporated from U.S. Provisional Application No. 61/785,054, Portions of which were Included as an Appendix in U.S. Provisional Application No. 61/785,927)

Moreover, some embodiments disclosed herein are directed to systems that include negative pressure therapy apparatuses and dressings, and methods for operating such negative pressure therapy apparatuses for use with negative pressure therapy dressings. In one embodiment, a wound treatment apparatus for treatment of a wound site comprises: a wound dressing comprising: an absorbent layer configured to retain fluid, a backing layer above the absorbent layer, and an obscuring layer configured to at least partly visually obscure fluid within the absorbent layer; and a fluidic connector configured to transmit negative pressure from a negative pressure source to the wound dressing for the application of topical negative pressure at the wound site.

In some embodiments, the obscuring layer is above or below the backing layer. The obscuring layer may configured to at least partially visually obscure fluid contained within the absorbent layer. The obscuring layer may comprise at least one viewing window configured to allow a visual determination of the saturation level of the absorbent layer. The at least one viewing window may comprise at least one aperture made through the obscuring layer. The at least one viewing window may comprise at least one uncolored region of the obscuring layer. The viewing window may comprise an array of dots. The array of dots may be distributed in a straight line of dots, the straight line of dots being positioned on a center line along a length of the absorbent layer. The straight line of dots may comprise an array of three dots. The straight line of dots may comprise an array of five dots. The straight line of dots may comprise an array of eight dots. The array of dots may be distributed in two straight lines of dots, the two straight lines of dots positioned to be an equal distance from a center line along a length of the absorbent layer, the two straight lines of dots having an equal number of dots. The two straight lines of dots may comprise an array of three dots. The two straight lines of dots may comprise an array of five dots. The array of dots may be distributed regularly over the obscuring layer to enable assessment of wound exudate spread. The viewing window may be selected from the group consisting of a graphical element or a typographical element. The obscuring layer may comprise an auxiliary compound, wherein the auxiliary compound may comprise activated charcoal configured to absorb odors and configured to color or tint the obscuring layer. The fluidic connector may comprise an obscuring element configured to substantially visually obscure wound exudate.

Some embodiments may further comprise an acquisition distribution layer between the wound contact layer and the absorbent material. The absorbent layer may comprise cellulose fibers and between 40% and 80% (or between about 40% and about 80%) superabsorbent particles. The obscuring layer, in a dry state, may be configured to yield a CIE y value of 0.4 or less and a CIE x value of 0.5 or less on a CIE x, y chromaticity diagram. The obscuring layer, in a dry state, may have a color of Bg, gB, B, pB, bP, P, rP, pPk, RP, O, rO, or yO on a CIE x, y chromaticity diagram.

In some embodiments, the wound dressing further comprises an orifice in the backing layer, the orifice configured to communicate negative pressure to the wound site. The orifice may comprise at least one orifice viewing window configured to be positioned adjacent to the orifice in the backing layer, the orifice viewing window configured to allow a visual determination of the saturation level of the absorbent layer adjacent to the orifice. The orifice viewing window may be cross-shaped. The wound dressing may comprise a first length corresponding to a first edge of a wound dressing and a first width corresponding to a second edge of the wound dressing, a first x axis runs along the first width and a first y axis runs along the first length, wherein the first x axis and the first y axis are in a perpendicular alignment. The viewing window may comprise a first arm and a second arm, the first arm of the viewing window define a second length and the second arm defines a second width, a second x axis runs along the second width and a second y axis runs along the second length, wherein the second x axis and the second y axis are in a perpendicular alignment. The second x axis and second y axis of the viewing window is offset from the first x axis and the first y axis of the absorbent layer. The second x axis and second y axis of the viewing window may be aligned with the first x axis and the first y axis of the absorbent layer. The cross-shaped transparent layer may comprise flared ends. The fluidic connector may be configured to transmit air. The fluidic connector may comprise a filter, the filter configured to block fluid transport past itself. The fluidic connector may comprise a secondary air leak channel, the secondary air leak channel configured to allow a flow of ambient air to the wound site. The secondary air leak channel may comprise a filter. The fluidic connector may comprise a soft fluidic connector. The soft fluidic connector may comprise a three dimensional fabric. In some embodiments, the three dimensional fabric is configured to transmit therapeutic levels of negative pressure while an external pressure up to 2 kg/cm$^2$ is applied thereto. The soft fluidic connector may be configured to be connected to a tube in fluid communication with the vacuum source. The soft fluidic connector may be configured to be connected directly to the vacuum source. The soft fluidic connector may comprise an enlarged distal end, the enlarged distal end configured to be connected to the wound dressing. The apparatus may further comprise a tube connected to the fluidic connector. The apparatus may further comprise a pump in fluid communication with the fluidic connector. In some embodiments, the absorbent layer comprises two or more lobes.

In another embodiment, a wound treatment apparatus for treatment of a wound site comprises: a wound dressing configured to be positioned over a wound site, the wound dressing comprising: a backing layer having an upper surface and a lower surface and defining a perimeter configured to be positioned over skin surrounding the wound site, the backing layer including an opening; a wound contact layer adhered to the lower surface of the backing layer, the wound contact layer comprising an adhesive on a lower surface thereof; an absorbent material positioned between the backing layer and the wound contact layer, wherein the absorbent material comprises a vertical hole positioned below the opening in the backing layer; an obscuring layer positioned at least partially over the absorbent material, wherein the obscuring layer comprises a vertical hole positioned between the opening in the backing layer and the vertical hole in the absorbent material; one or more viewing windows extending through the obscuring layer configured to allow visualization of wound exudate in the absorbent material; and a port positioned over the opening in the backing layer configured to transmit negative pressure through the port for the application of topical negative pressure at the wound site.

In some embodiments, the backing layer is transparent or translucent. The backing layer may define a perimeter with a rectangular or a square shape. The wound contact layer may be adhered to the lower surface of the backing layer along the perimeter of the backing layer. The hole in the obscuring layer may have a different diameter than the hole in the absorbent material or the opening in the backing layer. The one or more viewing windows may be arranged in a repeating pattern across the obscuring layer. The one or more viewing windows may have a circular shape.

Some embodiments may further comprise an acquisition distribution layer between the wound contact layer and the absorbent material. The absorbent layer may comprise cellulose fibers and between 40% and 80% (or between about 40% and about 80%) superabsorbent particles. The obscuring layer, in a dry state, may be configured to yield a color of Bg, gB, B, pB, bP, P, rP, pPk, RP, O, rO, or yO on the CIE x, y chromacity diagram.

Some embodiments further comprise a transmission layer between the absorbent material and the wound contact layer. In some embodiments, the apparatus further comprises a hydrophobic filter positioned in or below the port. The absorbent material may have a longitudinal length and a transverse width, wherein the length is greater than the width, and wherein the width of the absorbent material narrows in a central portion along the longitudinal length of the absorbent material. The obscuring layer may have substantially the same perimeter shape as the absorbent material. The apparatus may further comprise a pump In another embodiment, a wound treatment apparatus for treatment of a wound site comprises: a wound dressing configured to be conformable to a nonplanar wound comprising: an absorbent layer comprising a contoured shape, the contoured shape comprising a substantially rectangular body with a waisted portion, and a backing layer above the absorbent layer; and a fluidic connector configured to transmit negative pressure from a negative pressure source to the wound dressing for the application of topical negative pressure at a wound site.

Some embodiments may further comprise a wound contact layer. The backing layer may be rectangular. In some embodiments, the negative pressure source is a pump.

In some embodiments, the wound dressing has a longer axis and a shorter axis, and wherein the waisted portion configured to be on the longer axis. The apparatus may further comprise an obscuring layer configured to at least partly visually obscure fluid within the absorbent layer. The obscuring layer may comprise at least one viewing window configured to allow a visual determination of the saturation level of the absorbent layer. The viewing window may comprise an array of dots. The fluidic connector may be located along a side or corner of the rectangular body.

Some embodiments may further comprise an acquisition distribution layer between the wound contact layer and the absorbent material. The absorbent layer may comprise cellulose fibers and 40%-80% (or about 40% to about 80%) superabsorbent particles. The obscuring layer, in a dry state, may be configured to yield a color of Bg, gB, B, pB, bP, P, rP, pPk, RP, O, rO, or yO on the CIE x, y chromacity diagram.

In yet another embodiment, an apparatus for dressing a wound for the application of topical negative pressure at a wound site, comprises: an absorbent layer having one or more slits extending at least partially across the width of the absorbent layer; and a backing layer above the absorbent layer, the backing layer having an orifice for communicating negative pressure to the wound site, wherein the orifice is positioned over a portion of the absorbent layer having no slits.

In some embodiments, the one or more slits comprise one or more concentric arcs.

In another embodiment, a wound treatment apparatus comprises: a wound dressing configured to be conformable to a nonplanar wound comprising: an absorbent layer above the contact layer, the absorbent layer comprising a contoured shape, the contoured shape comprising two or more lobes, and a backing layer above the absorbent layer.

In some embodiments, the wound treatment apparatus comprises a pump. The wound dressing may comprise a fluidic connector configured to transmit negative pressure from a pump to the wound dressing for the application of topical negative pressure at a wound site. The wound dressing may also comprise a wound-facing contact layer. The contoured shape may comprise three lobes. The contoured shape may comprise four lobes. The two or more lobes may comprise rounded projections. The apparatus may comprise two or more lobes flared lobes. The contoured shape may be oval-shaped. The contoured shape may comprise six lobes. The apparatus may further comprise an obscuring layer disposed so as to obscure the absorbent layer. The apparatus may further comprise an obscuring layer configured to at least partly visually obscure fluid within the absorbent layer. The obscuring layer may comprise at least one viewing window configured to allow a visual determination of the saturation level of the absorbent layer. The viewing window may comprise an array of dots.

In yet another embodiment, an apparatus for dressing a wound for the application of topical negative pressure at a wound site, comprises: a wound contact layer; an acquisition distribution layer above the transmission layer; an absorbent layer over the acquisition and distribution layer, the absorbent layer comprising a matrix and superabsorbing particles within the matrix; and a backing layer above the absorbent layer.

Some embodiments of the apparatus may further comprise a transmission layer between the wound contact layer and the acquisition distribution layer. The acquisition distribution layer may comprise viscose, polyester, polypropylene, cellulose, polyethylene or a combination of some or all of these materials. The absorbent layer may comprise between 30% and 40% (or between about 30% and about 40%) cellulose matrix and between 60% and 70% (or between about 60% and about 70%) superabsorbing polymers. The backing layer may be transparent or translucent.

Some embodiments may further comprise an obscuring layer between the absorbent layer and the backing layer. There may be one or more viewing windows in the obscuring layer. At least the obscuring layer may be shaped with a narrowed central portion along its length. The obscuring layer may comprise two rows of three viewing windows, one row of three viewing windows, one row of eight viewing windows, two rows of five viewing windows, or one row of five viewing windows. At least the obscuring layer may be shaped with a narrowed central portion along both its width and its length. The obscuring layer may comprise a 3×3 array of viewing window or a quincunx array of viewing windows. In some embodiments, at least the obscuring layer may comprise a six-lobed shape. The absorbent layer and acquisition distribution layer may be substantially the same shape as the obscuring layer. The obscuring layer may further comprise a cross or maltese cross shaped hole over which a fluidic connector for transmitting negative pressure may be connected. The apparatus may further comprise a fluidic connector configured to connect the backing layer to a source of negative pressure.

In yet another embodiment, an apparatus for dressing a wound for the application of topical negative pressure at a wound site, comprises: an absorbent layer configured to retain fluid, a backing layer above the absorbent layer, and an obscuring layer configured to at least partly visually obscure fluid within the absorbent layer, wherein the obscuring layer, in a dry state, is configured to yield a color of Bg, gB, B, pB, bP, P, rP, pPk, RP, O, rO, or yO on the CIE x, y chromaticity diagram.

Some embodiments may further comprise one or more viewing windows in the backing layer. At least the obscuring layer may be shaped with a narrowed central portion along its length. The obscuring layer may comprise a 3×3 array of viewing window or a quincunx array of viewing windows. In some embodiments, at least the obscuring layer may comprise a six-lobed shape. The absorbent layer and acquisition distribution layer may be substantially the same shape as the obscuring layer. The obscuring layer may further comprise a cross or maltese cross shaped hole over which a fluidic connector for transmitting negative pressure may be connected. The apparatus may further comprise a fluidic connector configured to connect the backing layer to a source of negative pressure.

Figure 17:
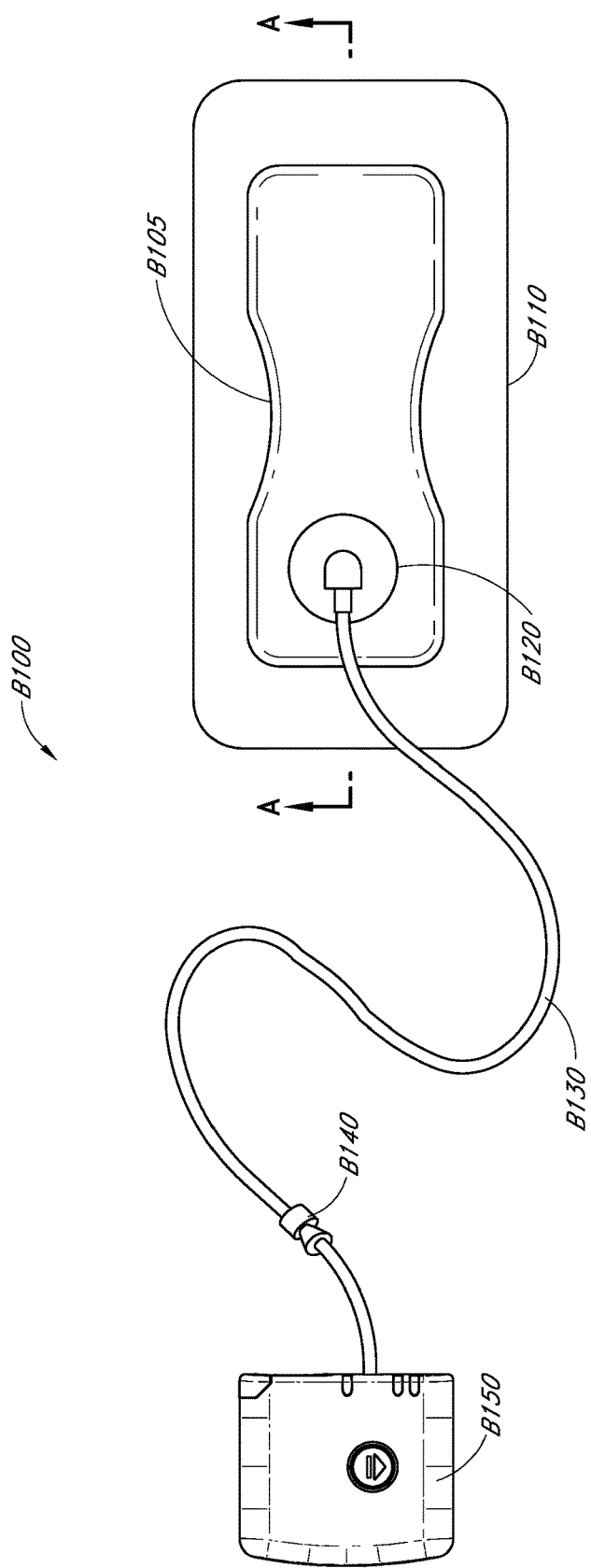
FIG. 17 illustrates an embodiment of a wound treatment system.

FIG. 17 illustrates an embodiment of a TNP wound treatment system B100 comprising a wound dressing B110 in combination with a pump B150. As stated above, the wound dressing B110 can be any wound dressing embodiment disclosed herein including without limitation dressing embodiment or have any combination of features of any number of wound dressing embodiments disclosed herein. Here, the dressing B110 may be placed over a wound as described previously, and a conduit B130 may then be connected to the port B120, although in some embodiments the dressing B101 may be provided with at least a portion of the conduit B130 preattached to the port B120. Preferably, the dressing B110 is provided as a single article with all wound dressing elements (including the port B120) pre-attached and integrated into a single unit. The wound dressing B110 may then be connected, via the conduit B130, to a source of negative pressure such as the pump B150. The pump B150 can be miniaturized and portable, although larger conventional pumps may also be used with the dressing B110. In some embodiments, the pump B150 may be attached or mounted onto or adjacent the dressing B110. A connector B140 may also be provided so as to permit the conduit B130 leading to the wound dressing B110 to be disconnected from the pump, which may be useful for example during dressing changes.

Figure 18A:
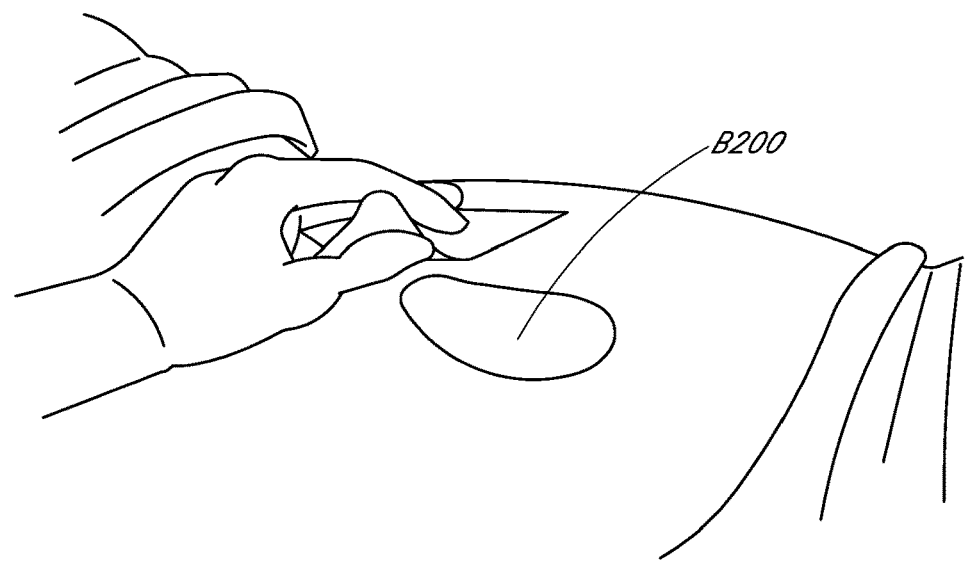
FIGS. 18A-D illustrate the use and application of an embodiment of a wound treatment system onto a patient.

FIGS. 18A-D illustrate the use of an embodiment of a TNP wound treatment system being used to treat a wound site on a patient. FIG. 18A—shows a wound site B200 being cleaned and prepared for treatment. Here, the healthy skin surrounding the wound site B200 is preferably cleaned and excess hair removed or shaved. The wound site B200 may also be irrigated with sterile saline solution if necessary. Optionally, a skin protectant may be applied to the skin surrounding the wound site B200. If necessary, a wound packing material, such as foam or gauze, may be placed in the wound site B200. This may be preferable if the wound site B200 is a deeper wound.

Figure 18B:
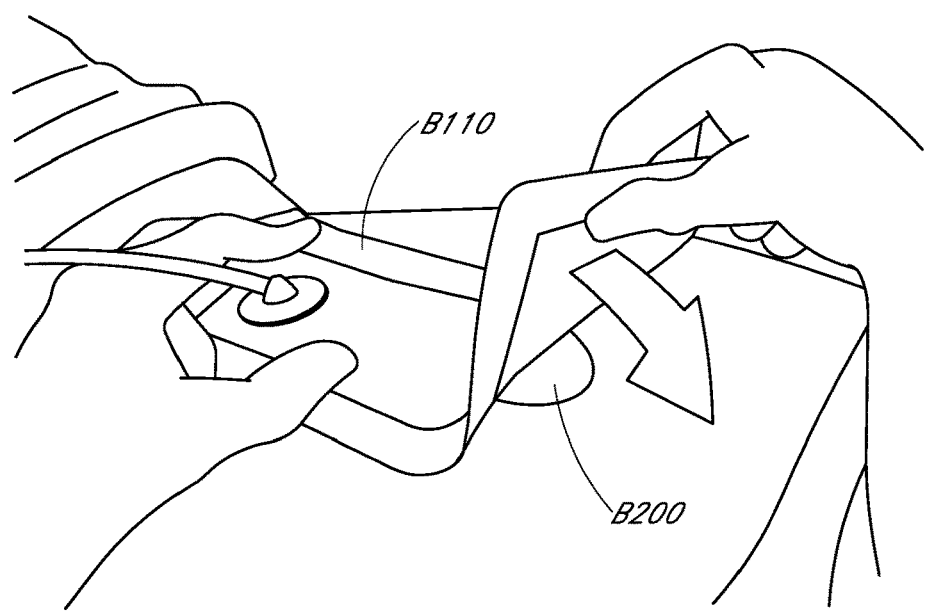

After the skin surrounding the wound site B200 is dry, and with reference now to FIG. 18B, the wound dressing B110 may be positioned and placed over the wound site B200. Preferably, the wound dressing B110 is placed with the wound contact layer B2102 over and/or in contact with the wound site B200. In some embodiments, an adhesive layer is provided on the lower surface B2101 of the wound contact layer B2102, which may in some cases be protected by an optional release layer to be removed prior to placement of the wound dressing B110 over the wound site B200. Preferably, the dressing B110 is positioned such that the port B2150 is in a raised position with respect to the remainder of the dressing B110 so as to avoid fluid pooling around the port. In some embodiments, the dressing B110 is positioned so that the port B2150 is not directly overlying the wound, and is level with or at a higher point than the wound. To help ensure adequate sealing for TNP, the edges of the dressing B110 are preferably smoothed over to avoid creases or folds.

Figure 18C:
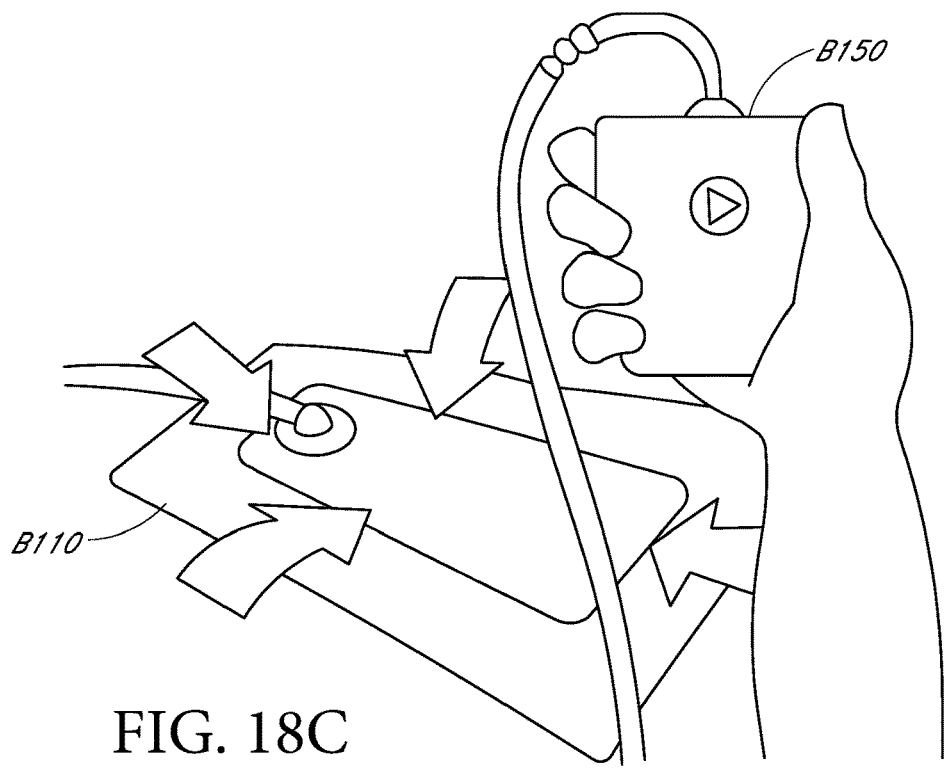

With reference now to FIG. 18C, the dressing B110 is connected to the pump B150. The pump B150 is configured to apply negative pressure to the wound site via the dressing B110, and typically through a conduit. In some embodiments, and as described above in FIG. 17, a connector may be used to join the conduit from the dressing B110 to the pump B150. Upon the application of negative pressure with the pump B150, the dressing B110 may, in some embodiments, partially collapse and present a wrinkled appearance as a result of the evacuation of some or all of the air underneath the dressing B110. In some embodiments, the pump B150 may be configured to detect if any leaks are present in the dressing B110, such as at the interface between the dressing B110 and the skin surrounding the wound site B200. Should a leak be found, such leak is preferably remedied prior to continuing treatment.

Figure 18D:
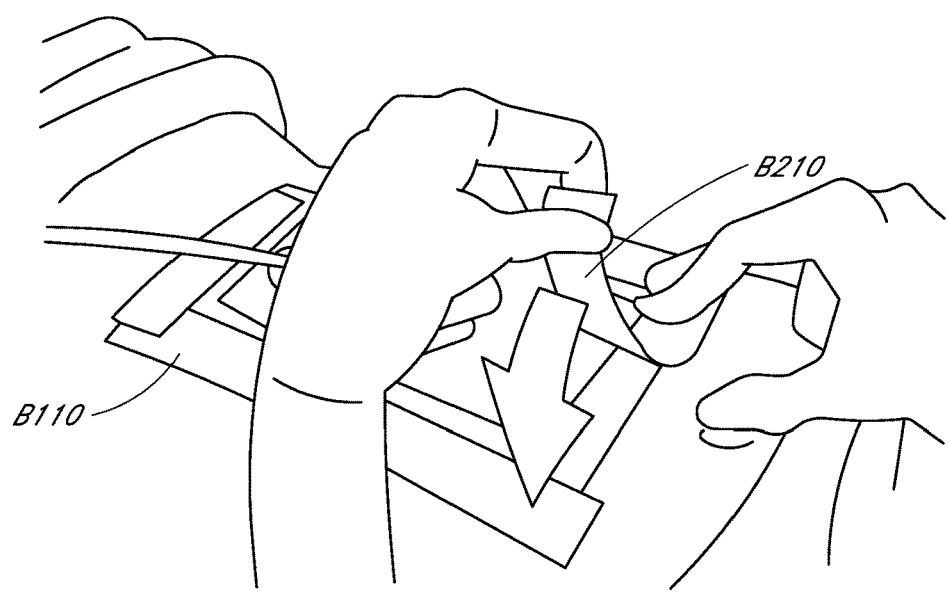

Turning to FIG. 18D, additional fixation strips B210 may also be attached around the edges of the dressing B110. Such fixation strips B210 may be advantageous in some situations so as to provide additional sealing against the skin of the patient surrounding the wound site B200. For example, the fixation strips B210 may provide additional sealing for when a patient is more mobile. In some cases, the fixation strips B210 may be used prior to activation of the pump B150, particularly if the dressing B110 is placed over a difficult to reach or contoured area.

Treatment of the wound site B200 preferably continues until the wound has reached a desired level of healing. In some embodiments, it may be desirable to replace the dressing B110 after a certain time period has elapsed, or if the dressing is full of wound fluids. During such changes, the pump B150 may be kept, with just the dressing B110 being changed.

Figure 19A:
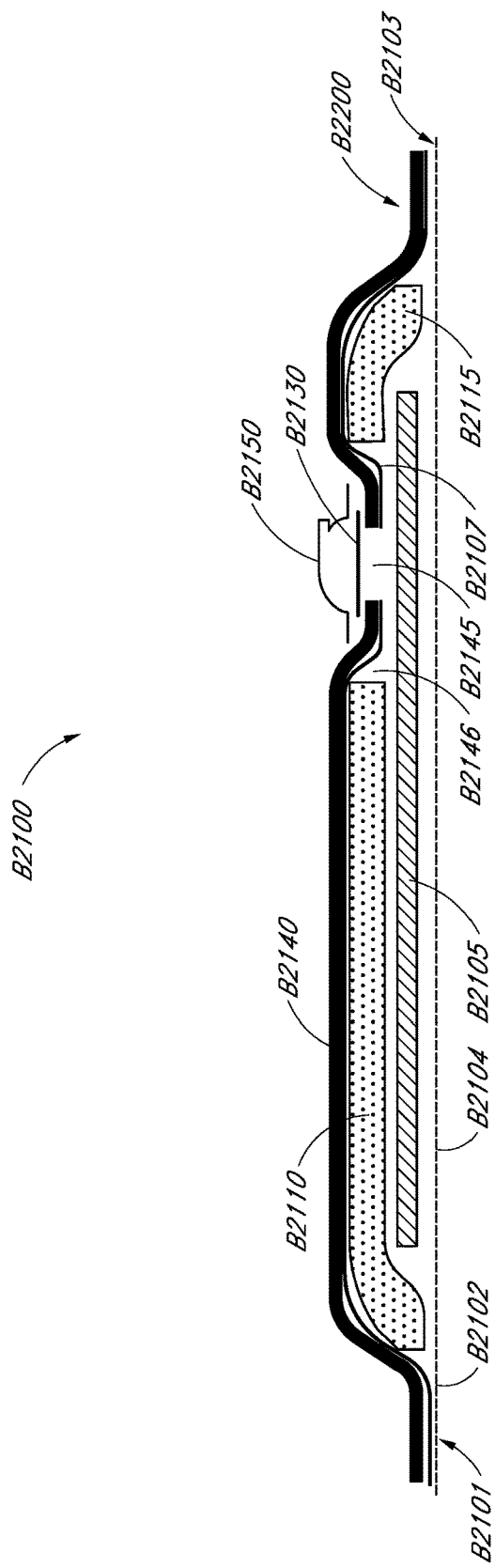
FIG. 19A illustrates an embodiment of a wound dressing in cross-section.
Figure 19B:
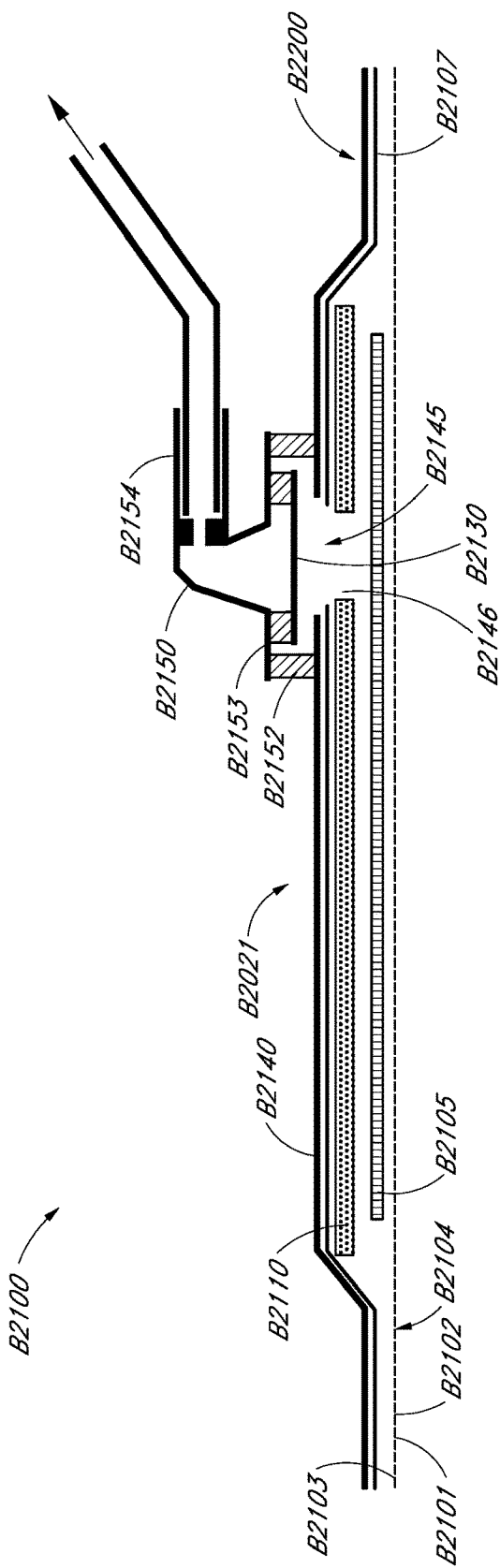
FIG. 19B illustrates another embodiment of a wound dressing in cross-section.
Figure 19C:
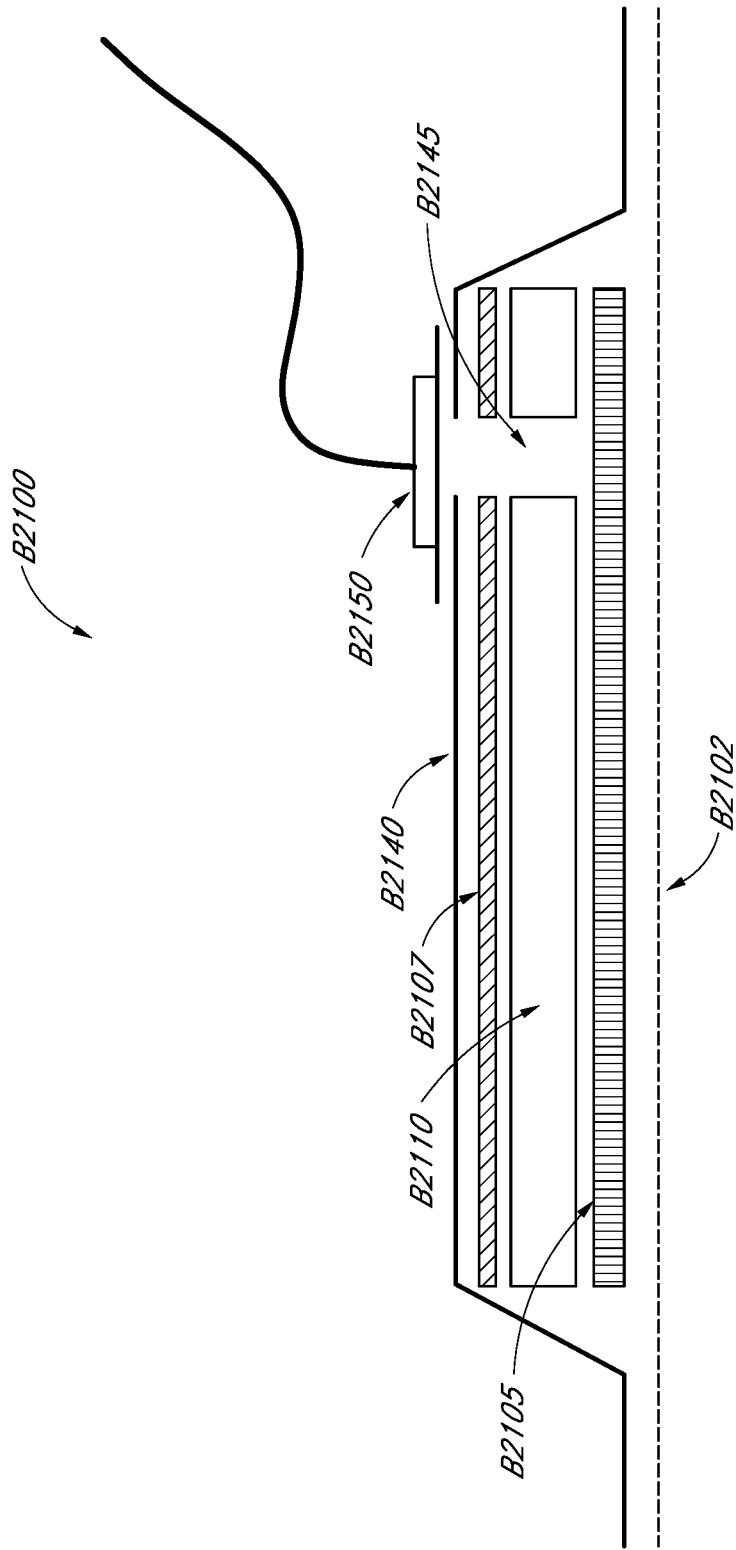
FIG. 19C illustrates another embodiment of a wound dressing in cross-section.

FIGS. 19A-C illustrate cross-sections through a wound dressing B2100 similar to the wound dressing of FIG. 17 according to an embodiment of the disclosure. A view from above the wound dressing B2100 is illustrated in FIG. 17 with the line A-A indicating the location of the cross-section shown in FIGS. 19A and 19B. The wound dressing B2100, which can alternatively be any wound dressing embodiment disclosed herein including without limitation wound dressing B110 or any combination of features of any number of wound dressing embodiments disclosed herein, can be located over a wound site to be treated. The dressing B2100 may be placed to as to form a sealed cavity over the wound site. In a preferred embodiment, the dressing B2100 comprises a backing layer B2140 attached to a wound contact layer B2102, both of which are described in greater detail below. These two layers B2140, B2102 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer B2105 and an absorbent layer B2110.

As illustrated in FIGS. 19A-C, a lower surface B2101 of the wound dressing B2100 may be provided with an optional wound contact layer B2102. The wound contact layer B2102 can be a polyurethane layer or polyethylene layer or other flexible layer which is perforated, for example via a hot pin process, laser ablation process, ultrasound process or in some other way or otherwise made permeable to liquid and gas. The wound contact layer B2102 has a lower surface B2101 and an upper surface B2103. The perforations B2104 preferably comprise through holes in the wound contact layer B2102 which enable fluid to flow through the layer B2102. The wound contact layer B2102 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer B2102 may help maintain the integrity of the entire dressing B2100 while also creating an air tight seal around the absorbent pad in order to maintain negative pressure at the wound.

Some embodiments of the wound contact layer B2102 may also act as a carrier for an optional lower and upper adhesive layer (not shown). For example, a lower pressure sensitive adhesive may be provided on the lower surface B2101 of the wound dressing B2100 whilst an upper pressure sensitive adhesive layer may be provided on the upper surface B2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing B2100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer B2105 of porous material can be located above the wound contact layer B2102. This porous layer, or transmission layer, B2105 allows transmission of fluid including liquid and gas away from a wound site into upper layers of the wound dressing. In particular, the transmission layer B2105 preferably ensures that an open air channel can be maintained to communicate negative pressure over the wound area even when the absorbent layer has absorbed substantial amounts of exudates. The layer B2105 should preferably remain open under the typical pressures that will be applied during negative pressure wound therapy as described above, so that the whole wound site sees an equalized negative pressure. The layer B2105 may be formed of a material having a three dimensional structure. For example, a knitted or woven spacer fabric (for example Baltex 7970 weft knitted polyester) or a non-woven fabric could be used.

A layer B2110 of absorbent material is provided above the transmission layer B2105. The absorbent material, which comprise a foam or non-woven natural or synthetic material, and which may optionally comprise a super-absorbent material, forms a reservoir for fluid, particularly liquid, removed from the wound site. In some embodiments, the layer B2100 may also aid in drawing fluids towards the backing layer B2140.

With reference to FIGS. 19A-C, a masking or obscuring layer B2107 can be positioned beneath at least a portion of the backing layer B2140. In some embodiments, the obscuring layer B2107 can have any of the same features, materials, or other details of any of the other embodiments of the obscuring layers disclosed herein, including but not limited to having any viewing windows or holes. Additionally, the obscuring layer B2107 can be positioned adjacent to the backing layer, or can be positioned adjacent to any other dressing layer desired. In some embodiments, the obscuring layer B2107 can be adhered to or integrally formed with the backing layer. Preferably, the obscuring layer B2107 is configured to have approximately the same size and shape as the absorbent layer B2110 so as to overlay it. As such, in these embodiments the obscuring layer B2107 will be of a smaller area than the backing layer B2140.

The material of the absorbent layer B2110 may also prevent liquid collected in the wound dressing B2100 from flowing freely within the dressing, and preferably acts so as to contain any liquid collected within the absorbent layer B2110. The absorbent layer B2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer B2110 may typically be manufactured from ALLEVYN™ foam, Freudenberg 114-224-4 and/or Chem-Posite™ 11C-450. In some embodiments, the absorbent layer B2110 may comprise a composite comprising superabsorbent powder, fibrous material such as cellulose, and bonding fibers. In a preferred embodiment, the composite is an airlaid, thermally-bonded composite.

An orifice B2145 is preferably provided in the backing layer B2140 to allow a negative pressure to be applied to the dressing B2100. A suction port B2150 is preferably attached or sealed to the top of the backing layer B2140 over an orifice B2145 made into the dressing B2100, and communicates negative pressure through the orifice B2145. A length of tubing B2220 may be coupled at a first end to the suction port B2150 and at a second end to a pump unit (not shown) to allow fluids to be pumped out of the dressing. The port may be adhered and sealed to the backing layer B2140 using an adhesive such as an acrylic, cyanoacrylate, epoxy, UV curable or hot melt adhesive. The port B2150 is formed from a soft polymer, for example a polyethylene, a polyvinyl chloride, a silicone or polyurethane having a hardness of 30 to 90 on the Shore A scale. In some embodiments, the port B2150 may be made from a soft or conformable material, for example using the embodiments described below in FIGS. 39A-B.

Preferably the absorbent layer B2110 and the obscuring layer B2107 include at least one through hole B2146 located so as to underlie the port B2150. The through hole B2146, while illustrated here as being larger than the hole through the obscuring layer B2107 and backing layer B2140, may in some embodiments be bigger or smaller than either. Of course, the respective holes through these various layers B2107, B2140, and B2110 may be of different sizes with respect to each other. As illustrated in FIGS. 19A-C a single through hole can be used to produce an opening underlying the port B2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer B2100 is near saturation.

The aperture or through-hole B2146 is preferably provided in the absorbent layer B2110 and the obscuring layer B2107 beneath the orifice B2145 such that the orifice is connected directly to the transmission layer B2105. This allows the negative pressure applied to the port B2150 to be communicated to the transmission layer B2105 without passing through the absorbent layer B2110. This ensures that the negative pressure applied to the wound site is not inhibited by the absorbent layer as it absorbs wound exudates. In other embodiments, no aperture may be provided in the absorbent layer B2110 and/or the obscuring layer B2107, or alternatively a plurality of apertures underlying the orifice B2145 may be provided.

The backing layer B2140 is preferably gas impermeable, but moisture vapor permeable, and can extend across the width of the wound dressing B2100. The backing layer B2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer B2140 and a wound site where a negative pressure can be established. The backing layer B2140 is preferably sealed to the wound contact layer B2102 in a border region B2200 around the circumference of the dressing, ensuring that no air is drawn in through the border area, for example via adhesive or welding techniques. The backing layer B2140 protects the wound from external bacterial contamination (bacterial barrier) and allows liquid from wound exudates to be transferred through the layer and evaporated from the film outer surface. The backing layer B2140 preferably comprises two layers; a polyurethane film and an adhesive pattern spread onto the film. The polyurethane film is preferably moisture vapor permeable and may be manufactured from a material that has an increased water transmission rate when wet.

The absorbent layer B2110 may be of a greater area than the transmission layer B2105, such that the absorbent layer overlaps the edges of the transmission layer B2105, thereby ensuring that the transmission layer does not contact the backing layer B2140. This provides an outer channel B2115 of the absorbent layer B2110 that is in direct contact with the wound contact layer B2102, which aids more rapid absorption of exudates to the absorbent layer. Furthermore, this outer channel B2115 ensures that no liquid is able to pool around the circumference of the wound cavity, which may otherwise seep through the seal around the perimeter of the dressing leading to the formation of leaks.

As shown in FIG. 19A, one embodiment of the wound dressing B2100 comprises an aperture B2146 in the absorbent layer B2110 situated underneath the port B2150. In use, for example when negative pressure is applied to the dressing B2100, a wound facing portion of the port B150 may thus come into contact with the transmission layer B2105, which can thus aid in transmitting negative pressure to the wound site even when the absorbent layer B2110 is filled with wound fluids. Some embodiments may have the backing layer B2140 be at least partly adhered to the transmission layer B2105. In some embodiments, the aperture B2146 is at least 1-2 mm larger than the diameter of the wound facing portion of the port B2150, or the orifice B2145.

A filter element B2130 that is impermeable to liquids, but permeable to gases is provided to act as a liquid barrier, and to ensure that no liquids are able to escape from the wound dressing. The filter element may also function as a bacterial barrier. Typically the pore size is 0.2 µm. Suitable materials for the filter material of the filter element B2130 include 0.2 micron Gore™ expanded PTFE from the MMT range, PALL Versapore™ B200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the backing layer B2140 over the orifice B2145. For example, the filter element B2130 may be molded into the port B2150, or may be adhered to both the top of the backing layer B2140 and bottom of the port B2150 using an adhesive such as, but not limited to, a UV cured adhesive.

In FIG. 19B, an embodiment of the wound dressing B2100 is illustrated which comprises spacer elements B2152, B2153 in conjunction with the port B2150 and the filter B2130. With the addition of such spacer elements B2152, B2153, the port B2150 and filter B2130 may be supported out of direct contact with the absorbent layer B2110 and/or the transmission layer B2105. The absorbent layer B2110 may also act as an additional spacer element to keep the filter B2130 from contacting the transmission layer B2105. Accordingly, with such a configuration contact of the filter B2130 with the transmission layer B2105 and wound fluids during use may thus be minimized. As contrasted with the embodiment illustrated in FIG. 19A, the aperture B2146 through the absorbent layer B2110 and the obscuring layer B2107 may not necessarily need to be as large or larger than the port B2150, and would thus only need to be large enough such that an air path can be maintained from the port to the transmission layer B2105 when the absorbent layer B2110 is saturated with wound fluids.

With reference now to FIG. 19C, which shares many of the elements illustrated in FIGS. 19A-C, the embodiment illustrated here comprises the backing layer B2140, masking layer B2107, and absorbent layer B2110, all of which have a cut or opening made therethrough which communicate directly to the transmission layer B2105 so as to form the orifice B2145. The suction port B2150 is preferably situated above it and communicates with the orifice B2145.

In particular for embodiments with a single port B2150 and through hole, it may be preferable for the port B2150 and through hole to be located in an off-center position as illustrated in FIGS. 19A-C and in FIG. 17. Such a location may permit the dressing B2100 to be positioned onto a patient such that the port B2150 is raised in relation to the remainder of the dressing B2100. So positioned, the port B2150 and the filter B2130 may be less likely to come into contact with wound fluids that could prematurely occlude the filter B2130 so as to impair the transmission of negative pressure to the wound site.

Figure 20A:
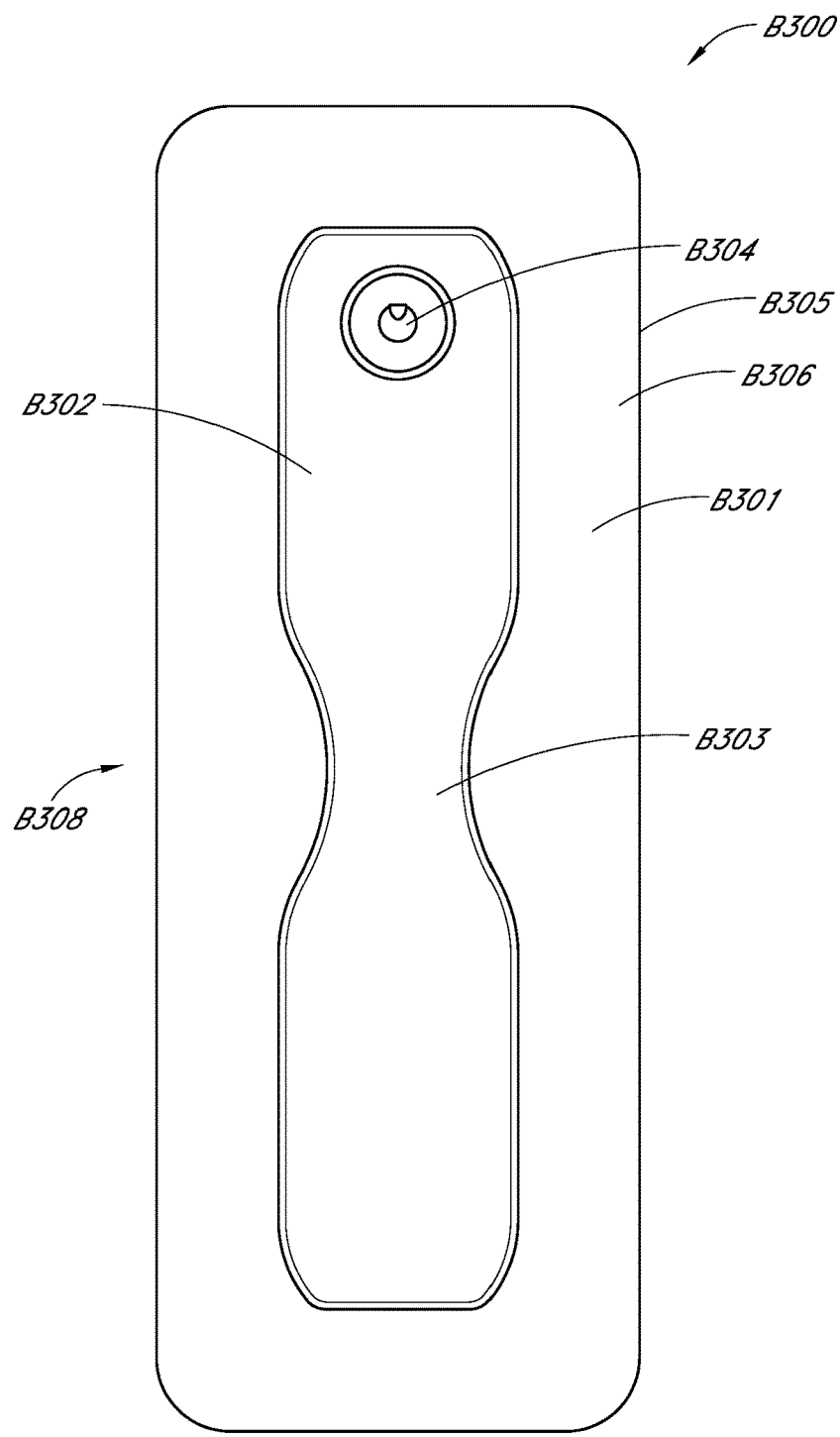
FIGS. 20A-C illustrate a top view of an embodiment of a wound dressing with a narrow central portion.
Figure 20B:
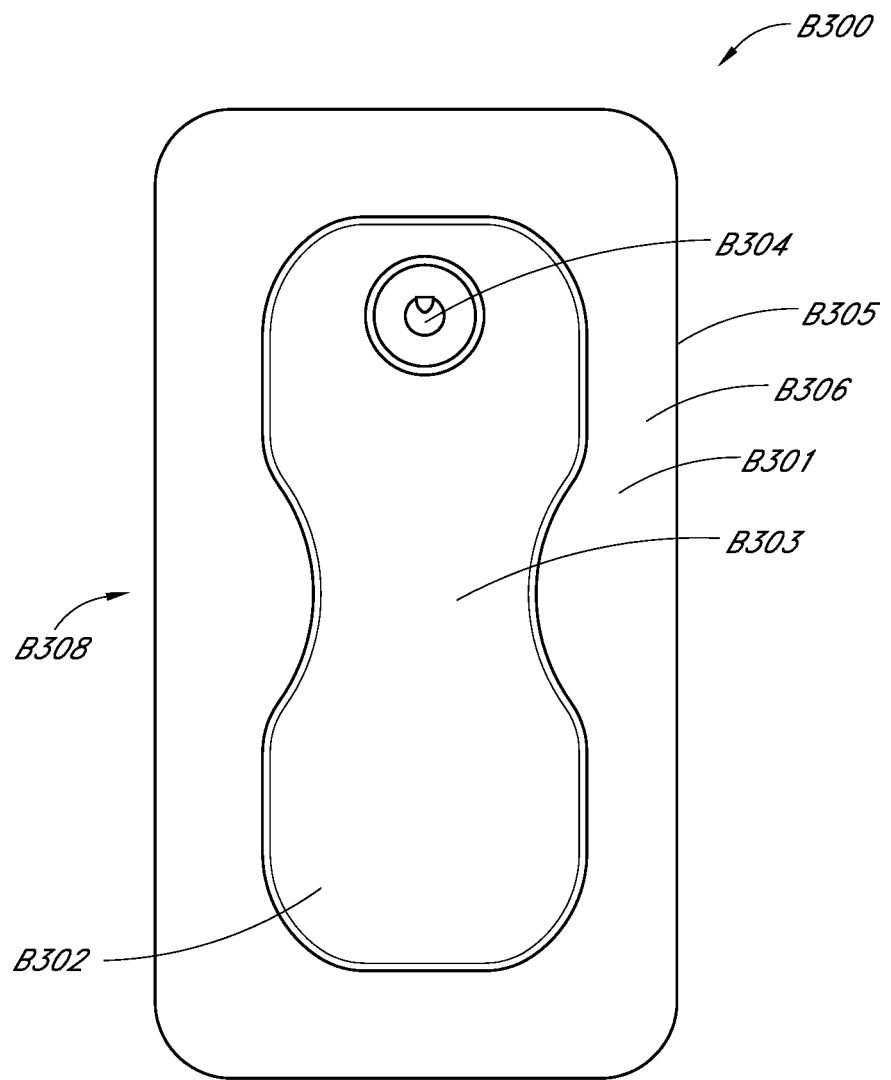
Figure 20C:
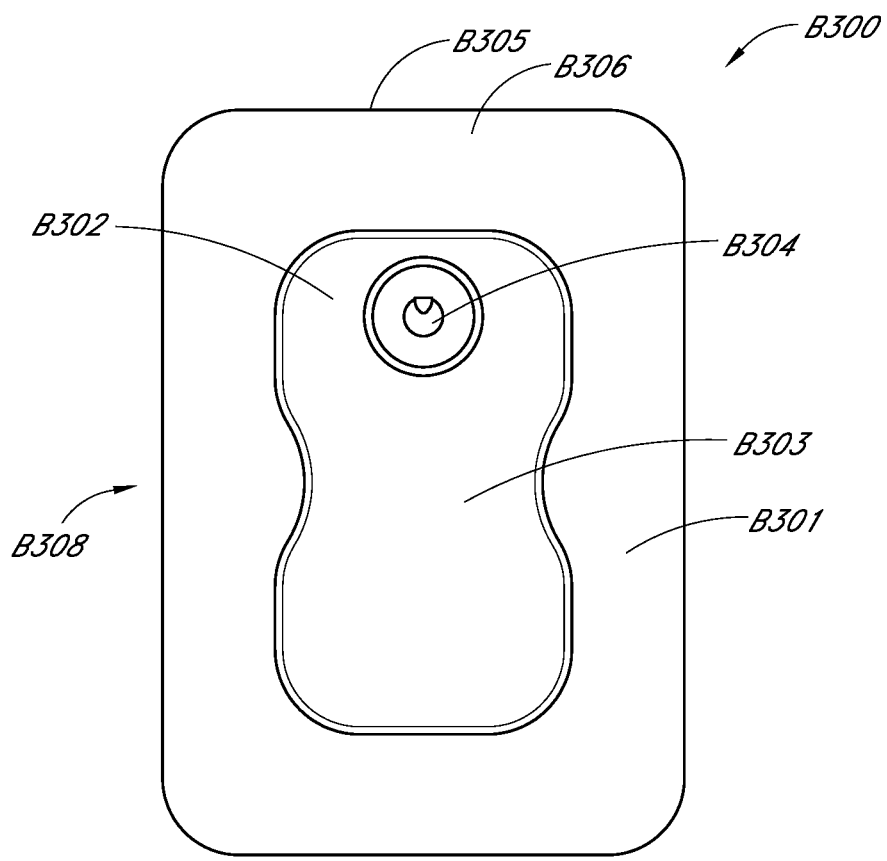

FIGS. 20A-C illustrate embodiments of wound dressings B300 similar to the embodiments described above and provided with a narrowed central portion in various lengths and widths. FIG. 20A illustrates an embodiment of a wound dressing B300 with a narrowed central portion or a waisted middle portion. The wound dressing B300 has a backing layer B301. The backing layer B301 can have a rectangular or square shaped perimeter and can be a transparent or translucent material. The backing layer B301 can have a lower surface B305 and an upper surface B306. The lower surface of the backing layer B301 can be configured to be placed on the skin surface surrounding the wound site as discussed previously with reference to FIGS. 19A-C. Additionally, the lower surface B305 can have a wound contact layer. The wound contact layer can have all the features and embodiments described herein, including without limitation wound dressing embodiments described in reference to FIGS. 19A-C. The wound contact layer can be adhered to the perimeter of the lower surface B305 of the backing layer B301. The wound contact layer can comprise an adhesive or any other method of attachment that allows attachment of the wound dressing to the skin surface as previously described.

In some embodiments, the wound dressing B300 can have a port B304 offset from the center of the dressing as described previously. The port B304 can be a domed port or a soft fluidic connector (described in detail below). Although the port B304 can be placed in a central location on the dressing, it is preferably offset from the center of the dressing to a particular side or edge. As such, the orientation of the port B304, when placed on the body, may thus permit the port B304 to be situated in an elevated position, thereby increasing the amount of time that the dressing B300 may be used before coming into contact with fluids. Although other orientations may be used, and may occur in practice (e.g., when the patient shifts positions), placing the port B304 at a lower position may cause the filter proximate the port (not illustrated here) to become saturated, which may cause the dressing to need changing even though there may still remain some absorptive capacity within the absorbent layer. Preferably, the port B304 has an orifice for the connection of a tube or conduit thereto; this orifice may be angled away from the center of the dressing B300 so as to permit the tube or conduit to extend away from the dressing B300. In some preferred embodiments, the port B304 comprises an orifice that permits the tube or conduit inserted therein to be approximately parallel to the top surface of the backing layer B301.

In various embodiments, the wound dressing B300 can have an absorbent material B302. The absorbent material B302 can be accompanied by the additional components within the wound dressing as described with reference to the wound dressing cross-section in FIGS. 19A-B, such as a transmission layer and a masking or obscuring layer (not shown).

In some embodiments, the wound dressing B300 can have an absorbent material B302 with a central portion B308. The absorbent material B302 can have a longitudinal length and a transverse width. In some embodiments, the longitudinal length is greater than the transverse width. In some embodiments, the longitudinal length and the transverse width are of equal size. In various embodiments, the absorbent material B302 can have a contoured shape with a substantially rectangular body.

The central portion B308 of the absorbent material B302 may comprise a waisted portion B303. The waisted portion B303 can be defined by the transverse width of the absorbent material B302 narrowing at the central portion B308 of the longitudinal length. For example, in some embodiments, the waisted portion B303 can be a narrow width at the central portion B308 of the absorbent material B302, as illustrated in FIGS. 20A-C. Additional embodiments of the waisted portion B303 are possible including those described herein. Further, the shape of the accompanying components within the wound dressing as described with reference to FIGS. 19A-C can be formed to the same contoured shape of the absorbent material including the waisted portion.

The waisted portion B303 can increase the flexibility of the wound dressing and can allow enhanced compatibility of the wound dressing to the patient's body. For example, the narrow central region may allow for improved contact and adhesion of the wound dressing to the skin surface when the wound dressing is used on non-planar surfaces and/or wrapped around an arm or leg. Further, the narrow central portion provides increased compatibility with the patient's body and patient movement.

As in FIGS. 31A-B, embodiments of wound dressings may comprise various configurations of slits (described in detail below) so as to further enhance conformability of the dressing in non-planar wounds. Also, as described below, the absorbent layers may be colored or obscured with an obscuring layer, and optionally provided with one or more viewing windows. The domed ports may also be replaced with one or more fluidic connectors of the type described below in FIGS. 39A-B. Further, the wound dressing B300 can comprise all designs or embodiments herein described or have any combination of features of any number of wound dressing embodiments disclosed herein.

FIG. 20B illustrates an embodiment of a wound dressing B300 with a waisted portion. A wound dressing B300 as illustrated in FIG. 20B can have the features and embodiments as described above with reference to FIG. 20A. However, FIG. 20B illustrates an embodiment with a shorter longitudinal length with respect to the transverse width. FIG. 20C illustrates an additional embodiment of a wound dressing B300 with a waisted portion. As illustrated in FIG. 20C, the wound dressing can have a longitudinal length and a transverse width that are not substantially different in size, as opposed to a longitudinal length that is substantially longer than the transverse width of the wound dressing as shown in the embodiments illustrated in FIGS. 20A and 20B. The embodiments of a wound dressing illustrated in FIGS. 20B and 20C can include all features and embodiments described herein for wound dressings including those embodiments of the waisted portion B303 described with reference to FIG. 20A.

FIGS. 21A-F, 22A-F, 23A-F, 24A-F, 25A-F, 26A-F, 27A-F, 28A-F, and 30 illustrate additional embodiments of wound dressings. In these embodiments, a waisted portion B408 is located inwardly with reference to an edge B409 of the absorbent layer B402. Preferably, the contour of the absorbent layer B402 is curved from the edge B409 to the waisted portion B408, so as to form a smooth contour.

Figure 21A:
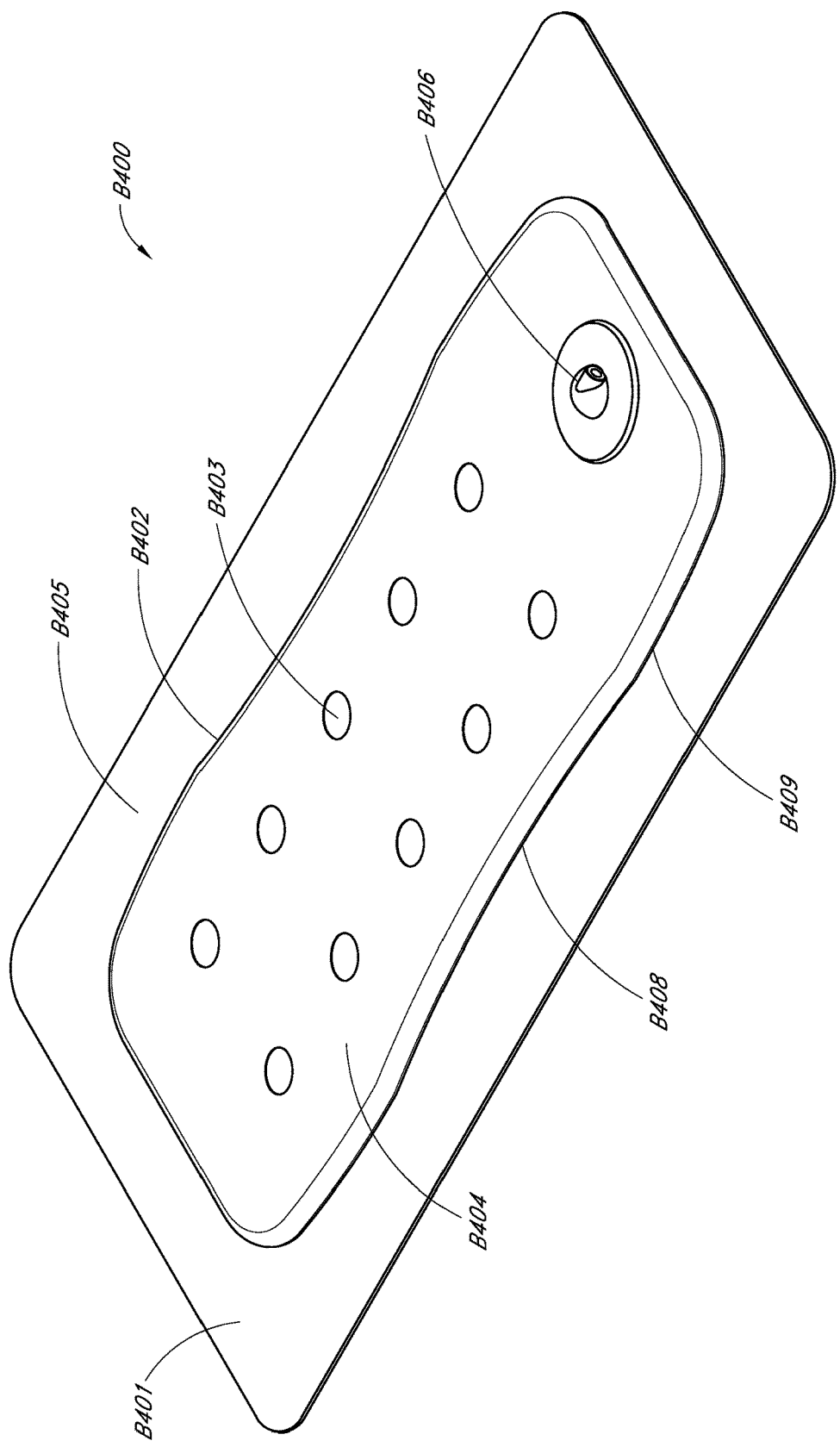

FIGS. 21A-F illustrate multiple views of an embodiment of a wound dressing with a waisted portion, obscuring layer, and viewing windows. FIG. 21A illustrates a perspective view of an embodiment of a wound dressing B400. The wound dressing B400 preferably comprises a port B406. The port B406 is preferably configured to be in fluid communication with a pump as described with reference to FIG. 17, and may include a tube or conduit pre-attached to the port. Alternatively, negative pressure can be supplied to the wound dressing through other suitable fluidic connectors, including but not limited to the fluidic connectors of the type described below in FIGS. 39A-B.

The wound dressing B400 can be constructed similar to the embodiments of FIGS. 19A and 19B above, and may comprise an absorbent material B402 underneath or within a backing layer B405. Optionally, a wound contact layer and a transmission layer may also be provided as part of the wound dressing B400 as described above. The absorbent material B402 can contain a narrowed central or waisted portion B408, as described previously to increase flexibility and conformability of the wound dressing to the skin surface. The backing layer B405 may have a border region B401 that extends beyond the periphery of the absorbent material B402. The backing layer B405 may be a translucent or transparent backing layer, such that the border region B401 created from the backing layer B405 can be translucent or transparent. The area of the border region B401 of the backing layer B405 can be approximately equal around the perimeter of the entire dressing with the exception of the narrowed central portion, where the area of the border region is larger. One will recognize that the size of the border region B401 will depend on the full dimensions of the dressing and any other design choices.

As illustrated in FIG. 21A, provided at least at the top of or over the absorbent layer B402 and under the backing layer B405 may be an obscuring layer B404 that optionally has one or more viewing windows B403. The obscuring layer B404 may partially or completely obscure contents (such as fluids) contained within the wound dressing B400 and/or the absorbent material (i.e., within the absorbent material B402 or under the backing layer B405). The obscuring layer may be a colored portion of the absorbent material, or may be a separate layer that covers the absorbent material. In some embodiments, the absorbent material B402 may be hidden (partially or completely), colored, or tinted, via the obscuring layer B404, so as to provide cosmetic and/or aesthetic enhancements, in a similar manner to what is described above. The obscuring layer is preferably provided between the topmost backing layer B405 and the absorbent material B402, although other configurations are possible. The cross-sectional view in FIGS. 19A and 19B illustrates this arrangement with respect to the masking or obscuring layer B2107. Other layers and other wound dressing components can be incorporated into the dressing as herein described.

The obscuring layer B404 can be positioned at least partially over the absorbent material B402. In some embodiments, the obscuring layer B404 can be positioned adjacent to the backing layer, or can be positioned adjacent to any other dressing layer desired. In some embodiments, the obscuring layer B404 can be adhered to or integrally formed with the backing layer and/or the absorbent material.

As illustrated in FIG. 21A, the obscuring layer B404 can have substantially the same perimeter shape and size as the absorbent material B402. The obscuring layer B404 and absorbent material B402 can be of equal size so that the entirety of the absorbent material B402 can be obscured by the obscuring layer B404. The obscuring layer B404 may allow for obscuring of wound exudate, blood, or other matter released from a wound. Further, the obscuring layer B404 can be completely or partially opaque having cut-out viewing windows or perforations.

In some embodiments, the obscuring layer B404 can help to reduce the unsightly appearance of a dressing during use, by using materials that impart partial obscuring or masking of the dressing surface. The obscuring layer B404 in one embodiment only partially obscures the dressing, to allow clinicians to access the information they require by observing the spread of exudate across the dressing surface. The partial masking nature of this embodiment of the obscuring layer enables a skilled clinician to perceive a different color caused by exudate, blood, by-products etc. in the dressing allowing for a visual assessment and monitoring of the extent of spread across the dressing. However, since the change in color of the dressing from its clean state to a state containing exudate is only a slight change, the patient is unlikely to notice any aesthetic difference. Reducing or eliminating a visual indicator of wound exudate from a patient's wound is likely to have a positive effect on their health, reducing stress for example.

In some embodiments, the obscuring layer can be formed from a non-woven fabric (for example, polypropylene), and may be thermally bonded using a diamond pattern with 19% bond area. In various embodiments, the obscuring layer can be hydrophobic or hydrophilic. Depending on the application, in some embodiments, a hydrophilic obscuring layer may provide added moisture vapor permeability. In some embodiments, however, hydrophobic obscuring layers may still provide sufficient moisture vapor permeability (i.e., through appropriate material selection, thickness of the obscuring layer), while also permitting better retention of dye or color in the obscuring layer. As such, dye or color may be trapped beneath the obscuring layer. In some embodiments, this may permit the obscuring layer to be colored in lighter colors or in white. In the preferred embodiment, the obscuring layer is hydrophobic. In some embodiments, the obscuring layer material can be sterilizable using ethylene oxide. Other embodiments may be sterilized using gamma irradiation, an electron beam, steam or other alternative sterilization methods. Additionally, in various embodiments the obscuring layer can colored or pigmented, e.g., in medical blue. The obscuring layer may also be constructed from multiple layers, including a colored layer laminated or fused to a stronger uncolored layer. Preferably, the obscuring layer is odorless and exhibits minimal shedding of fibers.

The absorbent layer B402, itself may be colored or tinted in some embodiments, however, so that an obscuring layer is not necessary. The dressing may optionally include a means of partially obscuring the top surface. This could also be achieved using a textile (knitted, woven, or non-woven) layer without openings, provided it still enables fluid evaporation from the absorbent structure. It could also be achieved by printing an obscuring pattern on the top film, or on the top surface of the uppermost pad component, using an appropriate ink or colored pad component (yarn, thread, coating) respectively. Another way of achieving this would be to have a completely opaque top surface, which could be temporarily opened by the clinician for inspection of the dressing state (for example through a window), and closed again without compromising the environment of the wound.

Additionally, FIG. 21A illustrates an embodiment of the wound dressing including one or more viewing windows B403. The one or more viewing windows B403 preferably extend through the obscuring layer B404. These viewing windows B403 may allow visualization by a clinician or patient of the wound exudate in the absorbent material below the obscuring layer. FIG. 21A illustrates an array of dots (e.g., in one or more parallel rows) that can serve as viewing windows B403 in the obscuring layer B404 of the wound dressing. In a preferred embodiment, two or more viewing windows B403 may be parallel with one or more sides of the dressing B400. In some embodiments, the one or more viewing windows may measure between 0.1 mm and 20 mm, preferably 0.4 mm to 10 mm, and even more preferably, 1 mm to 4 mm.

The viewing windows B403 may be cut through the obscuring layer B404 or may be part of an uncolored area of the obscuring layer B404 and therefore may allow visualization of the absorbent material B402. The one or more viewing windows B403 can be arranged in a repeating pattern across the obscuring layer B404 or can be arranged at random across the obscuring layer. Additionally, the one or more viewing windows can be a circular shape or dots. Preferably, the one or more viewing windows B403 are configured so as to permit not only the degree of saturation, but also the progression or spread of fluid toward the fluid port B406, as in some embodiments, dressing performance may be adversely affected when the level of fluid has saturated the fluid proximate the port B406. In some embodiments, a "starburst" array of viewing windows B403 emanating around the port B406 may be suitable to show this progression, although of course other configurations are possible.

In FIG. 21A, the viewing windows B403 correspond to the area of the absorbent material B402 that is not covered by the obscuring layer B404. As such, the absorbent material B402 is directly adjacent the backing layer B405 in this area. Since the obscuring layer B404 acts as a partial obscuring layer, the viewing windows B403 may be used by a clinician or other trained user to assess the spread of wound exudate throughout the dressing. In some embodiments, the viewing windows B403 can comprise an array of dots or crescent shaped cut-outs. For example, an array of dots as viewing windows B403 are illustrated in FIGS. 21A-F, 22A-F, 23A-F, 24A-F, 25A-F, 26A-F, 27A-F, and 28A-F in which the array of dots are arranged in an 5×2, 3×2, 8×1, 5×1, 3×1, 3×3, 3×3, and quincunx array respectively. Additionally, in some embodiments, the dot pattern can be distributed evenly throughout the obscuring layer and across the entire or substantially the entire surface of the obscuring layer. In some embodiments, the viewing windows B403 may be distributed randomly throughout the obscuring layer. Preferably, the area of the obscuring layer B404 uncovered by the one or more viewing windows B403 is balanced to as to minimize the appearance of exudate while permitting the inspection of the dressing B400 and/or absorbent material B402. In some embodiments, the area exposed by the one or more viewing windows B403 does not exceed 20% of the area of the obscuring layer B404, preferably 10%, and even more preferably 5%.

Figures 32, 33, 34:
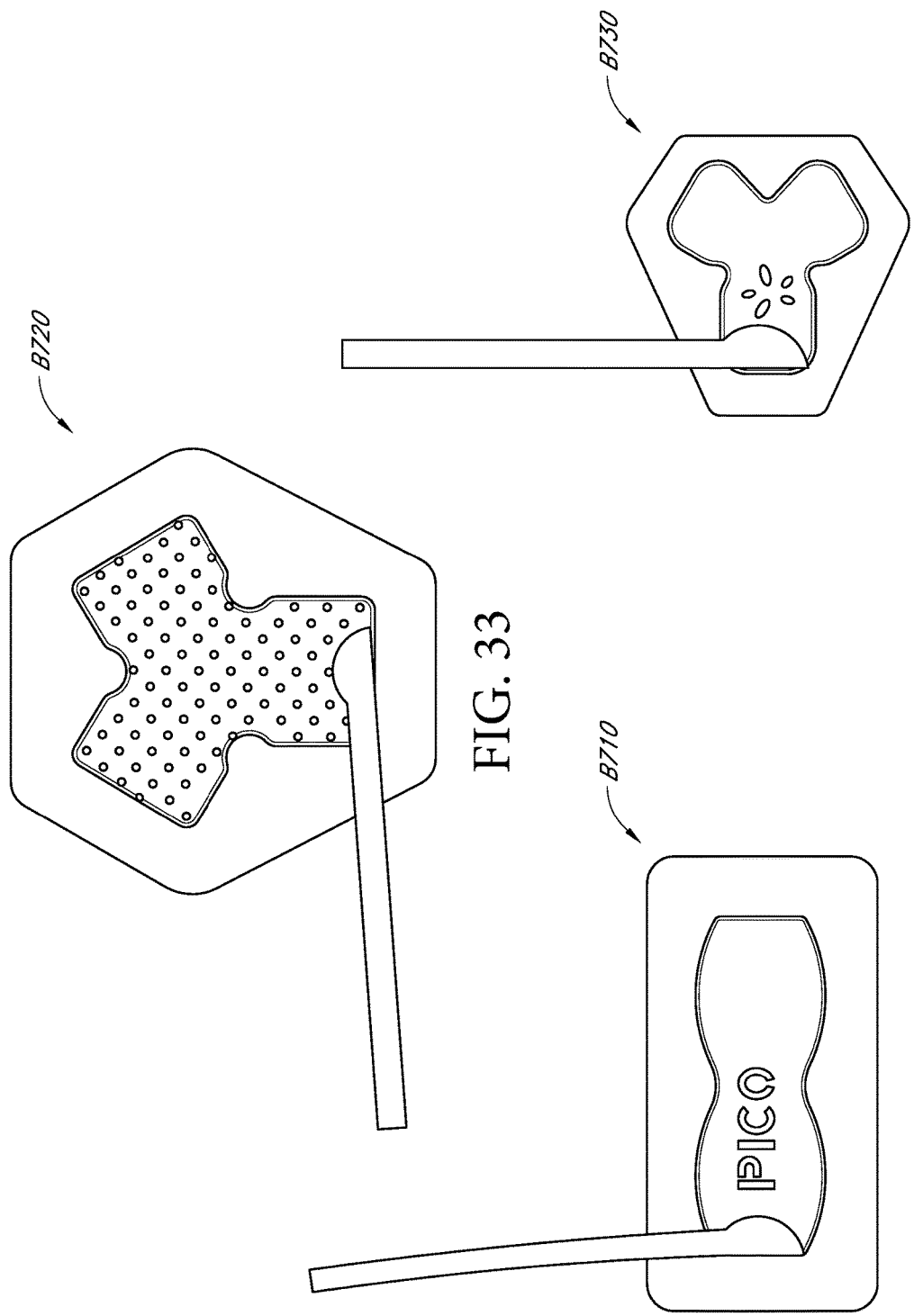
FIG. 32 illustrates an embodiment of a dressing comprising a viewing window in the shape of a trademarked brand name.
FIG. 33 illustrates a top view of an embodiment of a three-lobe configuration of a wound dressing and a dot pattern of viewing windows.
FIG. 34 illustrates a top view of an embodiment of a three-lobe configuration of a wound dressing and viewing windows in the shape of a logo.

The viewing windows B403 may take several configurations, as will be discussed in relation to FIGS. 32-34. In FIG. 33, the viewing windows B403 may comprise an array of regularly spaced uncolored dots (holes) made into the obscuring layer B404. While the dots illustrated here are in a particular pattern, the dots may be arranged in different configurations, or at random. The viewing windows B403 are preferably configured so as to permit a patient or caregiver to ascertain the status of the absorbent layer, in particular to determine its saturation level, as well as the color of the exudate (e.g., whether excessive blood is present). By having one or more viewing windows, the status of the absorbent layer can be determined in an unobtrusive manner that is not aesthetically unpleasing to a patient. Because a large portion of the absorbent layer may be obscured, the total amount of exudate may therefore be hidden. As such, the status and saturation level of the absorbent layer B402 may therefore present a more discreet external appearance so as to reduce patient embarrassment and visibility and thereby enhance patient comfort. In some configurations, the one or more viewing windows B403 may be used to provide a numerical assessment of the degree of saturation of the dressing B400. This may be done electronically (e.g., via a digital photograph assessment), or manually. For example, the degree of saturation may be monitored by counting the number of viewing windows B403 which may be obscured or tinted by exudate or other wound fluids.

In some embodiments, the absorbent layer B402 or the obscuring layer B404, in particular the colored portion of the absorbent layer, may comprise (or be colored because of) the presence of an auxiliary compound. The auxiliary compound may in some embodiments be activated charcoal, which can act to absorb odors. The use of antimicrobial, antifungal, anti-inflammatory, and other such therapeutic compounds is also possible. In some embodiments, the color may change as a function of time (e.g., to indicate when the dressing needs to be changed), if the dressing is saturated, or if the dressing has absorbed a certain amount of a harmful substance (e.g., to indicate the presence of infectious agents). In some embodiments, the one or more viewing windows B403 may be monitored electronically, and may be used in conjunction with a computer program or system to alert a patient or physician to the saturation level of the dressing B400.

FIG. 32 illustrates an embodiment of a dressing containing a viewing window in the shape of a trademarked brand name ("PICO"). FIG. 34 illustrates an embodiment of a dressing comprising a viewing window in the shape of a logo, here, the Smith & Nephew logo. Of course, many other configurations are possible, including other graphics, texts, or designs. The graphical or textual elements present in the viewing window may also be, for example, instructional in nature.

In other alternatives, instructions may be given to change the wound dressing when the exudate reaches a predetermined distance from the edge of the wound dressing, such as 5 mm from the wound dressing edge or 7 mm from the wound dressing edge, etc. Alternatively a 'traffic light' system may be implemented whereby an electronic indicator shows green, amber or red light to indicate the spread of exudate in the wound dressing. Alternatively or additionally, another suitable indicator may be used for indicating the spread of exudate over the dressing.

FIGS. 21A-F illustrate multiple views of the wound dressing B400. FIG. 21A illustrates a perspective view of a wound dressing with the dimensions of 300 mm×150 mm.

Figure 21B:
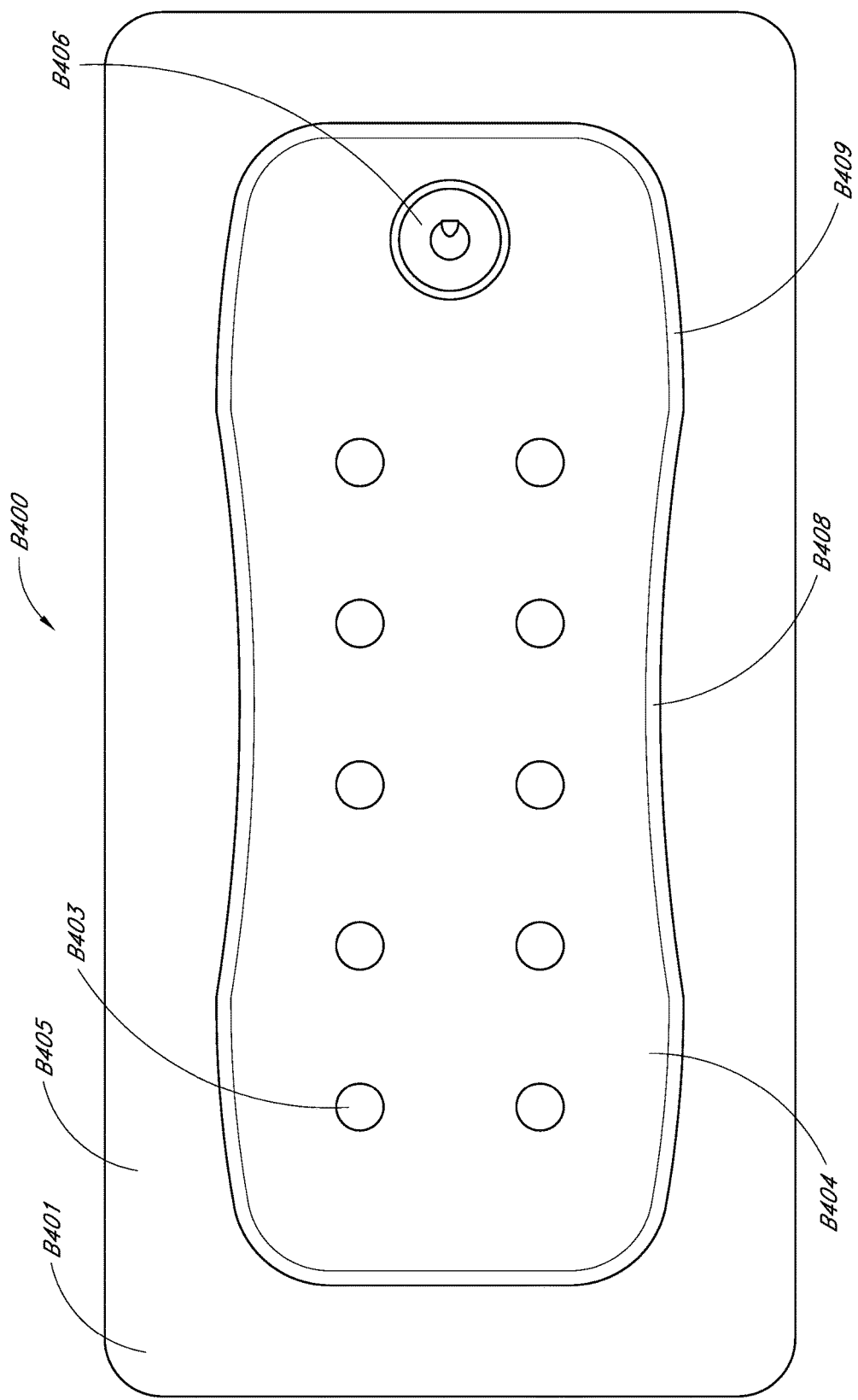
Figure 21C:
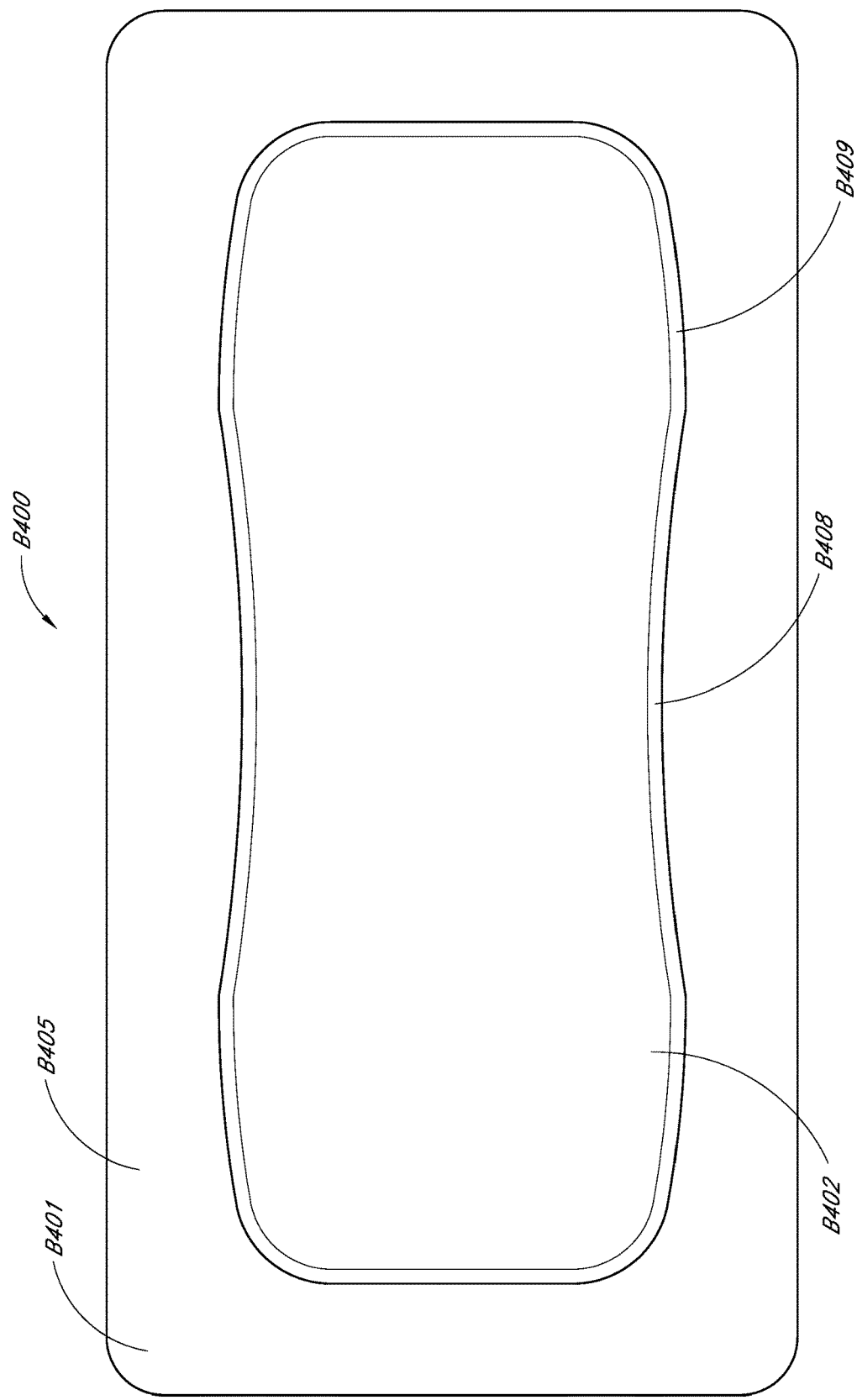
Figure 21F:
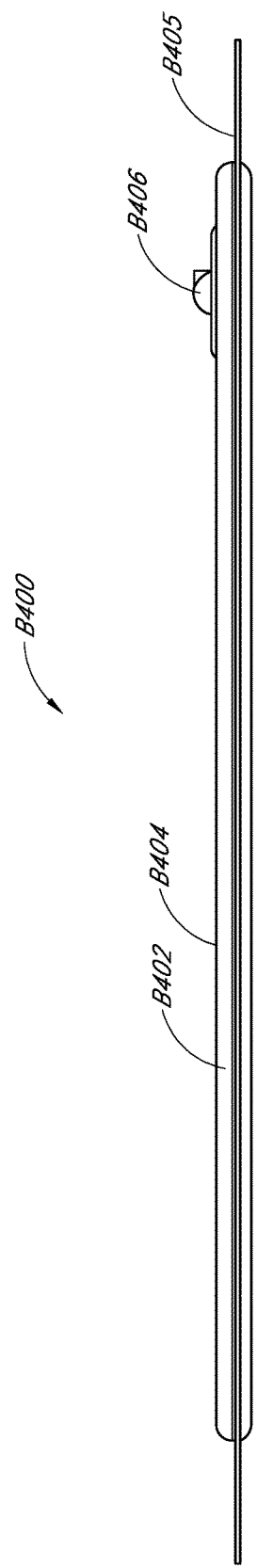
Figure 22A:
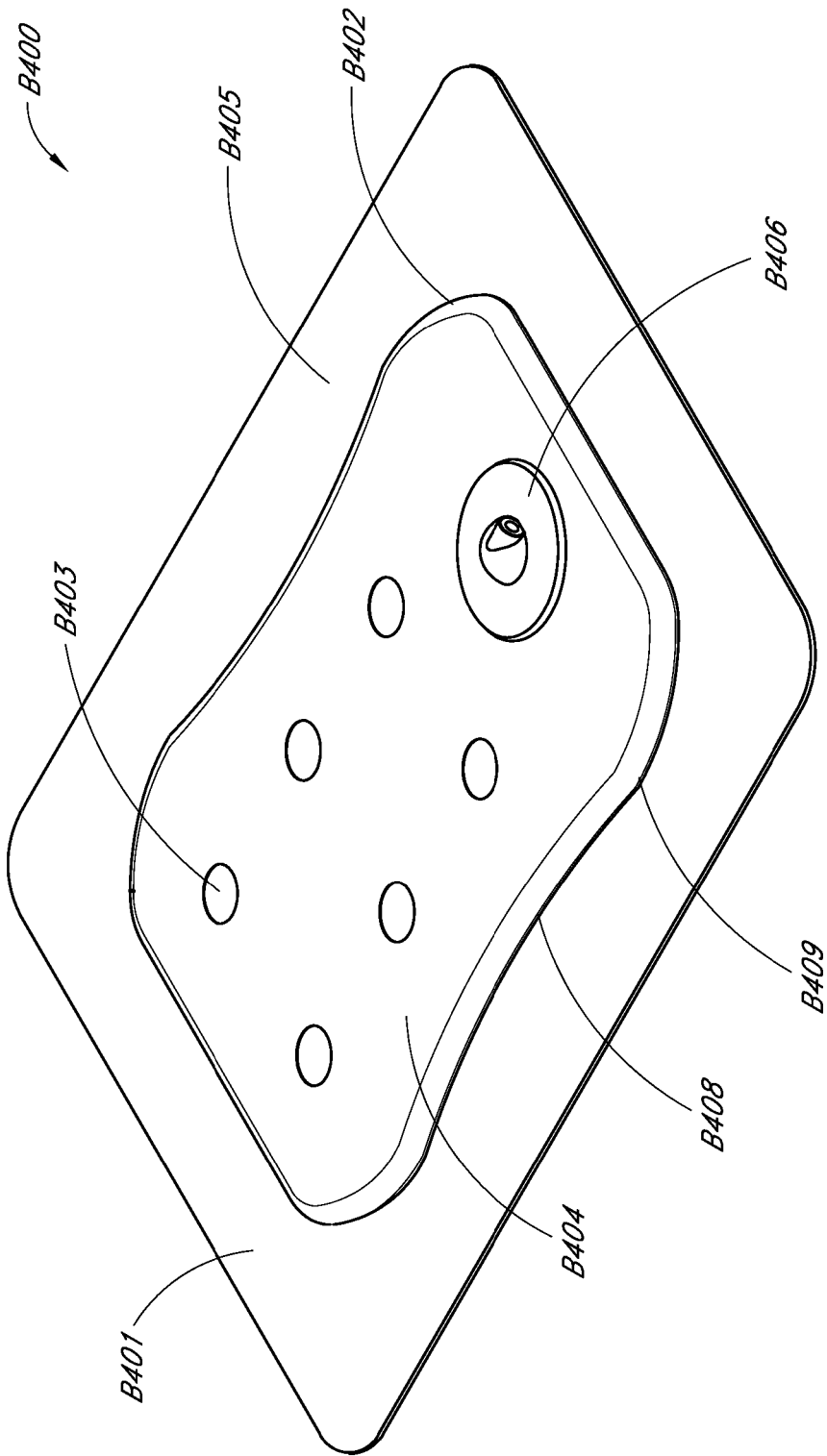
Figure 22B:
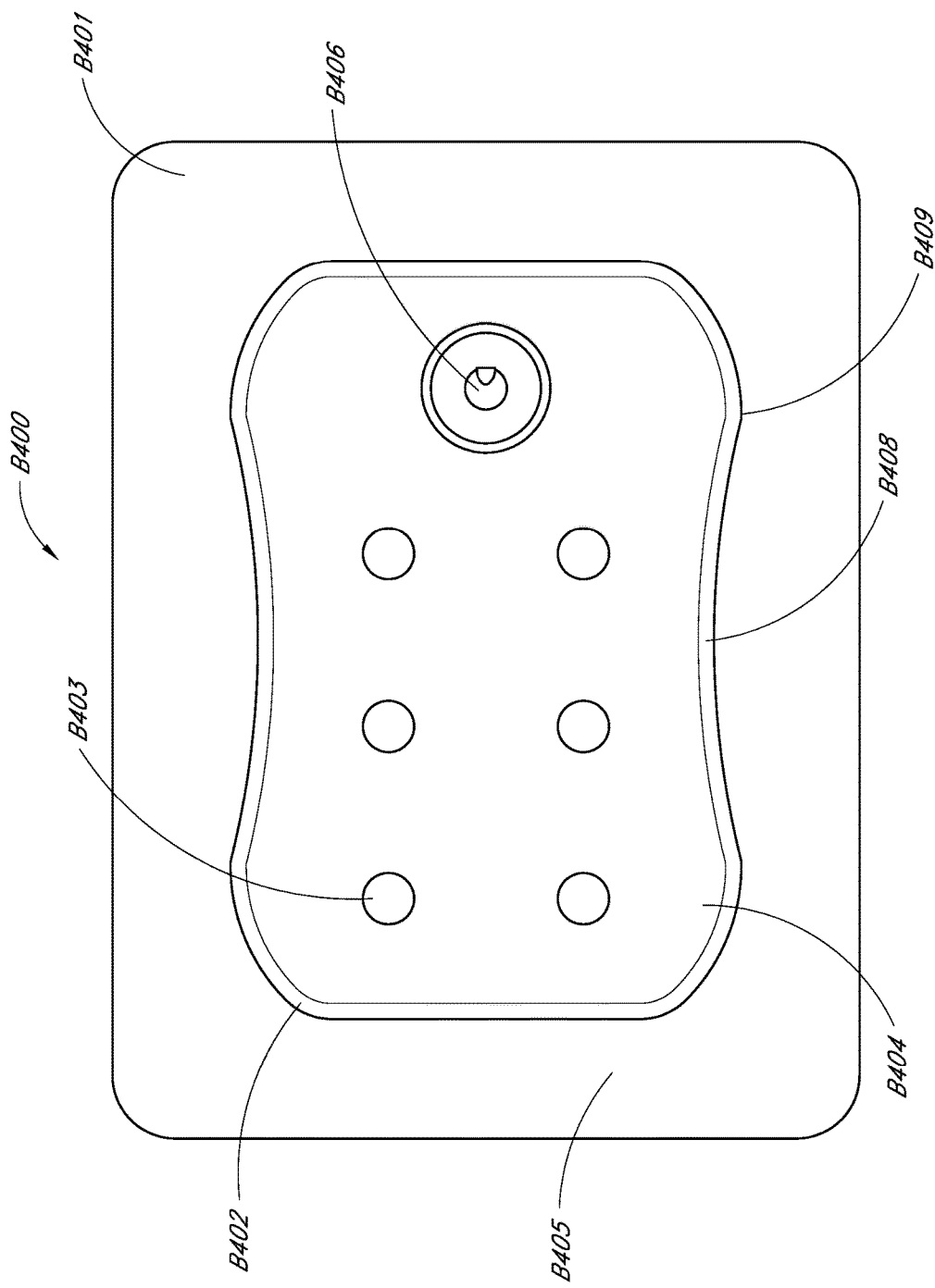
Figure 22C:
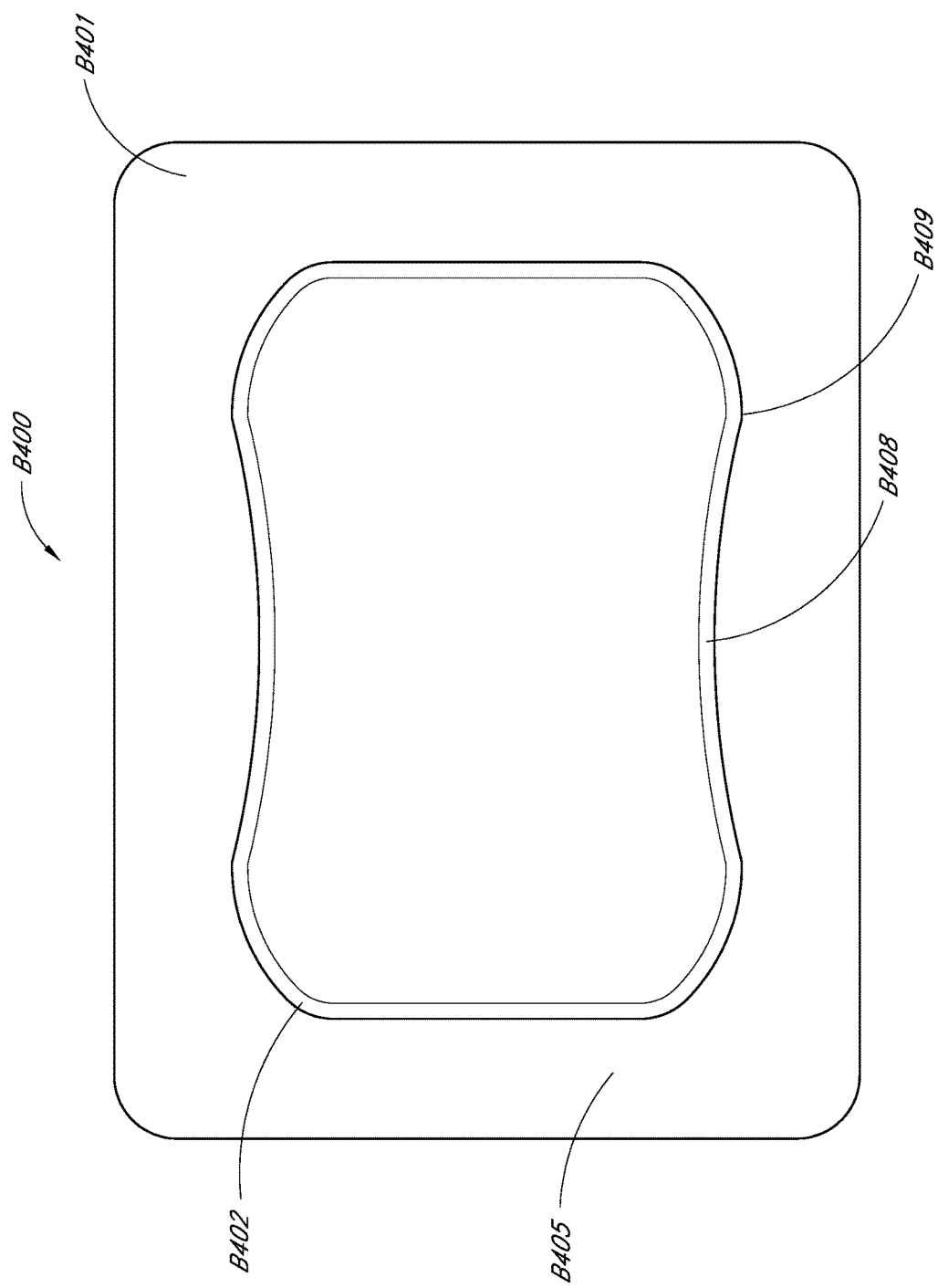
Figure 22D:
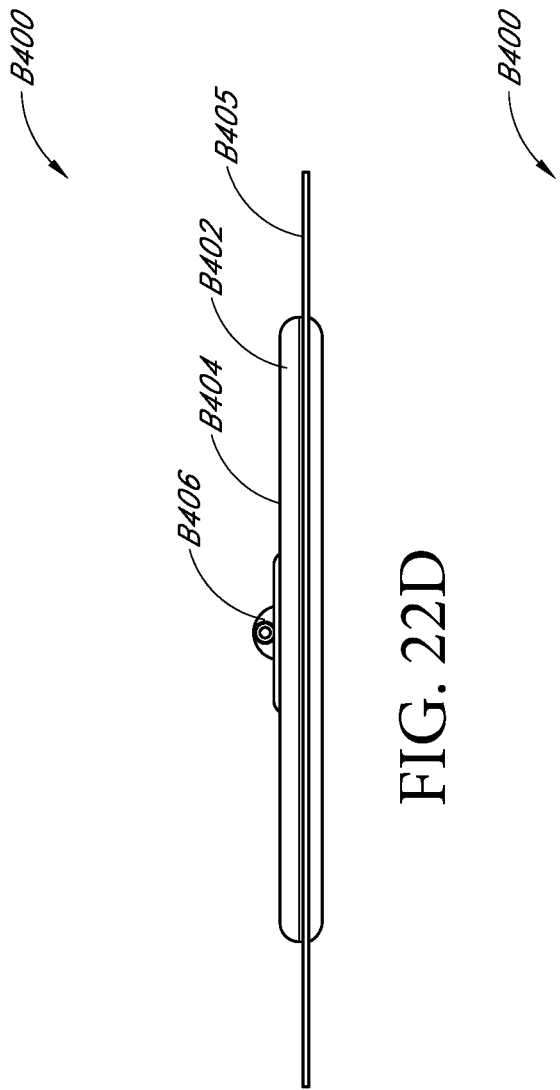
Figure 22E:
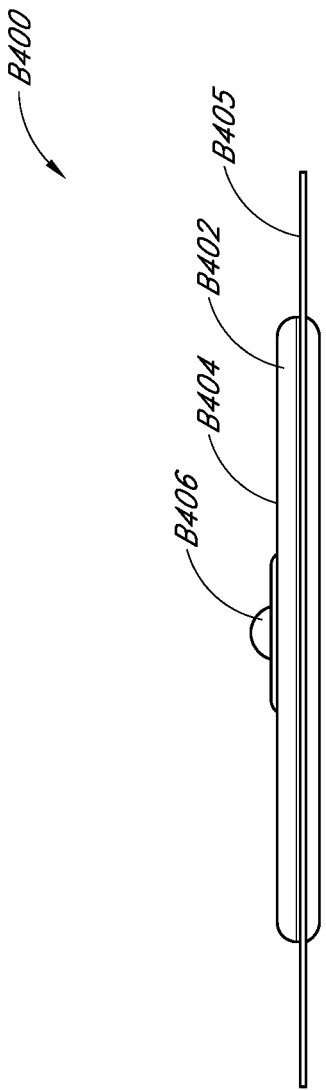
Figure 22F:
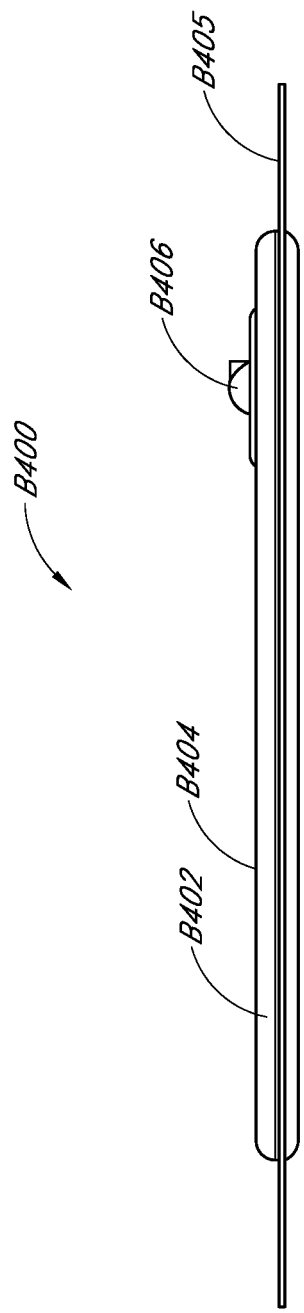
Figure 23A:
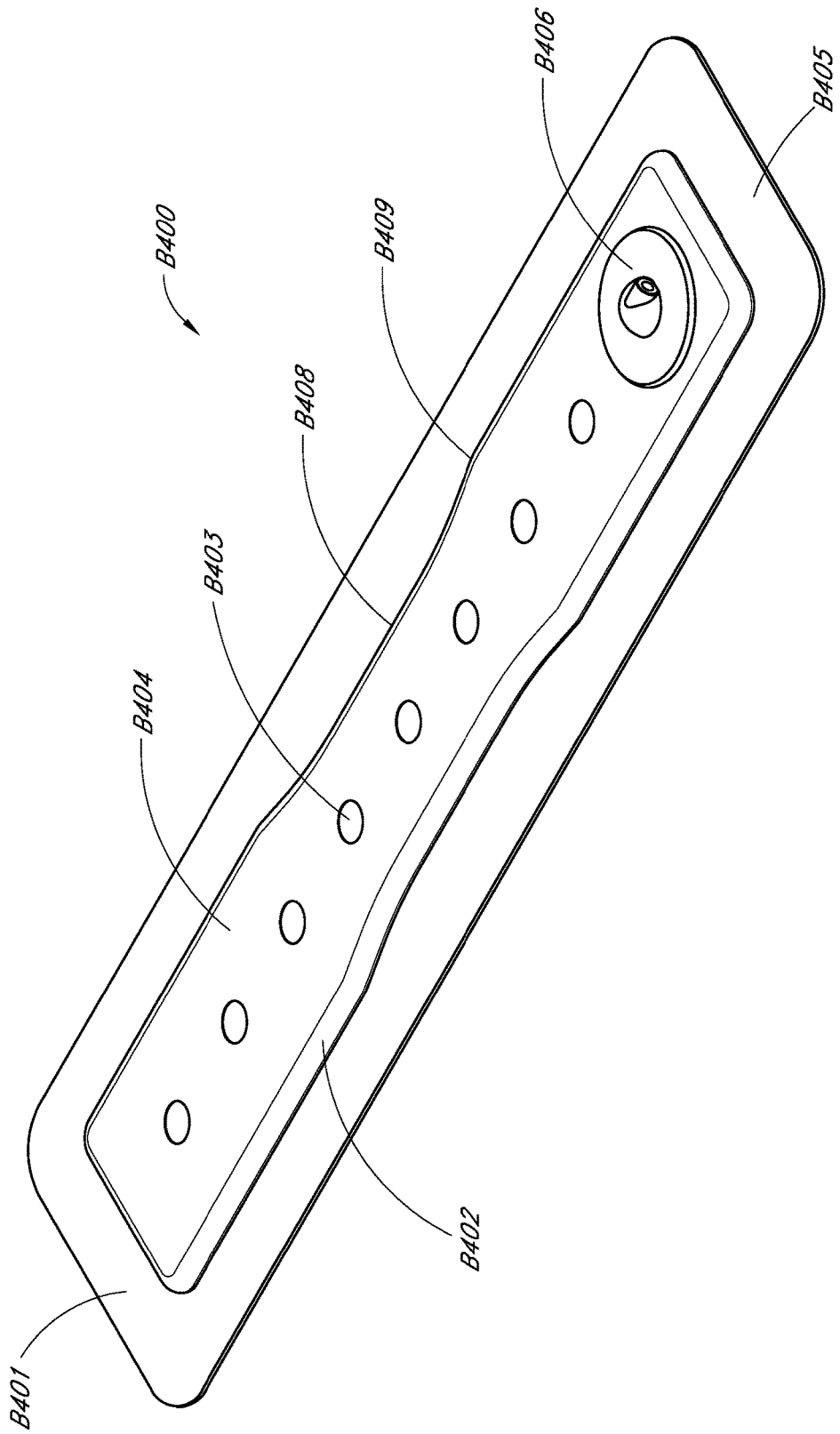
Figure 23B:
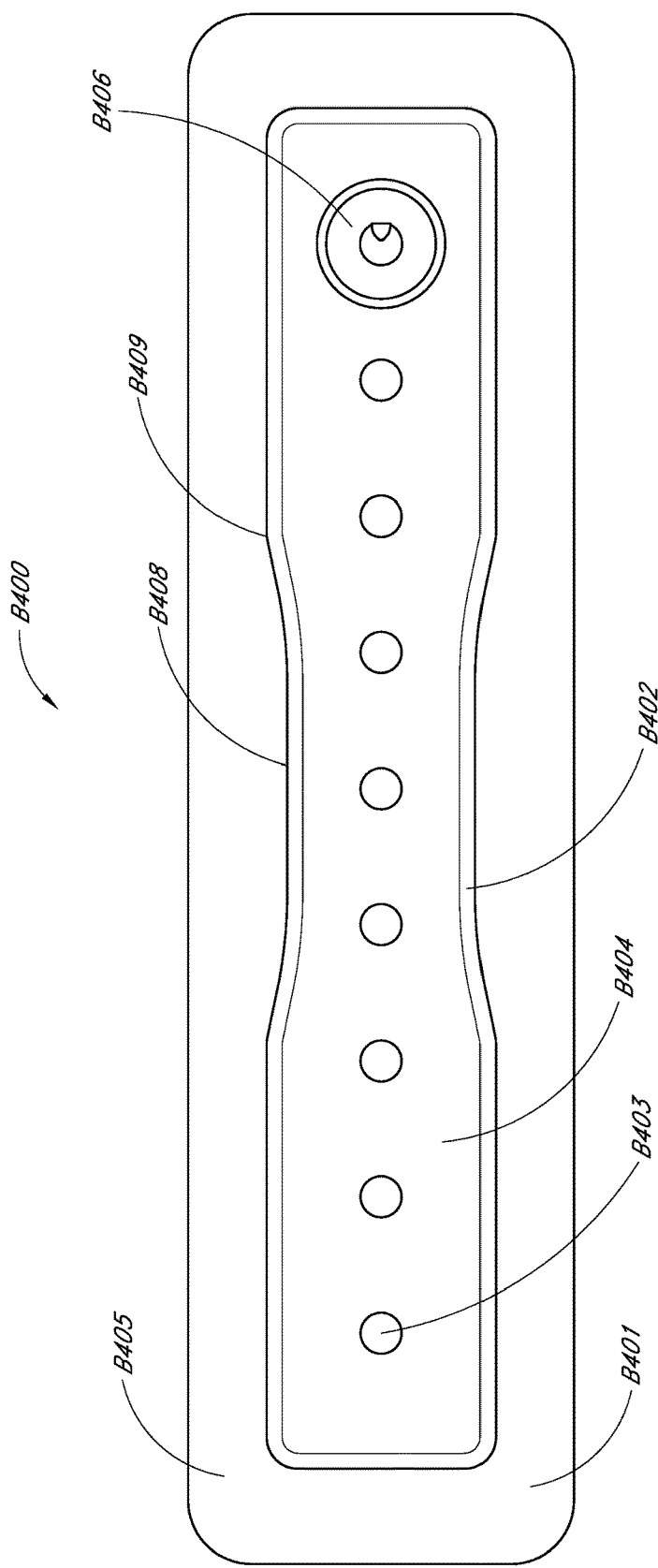
Figure 23C:
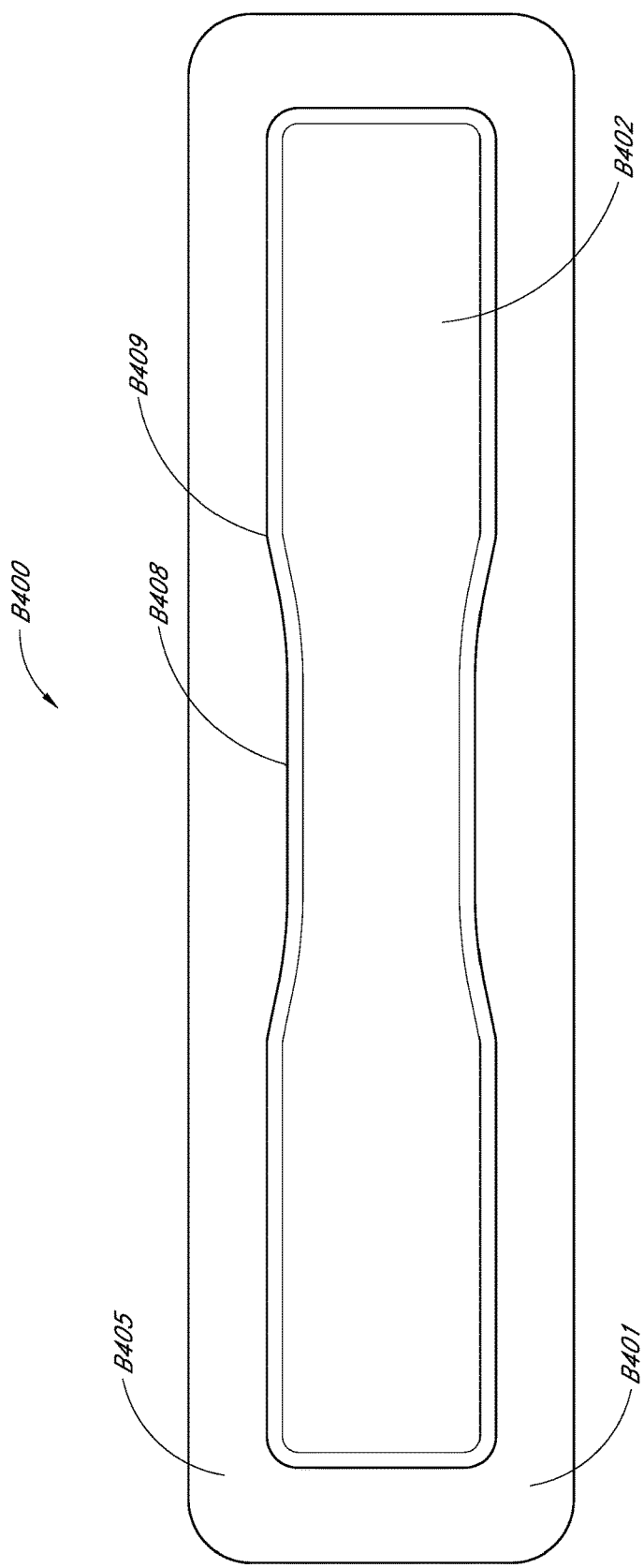
Figure 23F:
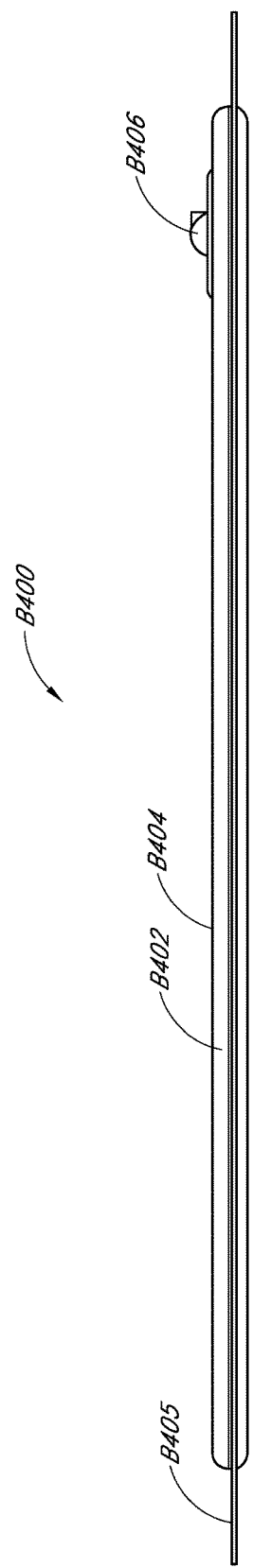
Figure 24A:
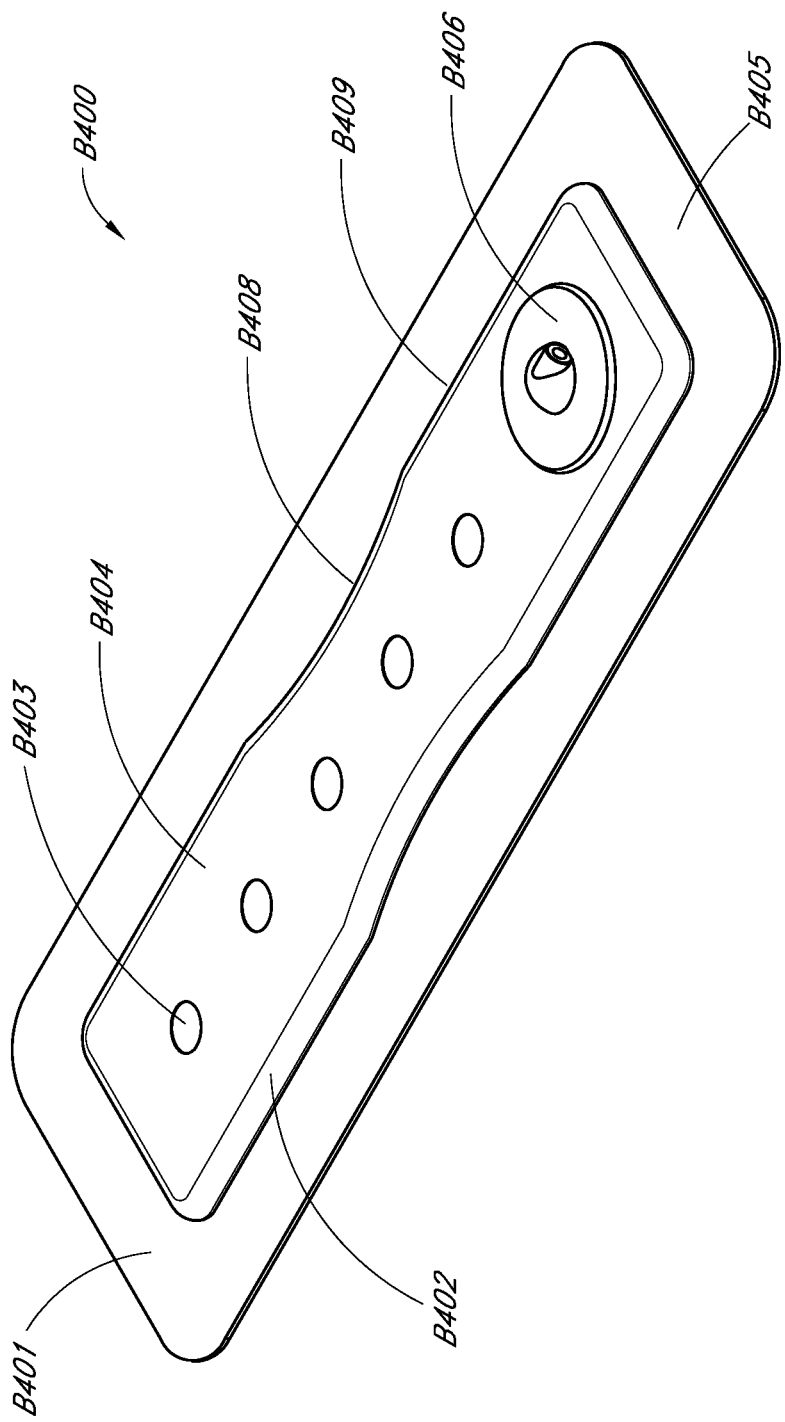
Figure 24B:
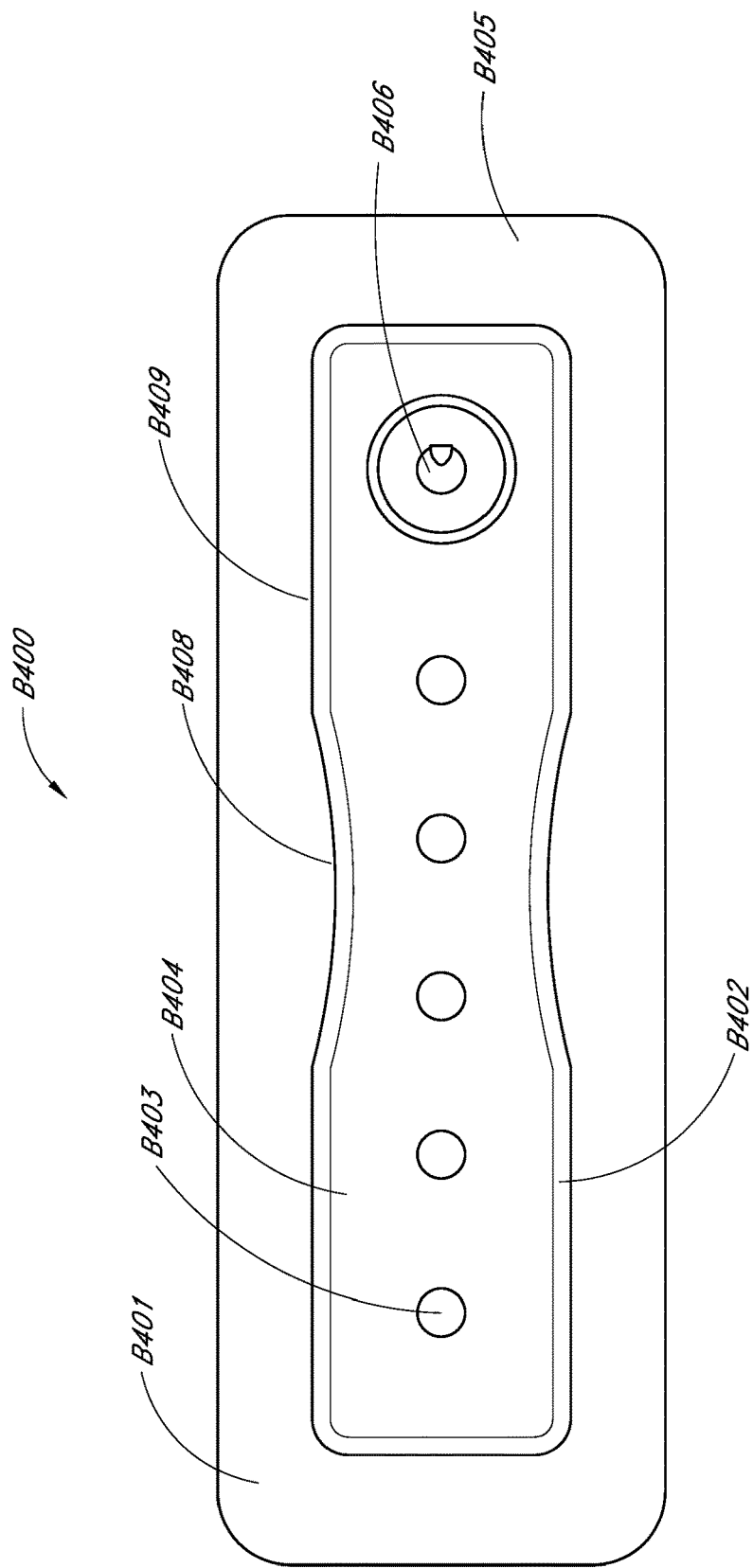
Figure 24C:
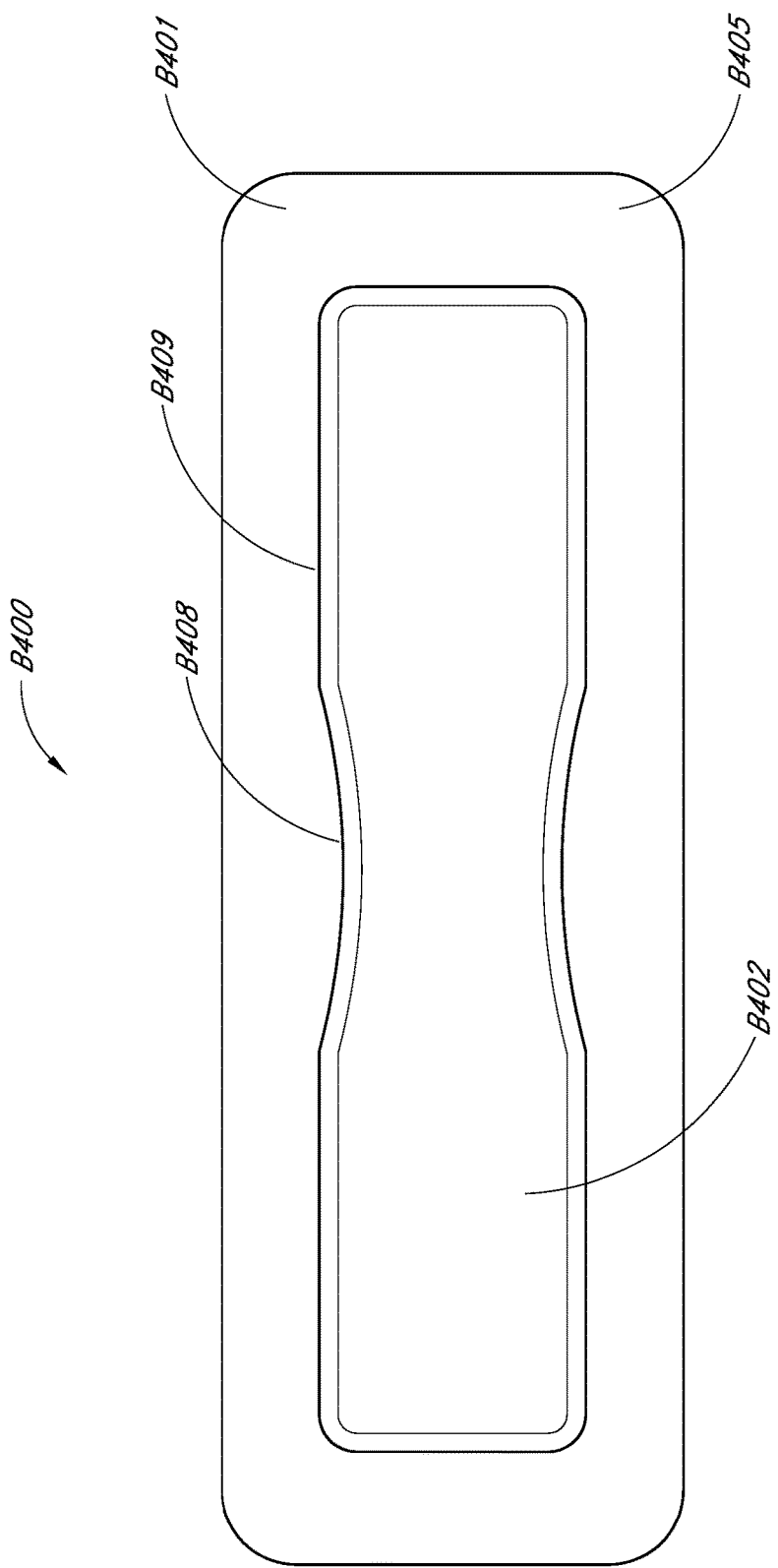
Figure 24F:
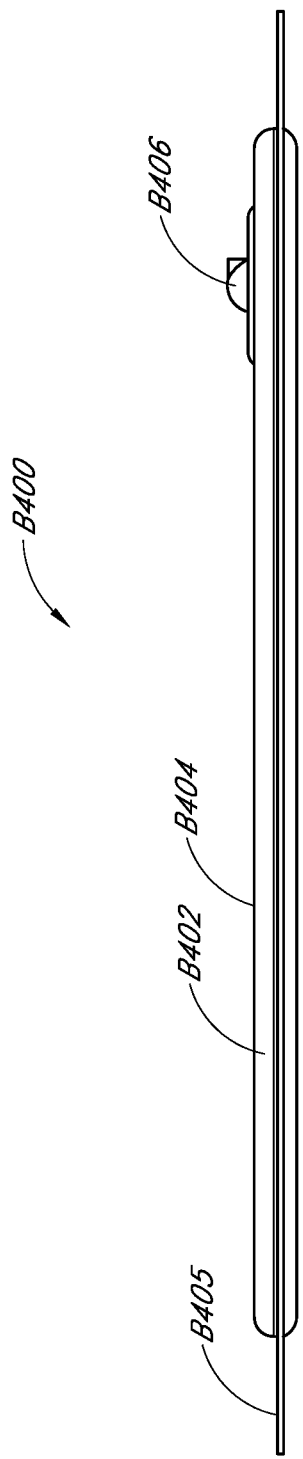
Figure 25A:
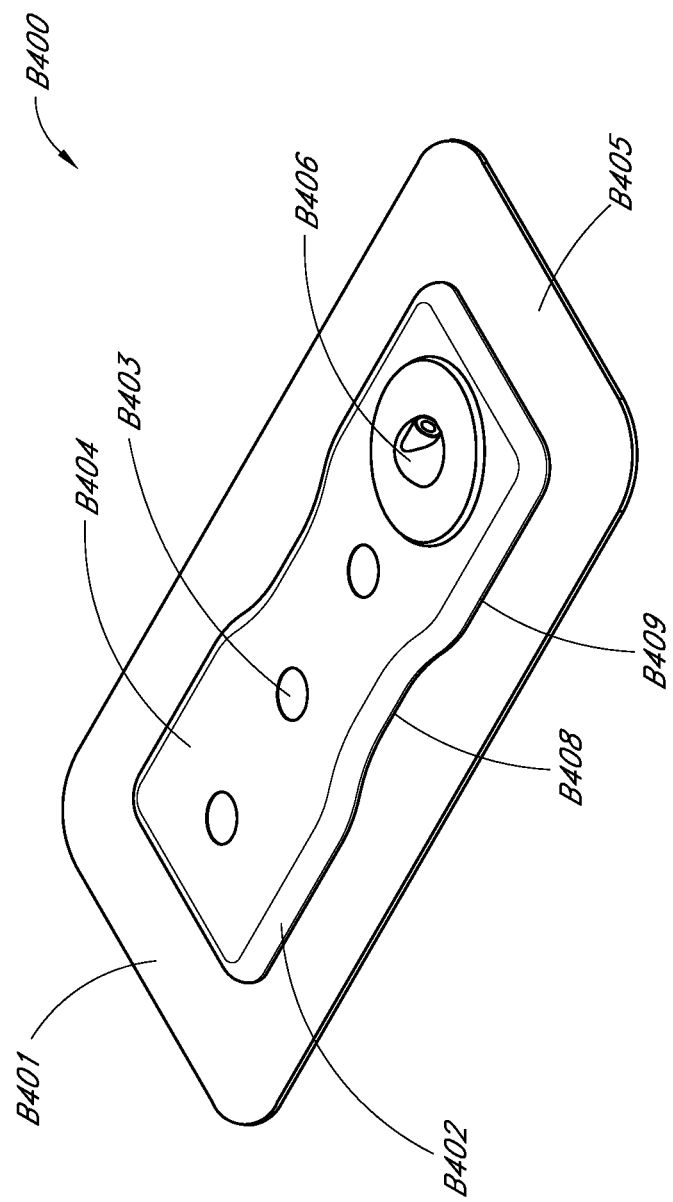
Figure 25B:
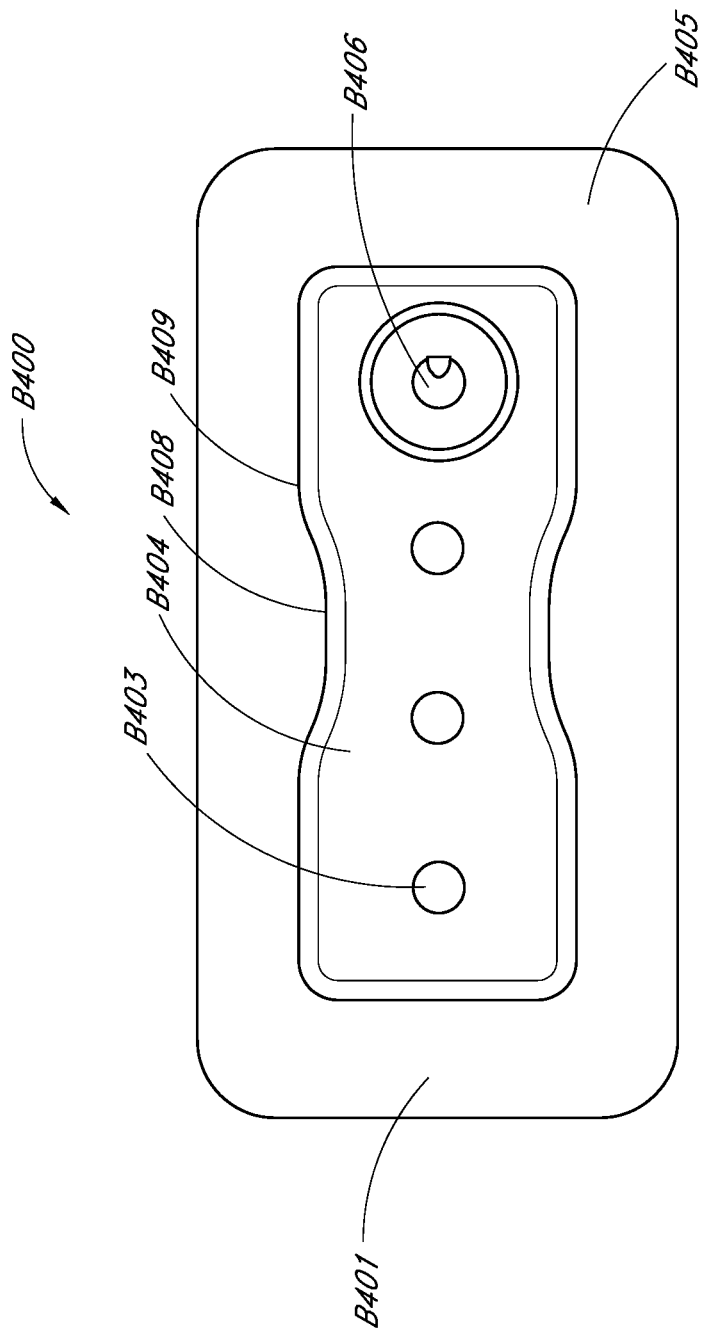
Figure 25C:
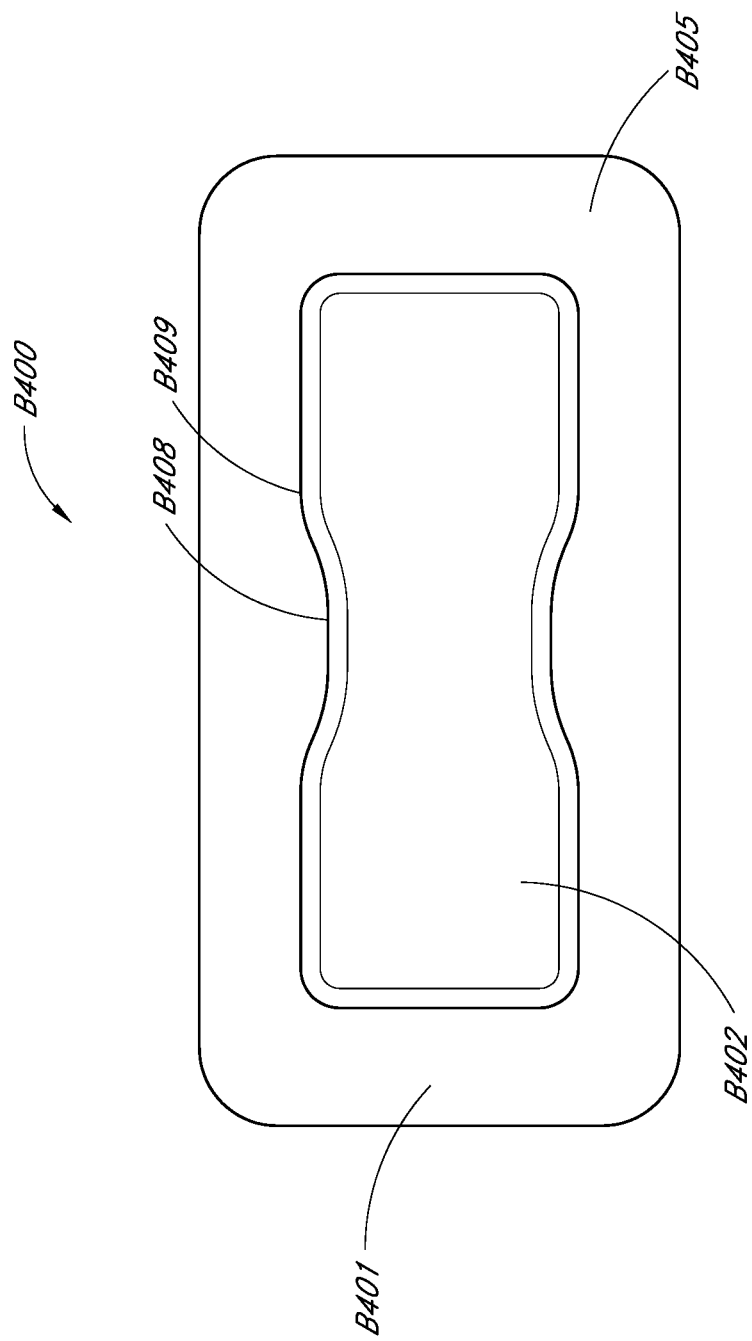
Figure 25F:
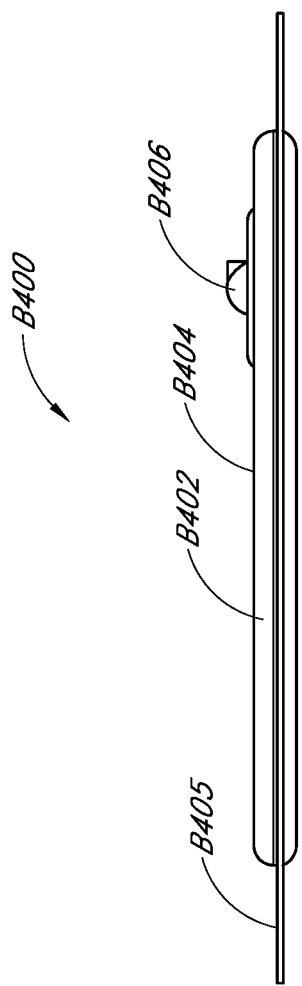
Figure 26A:
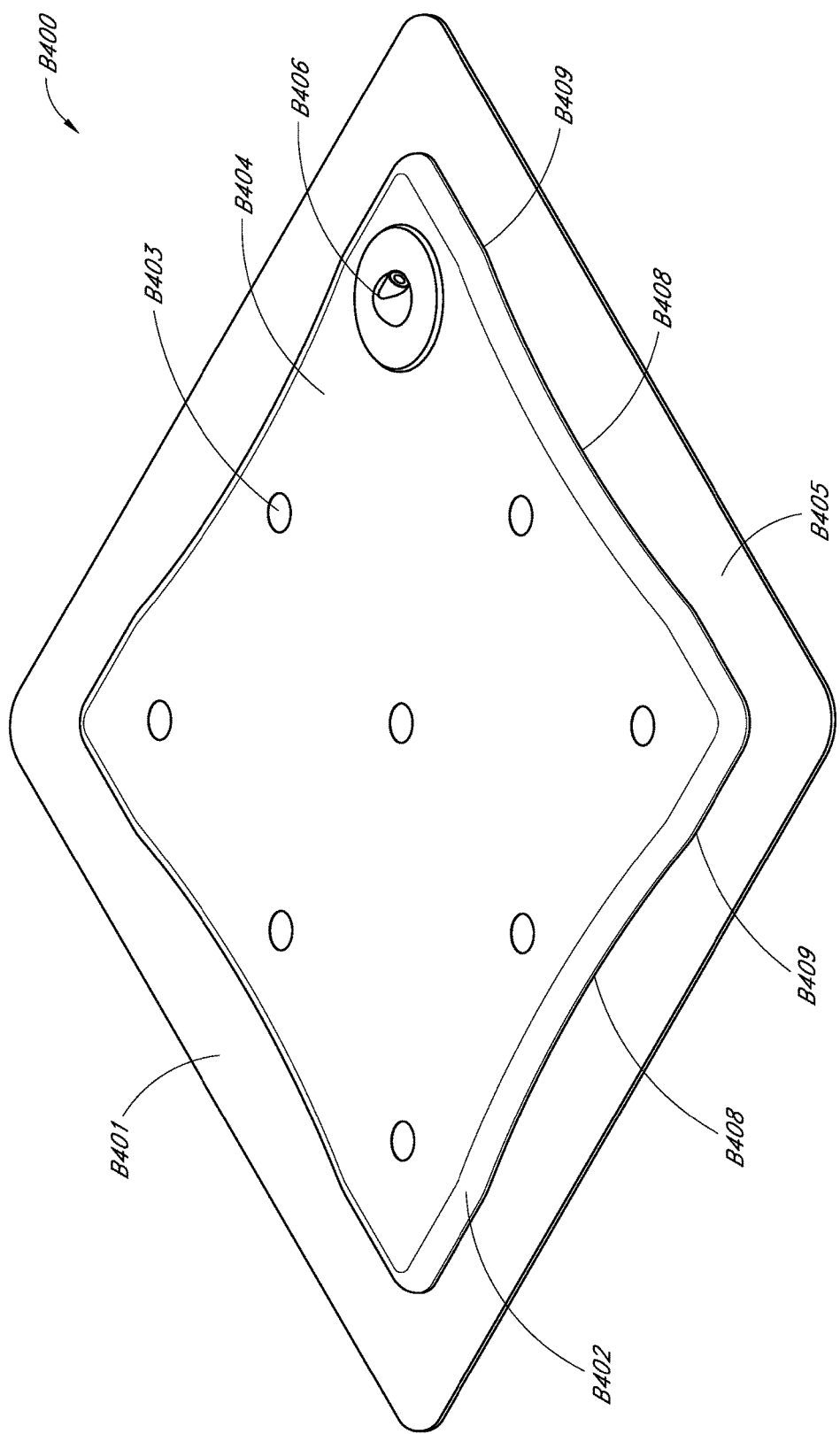
Figure 26B:
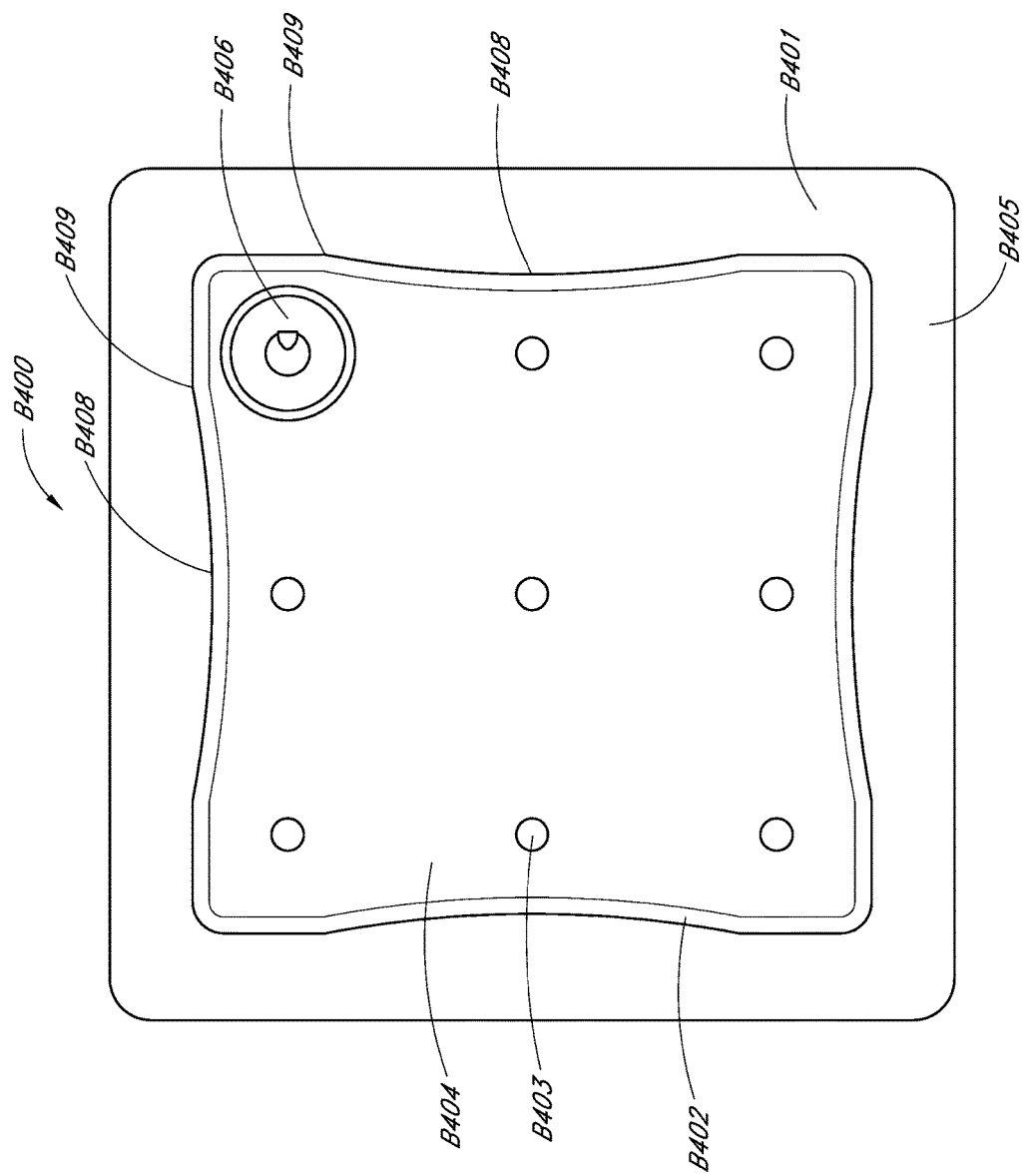
Figure 26C:
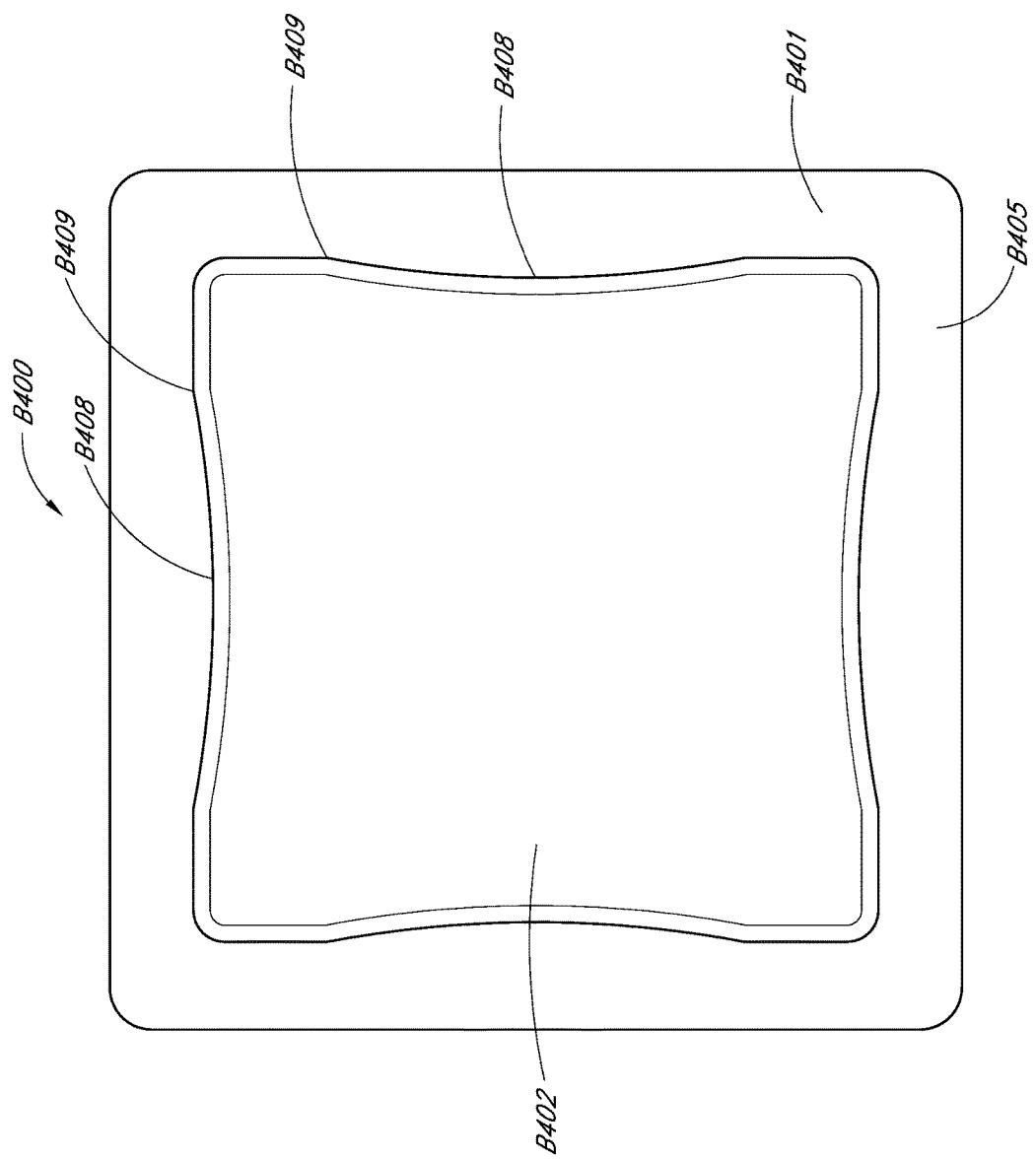
Figure 26F:
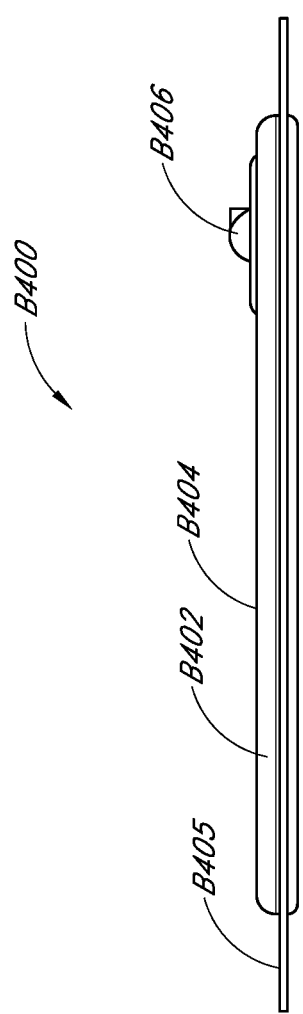
Figure 27A:
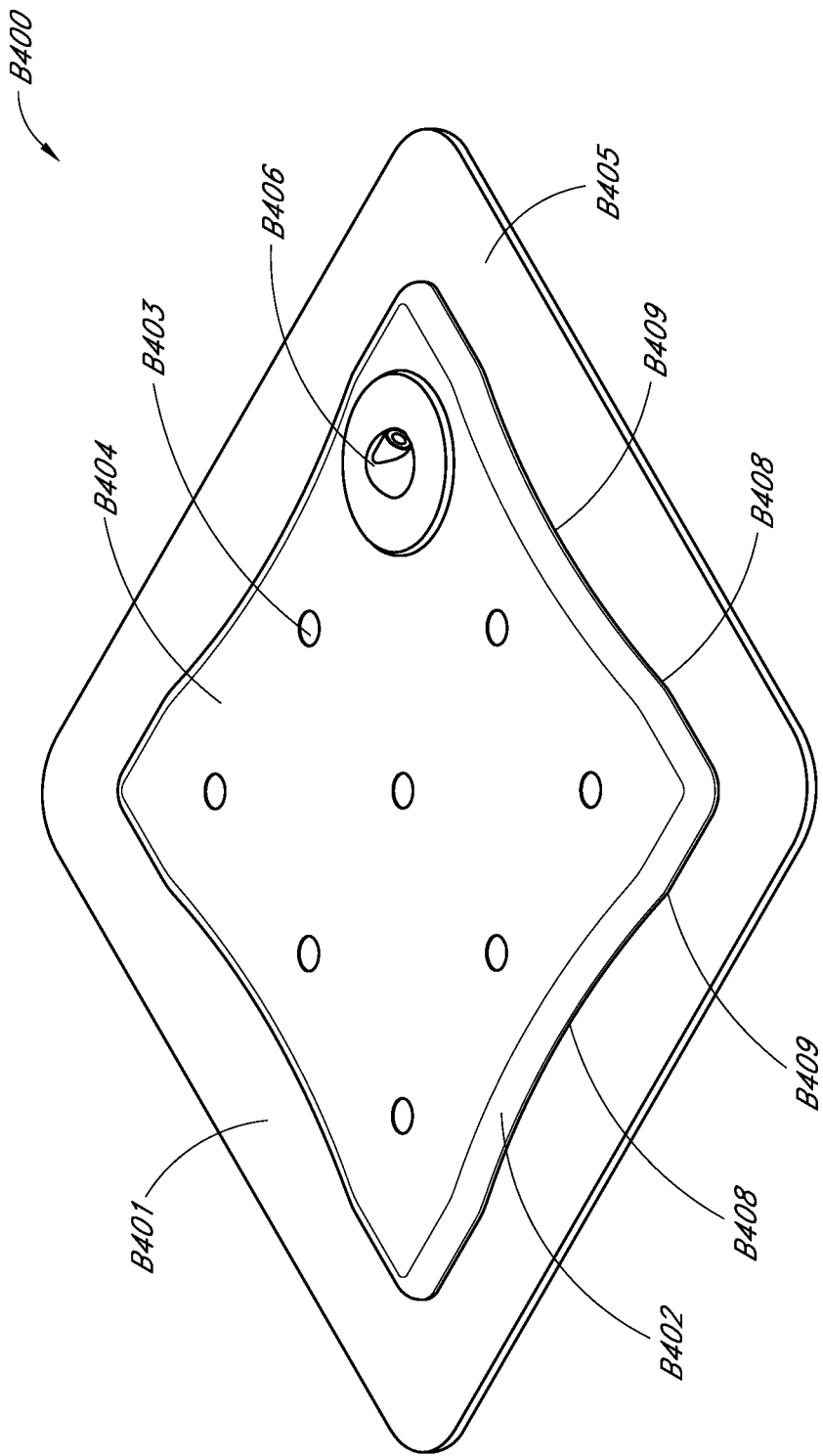
Figure 27B:
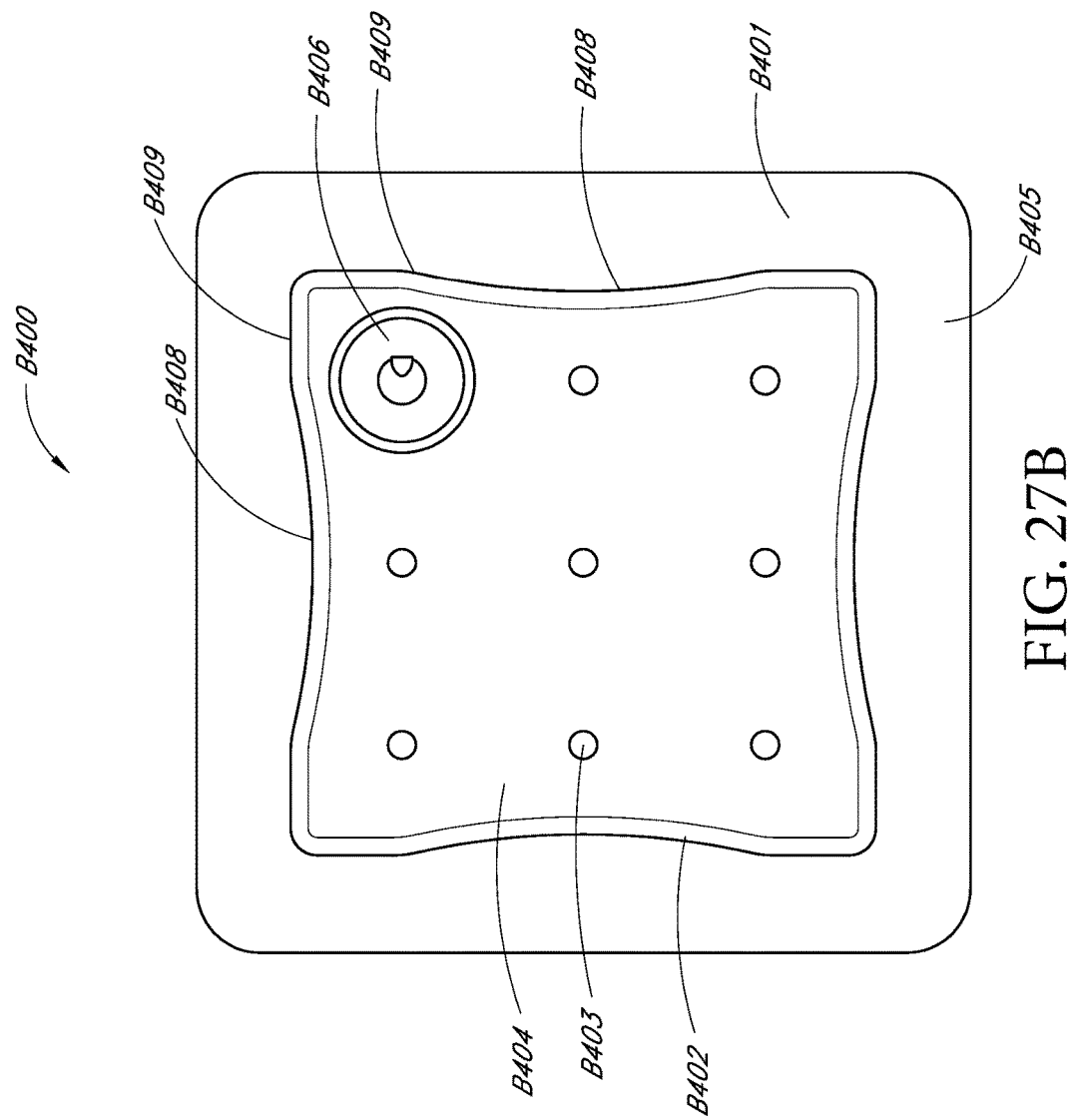
Figure 27C:
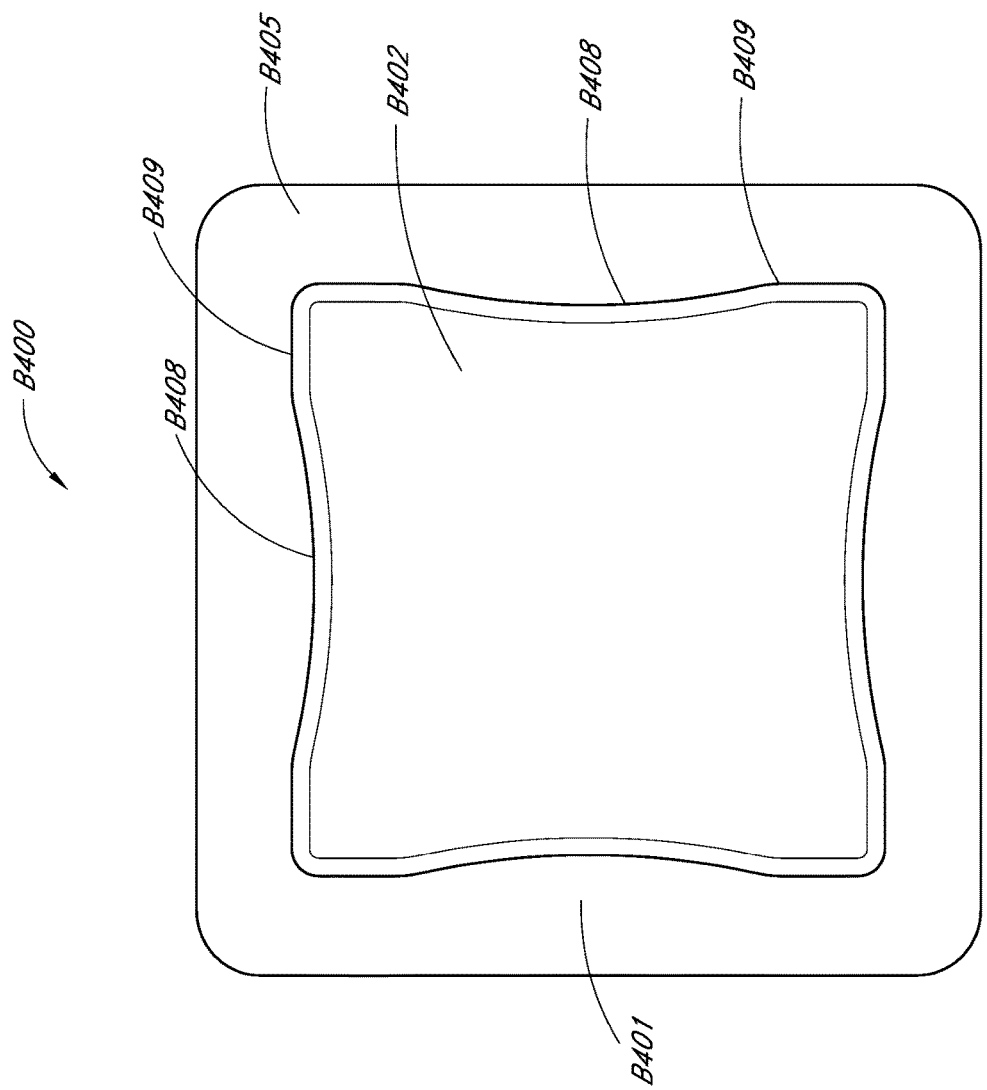
Figure 27F:
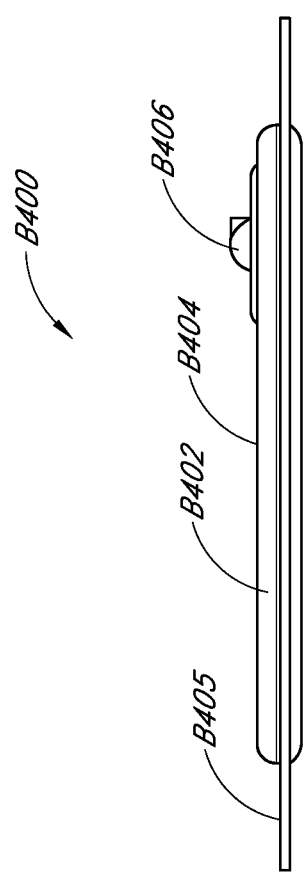
Figure 28A:
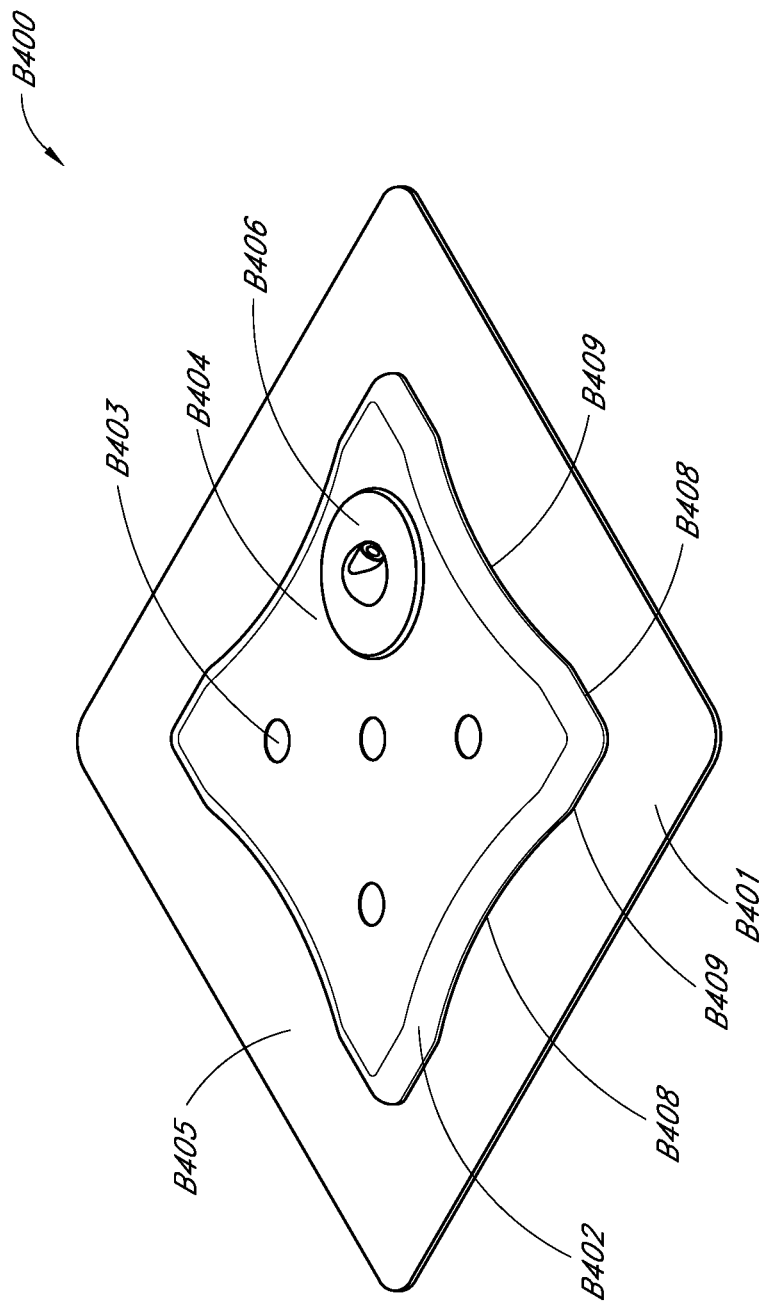
Figure 28B:
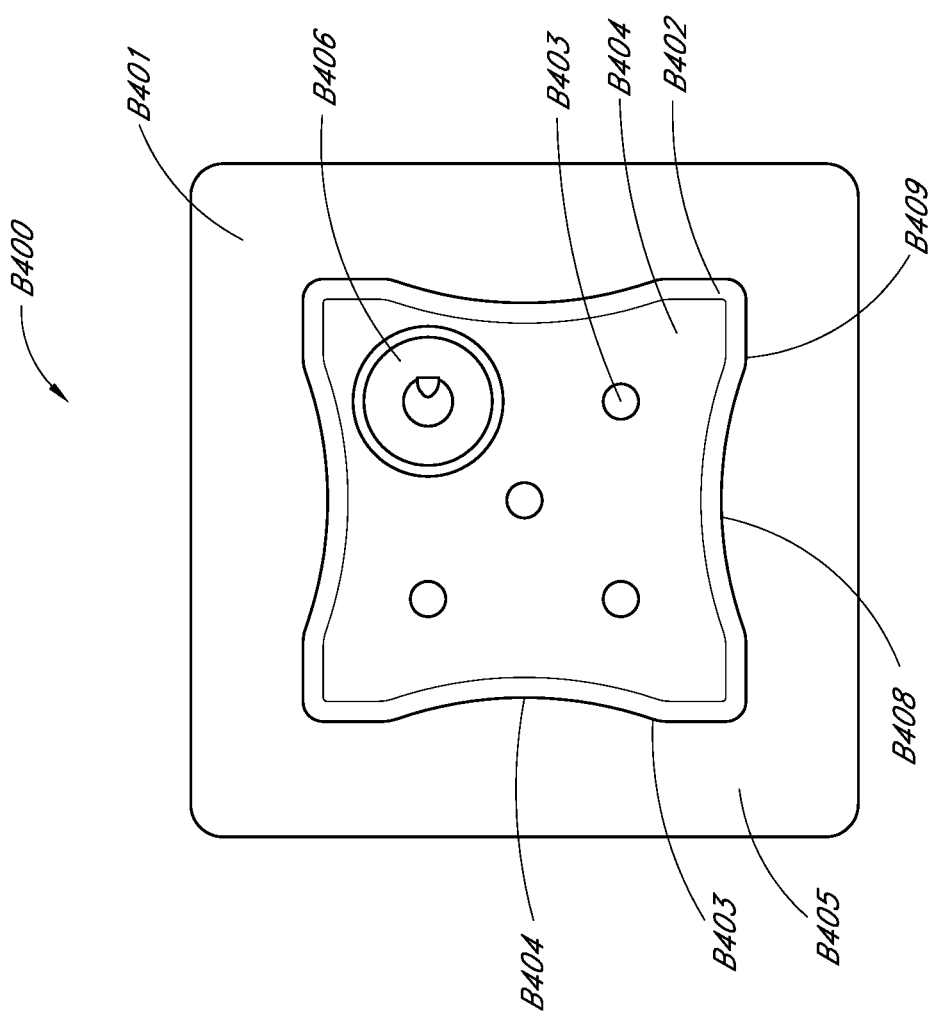
Figure 28C:
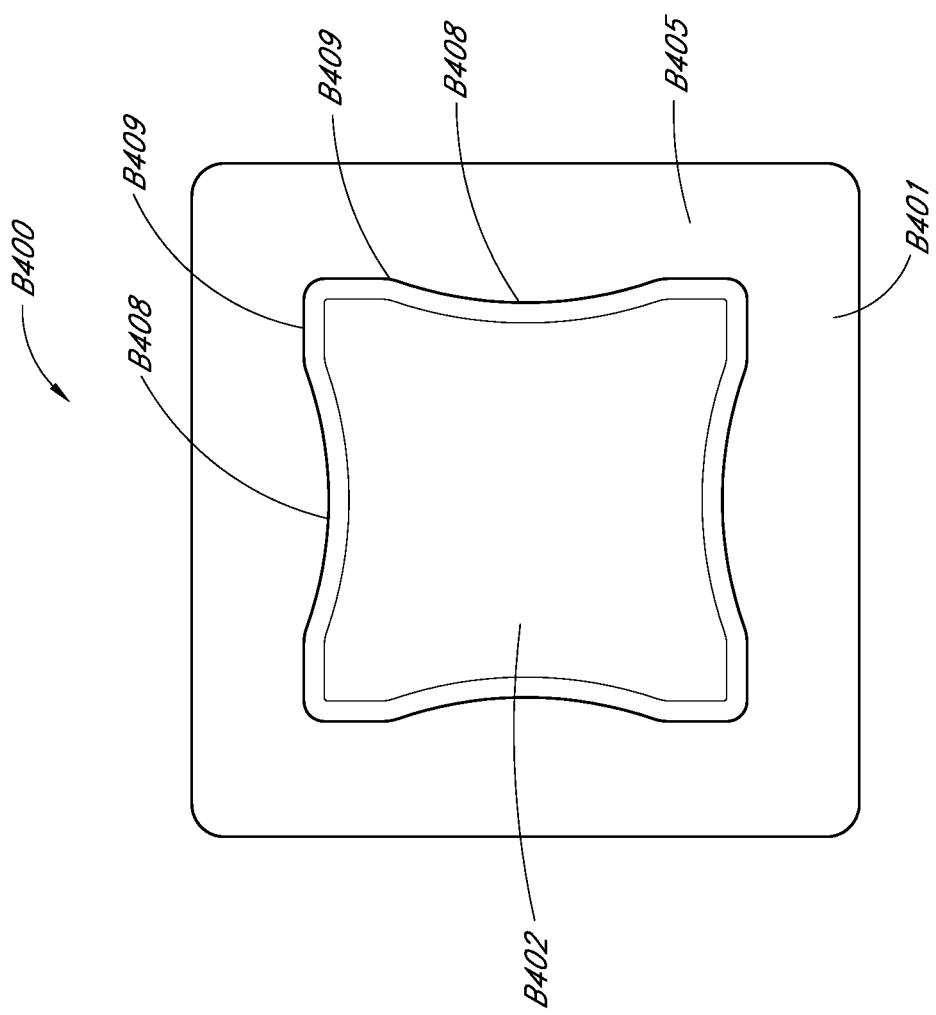
Figure 28D:
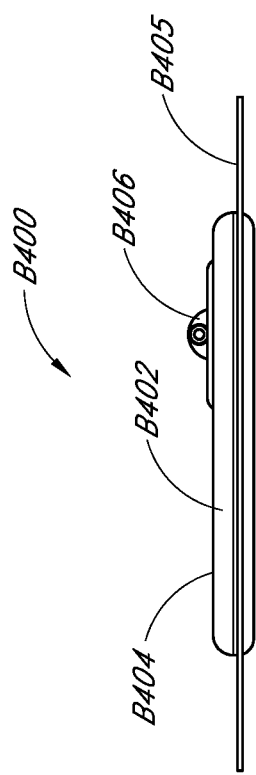
Figure 28E:
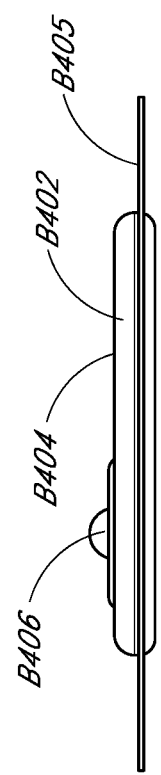
Figure 28F:
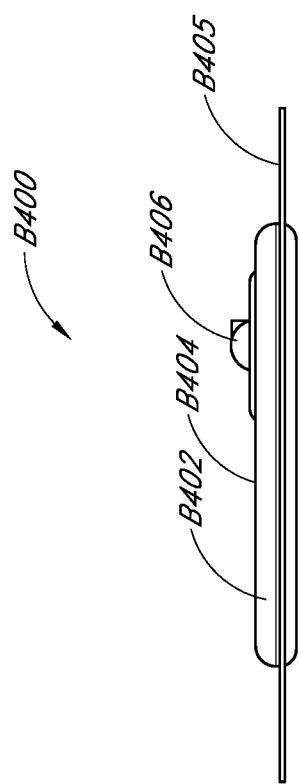

FIGS. 21B and 21C illustrate a top view and bottom view of the embodiment of a wound dressing described in FIG. 21A. FIGS. 21D and 21E illustrate a front and back view respectively of the wound dressing B400 described in FIG. 21A. FIG. 21F illustrates a side view of the wound dressing as described in FIG. 21A.

Embodiments of the wound dressings described herein may be arranged such that each embodiment may have enhanced compatibility with body movement. This can be achieved by using a different shape for different wound types or areas of the body. Wound dressing embodiments can be of any suitable shape or form or size as illustrated in FIGS. 21A-F, 22A-F, 23A-F, 24A-F, 25A-F, 26A-F, 27A-F, 28A-F, and 40A-F. The overall dimensions of the dressings as illustrated in FIGS. 21A-F, 22A-F, 23A-F, 24A-F, 25A-F, 26A-F, 27A-F, 28A-F may be, for example but without limitation, 300 mm×150 mm, 200 mm×150 mm, 400 mm×100 mm, 300 mm×100 mm, 200 mm×100 mm, 250 mm×250 mm, 200 mm×200 mm, and 150 mm×150 mm, respectively, although any total size may be used, and the size may be determined to match particular wound sizes. The oval-shaped dressing in FIGS. 40A-F may, in some embodiments, measure 190 mm×230 mm, or 145.5 mm×190 mm. Again, it will be understood that the embodiments described in the foregoing are simply illustrative embodiments illustrating possible sizes, dimensions, and configurations of wound dressings, and that other configurations are possible.

As noted above, the preceding embodiments illustrated in FIGS. 21A-F, 22A-F, 23A-F, 24A-F, 25A-F, 26A-F, 27A-F and 28A-F may comprise a waisted portion B408 located inwardly with reference to an edge B409 of the absorbent layer B402. The contour of the absorbent layer to the waisted portion B408 is preferably rounded and smooth. In the embodiments of FIGS. 21A-F, 22A-F, 23A-F, 24A-F and 25A-F, the inward distance between the edge B409 and the waisted portion B408 may range from 1 mm, 5 mm, 10 mm, 15 mm, 20 mm, and 30 mm. Preferably, the inward distance is 10 mm. In the embodiments of FIGS. 26A-F, 27A-F, and 28A-F the inward distance between the edge B409 and the waisted portion B408 may range from 5 mm, 10 mm, 20 mm, 30 mm, 40 mm, 45 mm, 50 mm, 60 mm, and 75 mm. FIGS. 22A-F illustrate a perspective view, a top view, a bottom view, a front view, a back view, and a side view, respectively, of an embodiment of a wound dressing B400. In some embodiments, the dressing may measure 200 mm×150 mm. The wound dressing B400 of FIGS. 22A-F can have a similar configuration and components as described above for FIGS. 21A-F, except the embodiments of FIG. 22A-F are of a smaller size. Additionally, in contrast to the embodiment of FIGS. 21A-F which comprises a 5×2 configuration of an array of dots viewing windows, the embodiment of FIGS. 22A-F comprises a viewing window configuration comprising a 3×2 array of dots.

FIGS. 23A-F illustrate a perspective view, a top view, a bottom view, a front view, a back view, and a side view, respectively, of an embodiment of a wound dressing B400. In some embodiments, the dressing may measure 400 mm×100 mm. The wound dressing B400 of FIGS. 23A-F can have a similar configuration and components as described above for FIGS. 21A-F, except the embodiments of FIG. 23A-F are of a different size. Additionally, in contrast to the embodiment of FIGS. 21A-F, the embodiment of FIGS. 23A-F comprises a viewing window configuration comprising an 8×1 array of dots.

FIGS. 24A-F illustrate a perspective view, a top view, a bottom view, a front view, a back view, and a side view, respectively, of an embodiment of a wound dressing B400. In some embodiments, the dressing may measure 300 mm×100 mm. The wound dressing B400 of FIGS. 24A-F can have a similar configuration and components as described above for FIGS. 21A-F, except the embodiments of FIG. 24A-F are of a different size. Additionally, in contrast to the embodiment of FIGS. 21A-F, the embodiment of FIGS. 24A-F comprises a viewing window configuration comprising a 5×1 array of dots.

FIGS. 25A-F illustrate a perspective view, a top view, a bottom view, a front view, a back view, and a side view, respectively, of an embodiment of a wound dressing B400. In some embodiments, the dressing may measure 200 mm×100 mm. The wound dressing B400 of FIGS. 25A-F can have a similar configuration and components as described above for FIGS. 21A-F, except the embodiments of FIG. 25A-F are of a different size. Additionally, in contrast to the embodiment of FIGS. 21A-F, the embodiment of FIGS. 25A-F comprises a viewing window configuration comprising a 3×1 array of dots.

FIGS. 28A-F illustrate a perspective view, a top view, a bottom view, a front view, a back view, and a side view, respectively, of an embodiment of a wound dressing B400. In some embodiments, the dressing may measure 150 mm×150 mm. The wound dressing B400 of FIGS. 28A-F can have a similar configuration and components as described above for FIGS. 21A-F, except the embodiments of FIGS. 25A-F are of a different size. Additionally, in contrast to the embodiment of FIGS. 21A-F, the embodiment of FIGS. 28A-F comprises a viewing window configuration comprising a quincunx array of dots. The quincunx array of dots configuration consists of five dots arranged in a cross, with four of the dots forming a square or rectangle where one dot is positioned at each of the four corners of the square or rectangle shaped wound dressing and a fifth dot in the center. However, one corner of the wound dressing preferably has the fluidic connector or port B406 in place of a dot in the quincunx dot array.

FIGS. 26A-F illustrate a perspective view, a top view, a bottom view, a front view, a back view, and a side view, respectively, of an embodiment of a wound dressing B400. In some embodiments, the dressing may measure 250 mm×250 mm. The wound dressing B400 of FIGS. 26A-F can have a similar configuration and components as described above for FIGS. 21A-F, except the embodiments of FIGS. 26A-Fare of a different size. Additionally, in contrast to the embodiment of FIGS. 21A-F, the embodiment of FIGS. 26A-F comprises a viewing window configuration comprising a 3×3 array of dots with an absent dot at a corner position of the wound dressing and in its place is a domed port or a fluidic connector B406 completing the 3×3 array.

FIGS. 27A-F illustrate a perspective view, a top view, a bottom view, a front view, a back view, and a side view, respectively, of an embodiment of a wound dressing B400. In some embodiments, the dressing may measure 200 mm×200 mm. The wound dressing B400 of FIGS. 27A-F can have a similar configuration and components as described above for FIGS. 21A-F, except the embodiments of FIGS. 27A-F are of a different size. Additionally, in contrast to the embodiment of FIGS. 21A-F, the embodiment of FIGS. 27A-F comprises a viewing window configuration comprising a 3×3 array of dots with an absent dot at a corner position of the wound dressing and in its place is a domed port or a fluidic connector completing the 3×3 array.

The additional sizes and shapes illustrated in FIGS. 21A-F, 22A-F, 23A-F, 24A-F, 25A-F, 26A-F, 27A-F, 28A-F, and 40 may incorporate the waisted portion B408, obscuring layer B404, viewing windows B403, and other components and embodiments described herein.

Figures 29A, 29B:
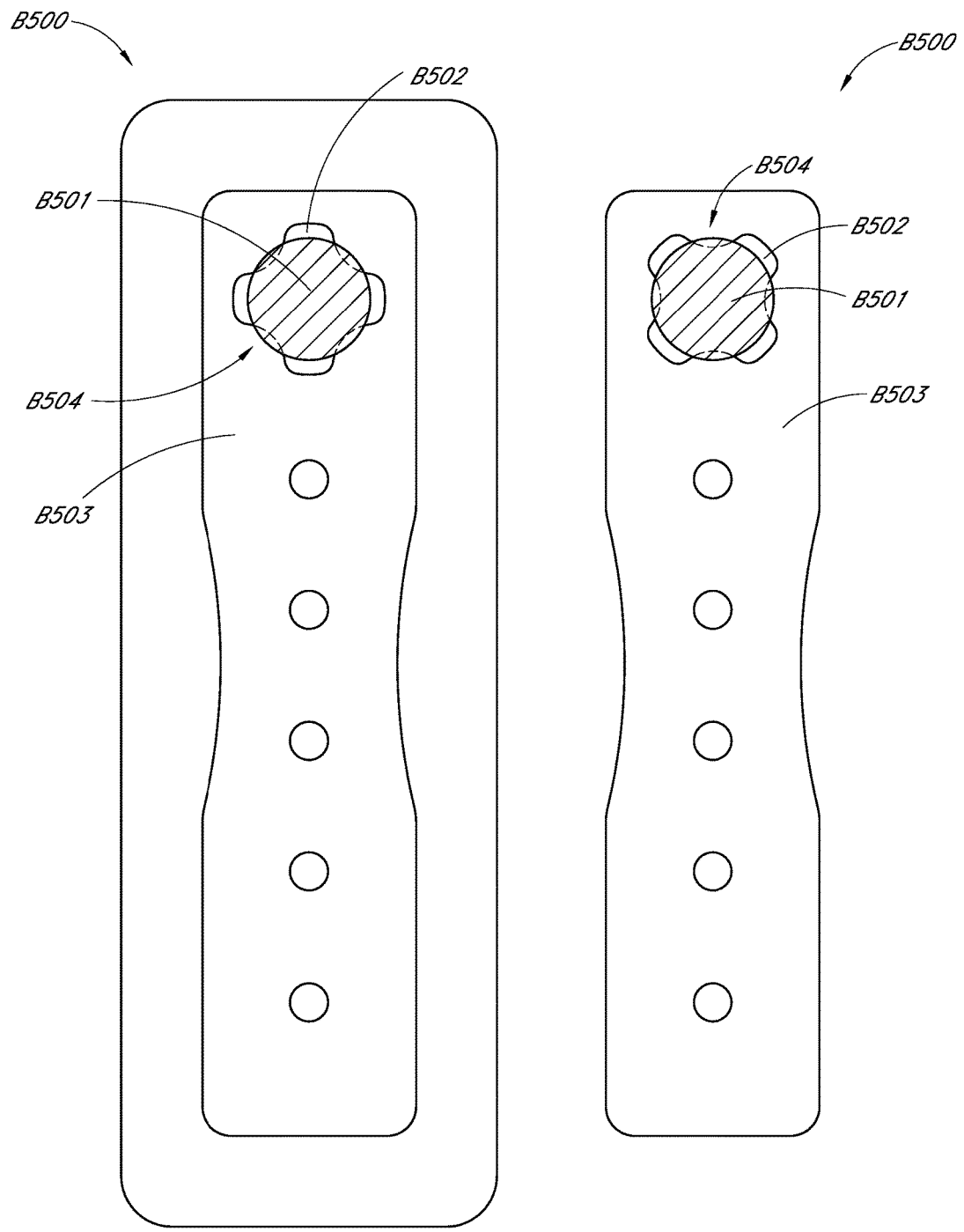
FIGS. 29A-B and 30 illustrate a top view of an embodiment of a wound dressing including a cross-shaped viewing window.
Figure 30:
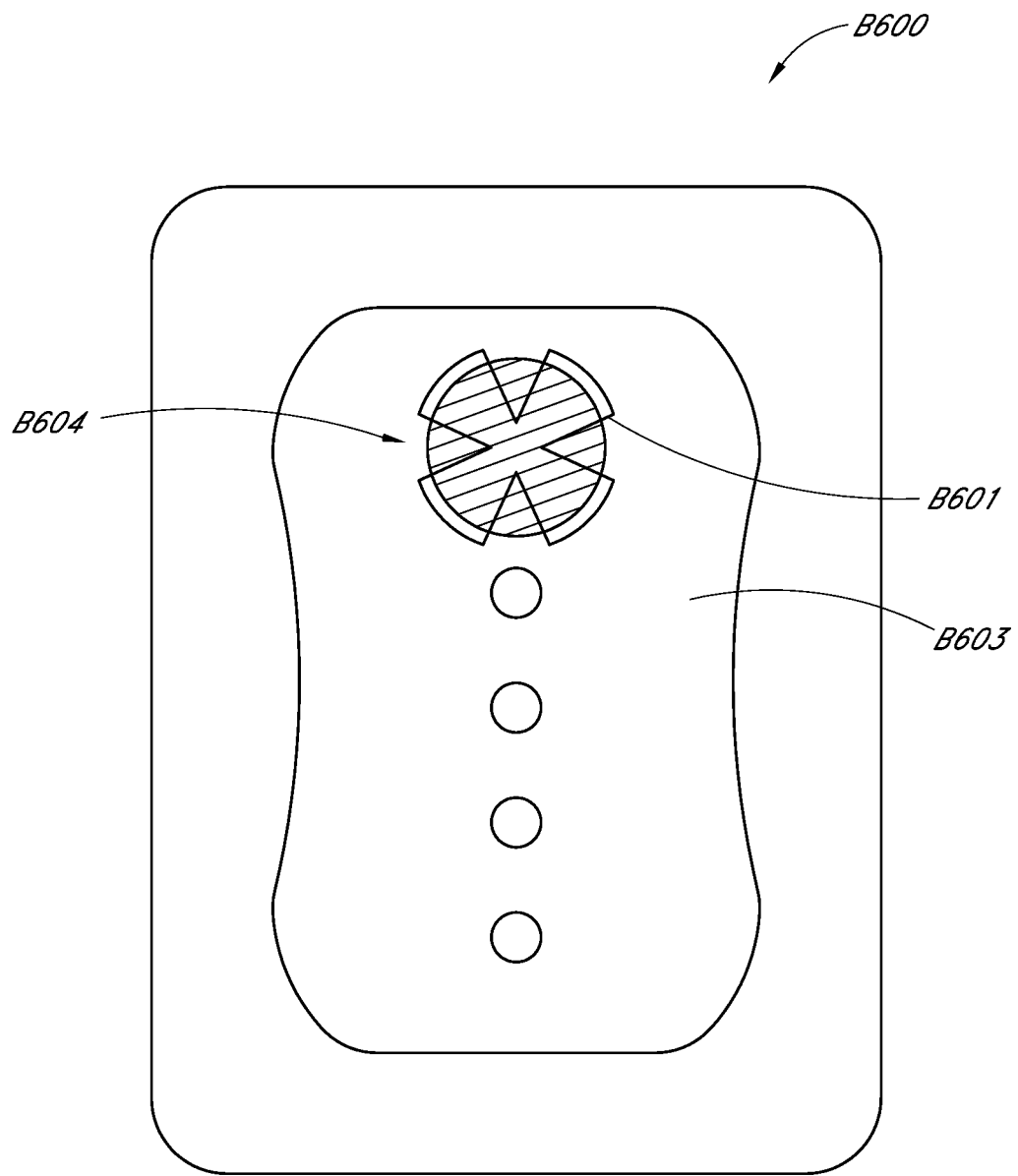

FIGS. 29A, 29B, and 30 illustrate embodiments of a dressing B500 comprising one or more orifice viewing windows B502 at, near, or adjacent to the port. The orifice viewing windows B502 can be provided at, near, adjacent to the port B504 in the backing layer for viewing of the absorbent material B503 present in proximity to the port B504. The orifice viewing windows B502 can have the same structure and/or function as the viewing windows herein described. In some embodiments, the orifice viewing window B502 can be formed from a cross-shaped or Maltese-cross-shaped aperture or cut-out B501 in the obscuring layer. The arms of the cross-shaped cut-out B501 can be aligned with the longitudinal length and transverse width of the absorbent material B503 as shown in FIG. 29A. Alternatively, the arms of the cross-shaped cut-out B501 can be offset from the longitudinal length and transverse width of the absorbent material, at an angle, for example, a 45° angle, as illustrated in FIG. 29B. The arms of the cross-shaped cut-out may span a larger dimension than a hole in the absorbent material below the cut-out B501. For example, the arms may span a dimension of about 25 mm, while the through-hole in the absorbent material may have a diameter of 10 mm.

Additionally, FIG. 30 illustrates an embodiment of a wound dressing B600 in which the arms of the cross-shaped aperture can have flared edges B601. The orifice viewing windows B502 at, near, or adjacent to the port B604 may be used to indicate that fluid is approaching the port B604 or that the dressing B600 is otherwise becoming saturated. This can assist the clinician or patient in maintaining the wound dressing and determining when to change the dressing, because once fluid contacts the center of the port, such fluid contact may at least partially occlude the hydrophobic filter that may be contained therein so as to interrupt or at least partially block the application of negative pressure. The orifice viewing windows B502 can be used with the fluidic connector as well as the domed port or any other suitable connector.

Figure 31A:
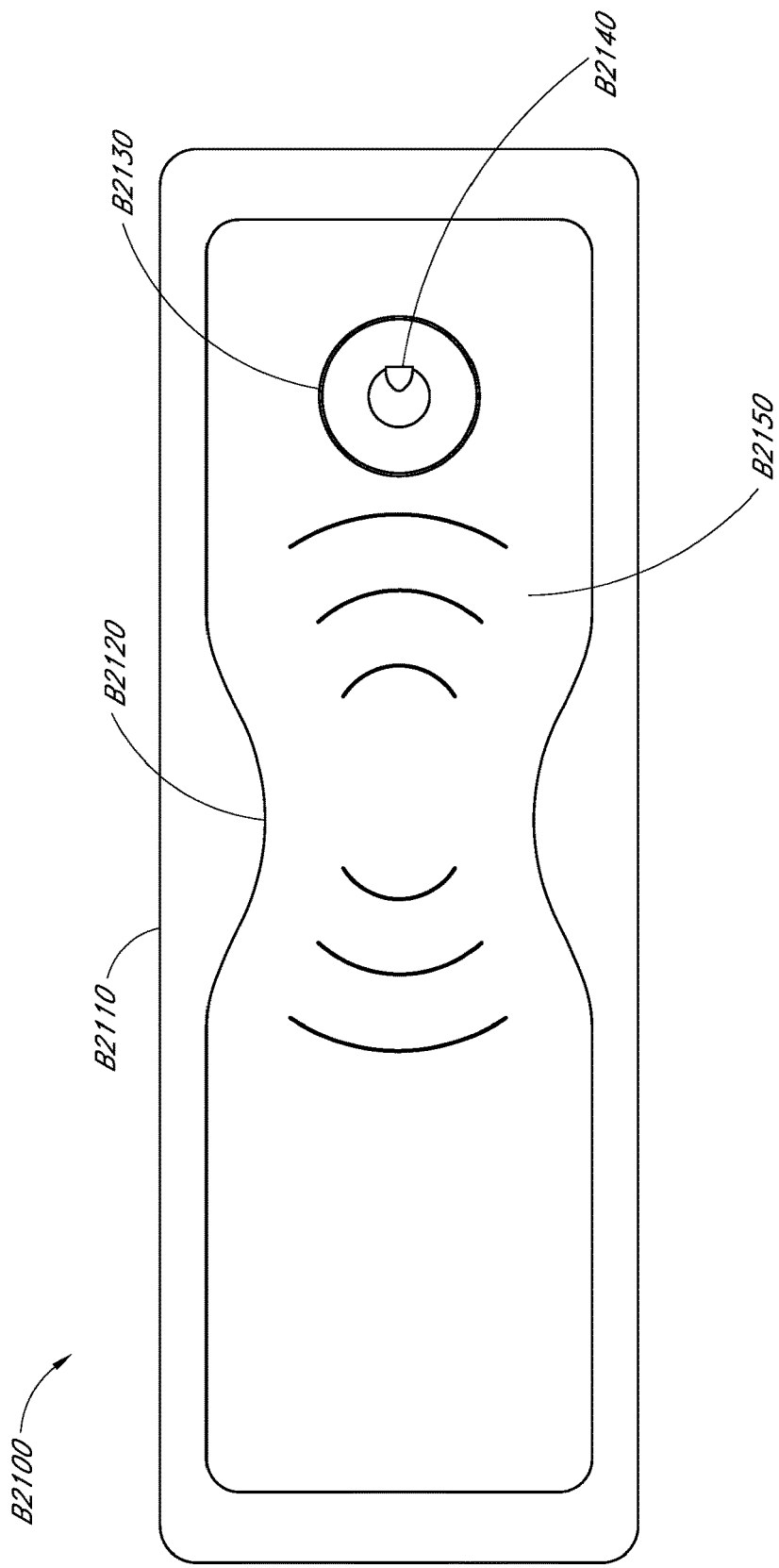
FIGS. 31A-B illustrate a top view of an embodiment of a wound dressing including slits in the wound dressing.
Figure 31B:
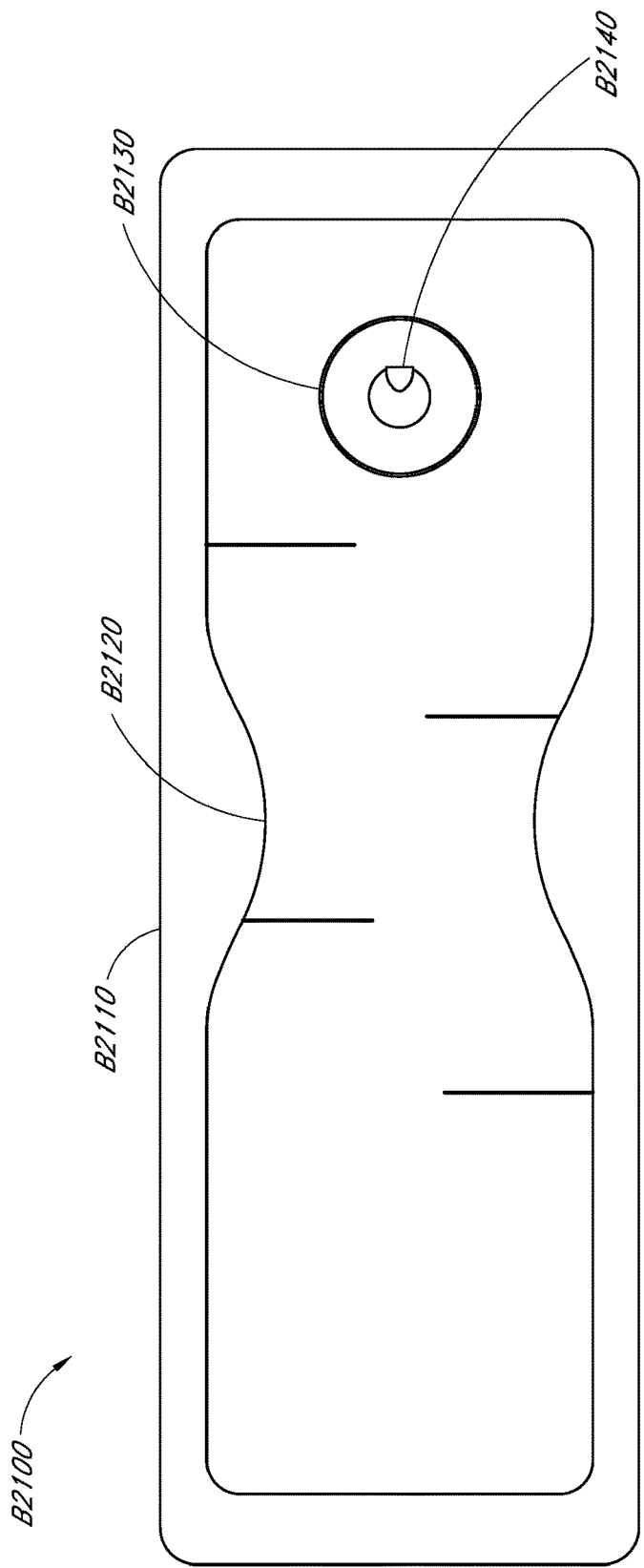

As with FIGS. 31A and 31B, the wound dressing may also be provided with one or more slits B2150 to aid the dressing in conforming to a non-planar area. FIG. 31A illustrates an embodiment of a wound dressing B2100 with a narrowed central portion or waisted portion B2120 and concentric slits B2150. This embodiment may be useful for the treatment of wounds on non-planar surfaces or otherwise contoured wounds, including, for example, feet, knees, sacral regions, or other such areas. In some embodiments, the wound dressing B2100 may provide for one or more slits B2150 cut into the dressing, preferably into the absorbent layer, that may enhance the conformability of the dressing. In this embodiment, the slits B2150 are cut in concentric ovoid arcs, although other configurations (as discussed below) are possible. Preferably, the area under the port B2130 or fluidic connector disposed at the top of the device is free from the slits B2150, as this may interfere with fluid transfer from the dressing. In some embodiments, the slits B2150 may be formed as part of, in addition to, or instead of baffles that may be present within the absorbent layer so as to may aid in distribution of wound exudate. In these embodiments, and with all other embodiments described herein, although a domed connector is shown attached to the dressing, this may be interchanged with any other suitable connector, including for example embodiments of the fluidic connectors described in FIGS. 39A and 39B (as described below).

FIG. 31B illustrates an embodiment of a wound dressing B2100 with a narrow central portion B2120. Here, however, one or more slits B2150 extending across the width of the dressing may be present. Preferably, these slits B2150 do not extend entirely across the width of the dressing, in order to promote fluid transfer within the absorbent layer. The slits B2150 may enhance conformability of the dressing, possibly in conjunction with the waisted configuration of the dressing, when applied to a non-planar or contoured wound area. For example, such a dressing B2100 may be useful when applied so as to wrap around an arm or a leg.

Figure 39A:
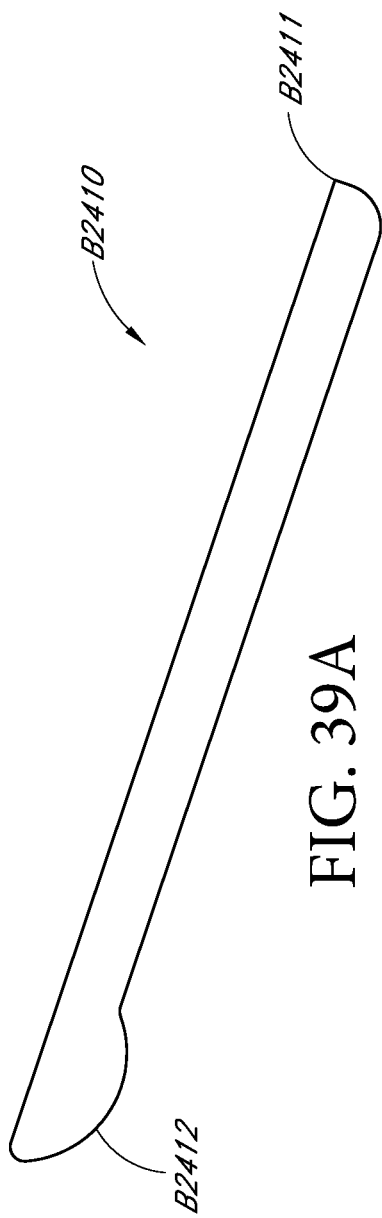
FIG. 39A-B illustrate embodiments of white and colored fluidic connectors, respectively.
Figure 39B:
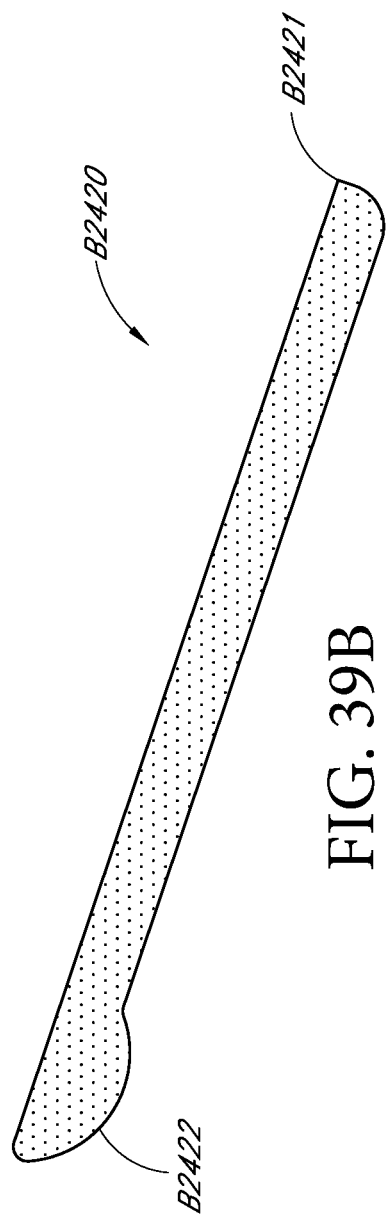

FIGS. 39A and 39B illustrate embodiments of white and black fluidic connectors B2410, B2420, respectively, that may be used to connect an embodiment of a wound dressing described herein to a source of negative pressure. In some embodiments, the domed port used in other embodiments discussed herein (e.g., as illustrated above in FIG. 17) may be replaced by the fluidic connector B2410, B2420, for example as illustrated in FIGS. 32-35. The fluidic connector B2410, B2420 may be flexible and/or enhance the comfort of the patient. The fluidic connector B2410, B2420 preferably comprises a fluidic connector body configured to transmit fluid through itself, including, for example, negative pressure and/or wound exudate. The fluidic connector body is preferably encapsulated within one or more layers of fluid-impermeable material. In some embodiments, the fluid-impermeable material is heat-sealed together to enclose the fluid connector body.

With reference now to FIG. 39A, the body of the fluidic connector B2410 is preferably be constructed from a material configured to transmit fluids therethrough, including fabrics such as 3D fabric. In some embodiments, the thickness of the fluidic connector body may measure between 0.5 to 4 mm, preferably 0.7 to 3 mm, and even more preferably between 1 and 2 mm; in a preferred embodiment the fluid connector body is 1.5 mm thick. Suitable materials that may be used for the fluidic connector body, including the 3D fabric, are disclosed in U.S. application Ser. No. 13/381,885, filed Dec. 30, 2011, published as US2012/0116334, titled "APPARATUSES AND METHODS FOR NEGATIVE PRESSURE WOUND THERAPY," and which is hereby incorporated by reference in its entirety. Use of the 3D fabric in the fluidic connector body may help alleviate fluid blockage when the connector is kinked, and may further provide for a soft fluidic connector that alleviates contact pressure onto a patient, for example when the patient's weight is pressed against the fluidic connector. This may enhance patient comfort and reduce the likelihood of pressure ulcers.

Testing of various weights in various configurations on embodiments of fluidic connectors comprising a 3D fabric was completed. The testing included weights above those believed to be likely to be encountered by a patient, as maximal pressure on a heel for a patient using dressings was found to be 1.3 kg/cm$^2$ in some studies. Preferably, embodiments of the fluidic connectors described herein, especially when comprising 3D fabric, can transmit therapeutic levels of negative pressure (i.e., in an amount sufficient to heal a wound) while a weight is pressed down thereupon. For example, embodiments are preferably able to transmit therapeutic levels of negative pressure while an external pressure applied on the dressing and/or 3D fabric of up to 1 kg/cm$^2$, preferably up to 2 kg/cm$^2$, and even more preferably up to 4 kg/cm$^2$. Certain embodiments, as described below, have been tested as being capable of transmitting therapeutic levels of negative pressure while an external pressure applied on the dressing and/or 3D fabric is above 6 kg/cm².

In the testing, a 400 ml wound cavity was used, and pressure was measured both at the wound and at the pump. Embodiments of a fluidic connector comprising 3D fabric were tested when laid flat with a weight placed thereupon. Testing indicated that when no pressure was applied to the fluidic connector, the pressure differential between the pressure at the pump and at the cavity was approximately 2 mmHg. Various different weights were applied, ranging between 2 and 12 kg/cm², in 2 kg increments, and the resulting pressure difference was approximately linear, with the pressure difference at 12 kg/cm² being calculated at 33 mmHg, while the pressure difference at 2 kg/cm² being only 16 mmHg. The relation between the pressure difference in mmHg was found to equal approximately 4.5 times the applied load in kg/cm². Testing also indicated that the relative pressure difference between the pressure at the pump and the pressure at the wound after five minutes was less than 10 mmHg when measured at the pump for loads under 4 kg/cm², and under 20 mmHg when measured at the wound for loads under 4 kg/cm².

Testing was also performed with a weight laid on an embodiment of a fluidic connector, while being bent at a 90° angle. Various different weights were applied, ranging between 2 and 12 kg/cm², in 2 kg increments, and the resulting pressure difference was approximately linear, with the pressure difference at 12 kg/cm² being calculated at 51 mmHg, while the pressure difference at 2 kg/cm² being 17 mmHg. The relation between the pressure difference in mmHg was found to equal approximately 8 times the applied load in kg/cm². Testing also indicated that the relative pressure difference between the pressure at the pump and the pressure at the wound after five minutes was approximately 20 mmHg when measured at the pump for loads under 4 kg/cm², and under 30 mmHg when measured at the wound for loads under 4 kg/cm².

Further testing was performed with a weight laid on an embodiment of a fluidic connector, while being bent at a 180° angle (i.e., folded over itself). Various different weights were applied, ranging between 2 and 12 kg/cm², in 2 kg increments, and the resulting pressure difference was approximately linear, with the pressure difference at 12 kg/cm² being calculated at 76 mmHg, while the pressure difference at 2 kg/cm² being 25 mmHg. The relation between the pressure difference in mmHg was found to equal approximately 10.7 times the applied load in kg/cm². Testing also indicated that the relative pressure difference between the pressure at the pump and the pressure at the wound after five minutes was approximately 20 mmHg when measured at the pump for loads under 4 kg/cm², and under 30 mmHg when measured at the wound for loads under 4 kg/cm².

Testing was also performed on different widths and thicknesses of 3D fabric that may be used in embodiments of fluidic connectors described herein. In a particular example, the maximum negative pressure that could be applied using 3D fabric measuring 1, 1.25, 1.5, 1.75, and 2 cm in width was found to be between 85 and 92 mmHg, respectively. Upon application of an applied load of 1 kg/cm², however, the maximum negative pressure applied for a 1 cm-width embodiment dropped to 75 mmHg, while the 1.25 and 1.5 cm-width embodiments were essentially unchanged, exhibiting pressures between 85 and 90 mmHg. Application of a 1 kg/cm² weight made the 1 cm-width embodiment maximum negative pressure drop to about 73 mmHg, while the 1.25 cm-width embodiment dropped to about 84 mmHg. The 1.5 cm-width embodiment showed a minimal maximum negative pressure change down to approximately 86 mmHg. As tested, the greatest increases in flow rate (as evidenced by the maximal negative pressures applied) were greatest when increasing the width of the 3D fabric from 1 cm to 1.25 cm, and stabilized above 1.5 cm. Similarly, increasing the width of the 3D fabric (i.e., above 1 cm) was found to slightly reduce the amount of time required to pump a wound cavity down to a target negative pressure.

Further testing with single and double layers of Baltex 3540 3D fabric, either single or double thickness, indicated that while the maximum negative pressure applied using a single thickness fabric dropped from about 88 mmHg with no applied weight to about 73 mmHg with a 2 kg/cm² weight. However, a double thickness fabric showed minimal change in the maximum amount of negative pressure applied, dropping from 90 mmHg with no weight applied to about 87 mmHg with an applied load of 2 kg/cm².

Depending on the particular application, using wider and/or thicker 3D fabric may permit improved air flow, together with greater pressure and kink resistance in some context; this may be useful especially if higher absolute negative pressure need to be applied to the wound. However, the greater kink and pressure resistance may need to be balanced with other concerns such as perceived bulk and size of the fluidic connector, aesthetics, and comfort, which may require use of a thinner 3D fabric.

In some embodiments, the proximal end B2411 of the fluidic connector B2410 is configured to be connected to a tube or other conduit that is in fluid communication with a source of negative pressure via the fluid connector body, although some embodiments may provide for the fluidic connector B2410 to be directly connectable to a source of negative pressure without needing a conventional tube. The distal end B2412 of the fluidic connector B2410 may be enlarged, and is configured to be attached and/or adhered to a dressing, for example via an aperture in the backing layer of the dressing and/or in the fluidic connector B2410, so that the fluid connector body is in fluid communication therewith.

In one configuration and as illustrated in FIG. 39A, the distal end B2412 of the fluidic connector B2410 may be convex on one side and flat on the opposite side. As illustrated in FIGS. 32-34 below, the flat side may be aligned with the edge of the absorbent layer with the convex side extending over the aperture in the backing layer. The fluidic connector B2410 may be provided preattached to the dressing portion, or may be provided in an unattached format so as to be connectable to the dressing portion by the patient or caregiver. The enlarged distal end B2412 may aid in providing a larger area capable of transmitting negative pressure to the dressing, although the distal end may be provided without any enlargement. Although preferred embodiments of the fluidic connector B2410 are used in dressings that contain substantially all wound exudate within the absorbent material, such that the fluidic connector transmits essentially only air, some embodiments of the fluidic connector may be configured so as to transfer exudate in addition to air. In embodiments of the fluidic connector that are configured to transfer essentially only air (while wound exudate remains substantially within the absorbent material), the distal end of the fluidic connector is preferably provided with a filter configured to block fluid transport beyond itself, such as a hydrophobic filter. An example of such a configuration is described in U.S. Provisional Application Ser. No. 61/650,904, filed May 23, 2012, titled "APPARATUSES AND METHODS FOR NEGATIVE PRESSURE WOUND THERAPY," and which is hereby incorporated into this present application in its entirety.

In embodiments of the fluidic connector that are configured to transfer exudate in addition to air, the fluidic connector may be provided with a secondary air leak channel configured to provide a flow of ambient air to the wound site. Preferably, the secondary air leak channel is provided with a filter to prevent contamination of the wound.

Turning now to FIG. 39B, this figure shows an embodiment similar to FIG. 39A, but where the fluidic connector B2420 may appear colored, for example as a result of an obscuring layer similar to that previously described. In some embodiments, obscuring coloration may be provided by dyeing the material used in the fluidic connector B2420, for example the 3D fabric that may be used therein. In some embodiments, the obscuring layer may be placed above the 3D fabric, either above or below the fluid-impermeable material. In some embodiments, the encapsulating fluid-impermeable material may be colored or tinted. Coloring the fluidic connector B2420 (e.g, via the obscuring layer) may enhance the aesthetic appeal of the device, help in disguising or making the device less obtrusive (in particular when the fluidic connector is visible to others), and, when the fluidic connector is used to transfer exudates away from the wound, may hide the presence of the exudates therein.

In some embodiments, the fluidic connector body may be colored as a result of an auxiliary compound such as activated charcoal. Further, some embodiments may provide for text or images to be printed thereon, for example for instructional or advertising purposes. Such improvements may enhance patient comfort and minimize embarrassment, thereby increasing patient compliance and satisfaction with the device. The obscuring layer in the fluidic connector can have all features described with reference to the obscuring layer of the wound dressing as herein described.

FIG. 33 illustrates an embodiment of a wound dressing B720 that comprises a hexagonal backing layer and a three-lobed configuration for the absorbent material and the obscuring layer. This wound dressing B720, as with several other embodiments described herein, may be advantageously applied to wounds or areas surrounding wounds that are located in non-planar areas. The embodiment illustrated here may be particularly advantageous when applied to protruding body portions, for example elbows and heels.

FIG. 34 illustrates a wound dressing B730 with a three-lobed configuration similar in some respects to the embodiment illustrated in FIG. 33. Here, however, the dressing is smaller and comprises more rounded projections. FIGS. 32-34 illustrate a fluidic connector B721, B731 similar to those described in FIGS. 39A and 39B attached to the device, with the flat end aligned with the edge of the absorbent material and the convex end extending over an aperture in the backing layer. This fluidic connector may enhance comfort and prevent pressure ulcers or other complications that may result from extended pressure of a conventional tube onto the wound or skin surrounding the wound (as described above). Of course, different connectors may be used, such as the domed port illustrated in FIG. 17.

Figure 36:
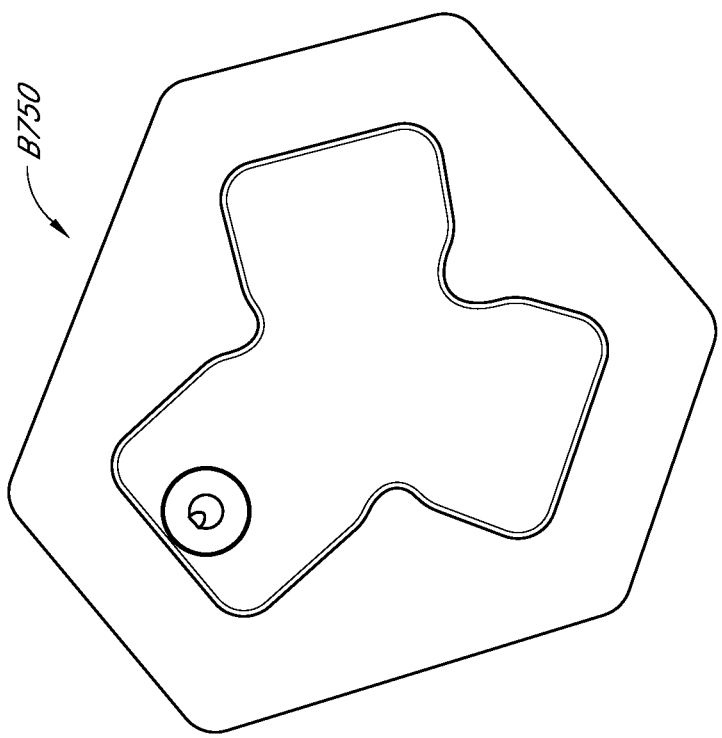
FIG. 36 illustrates a top view of an embodiment of a three-lobe wound dressing with flared ends on each lobe.
Figure 35:
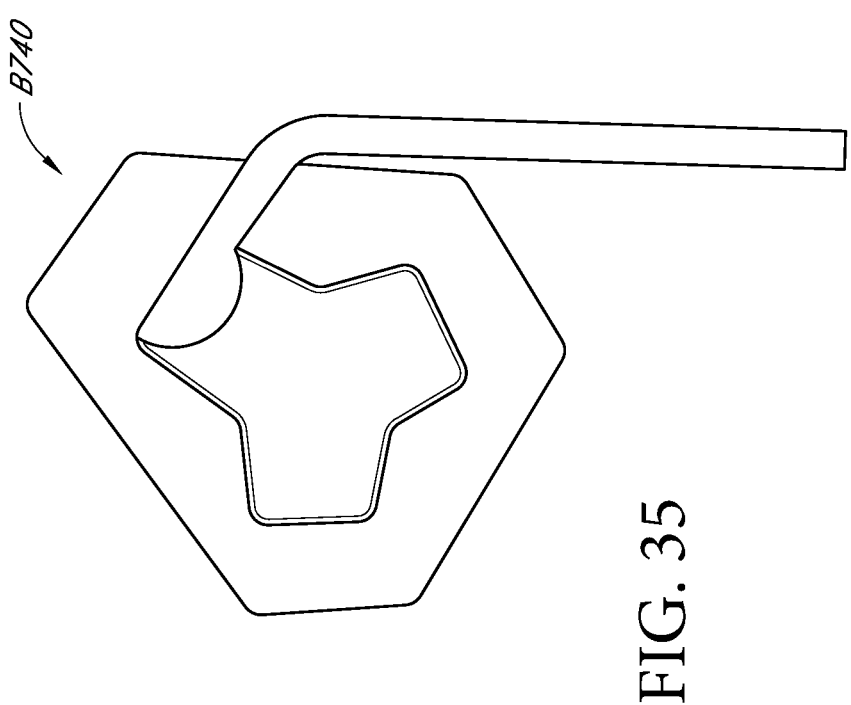
FIG. 35 illustrates a top view of an embodiment of a three-lobe wound dressing.

FIGS. 35-36 also illustrate additional embodiments of wound dressings B740, B750 with three-lobed configurations for the absorbent material and a hexagonal backing layer. The wound dressing B750 illustrated in FIG. 36 is larger where the lobes of the absorbent material comprises flared ends, while the wound dressing B740 illustrated in FIG. 35 is smaller and the absorbent material does not have flared ends. All suitable fluidic connectors or conduits may be used, and the domed port connector of FIG. 36 may be used in place of the fluidic connector of FIG. 35, and vice versa. As with the preceding embodiments, the absorbent layers may be colored or obscured, and one or more slits may be formed onto the absorbent layers to enhance conformability to non-planar surfaces. It will be appreciated that in the embodiments of FIGS. 33-36, the number of lobes may be varied, and the backing layer can have other shapes, and is not limited to being hexagonal.

Figure 37A:
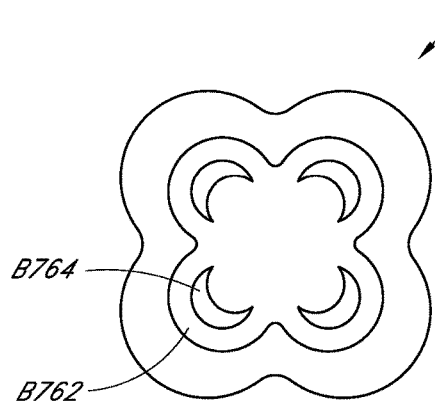
FIG. 37A illustrates a top view of an embodiment of a four-lobe wound dressing with crescent shaped cut-outs as viewing windows.
Figure 37B:
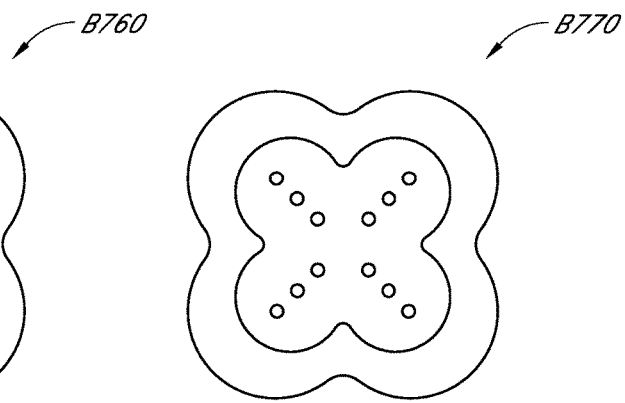
FIG. 37B illustrates a top view of an embodiment of a four-lobe wound dressing with an array of dots at viewing windows.
Figure 37C:
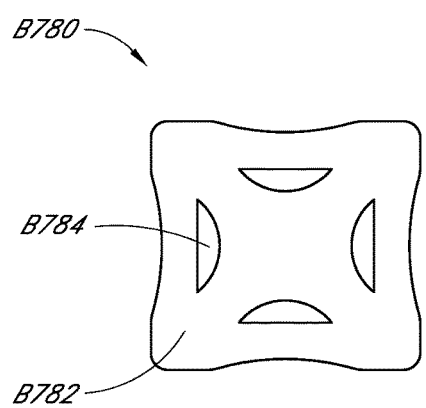
FIG. 37C illustrates a top view of an embodiment of a four-lobe wound dressing with viewing windows.

Additionally, FIGS. 37A-C and 38 illustrate embodiments of a wound dressing B760, B770, B780, B790 that comprises a four-lobed configuration. Although these embodiments are illustrated without a port or fluidic connector attached thereto, it will of course be understood that such ports and fluidic connectors are envisioned and may be attached in a similar fashion as described previously herein. FIGS. 37A-C comprise embodiments of a four-lobed wound dressing comprising an obscuring layer and viewing windows extending through the obscuring layer. The viewing windows can be used as discussed above for visualization of wound exudate in the absorbent layer. Examples of such viewing windows are illustrated in FIGS. 37A and 37B. The dressing B760 shown in FIG. 37A includes an obscuring layer B762 and crescent-shaped viewing windows B764 provided in the obscuring layer to extend through the obscuring layer allowing visibility of the dressing therebelow. The dressing B770 of FIG. 37B includes an obscuring layer B772 and a number of holes B774 therethrough acting as viewing windows for viewing the state of the dressing therebelow. FIG. 37C shows another dressing B780 including an obscuring layer B782 with viewing windows B784. With the dressings B760, B770, B780 the progress of exudate spread over the dressing and towards the edge of the dressing can be monitored.

Figure 38:
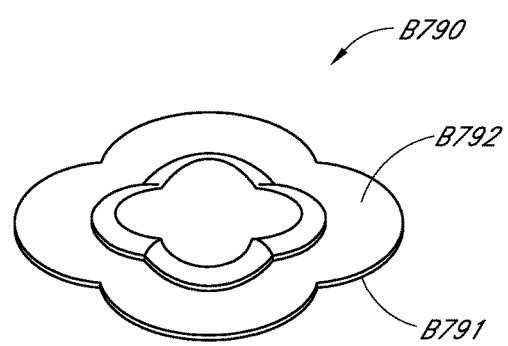
FIG. 38 illustrates a perspective view of an embodiment of a four-lobe wound dressing.

FIG. 38 illustrates a perspective view of an embodiment of a wound dressing B790 according to an embodiment of the four-lobe configuration. FIG. 38 shows a possible four-lobe configuration of a dressing, useful for enhanced compatibility with body movement, where each layer is shaped to reduce the incident angle of the pad edge, and to provide somewhat independently moving sub-sections of the dressing. The dressing border, including the wound contact layer B791 and the backing layer B792 can also comprise slits, provided to further enhance the conformability on application by allowing the borders to overlap if needed. The wound dressing with a four-lobe configuration, as well as other configurations, are described in detail in International Application PCT/GB2012/000587, titled "WOUND DRESSING AND METHOD OF TREATMENT" and filed on Jul. 12, 2012, published as WO 2013/007973 A2 on Jan. 17, 2013, which is incorporated by reference herein.

Additionally, FIGS. 40A-F illustrate an embodiment of a wound dressing B2300 with an oval shaped absorbent layer B2308 having multiple lobes B2301. FIGS. 40A-F illustrate, respectively, perspective, top, bottom, left, right, and side views of an embodiment of the dressing B2300. In some embodiments, the absorbent layer B2308 can have six lobes. Preferably, two or more lobes B2301 (e.g., six lobes) are provided on the wound dressing B2300; the lobes B2301, and specifically, the gaps between the lobes B2301, aid the wound dressing B2300 in conforming to nonplanar wounds. For example, it may be advantageous to use the dressing B2300 to conform around joints such as elbows and knees.

Figure 40B:
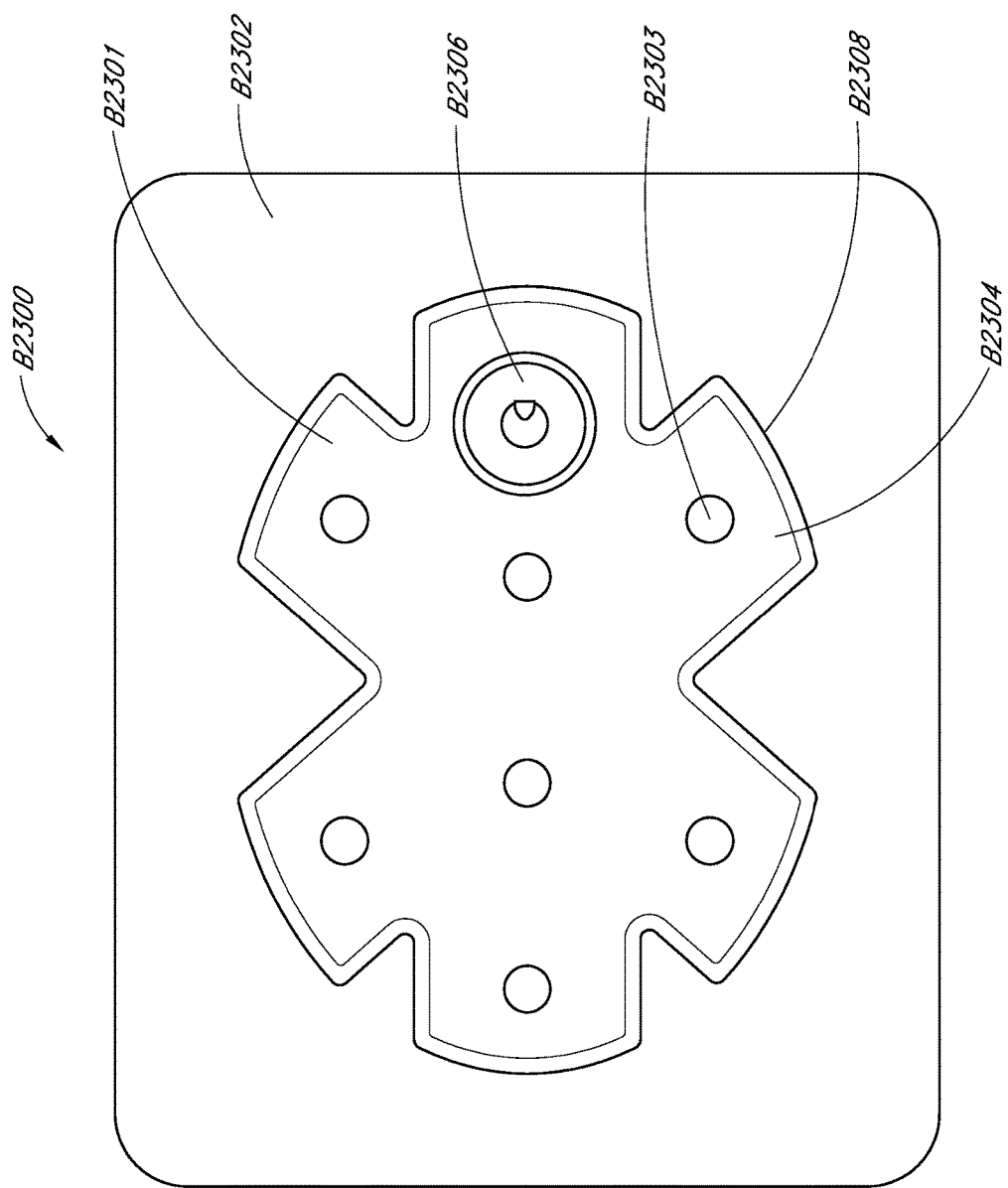
Figure 40C:
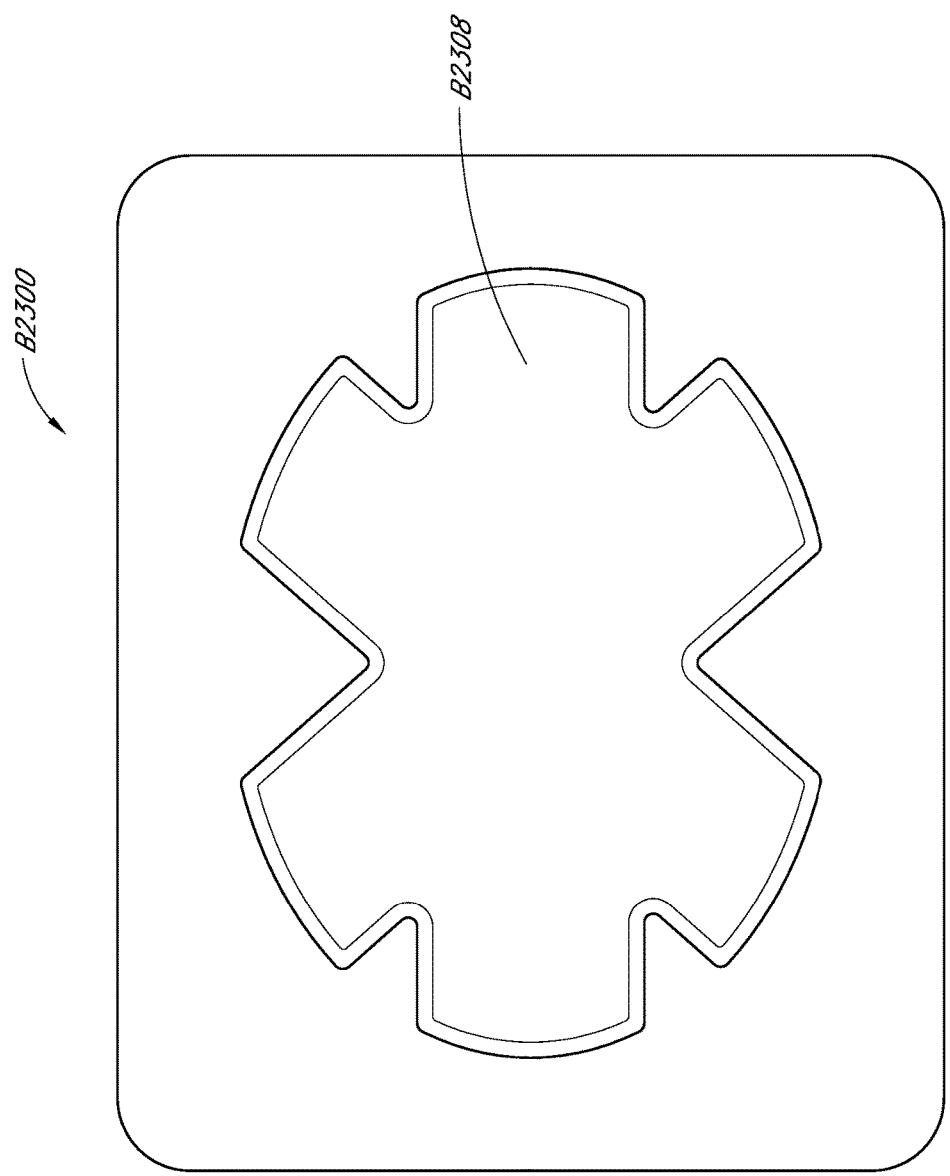
Figure 40D:
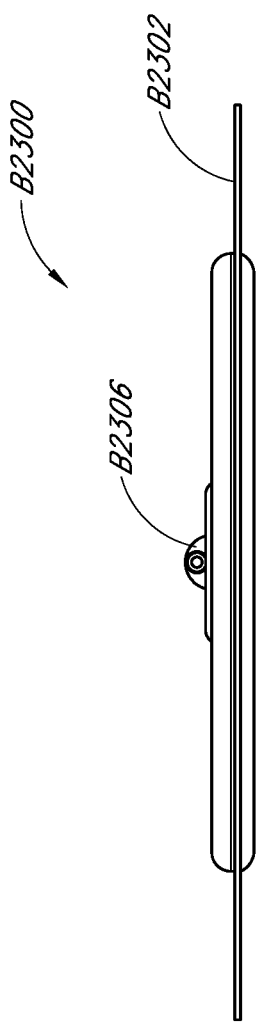
Figure 40E:
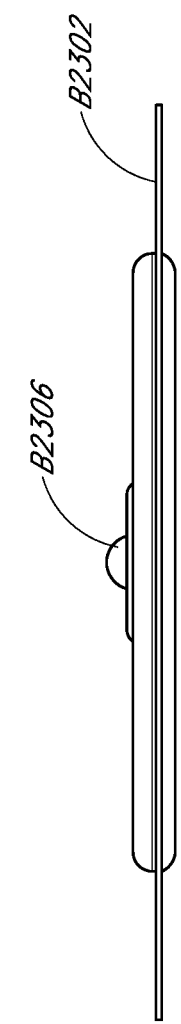
Figure 40F:

The dressing B2300 can have a rectangular or square shaped backing layer B2302, and in some embodiments, the overall dressing B2300 may measure 190 mm×230 mm, or 145.5 mm×190 mm. Preferably, a fluidic connector such as a port B2306 is attached to the dressing B2300, although it will of be recognized that the fluidic connector of FIGS. 39A-B may be used instead or in addition. Additionally, in some embodiments, the dressing B2300 can have an obscuring layer B2304 and one or more viewing windows B2303 similar to that described for other embodiments herein. FIG. 40A illustrates a perspective view of the dressing B2300, while FIG. 40B illustrates a top view, 40C a bottom view, and 40D-F represent views of the four sides of the dressing B2300.

Figure 41:
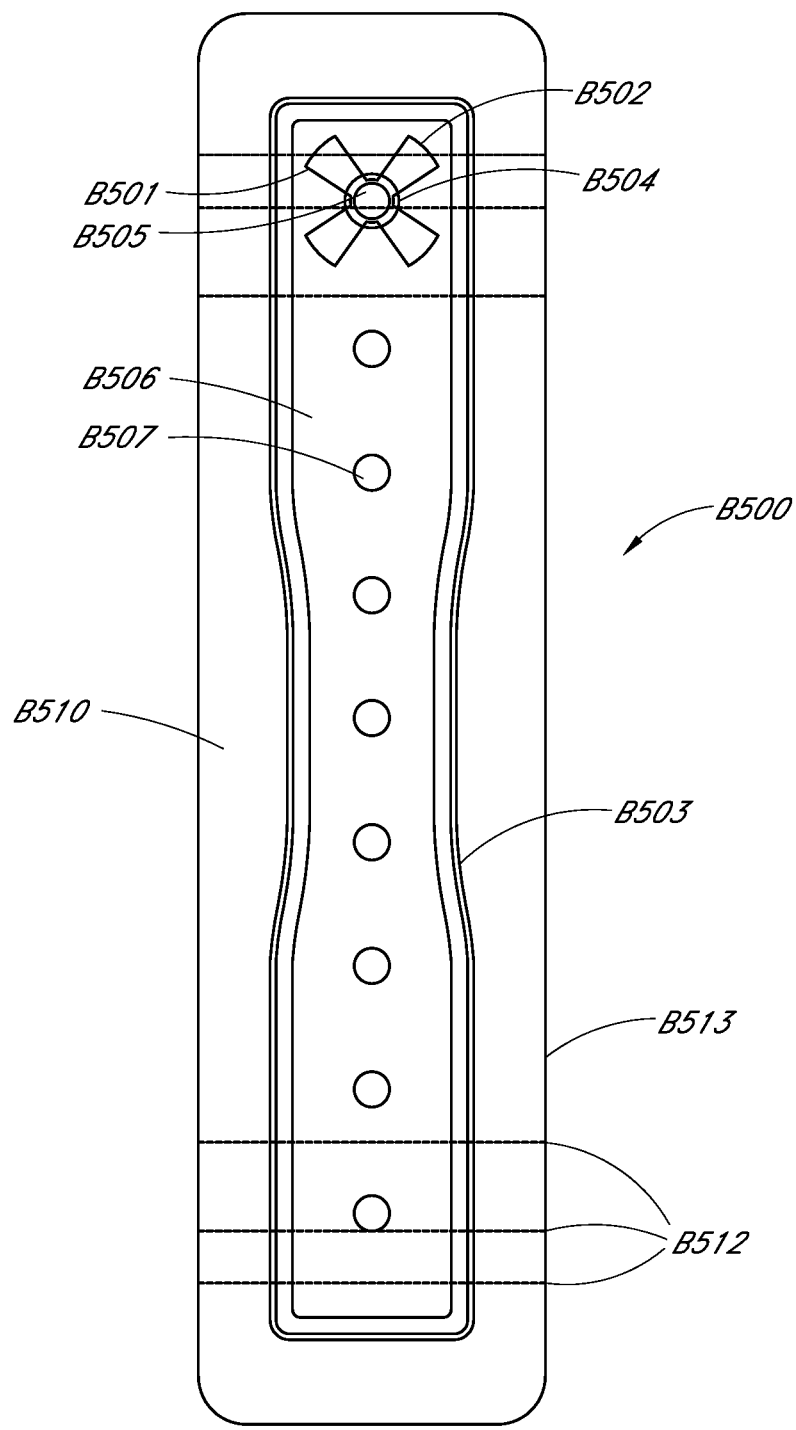
FIGS. 41-48 illustrate embodiments of a wound dressing including an obscuring layer and viewing windows including an orifice viewing window.

FIG. 41 illustrates an embodiment similar in shape and overall configuration to the embodiments illustrated above in FIGS. 23A-F. Here, however, the dressing B500 comprises an orifice viewing window B502 similar to that described in relation to FIGS. 29A-B and 30. The orifice viewing window B502 is preferably formed from a cross-shaped or Maltese-cross shaped aperture or cutout B501 in the obscuring layer B506. The backing layer B510 provided over the obscuring layer preferably has an orifice B504 located at the center of the orifice viewing window B502. Reference number B504 can also be considered to designate a port that may be provided in or over the backing layer B510 to provide a connection to a source of negative pressure, for example, a port provided over the orifice in the backing layer as described above. A smaller orifice B505 may be located in the absorbent layer B503 that is provided below the obscuring layer B506. The dressing B500 may comprise one or more viewing windows B507; here, eight viewing windows B507 are provided in a linear arrangement. The bottom side of the dressing B500 optionally comprises a layer of adhesive, over which a release layer B513 may be placed. Lines B512 illustrate possible locations where breaks in the release liner B513 may be provided.

In a preferred embodiment, the dressing B500 illustrated here has a longitudinal length of approximately 400 mm, and a transverse width of approximately 100 mm. The central axis of each arm of the cutout B501 of the orifice viewing window B502 is preferably offset from the longitudinal length and transverse width of the absorbent material, at an angle, for example, a 45° angle, as illustrated. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500. Although the location may be changed, it may be preferable to locate the port B504 near or along a side, edge, or corner of the dressing B500, which is then preferably elevated with respect to the remainder of the dressing. This configuration may extend the life of the dressing, as fluid would be slower in saturating the absorbent layer below or near the orifice or port B504.

Figure 42:
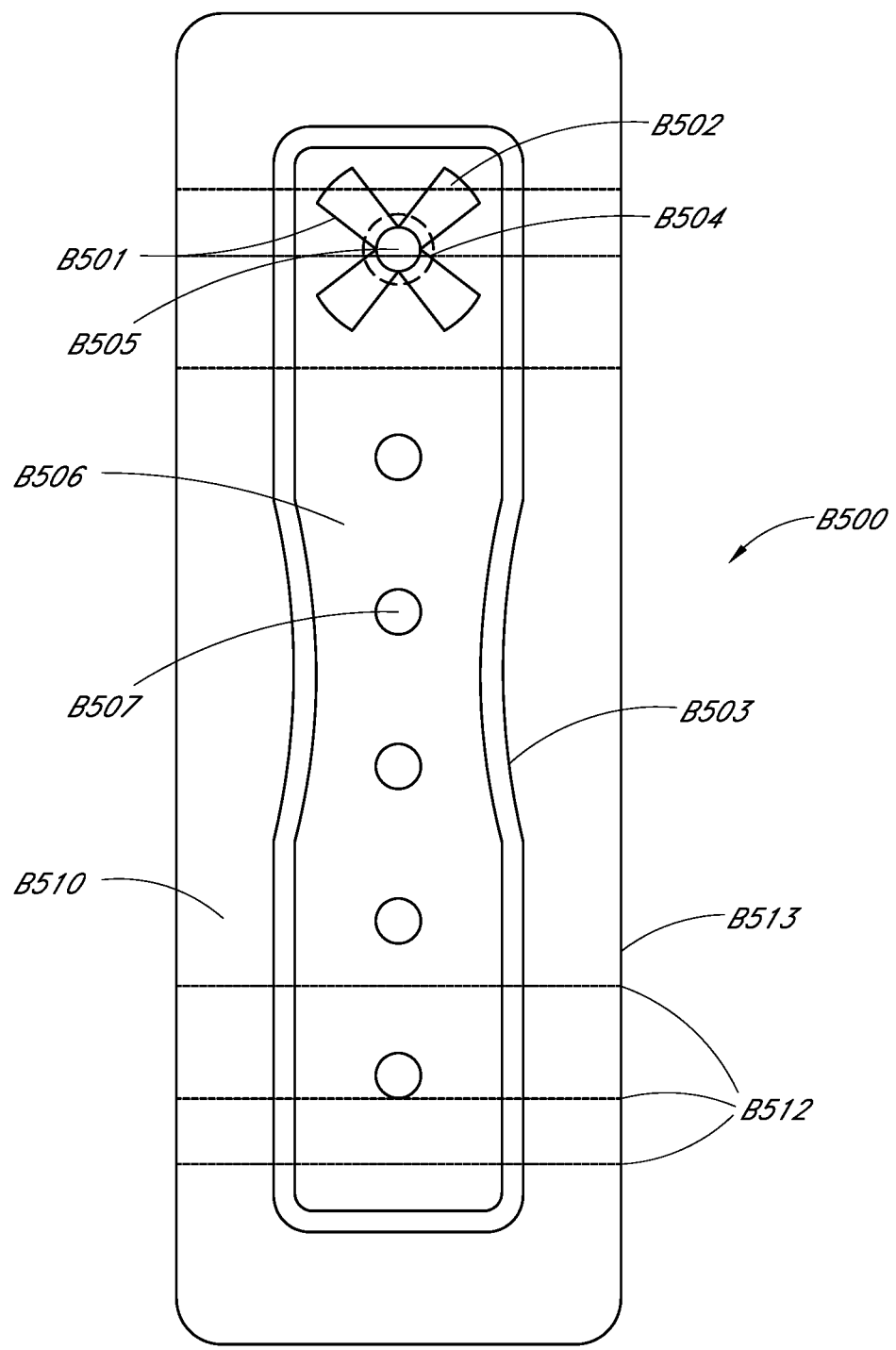

FIG. 42 illustrates an embodiment similar in shape and overall configuration to the embodiments illustrated above in FIGS. 24A-F. Here, however, the dressing B500 comprises an orifice viewing window B502 and cutout B501, with for example five linearly arranged viewing windows B507, among other parts, that are similar to that described above in relation to FIG. 41. In a preferred embodiment, the dressing B500 illustrated here has a longitudinal length of approximately 300 mm, and a transverse width of approximately 100 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 43:
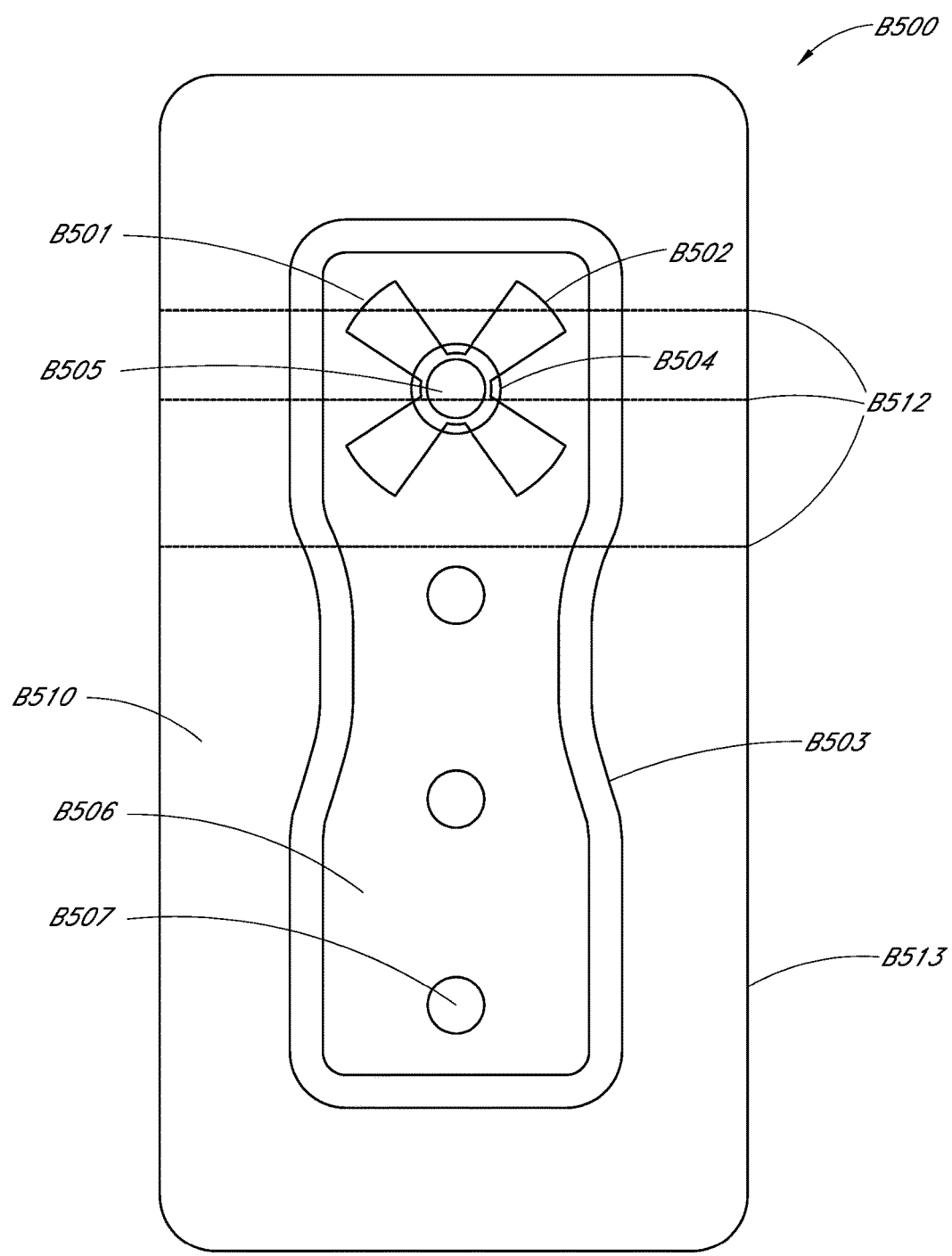

FIG. 43 illustrates an embodiment similar in shape and overall configuration to the embodiments illustrated above in FIGS. 25A-F. Here, however, the dressing B500 comprises an orifice viewing window B502 and cutout B501, with for example three linearly arranged viewing windows B507, among other parts, that are similar to that described above in relation to FIG. 41. In a preferred embodiment, the dressing B500 illustrated here has a longitudinal length of approximately 200 mm, and a transverse width of approximately 100 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 44:
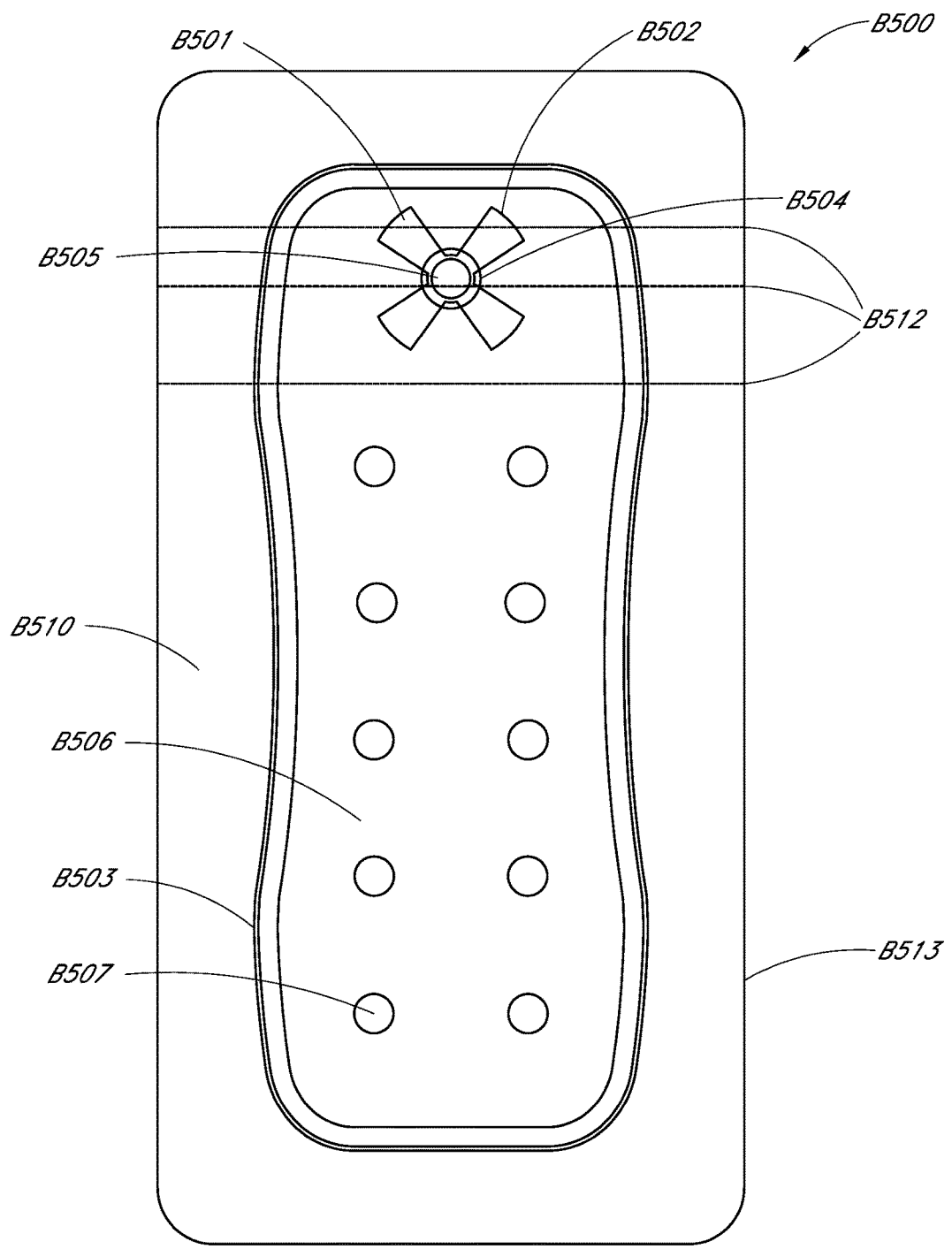

FIG. 44 illustrates an embodiment similar in shape and overall configuration to the embodiments illustrated above in FIGS. 21A-F. Here, however, the dressing B500 comprises an orifice viewing window B502 and cutout B501, with for example two rows of five linearly arranged viewing windows B507, among other parts, that are similar to that described above in relation to FIG. 41. In a preferred embodiment, the dressing B500 illustrated here has a longitudinal length of approximately 300 mm, and a transverse width of approximately 150 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 45:
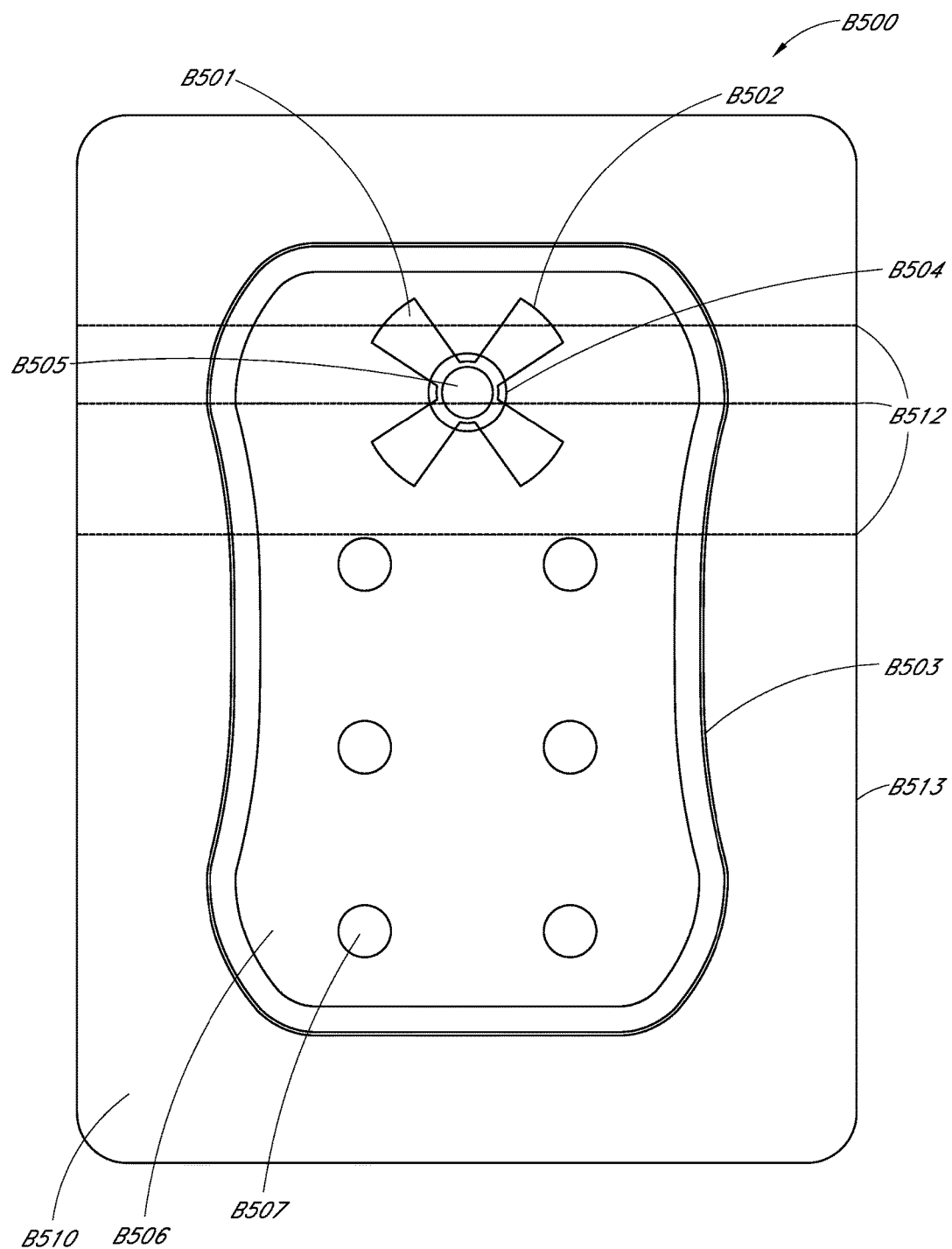

FIG. 45 illustrates an embodiment similar in shape and overall configuration to the embodiments illustrated above in FIGS. 22A-F. Here, however, the dressing B500 comprises an orifice viewing window B502 and cutout B501, with for example two rows of three linearly arranged viewing windows B507, among other parts, that are similar to that described above in relation to FIG. 41. In a preferred embodiment, the dressing B500 illustrated here has a longitudinal length of approximately 300 mm, and a transverse width of approximately 100 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 46:
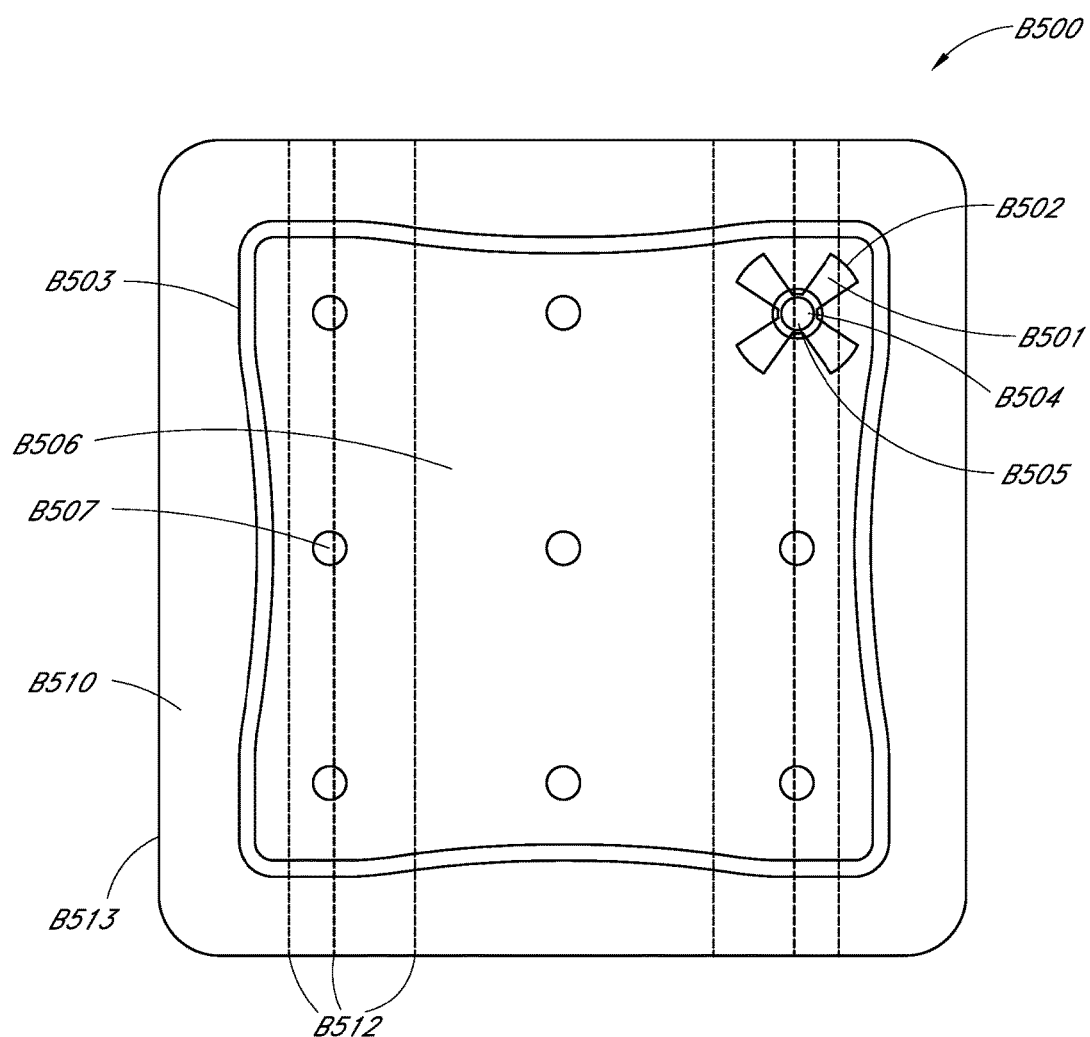

FIG. 46 illustrates an embodiment similar in shape and overall configuration to the embodiments illustrated above in FIGS. 26A-F. Here, however, the dressing B500 comprises an orifice viewing window B502 and cutout B501, with a 3×3 array of viewing windows absent a viewing window at a corner position of the wound dressing, among other parts, that are similar to that described above in relation to FIG. 41 but located in a corner of the dressing B500. In a preferred embodiment, the dressing B500 illustrated here is approximately square, with each side measuring approximately 250 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on a corner of the dressing B500, and situated approximately 52-55 mm from the top edge of the dressing B500.

Figure 47:
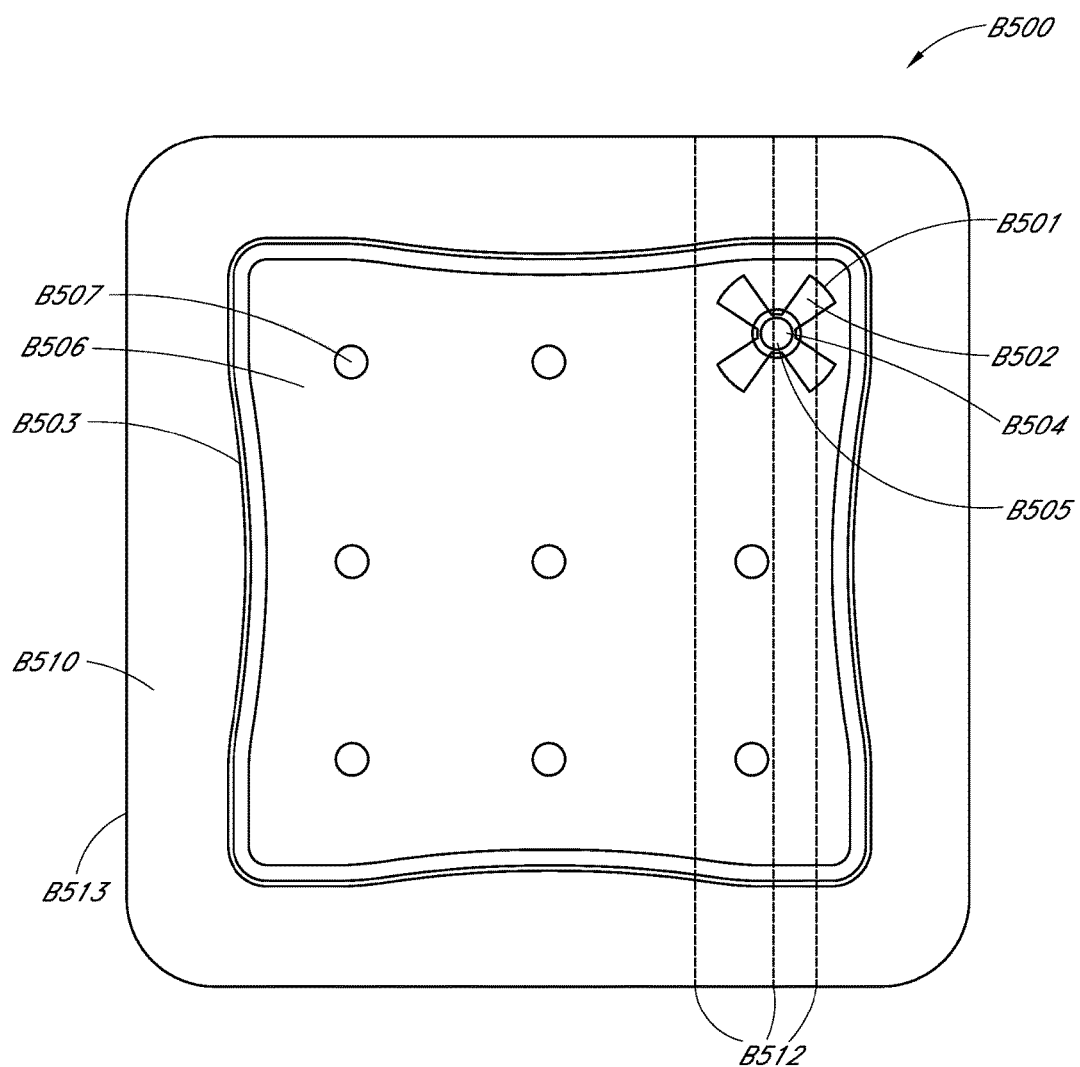

FIG. 47 illustrates an embodiment similar in shape and overall configuration to the embodiments illustrated above in FIGS. 27A-F. Here, however, the dressing B500 comprises an orifice viewing window B502 and cutout B501, with a 3×3 array of viewing windows absent a viewing window at a corner position of the wound dressing, among other parts, that are similar to that described above in relation to FIG. 41 but located in a corner of the dressing B500. In a preferred embodiment, the dressing B500 illustrated here is approximately square, with each side measuring approximately 200 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on a corner of the dressing B500, and situated approximately 52-55 mm from the top edge of the dressing B500.

Figure 48:
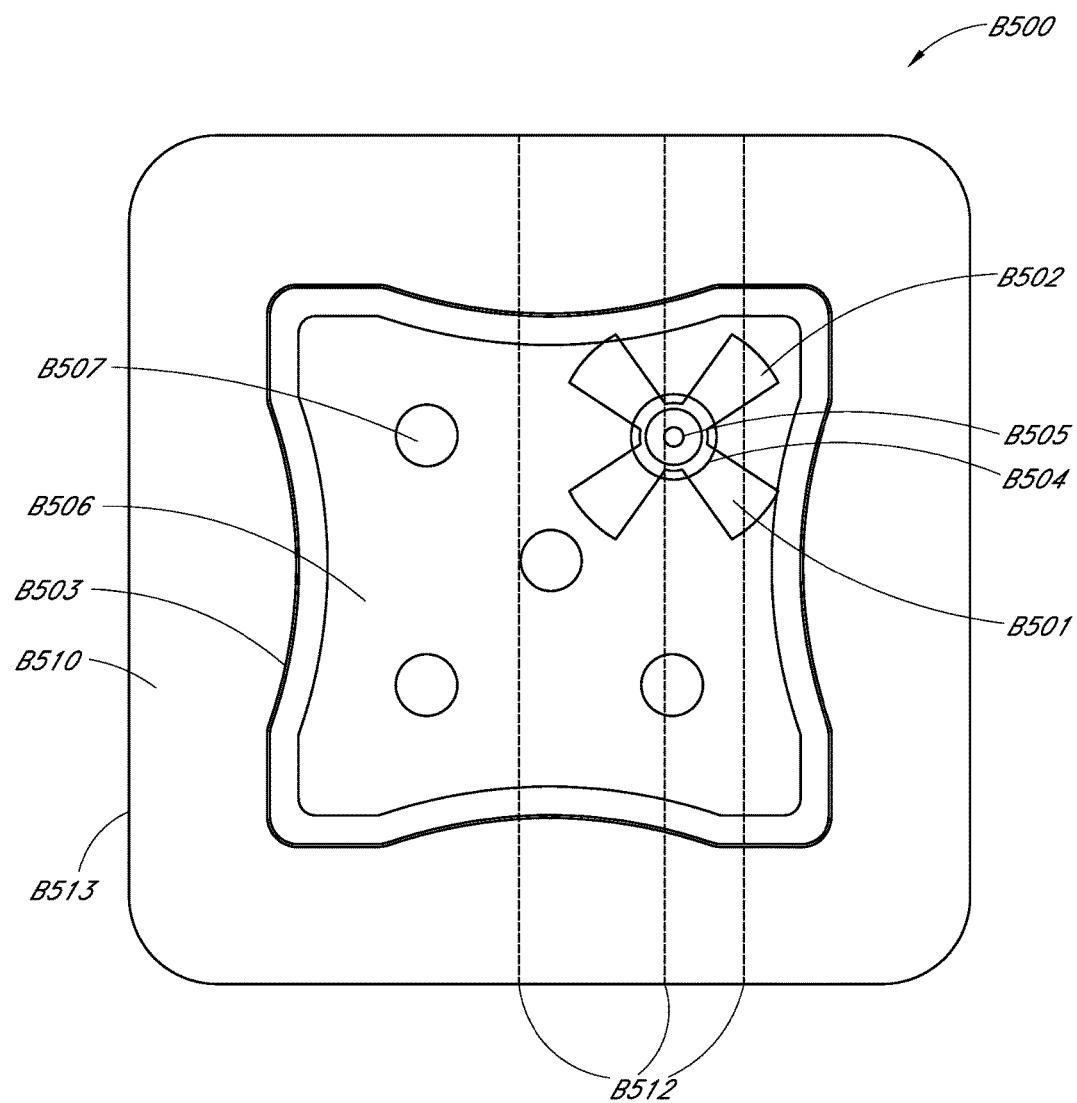

FIG. 48 illustrates an embodiment similar in shape and overall configuration to the embodiments illustrated above in FIGS. 28A-F. Here, however, the dressing B500 comprises an orifice viewing window B502 and cutout B501, with a quincunx array of viewing windows absent a viewing window at a corner position of the wound dressing, among other parts, that are similar to that described above in relation to FIG. 41 but located in a corner of the dressing B500. In a preferred embodiment, the dressing B500 illustrated here is approximately square, with each side measuring approximately 150 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, B40±4 mm, and 25±4 mm from each of the top and bottom edges of the dressing B500. As illustrated, the port B504 (and cutout B501) are preferably centered on a corner of the dressing B500, and situated approximately 52-55 mm from the top edge of the dressing B500.

Figures 49A, 49B:
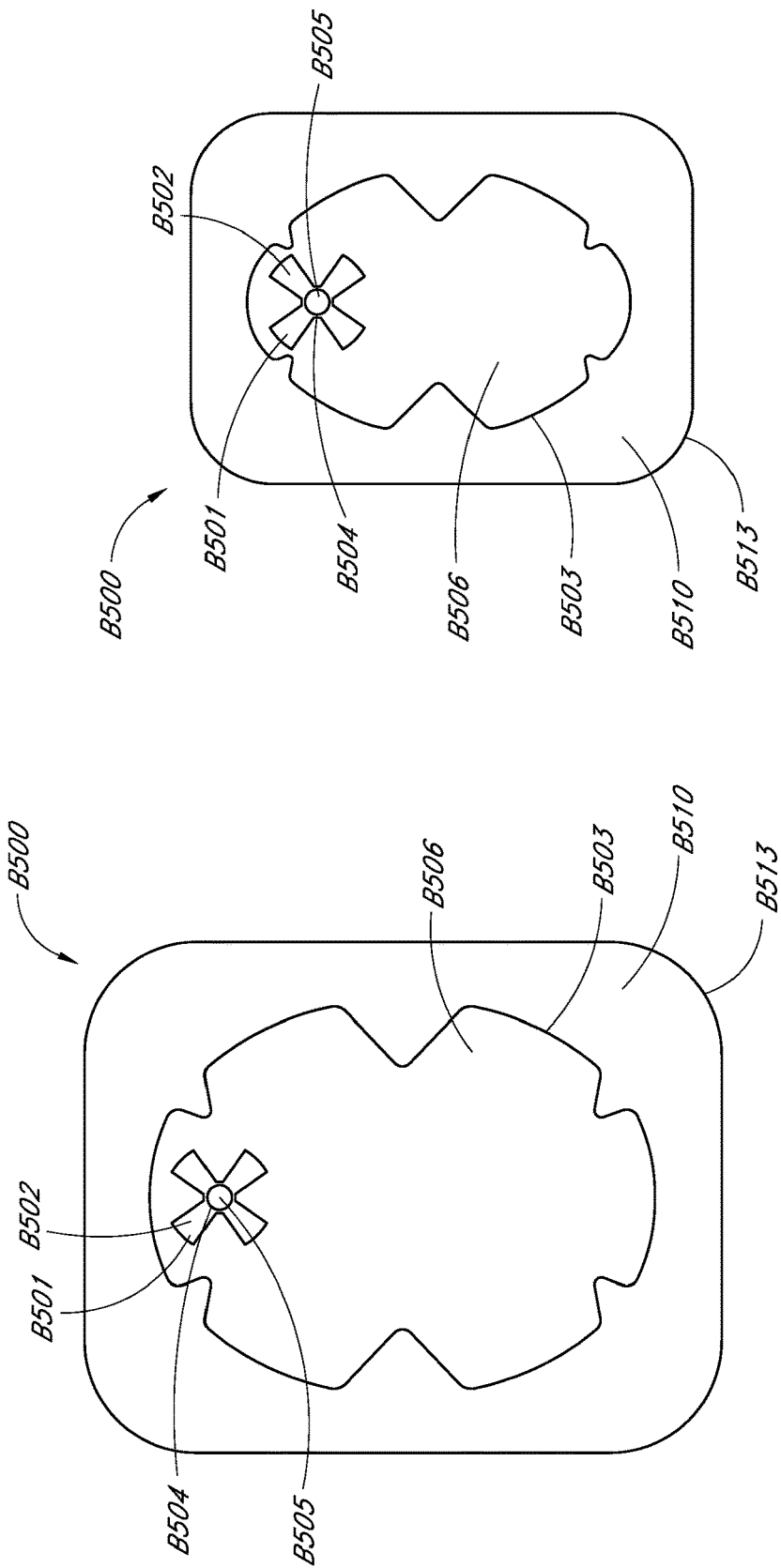
FIGS. 49A-B illustrate embodiments of an oval-shaped wound dressing comprising an obscuring layer and an orifice viewing window.

FIG. 49A-B illustrates an embodiment somewhat similar in shape and overall configuration to the embodiments illustrated above in FIGS. 40A-F. Here, however, the oval-shaped dressing B500 comprises an orifice viewing window B502 and cutout B501, among other parts, that are similar to that described above in relation to FIG. 41. Viewing windows are not shown, but may be provided as in one embodiment as described above. In a preferred embodiment, the dressing B500 illustrated in FIG. 49A has a longitudinal length of approximately 250 mm, and a transverse width of approximately 200 mm. The longitudinal length of the absorbent layer B503 (and corresponding obscuring layer, if so provided) measures approximately 200 mm, with a transverse width of approximately 150 mm. The embodiment of the dressing B500 illustrated in FIG. 49B has a longitudinal length of approximately 200 mm, and a transverse width of approximately 150 mm. The longitudinal length of the absorbent layer B503 (and corresponding obscuring layer, if so provided) measures approximately 150 mm, with a transverse width of approximately 100 mm. Although no viewing windows B507 are illustrated, it will of course be understood that one or more such windows B507 may be provided on the dressing B500. The spacing between each arm of the cutout B501 may be 72°, although it will of course be recognized that other angles and configurations are possible. As illustrated, the orifice or port B504 (and cutout B501) are preferably centered on the transverse midline of the dressing B500, and situated approximately 52-55 mm from the top edge of the dressing B500.

Figure 50A:
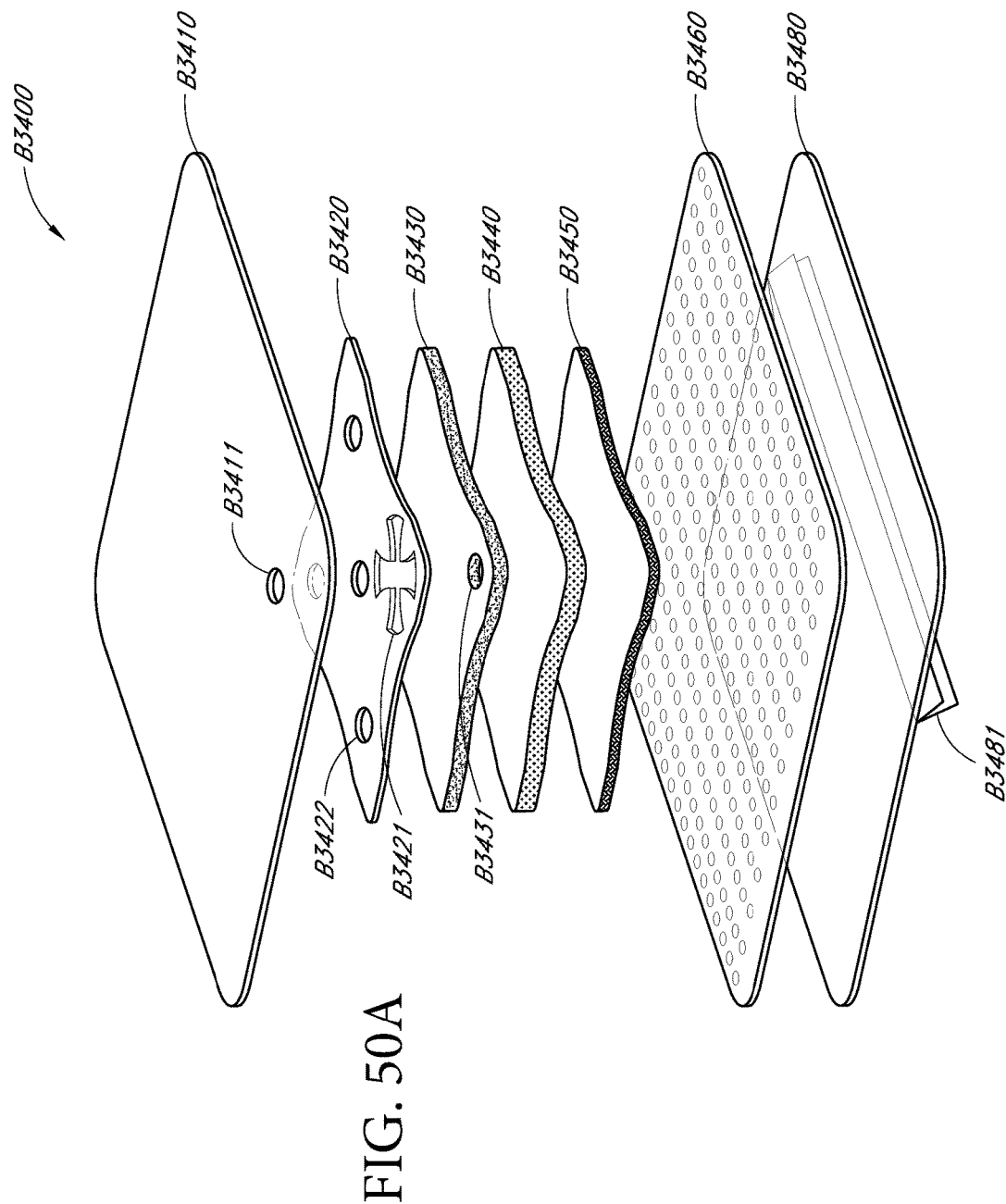
FIG. 50A illustrates an exploded view of an embodiment of a wound dressing.

FIG. 50A illustrates an exploded view of a dressing B3400 for use in negative pressure wound therapy. Although this figure illustrates a dressing having one particular shape, the construction of the layers can be applied to any of the embodiments identified above, including FIGS. 20A-30, 32-38, and 40A-49B. The dressing B3400 comprises a release layer B3480, wound contact layer B3460, a transmission layer B3450, an acquisition distribution layer B3440, an absorbent layer B3430, an obscuring layer B3420, and a backing layer B3410. The dressing B3400 may be connected to a port, such as described below with respect to FIGS. 51 and 52. At least the wound contact layer B3460, transmission layer B3450, absorbent layer B3430, obscuring layer B3420, and backing layer B3410 may have properties as described with respect to particular embodiments above, such as the embodiments of FIGS. 19A-38, and 40A-49B, as well as or instead of the properties described below.

The dressing B3400 may comprise a wound contact layer B3460 for sealing the dressing B3400 to the healthy skin of a patient surrounding a wound area. Certain embodiments of the wound contact layer may comprise three layers: a polyurethane film layer, a lower adhesive layer and an upper adhesive layer. The upper adhesive layer may assist in maintaining the integrity of the dressing B3400, and the lower adhesive layer may be employed for sealing the dressing B3400 to the healthy skin of a patient around a wound site. As described above, in some embodiments with respect to FIGS. 19A-C, some embodiments of the polyurethane film layer may be perforated. Some embodiments of the polyurethane film layer and upper and lower adhesive layers may be perforated together after the adhesive layers have been applied to the polyurethane film. In some embodiments a pressure sensitive adhesive, which may be a silicone, hot melt, hydrocolloid or acrylic based adhesive or other such adhesives, may be formed on both sides or optionally on a selected one side of the wound contact layer. In certain embodiments, the upper adhesive layer may comprise an acrylic pressure sensitive adhesive, and the lower adhesive layer may comprise a silicone pressure sensitive adhesive. In other embodiments the wound contact layer B3460 may not be provided with adhesive. In some embodiments, the wound contact layer B3460 may be transparent or translucent. The film layer of the wound contact layer B3460 may define a perimeter with a rectangular or a square shape. A release layer B3480 may be removably attached to the underside of the wound contact layer B3460, for example covering the lower adhesive layer, and may be peeled off using flaps B3481. Some embodiments of the release layer B3480 may have a plurality of flaps extending along the length of the layer B3480.

Some embodiments of the dressing B3400 may comprise an optional spacer or transmission layer B3450. The transmission layer B3450 may comprise a porous material or 3D fabric configured to allow for the passage of fluids therethrough away from the wound site and into the upper layers of the dressing B3400. In particular, the transmission layer B3450 can ensure that an open air channel can be maintained to communicate negative pressure over the wound area even when the absorbent layer B3430 has absorbed substantial amounts of exudates. The transmission layer B3450 should remain open under the typical pressures that will be applied during negative pressure wound therapy as described above, so that the whole wound site sees an equalized negative pressure.

Some embodiments of the transmission layer B3450 may be formed of a material having a three dimensional structure. For example, a knitted or woven spacer fabric (for example Baltex 7970 weft knitted polyester) or a non-woven fabric can be used. In some embodiments, the transmission layer B3450 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing B3400 where the absorbent layer B3430 helps lock the liquid away or itself wicks the liquid onwards towards the cover layer B3410 where it can be transpired. Other materials can be utilized, and examples of such materials are described in U.S. Patent Pub. No. 2011/0282309, which are hereby incorporated by reference and made part of this disclosure. However, the transmission layer B3450 may be optional, and for example may be optional in embodiments of the dressing B3400 which comprise the acquisition distribution layer B3440, described below.

Some embodiments may comprise a wicking or acquisition distribution layer (ADL) B3440 to horizontally wick fluid such as wound exudate as it is absorbed upward through the layers of the dressing B3400. Lateral wicking of fluid may allow maximum distribution of the fluid through the absorbent layer B3430 and may enable the absorbent layer B3430 to reach its full holding capacity. This may advantageously increase moisture vapor permeation and efficient delivery of negative pressure to the wound site. Some embodiments of the ADL B3440 may comprise viscose, polyester, polypropylene, cellulose, or a combination of some or all of these, and the material may be needle-punched. Some embodiments of the ADL B3440 may comprise polyethylene in the range of 40-150 grams per square meter (gsm).

The dressing B3400 may further comprise an absorbent or superabsorbent layer B3430. The absorbent layer can be manufactured from ALLEVYN™ foam, Freudenberg 114-224-4 and/or Chem-Posite™ 11C-450, or any other suitable material. In some embodiments, the absorbent layer B3430 can be a layer of non-woven cellulose fibers having superabsorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid.

For example, some embodiments of the absorbent layer B3430 may comprise a layered construction of an upper layer of non-woven cellulose fibers, superabsorbent particles (SAP), and a lower layer of cellulose fibers with 40-80% SAP. In some embodiments, the absorbent layer B3430 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer B3430 can have one or more through holes B3431 located so as to underlie the suction port.

Some embodiments of the present disclosure may employ a masking or obscuring layer B3420 to help reduce the unsightly appearance of a dressing B3400 during use due to the absorption of wound exudate. The obscuring layer B3420 may be a colored portion of the absorbent material, or may be a separate layer that covers the absorbent material. The obscuring layer B3420 may be one of a variety of colors such as blue, orange, yellow, green, or any color suitable for masking the presence of wound exudate in the dressing B3400. For example, a blue obscuring layer B3420 may be a shade of blue similar to the shade of blue commonly used for the material of medical gowns, scrubs, and drapes. Some embodiments of the obscuring layer B3420 may comprise polypropylene spunbond material. Further, some embodiments of the obscuring layer B3420 may comprise a hydrophobic additive or coating. Other embodiments may comprise a thin fibrous sheet of B60, 70, or 80 gsm.

The obscuring layer may comprise at least one viewing window B3422 configured to allow a visual determination of the saturation level of the absorbent layer. The at least one viewing window B3422 may comprise at least one aperture made through the obscuring layer. The at least one viewing window B3422 may comprise at least one uncolored region of the obscuring layer. Some embodiments of the obscuring layer may comprise a plurality of viewing windows or an array of viewing windows, as discussed above with respect to FIGS. 41-48.

The masking capabilities of the obscuring layer B3420 should preferably only be partial, to allow clinicians to access the information they require by observing the spread of exudate across the dressing surface. An obscuring layer B3420 may be partial due to material properties allowing wound exudate to slightly alter the appearance of the dressing or due to the presence of at least one viewing window B3422 in a completely obscuring material. The partial masking nature of the obscuring layer B3420 enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

Tests performed upon various dressings with respect to the transmittance properties of the dressing indicate the ability of various samples to mask colour. The ability to mask colour may be calculated, for example, by measuring the reduction in absorption of light radiation at particular wavelengths. The tests utilized a UV-Vis spectrophotometer Jasco with integrating sphere, with a scanning range 340 to 800 nm, bandwidth 5 nm and B1000 nm/sec scanning speed. The data labelled black background represents the extreme of exudate colour (the most colour an exudate might have)—the highest level of radiation absorbed and the least amount of radiation reflected from the sample. The data for white background represents the upper limit for total masking—generally the lowest level of radiation absorbed and the highest level of reflection. Sample 1 was a tinted polymer film placed over a black background, which was judged not to sufficiently mask the black background (representing wound exudate) satisfactorily. Sample 2 was a sheet of 3-dimensional spacer fabric (Baltex 3D) placed over a black background, and was judged to provide adequate masking of the black background. Sample 3 was a sheet of non-woven material dyed green placed over a black background, and provided complete masking of the black background.

Wound exudate may have dark yellow, red and/or brown tones. Therefore, to appropriately mask these colours, an obscuring layer B3420 would preferably shield light wavelengths of below 600 nm.

Measuring the reduction in absorption of light radiation at particular wavelengths may be performed by calculating:

$$\% \text{ reduction} = (A_{background} - A_{sample\ placed\ on\ background}) / (A_{background}) \times 100$$

where A is the absorption of light radiation at the particular wavelength.

Using this formula, using light at a wavelength of 460 nm, the percentage of absorption reduction was calculated as shown in Table 3 below.

TABLE 3

| Sample | Absorption reduction at 460 nm | Appropriate masking observed |
|---|---|---|
| Sample 1 | 34% | No |
| Sample 2 | 77% | Yes-partial |
| Sample 3 | 69% | Yes-complete |

It has been found that materials that reduce light absorption by about 50% or more will provide enough partial or complete masking of wound exudate (as judged by the inventors). Of course a complete masking element would preferably require a means for a clinician to judge the spread of wound exudate in the dressing below the obscuring layer B3420, e.g. the masking element not completely covering the entire dressing. For example, as described above with respect to FIGS. 41-49, a plurality of viewing windows may be provided in the obscuring layer B3420 such that the spread of exudate in the dressing below may be adequately assessed. Alternatively a partial masking element may allow a clinician to judge the spread of exudate in the dressing below without additional means.

It will be understood that the wetting of a masking material (by exudate for example) will also affect the masking performance of the masking element, since hydrophilic materials will allow chromophore-carrying species to travel through them more easily. As such, the absorption reduction rate should also be tested on wet materials.

The above-mentioned Samples 1, 2 and 3 were also tested for their masking properties by measuring CIE L*a*b* values (a known 3-dimensional model for representing colour space). The analysis employed Jasco software using the range 380 to 780 nm, stard observed 2 (deg), lightsource D65, colour matching JIS Z8701-1999.

Table 4 below shows the L*a*b* values found when Samples 1, 2 and 3 were respectively placed over a black background. The results for the black background alone and a white background are also shown.

TABLE 4

| Sample | CIE L*a*b* values recorded | | | Appropriate masking observed? |
|---|---|---|---|---|
| | L* | a* | b* | |
| Black background | 0 | 0 | 0 | n/a |
| Sample 1 (on black) | 36.59 | 3.76 | −1.80 | No |
| Sample 2 (on black) | 71.76 | −0.20 | −1.08 | Yes-partial |
| Sample 3 (on black) | 70.64 | −0.25 | −1.23 | Yes-complete |
| White background | 100 | 0 | 0 | n/a |

Generally, samples which lead to an increase in L* value will provide a lighter colour tone than the reference surface, which is the main contributor to masking a dark colour. From the values above, apt partial masking materials will yield an L* value above 50, or more aptly above 70.

However, completely opaque masking layers, such as for example a tinted polymeric film, may cover the area to be masked with a darker tone altogether, in which case the measure of L* is not relevant. Once again these values should also be considered on wet material, for the reasons stated above.

Figure 54:
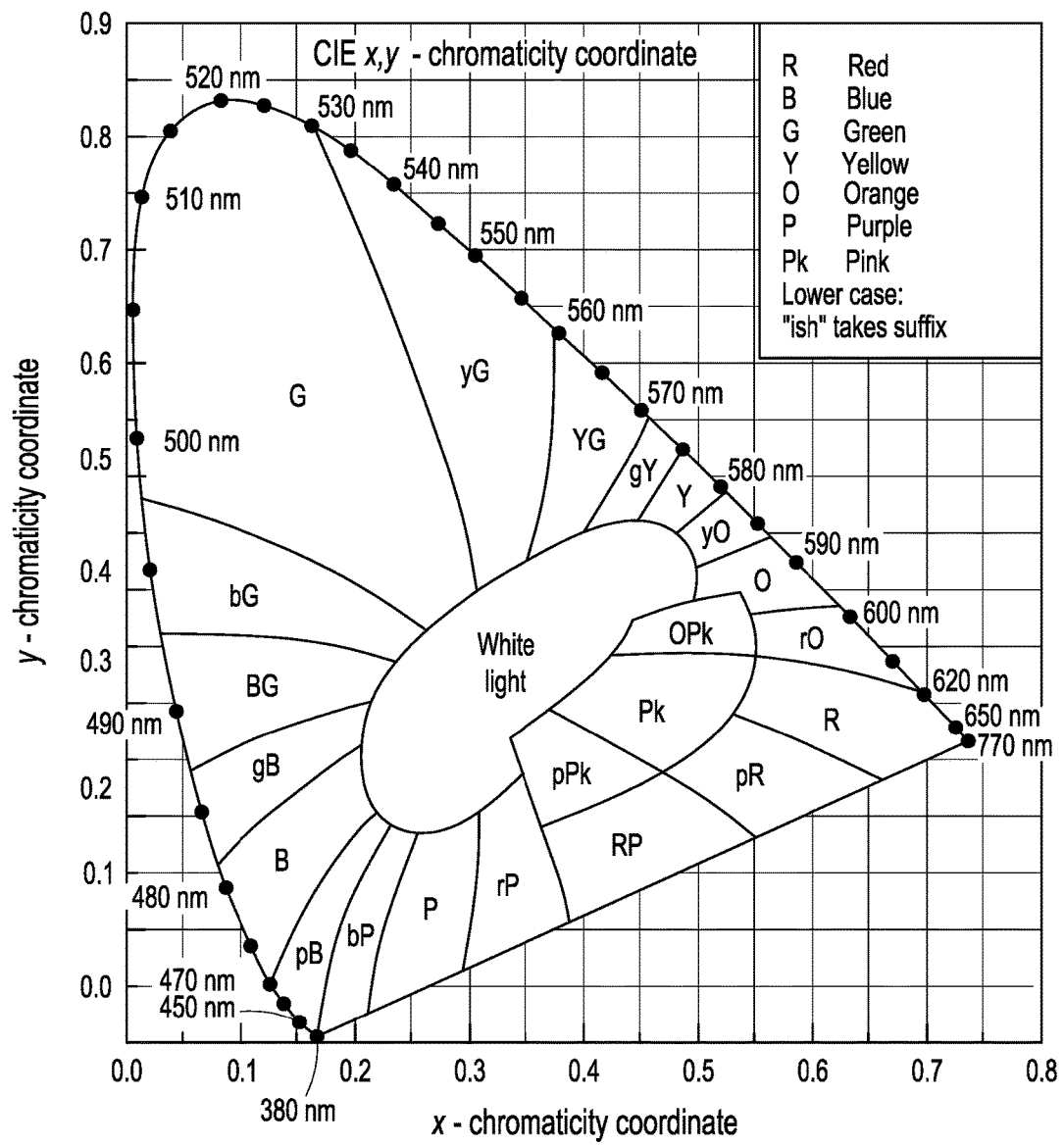
FIG. 54 illustrates a CIE chromacity scale.

In addition to transmittance properties, the color of the obscuring layer B3420 may affect the masking ability of the layer. In liquid permeable embodiments of the obscuring layer, various colors are suitable for masking the usual colors of wound exudate, while other colors may not provide optimal masking of the exudate. For example, with reference to the CIE chromacity diagram illustrated in FIG. 54, some embodiments of the obscuring layer, in a dry state, may be configured to yield a CIE y value of 0.4 or less and a CIE x value of 0.5 or less. Some embodiments of the obscuring layer, in a dry state, may have a color of Bg, gB, B, pB, bP, P, rP, pPk, RP, O, rO, or yO on the CIE x, y chromacity diagram. It will be appreciated that liquid impermeable embodiments of the obscuring layer may be configured with any color.

The obscuring layer B3420 can have one or more through holes located so as to underlie the suction port. Some embodiments may have a maltese cross B3421 or other shaped cutout underlying the suction port, wherein the diameter of the maltese cross B3421 is greater than the diameter of the port. This may allow a clinician to easily asses the amount of wound exudate absorbed into the layers beneath the port.

The dressing B3400 may also comprise a backing layer, or cover layer B3410 extending across the width of the wound dressing. The cover layer B3410 may be gas impermeable but moisture vapor permeable. Some embodiments may employ a polyurethane film (for example, Elastollan SP9109) or any other suitable material. For example, certain embodiments may comprise translucent or transparent 30 gsm EU33 film. The cover layer B3410 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer B3410 can have an orifice B3411 located so as to underlie the suction port. The orifice B3411 may allow transmission of negative pressure through the cover layer B3410 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

Figure 50B:
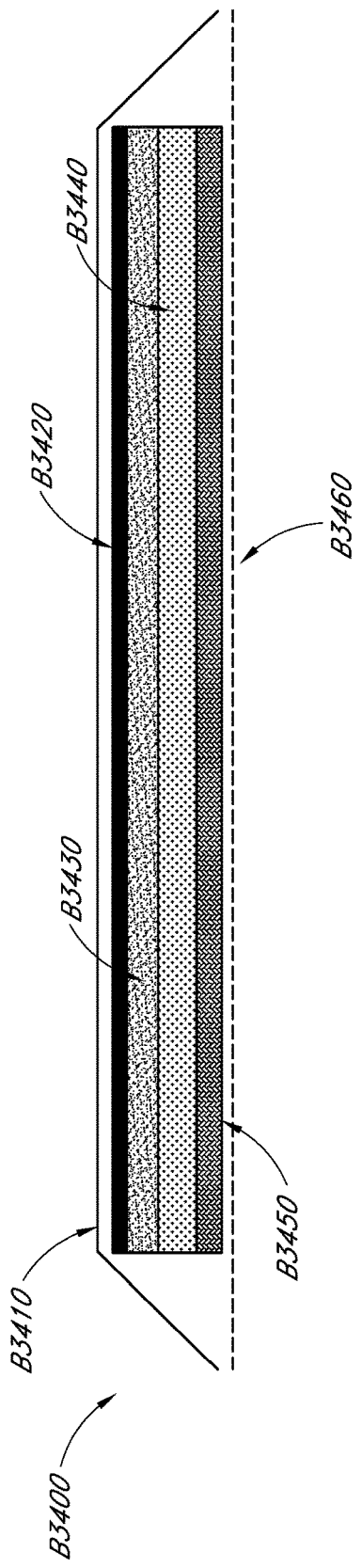
FIG. 50B illustrates a cross sectional view of an embodiment of a wound dressing.

FIG. 50B illustrates a cross sectional view of the wound dressing B3400, displaying an embodiment of the relative thicknesses of layers of the dressing B3400. In some embodiments, the wound contact layer B3460 may be flat and the top film layer B3410 may be contoured over the inner layers of the dressing B3400. The spacer layer B3450 may be half as thick as the acquisition distribution layer B3440 in some embodiments. In some embodiments, the absorbent layer B3430 may be about 1.5 times thicker than the spacer layer B3450. The obscuring layer B3420 may be about half the thickness of the spacer layer B3450.

Figure 51:
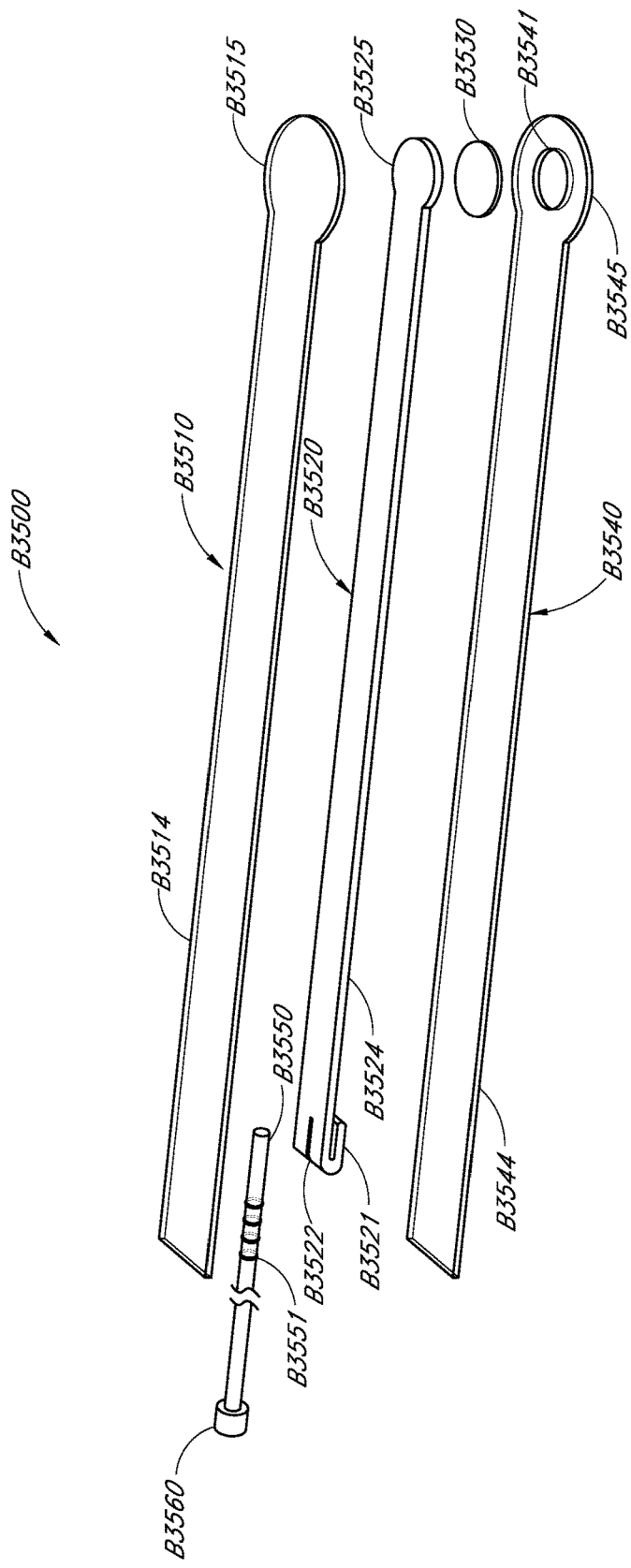
FIG. 51 illustrates an exploded view of an embodiment of a soft or flexible port for transmitting negative pressure to a wound dressing.

FIG. 51 illustrates a perspective exploded view of an embodiment of a flexible port or fluidic connector B3500 that may be used to connect any of the wound dressings described herein to a source of negative pressure. The port B3500 comprises a top layer B3510, a spacer layer B3520, a filter element B3530, a bottom layer B3540, and a conduit B3550. The conduit optionally comprises a connector B3560. The distal end of the port B3500 (the end connectable to the dressing B3400) is depicted as having an enlarged circular shape, although it will be appreciated that any suitable shape may be used and that the distal end need not be enlarged. For example, the distal end can have any of the shapes shown in FIGS. 39A and 39B above. The distal end can also have the shape shown in FIGS. 19A-19C above.

The bottom layer B3540 may comprise an elongate bridge portion B3544, an enlarged (e.g., rounded or circular) sealing portion B3545, and an orifice B3541. In some embodiments a plurality of orifices may be provided in the bottom layer. Some embodiments of the rounded sealing portion B3545 may comprise a layer of adhesive, for example a pressure sensitive adhesive, on the lower surface for use in sealing the port B3500 to a dressing. For example, the port may be sealed to the cover layer B3410 of the dressing in FIG. 50. The orifice B3541 in the bottom layer B3540 of the port B3500 may be aligned with the orifice B3411 in the cover layer B3410 of the dressing B3400 in order to transmit negative pressure through the dressing B3400 and into a wound site.

The top layer B3515 may be substantially the same shape as the bottom layer in that it comprises an elongate bridge B3514 and an enlarged (e.g., rounded or circular) portion B3515. The top layer B3515 and the bottom layer B3545 may be sealed together, for example by heat welding. In some embodiments, the bottom layer B3545 may be substantially flat and the top layer B3515 may be slightly larger than the bottom layer B3545 in order to accommodate the height of the spacer layer B3520 and seal to the bottom layer B3545. In other embodiments, the top layer B3515 and bottom layer B3545 may be substantially the same size, and the layers may be sealed together approximately at the middle of the height of the spacer layer B3520. In some embodiments, the elongate bridge portions B3544, B3514 may have a length of 10 cm (or about 10 cm) or more, more preferably a length of 20 cm (or about 20 cm) or more and in some embodiments, may be about 27 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions B3544, B3514 to their widths may in some embodiments exceed 6:1, and may more preferably exceed 8:1 or even 10:1. The diameter of the circular portion B3545, B3515 may be about 3.5 cm in some embodiments.

The bottom and top layers may comprise at least one layer of a flexible film, and in some embodiments may be transparent. Some embodiments of the bottom layer B3540 and top layer B3515 may be polyurethane, and may be liquid impermeable.

The port B3500 may comprise a spacer layer B3520, such as the 3D fabric discussed above, positioned between the lower layer B3540 and the top layer B3510. The spacer layer B3520 may be made of any suitable material, for example material resistant to collapsing in at least one direction, thereby enabling effective transmission of negative pressure therethrough. The spacer layer B3520 may comprise an enlarged (e.g., rounded or circular) portion B3525, and may optionally include a fold B3521. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion B3525 may be slightly smaller than the diameters of the enlarged ends B3545, B3515, and in one embodiment is about 2 cm. Some embodiments of the spacer layer B3520 may have adhesive on one or both of its proximal and distal ends (e.g., one or more dabs of adhesive) in order to secure the spacer layer B3520 to the top layer B3510 and/or the bottom layer B3540. Adhesive may also be provided along a portion or the entire length of the spacer layer. In other embodiments, the spacer layer B3520 may be freely movable within the sealed chamber of the top and bottom layers.

The fold B3521 of the spacer fabric may make the end of the port B3500 softer and therefore more comfortable for a patient, and may also help prevent the conduit B3550 from blockage. The fold B3521 may further protect the end of the conduit B3550 from being occluded by the top or bottom layers. The fold B3521 may, in some embodiments, be between 1 cm and 3 cm (or between about 1 cm and about 3 cm) long, and in one embodiment is 2 cm (or about 2 cm) long. The spacer fabric may be folded underneath itself, that is toward the bottom layer B3540, and in other embodiments may be folded upward toward the top layer B3510. Other embodiments of the spacer layer B3520 may contain no fold. A slot or channel 3522 may extend perpendicularly away from the proximal end of the fold B3521, and the conduit B3550 may rest in the slot or channel B3522. In some embodiments the slot B3522 may extend through one layer of the fold, and in others it may extend through both layers of the fold. The slot B3522 may, in some embodiments, be 1 cm (or about 1 cm) long. Some embodiments may instead employ a circular or elliptical hole in the fold B3521. The hole may face proximally so that the conduit B3550 may be inserted into the hole and rest between the folded layers of spacer fabric. In some embodiments, the conduit B3550 may be adhered to the material of the fold B3521, while in other embodiments it may not.

The port B3500 may have a filter element B3530 located adjacent the orifice B3541, and as illustrated is located between the lower layer B3540 and the spacer layer B3520. As illustrated, the filter element B3530 may have a round or disc shape. The filter element B3530 is impermeable to liquids, but permeable to gases. The filter element B3530 can act as a liquid barrier, to substantially prevent or inhibit liquids from escaping from the wound dressing, as well as an odor barrier. The filter element B3530 may also function as a bacterial barrier. In some embodiments, the pore size of the filter element B3530 can be approximately 0.2 µm. Suitable materials for the filter material of the filter element include 0.2 micron Gore™ expanded PTFE from the MMT range, PALL Versapore™ B200R, and Donaldson™ TX6628. The filter element B3530 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element B3530 may be adhered to one or both of top surface of the bottom layer B3540 and the bottom surface of the spacer layer B3520 using an adhesive such as, but not limited to, a UV cured adhesive. In other embodiments, the filter B3530 may be welded to the inside of the spacer layer B3520 and to the top surface of the bottom layer B3540. The filter may also be provided adjacent the orifice on a lower surface of the bottom layer B3540. Other possible details regarding the filter are disclosed in U.S. Patent Pub. No. 2011/0282309 and incorporated by reference herein.

The proximal end of the port B3500 may be connected to the distal end of a conduit B3550. The conduit B3550 may comprise one or more circular ribs B3551. The ribs B3551 may be formed in the conduit B3550 by grooves in a mold during the manufacturing of the conduit. During heat welding of the upper and lower layers B3515, B3545 melted material from those layers may flow around the ribs B3551, advantageously providing a stronger connection between the conduit B3550 and the layers. As a result, it may be more difficult to dislodge the conduit B3550 out from between the layers during use of the port B3500.

The proximal end of the conduit B3550 may be optionally attached to a connector B3560. The connector B3560 may be used to connect the port B3500 to a source of negative pressure, or in some embodiments to an extension conduit which may in turn be connected to a source of negative pressure. The distal end of the conduit B3550, which is inserted into the spacer layer B3520, may be shaped in such a way to reduce the possibility of occlusion.

Figure 52:
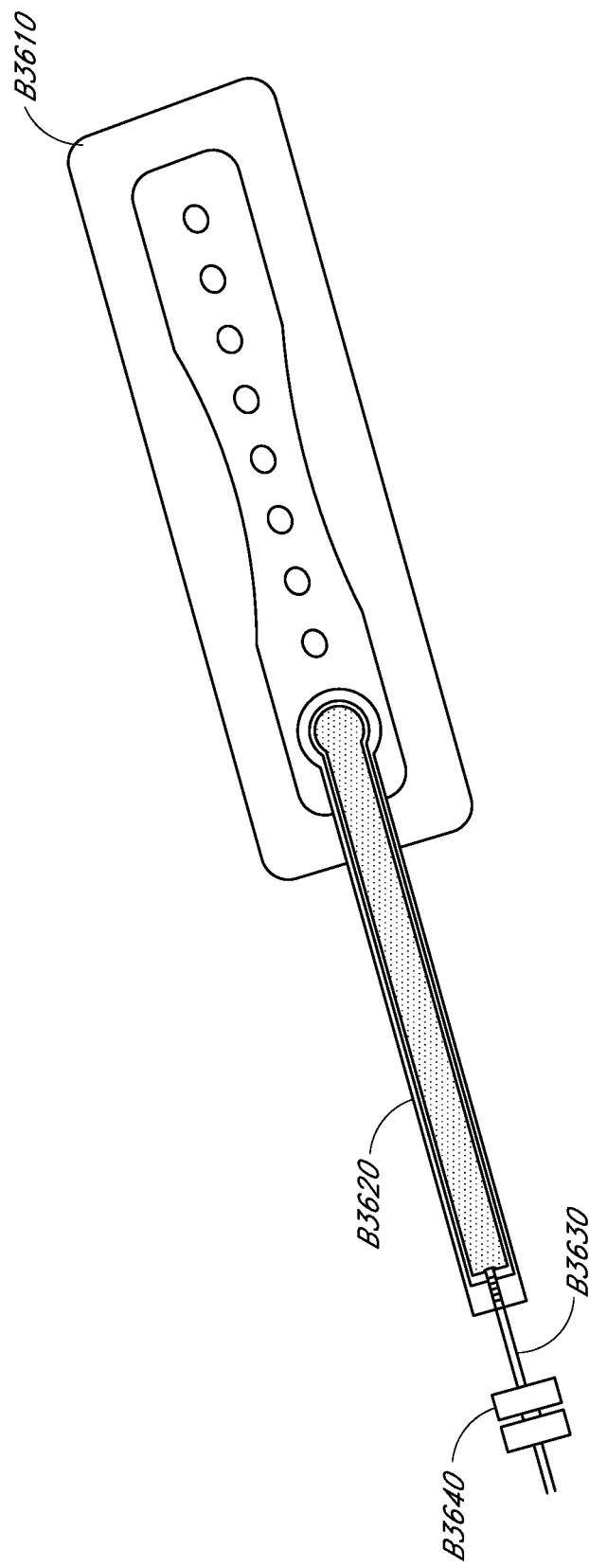
FIG. 52 illustrates an embodiment of a soft or flexible port attached to a wound dressing.

FIG. 52 illustrates an embodiment of a wound dressing B3610 with a flexible port B3620 such as described with respect to FIG. 51 attached. The port B3620 comprises a conduit 3630 and a connector 3640 for connecting the port to a source of negative pressure or to an extension conduit. The dressing B3610 comprises an obscuring layer with one row of eight holes in a linear arrangement, and is described above in more detail with respect to FIG. 41. Although in this depiction the port B3620 is connected over a circular window in the obscuring layer of the dressing B3610, in other embodiments the port B3620 may be connected over a maltese cross in the obscuring layer. In some embodiments, the maltese cross may be of a larger diameter than the port and may be at least partially viewable after the port is attached to the dressing.

Figure 53A:
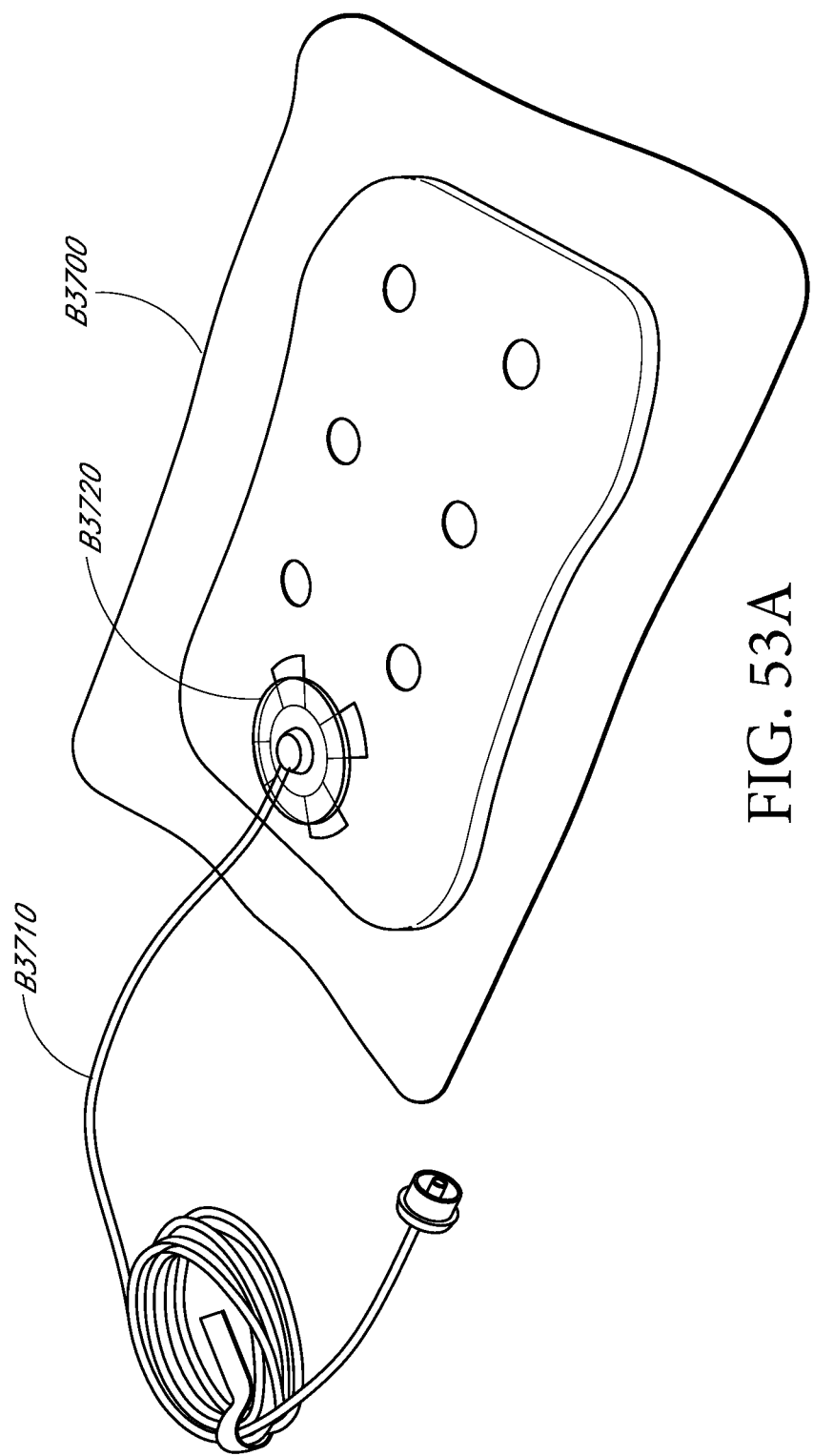
FIG. 53A illustrates a perspective view of a wound dressing.

FIG. 53A illustrates a perspective view of an embodiment of the dressing. Although the configuration as depicted is similar to the embodiment of FIG. 45B, the dressing can have any of the constructions of different layers previously described. Conduit B3710 is connected to the dressing B3700 via port B3720, however other embodiments of ports may be connected to the dressing, for example the flexible port of FIG. 51.

Figure 53B:
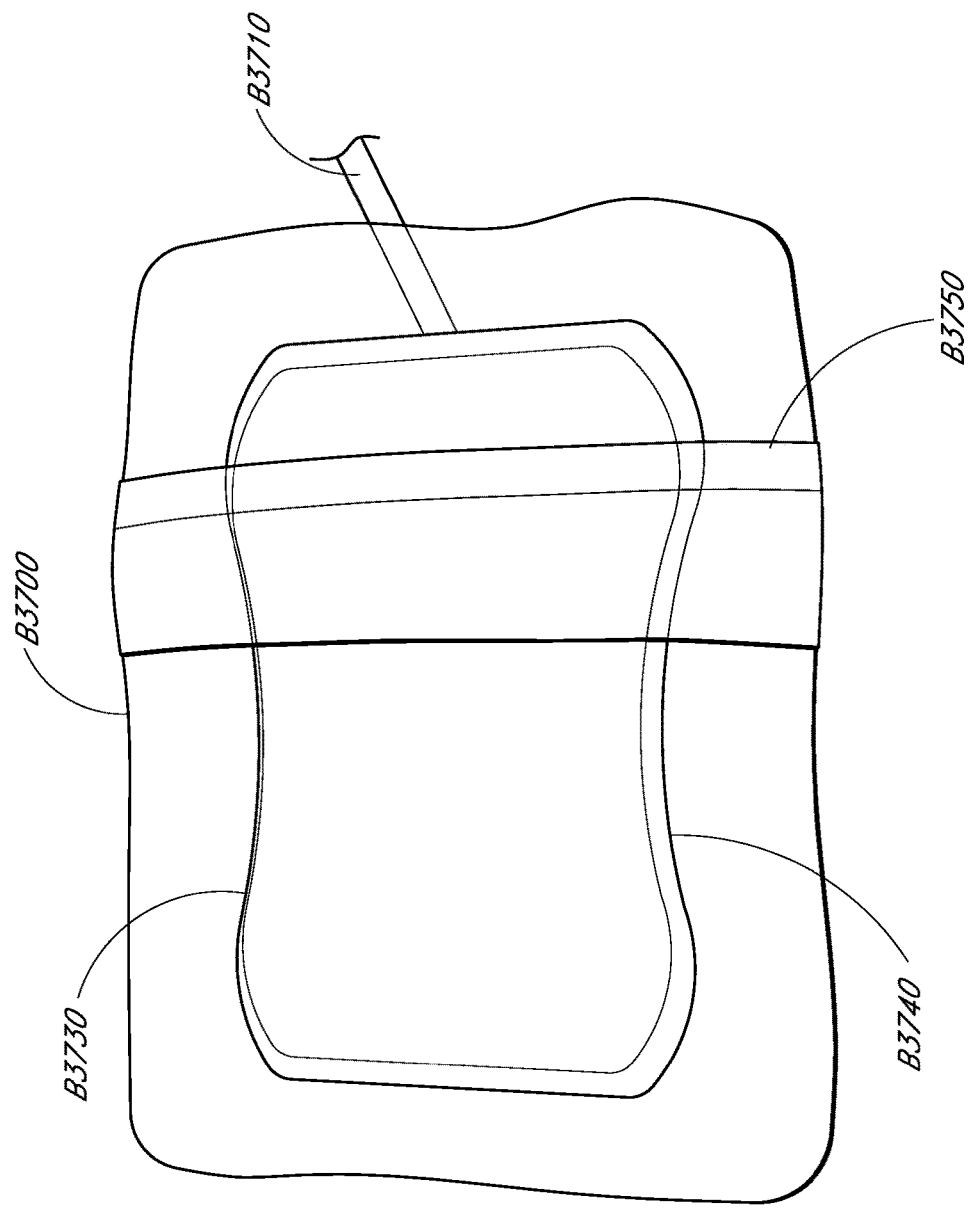
FIG. 53B illustrates a bottom view of the wound dressing of FIG. 53A.

FIG. 53B illustrates a bottom view of the dressing B3700. The view illustrates a transmission layer B3730 and an acquisition distribution layer B3740, which may be similar to the transmission layer B3450 and acquisition distribution layer B3440 of FIGS. 50A and 50B. In some embodiments, the perimeter of the transmission layer B3730 may be slightly smaller than the perimeter of the acquisition distribution layer B3740. The view also illustrates one embodiment of a release layer B3750 similar to release layer B3480 previously described for use in protecting the adhesive side of the wound contact layer. The release layer B3750 as illustrated is made of two separate layers of material that can be removed from the adhesive side of the wound contact layer by pulling on flaps attached to the release layer.

It will be of course appreciated that other dressing configurations are possible other than a narrow central portion configuration, a three-lobed configuration, a four-lobed configuration, including, for example, hexagonal or circular shaped backing layers for use in dressings. As illustrated in FIGS. 31A-B, these embodiments may also comprise various configurations of slits, described previously, so as to enhance conformability of the dressing in non-planar wounds. Also, as described previously, the absorbent layers of these embodiments may be colored or obscured with an obscuring layer, and optionally provided with one or more viewing windows. Further, the domed ports of these embodiments may also be replaced with one or more fluidic connectors of the type described below in FIGS. 39A-B, and vice versa. Additionally, all features and structures described for wound dressings with the waisted portion configuration can be incorporated into any shape or dressing configuration as described herein.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. An apparatus to provide suction to a wound site comprising:
    a wound dressing comprising:
        an absorbent layer for absorbing wound exudate from the wound site,
        a transparent cover layer overlying the absorbent layer and extending over the entirety of the absorbent layer, the transparent cover layer_comprising an opening; and
        an obscuring layer between the absorbent layer and the transparent cover layer that at least partially obscures visualization of the absorbent layer from above the transparent cover layer;
    a fluidic connector attached to the wound dressing comprising:
        a spacer layer comprising a proximal end, an elongate middle portion, and a distal end;
        a transparent top layer constructed from a liquid impermeable material provided over the spacer layer, the transparent top layer defining an upper surface of the fluidic connector;
        a bottom layer constructed from a liquid impermeable material provided below the spacer layer, wherein the transparent top layer and the bottom layer are sealed together around a perimeter thereof to enclose the spacer layer and wherein the spacer layer is in contact with the transparent top layer and the bottom layer; and
        one or more apertures in the bottom layer beneath the distal end of the spacer layer, wherein a distal end of the bottom layer of the fluidic connector is positioned over the transparent cover layer of the wound dressing with the one or more apertures in the bottom layer being positioned over the opening in the transparent cover layer; and
    a portion of absorbent material positioned below the distal end of the spacer layer, wherein the portion of absorbent material is visible around an outer perimeter of the spacer layer of the fluidic connector through the transparent top layer of the fluidic connector and is configured to indicate saturation of the absorbent layer by the wound exudate.

2. The apparatus of claim 1, wherein the apparatus is configured to prevent the wound exudate from escaping the wound dressing through the opening in the transparent cover layer.

3. The apparatus of claim 1, wherein the transparent top layer and the bottom layer are heat sealed together around the perimeter.

4. The apparatus of claim 1, wherein the distal end of the spacer layer is enlarged relative to a width of the elongate middle portion of the spacer layer and a width of the proximal end of the spacer layer.

5. The apparatus of claim 1, wherein the distal end of each of the transparent top layer and the bottom layer is enlarged relative to a width of the elongate middle portion of the transparent top layer and the bottom layer, respectively, and a width of the proximal end of the transparent top layer and the bottom layer, respectively.

6. The apparatus of claim 1, wherein the spacer layer comprises one of a 3D knitted or 3D fabric material, foam, a porous material and non-woven material.

7. The apparatus of claim 1, wherein the distal end of the bottom layer comprises adhesive.

8. The apparatus of claim 1, wherein the spacer layer has a substantially rectangular cross-sectional dimension.

9. The apparatus of claim 1, wherein the spacer layer is adhered to at least one of the transparent top layer and the bottom layer.

10. The apparatus of claim 1, wherein the absorbent layer comprises superabsorber material.

11. The apparatus of claim 10, wherein said superabsorber material comprises sodium polyacrylate superabsorber particles.

12. The apparatus of claim 10, wherein said superabsorber material comprises superabsorber fibers comprising carbomethoxycellulose materials.

13. The apparatus of claim 1, wherein the wound dressing comprises a wound contact layer comprising openings for transmission of the suction to the wound site.

14. The apparatus of claim 13, wherein the transparent cover layer is attached to the wound contact layer around a perimeter, thereby defining an interior space comprising the absorbent layer and the obscuring layer.

* * * * *

UNITED STATES PATENT AND TRADEMARK OFFICE
CERTIFICATE OF CORRECTION

PATENT NO. : 10,507,141 B2
APPLICATION NO. : 15/890218
DATED : December 17, 2019
INVENTOR(S) : Julie Allen It is certified that error appears in the above-identified patent and that said Letters Patent is hereby corrected as shown below:

In the Specification

Column 5, Line 43, delete "FIG." and insert --FIGS.--.

Column 6, Line 54, delete "FIG." and insert --FIGS.--.

Column 7, Line 12, delete "chromacity" and insert --chromaticity--.

Column 9, Line 32, delete "(that" and insert --that--.

Column 10, Line 60, delete "carbomethoxycellulose" and insert --carboxymethylcellulose--.

Column 22, Line 11, delete "chromacity" and insert --chromaticity--.

Column 22, Line 13, delete "chromacity" and insert --chromaticity--.

Column 23, Line 35, delete "chromacity" and insert --chromaticity--.

Column 23, Line 46, after "pump" insert --.--.

Column 24, Line 9, delete "chromacity" and insert --chromaticity--.

Column 25, Line 28, delete "chromacity" and insert --chromaticity--.

Column 38, Line 6, delete "Fare" and insert --F are--.

Column 38, Line 47, delete "Fare" and insert --F are--.

Column 50, Line 34, delete "carbomethoxycellulose" and insert --carboxymethylcellulose--.

Signed and Sealed this
Twenty-sixth Day of May, 2020

Andrei Iancu
*Director of the United States Patent and Trademark Office*

CERTIFICATE OF CORRECTION (continued)
U.S. Pat. No. 10,507,141 B2

Column 52, Line 63, delete "chromacity" and insert --chromaticity--.

Column 53, Line 1, delete "chromacity" and insert --chromaticity--.

In the Claims

Column 58, Lines 53-54, Claim 12, delete "carbomethoxycellulose" and insert --carboxymethylcellulose--.